United States Patent
Machii et al.

[11] Patent Number: 5,891,902
[45] Date of Patent: Apr. 6, 1999

[54] INDOLE DERIVATIVES

[75] Inventors: Daisuke Machii, Sunto-gun; Haruki Takai, Yokohama; Nobuo Kosaka; Hisakatsu Seo, both of Sunto-gun; Tomomi Sugiyama, Mishima; Joji Nakamura, Sunto-gun, all of Japan; Hiroyuki Ishida, Mountain View, Calif.; Katsushige Gomi, Susono, Japan; Soichiro Sato, Mishima, Japan; Masako Uchii, Mishima, Japan; Koji Suzuki, Mishima, Japan

[73] Assignee: Kyowa Hakko Kogyo Co., Ltd., Tokyo, Japan

[21] Appl. No.: 676,177

[22] Filed: Jul. 15, 1996

Related U.S. Application Data

[63] Continuation of PCT/JP95/00019, Jan. 11, 1995.

[30] Foreign Application Priority Data

| Jan. 18, 1994 | [JP] | Japan | 6-003334 |
| Jul. 18, 1995 | [JP] | Japan | 7-181950 |
| Jul. 18, 1995 | [JP] | Japan | 7-181951 |
| Jul. 18, 1995 | [JP] | Japan | 7-181952 |

[51] Int. Cl.⁶ ............ A61K 31/40; C07D 209/12; C07D 209/14; C07D 209/30
[52] U.S. Cl. ............ 514/415; 514/418; 514/235.2; 514/323; 514/339; 514/397; 514/399; 514/253; 548/469; 548/486; 548/490; 548/491; 548/335.1; 548/341.1; 548/342.1; 546/201; 546/277.4; 546/277.7; 544/143; 544/144; 544/373
[58] Field of Search ............ 514/253, 415, 514/418; 544/373, 143, 144; 548/469, 486, 490, 491, 335.1, 341.1, 342.1; 546/201, 277.4, 277.6

[56] References Cited

U.S. PATENT DOCUMENTS

| 5,296,499 | 3/1994 | Sohda et al. | 514/419 |
| 5,413,997 | 5/1995 | Kinoshita et al. | 514/183 |

FOREIGN PATENT DOCUMENTS

| 62141070 | 6/1987 | Japan. |
| 63208571 | 8/1988 | Japan. |
| 76586 | 3/1995 | Japan. |

OTHER PUBLICATIONS

J. Med. Chem., vol. 17, No. 12 (1974) 1298–1304.

*Primary Examiner*—Johann Richter
*Assistant Examiner*—Jane C. Oswecki
*Attorney, Agent, or Firm*—Fitzpatrick, Cella, Harper & Scinto

[57] ABSTRACT

The present invention relates to indole derivatives represented by formula (I):

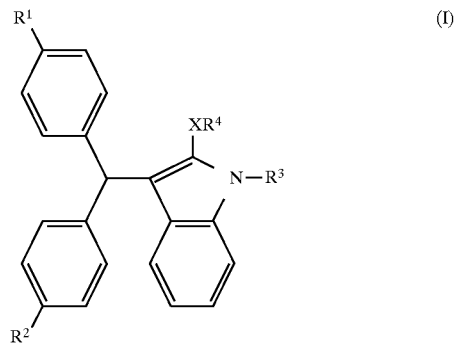

wherein $R^1$ and $R^2$ independently represent hydrogen, lower alkyl, hydroxy, lower alkoxy, halogen, —O—$(CH_2)_n$—$OR^5$, or

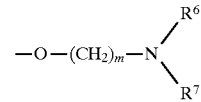

$R^3$ represents hydrogen, lower alkyl, or

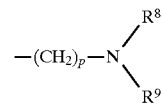

$R^4$ represents hydroxy, lower alkoxy, substituted or unsubstituted aryloxy, or —$NR^{10}R^{11}$, and X represents CO or $SO_2$, with the proviso that when $R^3$ is hydrogen or lower alkyl, and X is CO, $R^4$ is —$NR^{10}R^{11}$, or pharmaceutically acceptable salts thereof.

16 Claims, No Drawings

INDOLE DERIVATIVES

CROSS REFERENCE TO RELATED APPLICATION

This application is a continuation-in-part of application PCT/JP95/00019, filed Jan. 11, 1995.

1. Technical Field

The present invention relates to indole derivatives which are useful as therapeutic agents for osteoporosis.

2. Background Art

It is disclosed in Japanese Published Unexamined Patent Application No. 215461/91 that a triphenylmethane derivative having a substituent such as carbamoyl is useful as a therapeutic agent for osteoporosis. Further, it is disclosed in Japanese Published Unexamined Patent Application No. 211651/92 that an indole derivative having a phenyl group is useful as a therapeutic agent for osteoporosis. Further, an indole derivative having a carbamoyl group is disclosed in Japanese Published Unexamined Patent Application No. 76586/95. Further, an indole derivative having a benzhydryl group is disclosed in J. Med. Chem., 17, 1298 (1974).

DISCLOSURE OF THE INVENTION

The present invention relates to indole derivatives represented by formula (I):

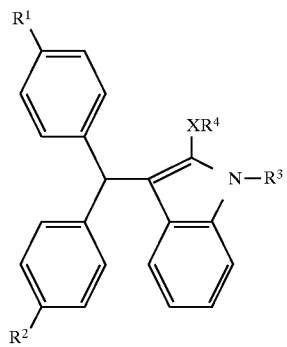

wherein $R^1$ and $R^2$ independently represent hydrogen, lower alkyl, hydroxy, lower alkoxy, halogen, —O—$(CH_2)_n$—$OR^5$ (wherein $R^5$ represents hydrogen or lower alkyl, and n is an integer of 1 to 6), or

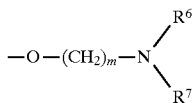

(wherein $R^6$ and $R^7$ independently represent hydrogen or lower alkyl, or $R^6$ and $R^7$ are combined together with the adjacent nitrogen atom to form a substituted or unsubstituted alicyclic heterocyclic group, and m represents an integer of 2 to 6), $R^3$ represents hydrogen, lower alkyl, or

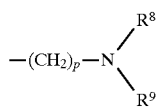

(wherein $R^8$ and $R^9$ independently represent hydrogen or lower alkyl, or $R^8$ and $R^9$ are combined together with the adjacent nitrogen atom to form a substituted or unsubstituted alicyclic heterocyclic group, and p represents an integer of 2 to 6), $R^4$ represents hydroxy, lower alkoxy, substituted or unsubstituted aryloxy, or —$NR^{10}R^{11}$ {wherein $R^{10}$ and $R^{11}$ independently represent hydrogen, lower alkyl, alicyclic alkyl, lower alkenyl, substituted or unsubstituted aryl, a substituted or unsubstituted heterocyclic group,

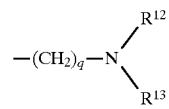

(wherein $R^{12}$ and $R^{13}$ independently represent hydrogen or lower alkyl, or $R^{12}$ and $R^{13}$ are combined together with the adjacent nitrogen atom to form a substituted or unsubstituted alicyclic heterocyclic group, and q represents an integer of 2 to 6), or —$(CH_2)_r$—$R^{14}$ (wherein $R^{14}$ represents substituted or unsubstituted aryl or a substituted or unsubstituted heterocyclic group, and r is an integer of 1 to 6), or $R^{10}$ and $R^{11}$ are combined together with the adjacent nitrogen atom to form a substituted or unsubstituted alicyclic heterocyclic group}, and X represents CO or $SO_2$, with the proviso that when $R^3$ is hydrogen or lower alkyl, and X is CO, $R^4$ is —$NR^{10}R^{11}$, or pharmaceutically acceptable salts thereof.

The compounds represented by formula (I) are hereinafter referred to as Compounds (I). The same applies to the compounds of other formula numbers.

In the definitions of the group in formula (I), the lower alkyl and the lower alkyl moiety of the lower alkoxy mean a straight or branched alkyl group having 1 to 8 carbon atoms such as methyl, ethyl, propyl, isopropyl, butyl, isobutyl, sec-butyl, tert-butyl, pentyl, neopentyl, hexyl, heptyl, and octyl. The alicyclic alkyl means an alicyclic alkyl group having 3 to 8 carbon atoms such as cyclopropyl, cyclobutyl, cyclopentyl, cyclohexyl, cycloheptyl, and cyclooctyl. The lower alkenyl means a straight or branched alkenyl group having 2 to 8 carbon atoms such as vinyl, allyl, methacryl, crotyl, 3-butenyl, 2-pentenyl, 4-pentenyl, 2-hexenyl, 5-hexenyl, 2-heptenyl, 6-heptenyl, 2-octenyl, and 7-octenyl. The halogen means fluorine, chlorine, bromine, and iodine. The aryl and the aryl moiety of the aryloxy mean phenyl and naphthyl. The alicyclic heterocyclic group means a group such as pyrrolidinyl, imidazolidinyl, pyrazolidinyl, piperidino, piperazinyl, homopiperazinyl, morpholino, and thiomorpholino. The heterocyclic group means a group such as an aromatic heterocyclic group (e.g., pyridyl, pyrazinyl, pyrimidinyl, pyridazinyl, quinolyl, isoquinolyl, phthalazinyl, naphthylidinyl, quinoxalinyl, thienyl, furyl, pyrrolyl, imidazolyl, pyrazolyl, triazolyl, tetrazolyl, thiazolyl, oxazolyl, indolyl, indazolyl, benzimidazolyl, purinyl), pyranyl, piperidyl, and tetrahydrofuranyl, in addition to the above-mentioned alicyclic heterocyclic groups.

The substituted alicyclic heterocyclic group, the substituted heterocyclic group, the substituted aryloxy, and the substituted aryl each has 1 to 3 independently selected substituents. Examples of the substituents are lower alkyl, hydroxy, lower alkoxy, lower alkylthio, aralkyl, carboxy, lower alkoxycarbonyl, lower alkanoyl, aroyl, halogen, nitro, amino, mono- or di(lower alkyl)amino, trifluromethyl, oxo, substituted or unsubstituted phenyl, pyridyl, and pyrimidinyl.

In the definitions of the substituents, the lower alkyl and the lower alkyl moiety of the lower alkoxy, lower alkylthio, lower alkoxycarbonyl, and mono- or di(lower alkyl)amino have the same meaning as defined for the above-mentioned lower alkyl. The aralkyl means an aralkyl group having 7 to 13 carbon atoms such as benzyl, phenethyl, benzhydryl, and naphthylmethyl. The lower alkanoyl means an alkanoyl group having 1 to 7 carbon atoms such as formyl, acetyl, propionyl, butyryl, isobutyryl, valeryl, pivaloyl, hexanoyl, and heptanoyl. The aroyl has the same meaning as defined for the above-mentioned aroyl. The halogen has the same meaning as defined for the above-mentioned halogen. The substituted phenyl has 1 to 3 independently selected substituents such as lower alkyl, hydroxy, lower alkoxy, lower alkylthio, aralkyl, carboxy, lower alkoxycarbonyl, lower alkanoyl, aroyl, halogen, nitro, amino, mono- or di(lower alkyl)amino, and trifluoromethyl. The lower alkyl, lower alkoxy, lower alkylthio, aralkyl, lower alkoxy carbonyl, lower alkanoyl, aroyl, halogen, and mono- or di(lower alkyl)amino have the same definitions as defined above.

The pharmaceutically acceptable salts of Compounds (I) include inorganic acid addition salts such as hydrochloride, sulfate, nitrate, and phosphate, organic acid addition salts such as acetate, maleate, fumarate, tartrate, citrate, lactate, glyoxylate, aspartate, methane sulfonate, ethane sulfonate, and benzene sulfonate, metal salts such as sodium salt, potassium salt, and calcium salt, ammonium salt, tetramethylammonium salt, and amine addition salts such as a salt with morpholine.

The processes for producing Compounds (I) are described below.

Compound (I) can be prepared according to the following reaction step:

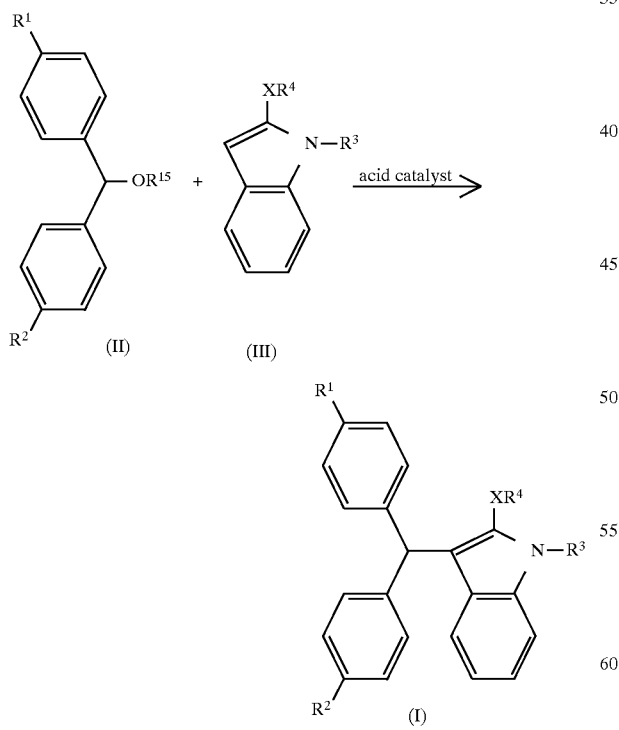

{In the formulae, $R^{15}$ represents hydrogen, lower alkyl, lower alkanoyl, or

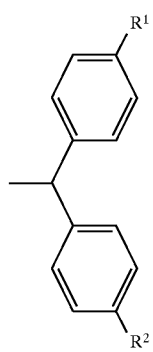

(wherein $R^1$ and $R^2$ have the same meanings as defined above), and $R^1$, $R^2$, $R^3$, $R^4$, and X have the same meanings as defined above.}

The lower alkyl and lower alkanoyl in the definition of $R^{15}$ have the same meanings as defined above.

Compound (I) can be obtained by reacting Compound (II) with Compound (III) in the presence of 0.1 equivalence to an excess amount of an acid catalyst such as boron trifluoride-ether complex, methanesulfonic acid, paratoluenesulfonic acid, and trifluoroacetic acid, in a solvent such as methylene chloride, chloroform, ether, and tetrahydrofuran, at a temperature of −20° C. to the boiling point of the solvent employed for 0.5 to 48 hours.

Compound (Ib), which is Compound (I) in which $R^1$ and $R^2$ are groups other than hydroxy, and $R^3$ is a group other than hydrogen, can also be prepared from Compound (Ia), which is Compound (I) in which $R^1$ and $R^2$ are groups other than hydroxy, and $R^3$ is hydrogen, according to the following reaction step:

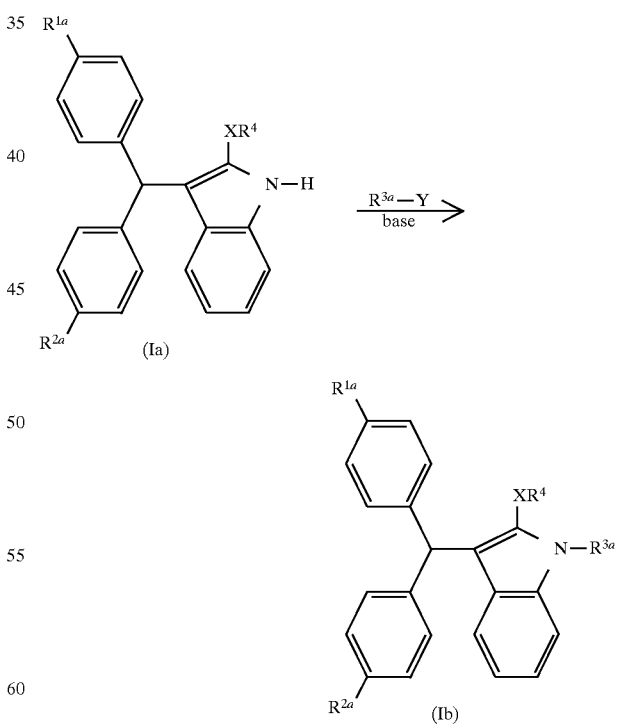

(In the formulae, $R^{1a}$ and $R^{2a}$ each represents a group other than hydroxy in the definition of $R^1$ and $R^2$, $R^{3a}$ represents a group other than hydrogen in the definition of $R^3$, Y represents chlorine, bromine, or iodine, and $R^4$ and X have the same meanings as defined above.)

Compound (Ib) can be obtained by reacting Compound (Ia) with a halogenated alkyl or halogenated aminoalkyl in the presence of a base such as sodium hydride and potassium tert-butoxide, in a solvent such as a lower alcohol (e.g., methanol, ethanol), N,N-dimethylformamide, dimethyl sulfoxide, and tetrahydrofuran, at a temperature of 0° C. to the boiling point of the solvent employed for 0.5 to 24 hours.

Compound (Iba), which is Compound (Ib) in which $R^{3a}$ is

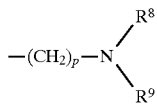

(wherein $R^8$, $R^9$, and p have the same meanings as defined above), can be prepared from Compound (Ia) according to the following reaction steps:

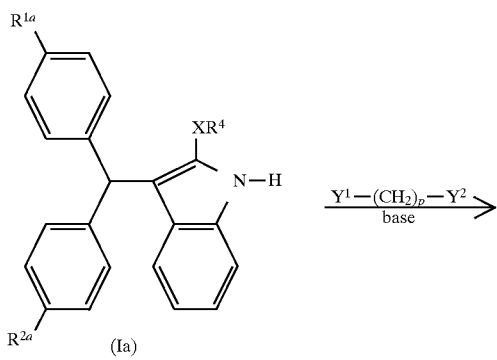

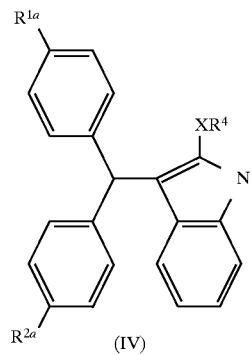

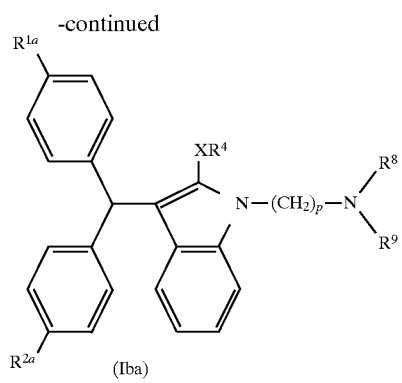

(In the formulae, $Y^1$ and $Y^2$ independently represent chlorine, bromine, or iodine, and $R^{1a}$, $R^{2a}$, $R^4$, $R^8$, $R^9$, X, and p have the same meanings as defined above.)

Compound (IV) can be obtained by reacting Compound (Ia) with a,w-dihalogenated alkyl in the presence of a base such as sodium hydride and potassium tert-butoxide, in a solvent such as a lower alcohol (e.g., methanol, ethanol), N,N-dimethylformamide, dimethyl sulfoxide, and tetrahydrofuran, at a temperature of 0° C. to the boiling point of the solvent employed for 0.5 to 24 hours. Then, Compound (Iba) can be obtained by reacting Compound (IV) with 1 equivalence to an excess amount of ammonia, a primary amine, or a secondary amine, in a solvent such as a lower alcohol (e.g., methanol, ethanol), N,N-dimethylformamide, dimethyl sulfoxide, tetrahydrofuran, and water, or a mixed solvent thereof, if necessary, in the presence of an inorganic base such as potassium carbonate and sodium carbonate, at a temperature of 0° C. to the boiling point of the solvent employed for one hour to 7 days.

Compound (Ibb), which is Compound (Ib) in which $R^{1a}$ is

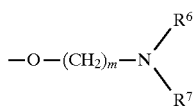

(wherein $R^6$, $R^7$, and m have the same meanings as defined above), can be prepared from Compound (V) and Compound (IIIa), which is Compound (III) in which $R^3$ is a group other than hydrogen, according to the following reaction steps:

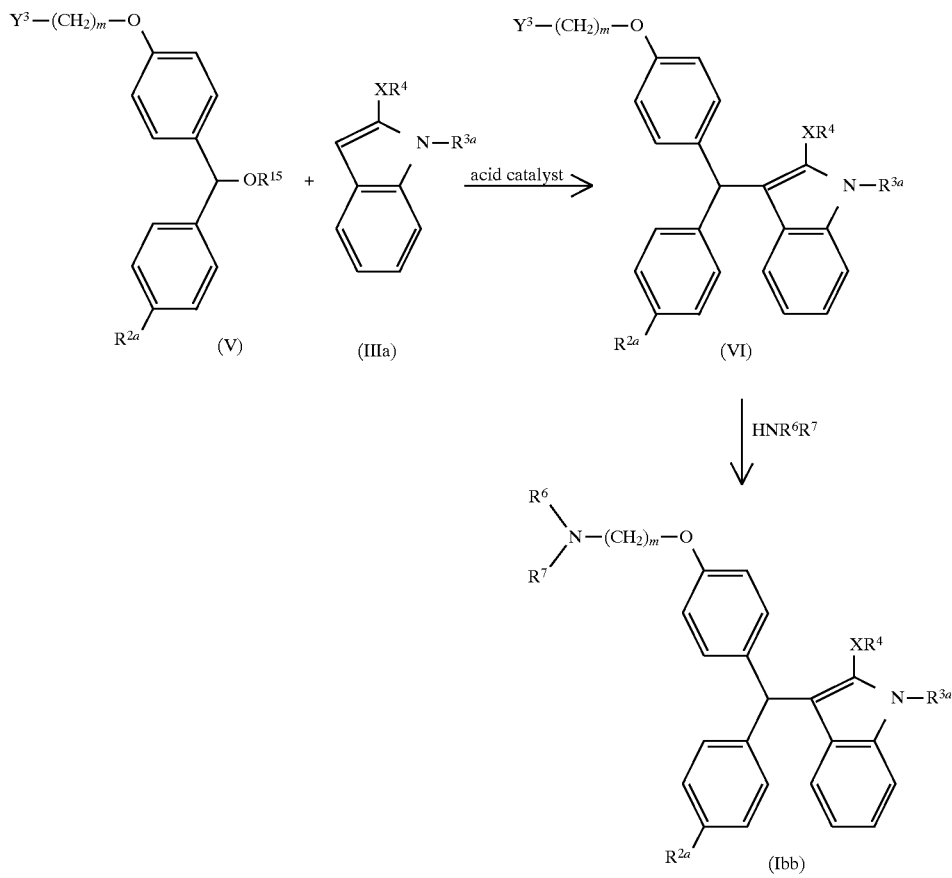

(In the formulae, $Y^3$ represents chlorine, bromine, or iodine, and $R^{2a}$, $R^{3a}$, $R^4$, $R^6$, $R^7$, $R^{15}$, X, and m have the same meanings as defined above.)

Compound (VI) can be obtained from Compound (V) and Compound (IIIa) according to a method similar to that in producing Compound (I) from Compound (II) and Compound (III). Compound (Ibb) can be obtained from Compound (VI) according to a method similar to that in producing Compound (Iba) from Compound (IV).

Compound (V) can be obtained from Compound (IIb), which is Compound (II) in which $R^1$ is hydroxy, and $R^2$ is a group other than hydroxy, and a,w-dihalogenated alkyl according to a method similar to that in producing Compound (IV) from Compound (Ia) and a,w-dihalogenated alkyl.

Compound (Id), which is Compound (I) in which both of $R^1$ and $R^2$ are hydroxy, can be prepared from Compound (Ic), which is Compound (I) in which both of $R^1$ and $R^2$ are methoxymethoxy, according to the following reaction step:

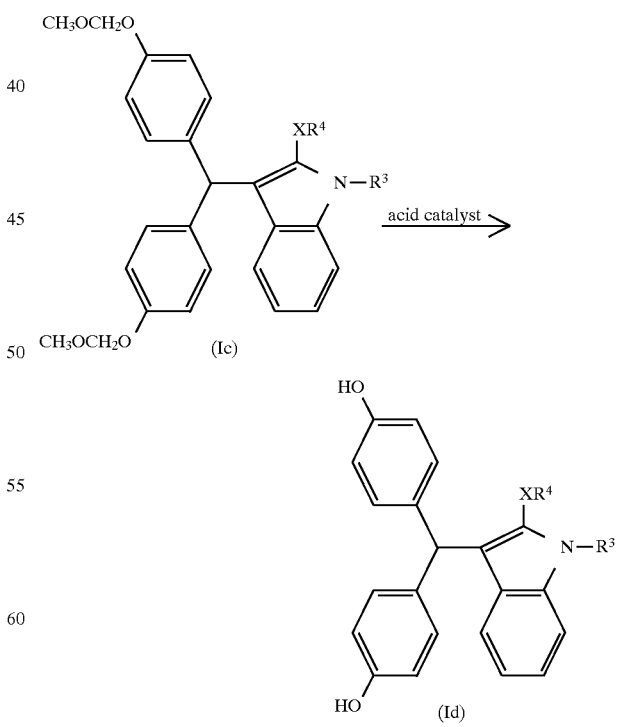

(In the formulae, $R^3$, $R^4$, and X have the same meanings as defined above.)

Compound (Id) can be obtained by treating Compound (Ic) in the presence of an acid catalyst such as hydrochloric acid, sulfuric acid, and paratoluenesulfonic acid, in a solvent such as a lower alcohol (e.g., methanol, ethanol), N,N-dimethylformamide, dimethyl sulfoxide, tetrahydrofuran, and water, or a mixed solvent thereof, at a temperature of room temperature to the boiling point of the solvent employed for 0.5 to 24 hours.

Compound (Ie), which is Compound (I) in which only one of $R^1$ and $R^2$ is hydroxy, can be prepared from Compound (If), which is Compound (I) in which only one of $R^1$ and $R^2$ is methoxymethoxy, according to a method similar to that in producing Compound (Id) from Compound (Ic).

Compound (Id) can also be prepared from Compound (VII) according to the following reaction step:

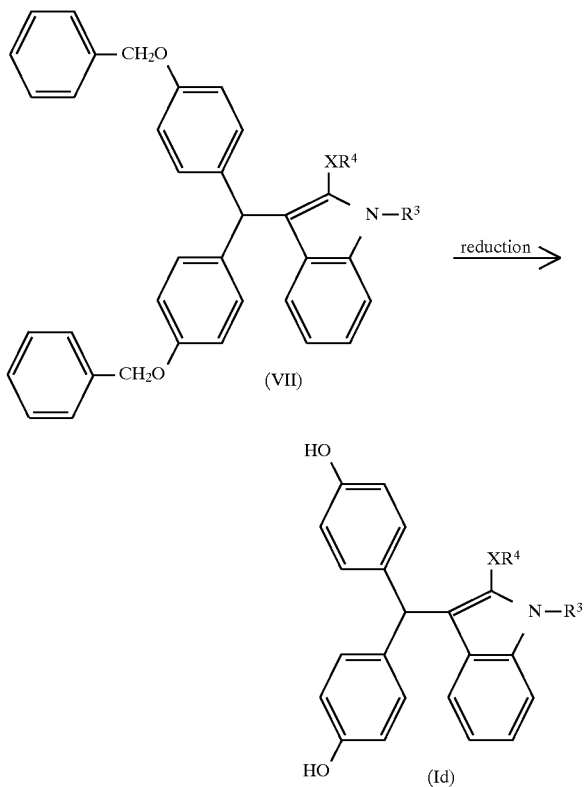

(In the formulae, $R^3$, $R^4$, and X have the same meanings as defined above.)

Compound (Id) can be obtained by hydrogenating Compound (VII) in the presence of a catalyst such as palladium on carbon, in a solvent such as a lower alcohol (e.g., methanol, ethanol), N,N-dimethylformamide, dimethyl sulfoxide, and tetrahydrofuran, or a mixed solvent thereof, under a hydrogen atmosphere, at a temperature of room temperature to the boiling point of the solvent employed for 0.5 to 24 hours.

Compound (VII) can be obtained from Compound (VIII), which is a compound in which the parts of $R^1$ and $R^2$ are replaced by benzyloxy groups in Compound (II), and Compound (III) according to a method similar to that in producing Compound (I) from Compound (II) and Compound (III).

Compound (Ig), which is Compound (I) in which only one of $R^1$ and $R^2$ is hydroxy, can be prepared from Compound (IX), which is Compound (I) in which only one of $R^1$ and $R^2$ is benzyloxy, according to a method similar to that in producing Compound (Id) from Compound (VII).

Compound (IX) can be obtained from Compound (X), which is a compound in which only one of $R^1$ and $R^2$ is replaced by a benzyloxy group in Compound (II), and Compound (III) according to a method similar to that in producing Compound (I) from Compound (II) and Compound (III).

Compound (Ii), which is Compound (I) in which $R^4$ is $-NR^{10}R^{11}$ and X is CO, can be prepared from Compound (Ih), which is Compound (I) in which $R^4$ is hydroxy and X is CO, or Compound (XI) according to the following reaction step:

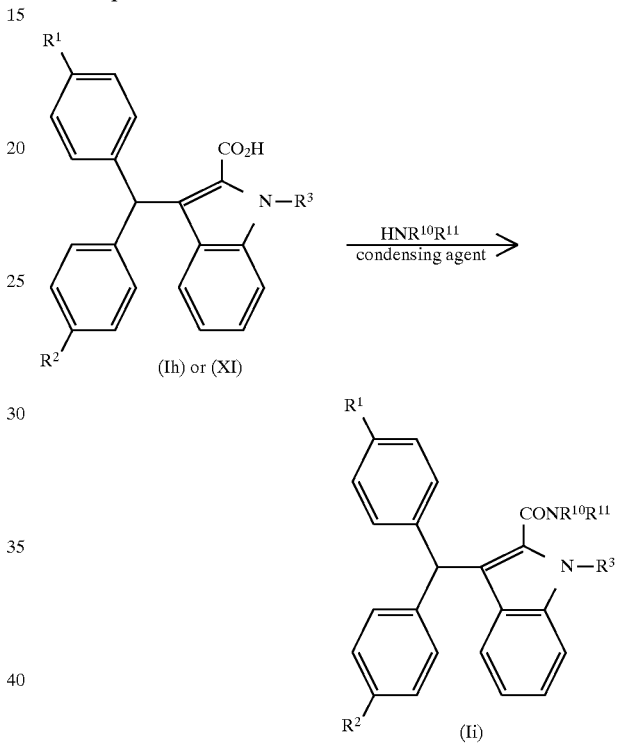

(In the formulae, $R^1$, $R^2$, $R^3$, $R^{10}$, and $R^{11}$ have the same meanings as defined above.)

Compound (Ii) can be obtained by reacting Compound (Ih) or Compound (XI) with ammonia, a primary amine, or a secondary amine in the presence of a condensing agent such as dicyclohexylcarbodiimide and 1-(3-dimethylaminopropyl)-3-ethylcarbodiimide hydrochloride, in a solvent such as methylene chloride, chloroform, and tetrahydrofuran, at a temperature of room temperature to the boiling point of the solvent employed for 1 to 24 hours.

Compound (Iha), which is Compound (Ih) in which $R^1$ and $R^2$ are groups other than hydroxy, or Compound (XIa), which is Compound (XI) in which $R^1$ and $R^2$ are groups other than hydroxy and $R^3$ is lower alkyl, can be prepared from Compound (IIa), which is Compound (II) in which $R^1$ and $R^2$ are groups other than hydroxy, and Compound (IIIb), which is Compound (III) in which $R^3$ is hydrogen, $R^4$ is lower alkoxy, and X is CO, according to the following reaction steps:

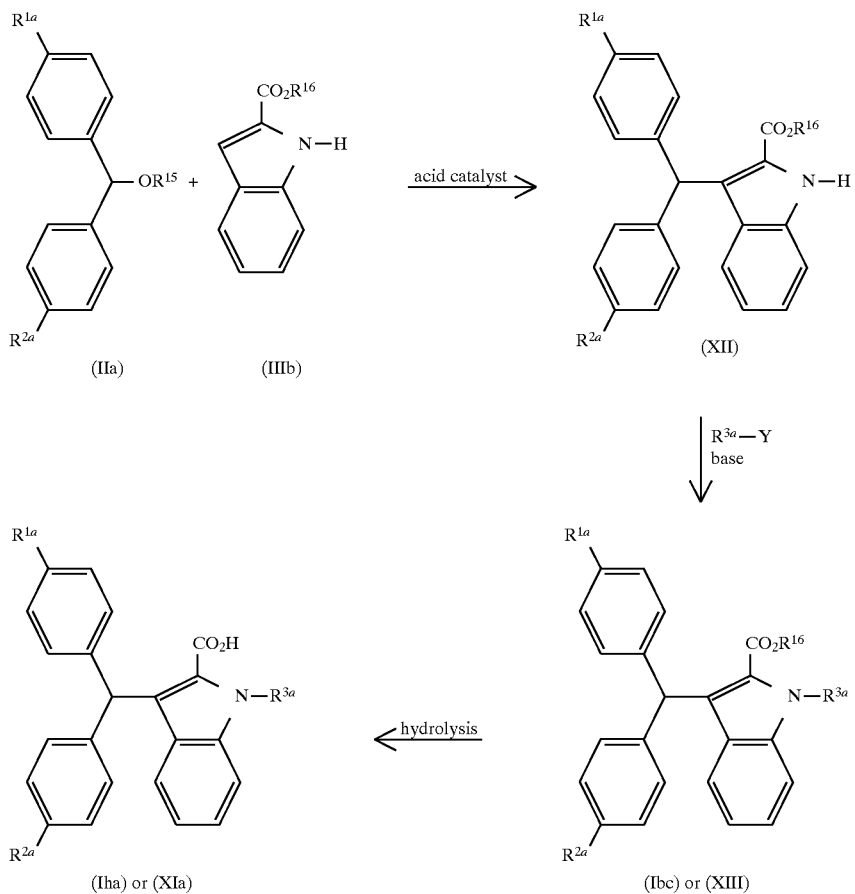

(In the formulae, $R^{16}$ represents lower alkyl or substituted or unsubstituted aryloxy, and $R^{1a}$, $R^{2a}$, $R^{3a}$, and $R^{15}$ have the same meanings as defined above.)

The lower alkyl and substituted or unsubstituted aryloxy in the definition of $R^{16}$ have the same meanings as defined above.

Compound (XII) can be obtained from Compound (IIa) and Compound (IIIb) according to a method similar to that in producing Compound (I) from Compound (II) and Compound (III). Compound (Ibc), which is Compound (Ib) in which $R^4$ is lower alkoxy or substituted or unsubstituted aryloxy and X is CO, or Compound (XIII) can be obtained from Compound (XII) according to a method similar to that in producing Compound (Ib) from Compound (Ia). Then, Compound (Iha) or Compound (XIa) can be obtained from Compound (Ibc) or Compound (XIII), respectively, under the normal hydrolytic condition, for example, treating Compound (Ibc) or Compound (XIII), respectively, in the presence of a base such as lithium hydroxide, sodium hydroxide, and potassium hydroxide, in a solvent such as a lower alcohol (e.g., methanol, ethanol), tetrahydrofuran, N,N-dimethylformamide, and dimethyl sulfoxide, if necessary, in the presence of water, at a temperature of room temperature to the boiling point of the solvent employed for 0.5 to 24 hours.

Compound (XIb), which is Compound (XI) in which $R^1$ and $R^2$ are groups other than hydroxy and $R^3$ is hydrogen, can be prepared from Compound (XII) by hydrolysis of the ester moiety according to the method of producing Compound (Iha) or Compound (XIa) from Compound (Ibc) or Compound (XIII), respectively, or a similar method thereto.

Compound (XIc), which is Compound (XI) in which $R^1$ and $R^2$ are hydroxy and $R^3$ is hydrogen, Compound (Ihb), which is Compound (Ih) in which $R^1$ and $R^2$ are hydroxy, or Compound (XId), which is Compound (XI) in which $R^1$ and $R^2$ are hydroxy and $R^3$ is lower alkyl, can be prepared from Compound (XIIa), which is Compound (XII) in which both of $R^{1a}$ and $R^{2a}$ are methoxymethoxy, from Compound (Ibca), which is Compound (Ibc) in which both of $R^{1a}$ and $R^{2a}$ are methoxymethoxy, or from Compound (XIIIa), which is Compound (XIII) in which $R^{1a}$ and $R^{2a}$ are methoxymethoxy, respectively, by carrying out demethoxymethylation according to the method of producing Compound (Id) from Compound (Ic) or a similar method thereto, followed by hydrolysis of the ester moiety according to the method of producing Compound (Iha) or Compound (XIa) from Compound (Ibc) or Compound (XIII), respectively, or a similar method thereto.

Compound (Ij), which is Compound (I) in which $R^1$ and $R^2$ are groups other than hydroxy, $R^4$ is —$NR^{10a}H$ (wherein $R^{10a}$ represents a group other than hydrogen in the definition of $R^{10}$), and X is $SO_2$, can be prepared according to the following reaction step:

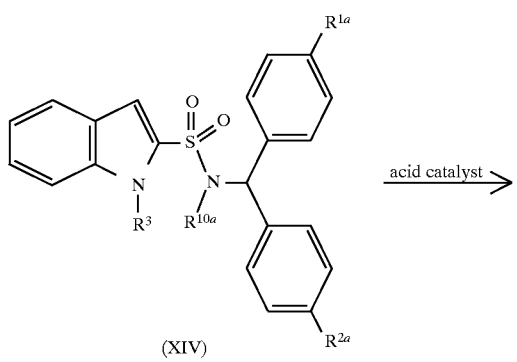

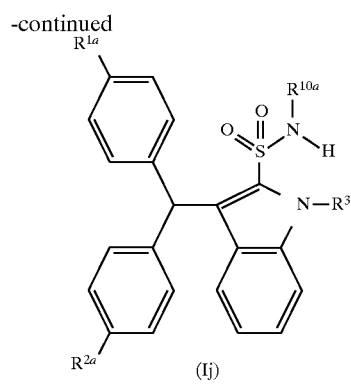

(In the formulae, $R^{1a}$, $R^{2a}$, $R^3$, and $R^{10a}$ have the same meanings as defined above.)

Compound (Ij) can be obtained by treating Compound (XIV) in the presence of 0.1 equivalence to an excess amount of an acid catalyst such as boron trifluoride-ether complex, methanesulfonic acid, paratoluenesulfonic acid, and trifluoroacetic acid, in a solvent such as methylene chloride, chloroform, ether, and tetrahydrofuran, at a temperature of −20° C. to the boiling point of the solvent employed for 0.5 to 48 hours.

Compound (XIV) can be prepared from Compound (XV) or Compound (XVI), which are both obtained according to the method described in J. Med. Chem., 33, 749 (1990) or a similar method thereto, according to the following reaction steps:

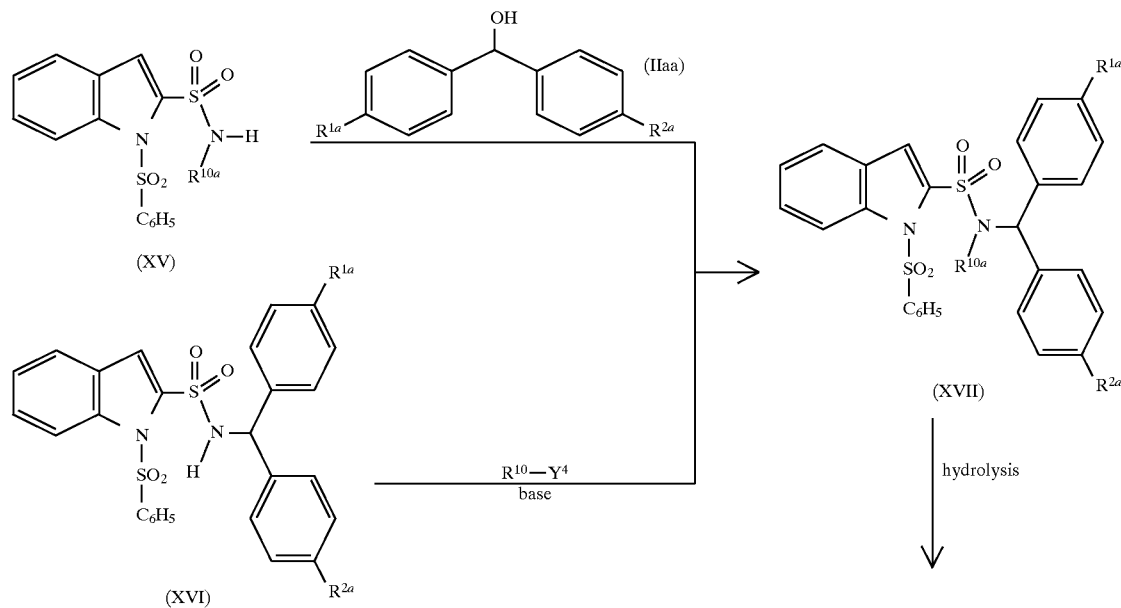

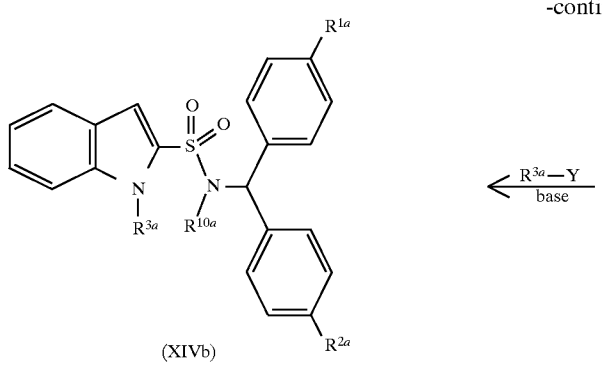

(XIVb)

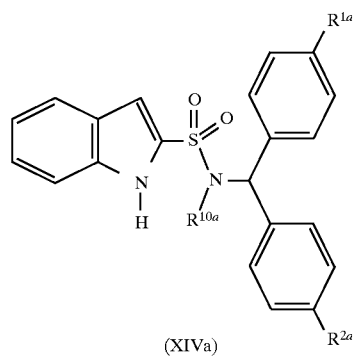

(XIVa)

(In the formulae, $Y^4$ represents chlorine, bromine, or iodine, and $R^{1a}$, $R^{2a}$, $R^{3a}$, $R^{10a}$, and Y have the same meanings as defined above.)

Compound (XVII) can be obtained by reacting Compound (XV) with Compound (IIaa), which is Compound (IIa) in which $R^{15}$ is hydrogen, in the presence of triphenylphosphine and the like, and diethyl azodicarboxylate and the like, in a solvent such as tetrahydrofuran, at a temperature of 0° C. to the boiling point of the solvent employed for 0.5 to 48 hours. Compound (XVII) can also be obtained by reacting Compound (XVI) with a compound represented by formula $R^{10a}$—$Y^4$ (wherein $R^{10a}$ and $Y^4$ have the same meanings as defined above) according to a method similar to that in producing Compound (Ib) from Compound (Ia). Then, Compound (XIVa), which is Compound (XIV) in which $R^3$ is hydrogen, can be obtained from Compound (XVII) according to a method similar to that in producing Compound (Iha) or Compound (XIa) from Compound (Ibc) or Compound (XIII), respectively. Compound (XIVb), which is Compound (XIV) in which $R^3$ is a group other than hydrogen, can be obtained from Compound (XIVa) according to a method similar to that in producing Compound (Ib) from Compound (Ia).

Compound (Ibaa), which is Compound (Iba) in which $R^4$ is —$NR^{10}N^{11}$, $R^8$ is lower alkyl, $R^9$ is hydrogen, and X is CO, can be prepared according to the following reaction step:

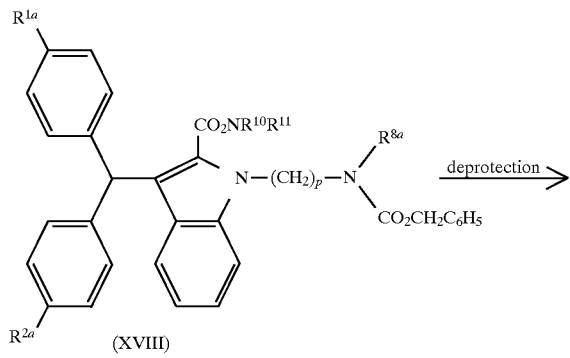

(XVIII)

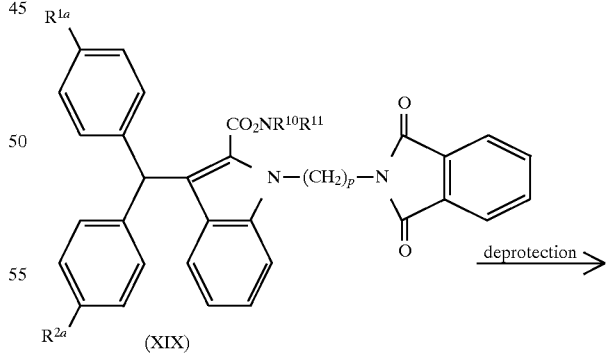

(Ibaa)

(In the formulae, $R^{8a}$ represents lower alkyl in the definition of $R^8$, and $R^{1a}$, $R^{2a}$, $R^{10}$, $R^{11}$, and p have the same meanings as defined above.)

Compound (Ibaa) can be obtained from Compound (XVIII) according to a method similar to that in producing Compound (Id) from Compound (VII).

Compound (Ibab), which is Compound (Iba) in which $R^4$ is —$NR^{10}N^{11}$, $R^8$ and $R^9$ are both hydrogen, and X is CO, can be prepared according to the following reaction step:

(XIX)

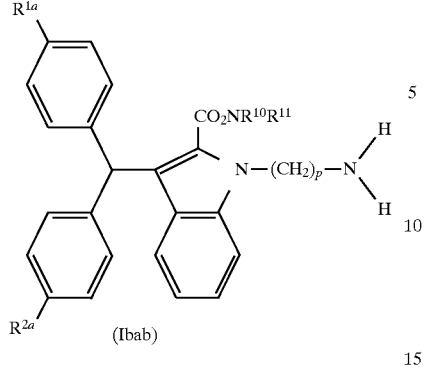

(In the formulae, $R^{1a}$, $R^{2a}$, $R^{10}$, $R^{11}$, and p have the same meanings as defined above.)

Compound (Ibab) can be obtained by treating Compound (XIX) with 1 equivalence to an excess amount of hydrazine hydrate in a solvent such as a lower alcohol (e.g., methanol, ethanol), N,N-dimethylformamide, dimethyl sulfoxide, and tetrahydrofuran, at a temperature of room temperature to the boiling point of the solvent employed for 0.5 to 24 hours.

Compound (XVIII) can be prepared according to the following reaction steps:

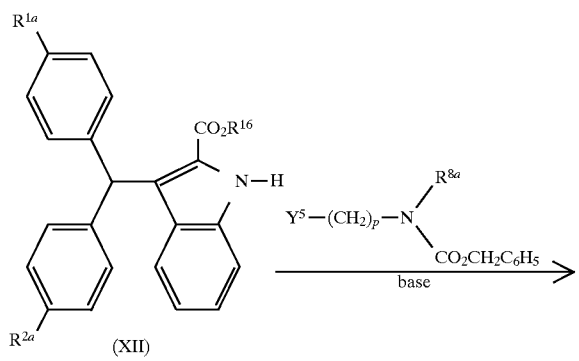

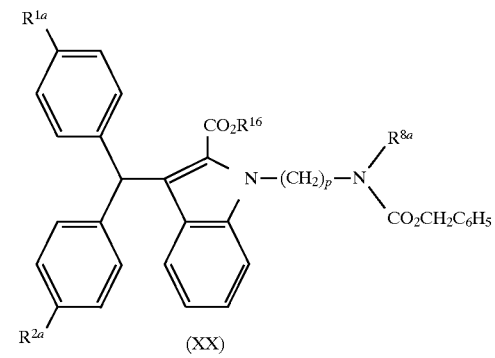

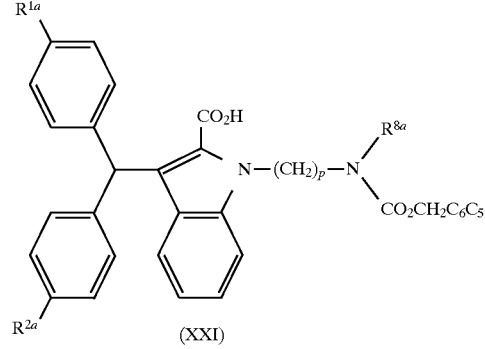

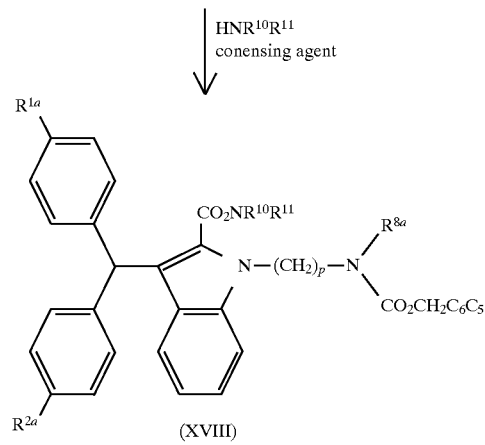

(In the formulae, $Y^5$ represents chlorine, bromine, or iodine, and $R^{1a}$, $R^{2a}$, $R^{8a}$, $R^{10}$, $R^{11}$, $R^{16}$, and p have the same meanings as defined above.)

Compound (XX) can be obtained from Compound (XII) and a halogenated aminoalkyl protected by a carboxybenzyl group according to the method of producing Compound (Ib) from Compound (Ia) or a similar method thereto. Compound (XXI) can be obtained from Compound (XX) according to the method of producing Compound (Iha) or Compound (XIa) from Compound (Ibc) or Compound (XIII), respectively, or a similar method thereto. Then, Compound (XVIII) can be obtained from Compound (XXI) according to the method of producing Compound (Ii) from Compound (Ih) or Compound (XI) or a similar method thereto.

Compound (XIX) can be prepared from Compound (XII) and a halogenated alkylphthalimide according to the method of producing Compound (XVIII) from Compound (XII) or a similar method thereto.

Compound (XIXa), which is Compound (XIX) in which p is 2, can also be prepared according to the following reaction steps:

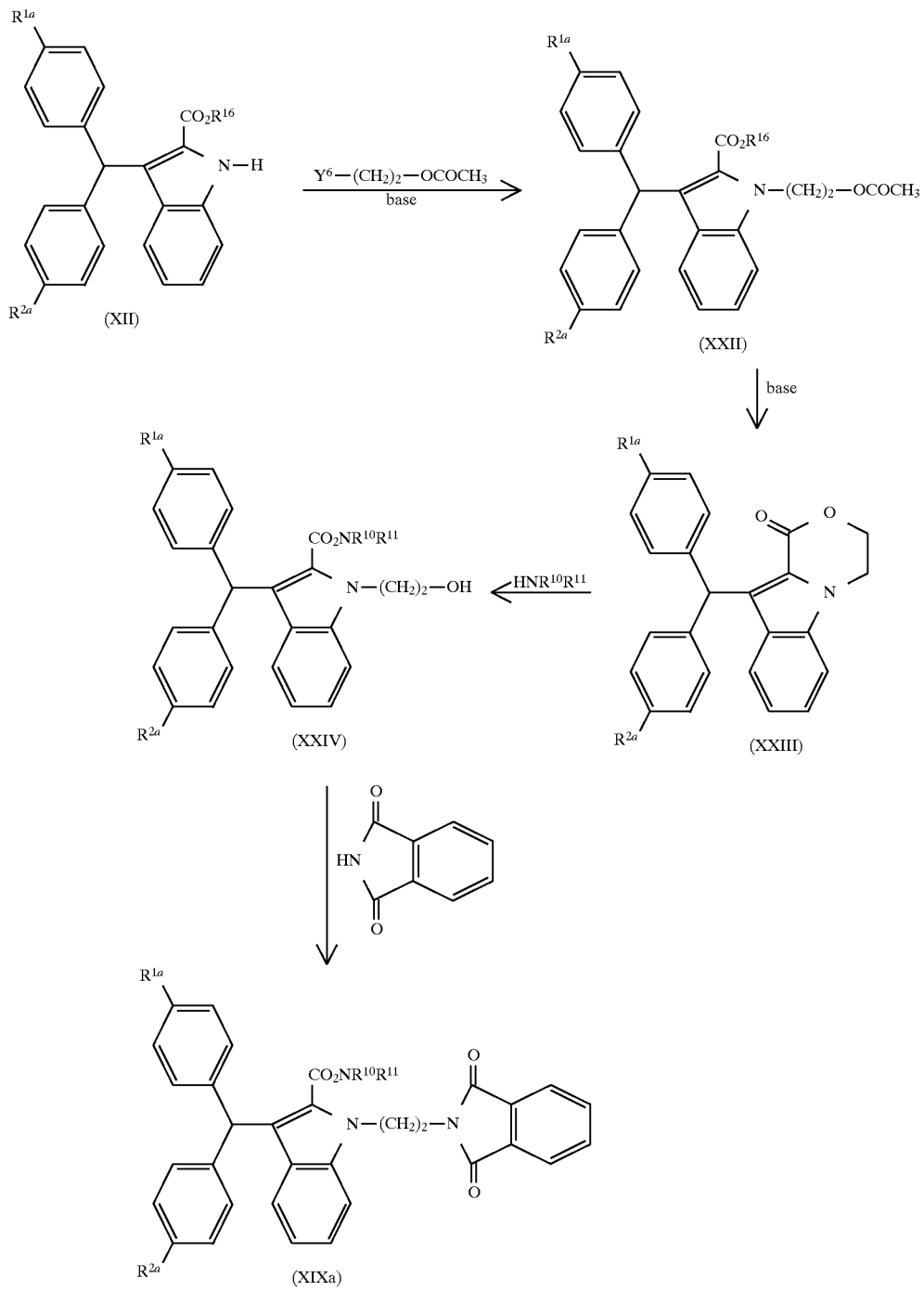

(In the formulae, $Y^6$ represents chlorine, bromine, or iodine, and $R^{1a}$, $R^{2a}$, $R^{10}$, $R^{11}$, and $R^{16}$ have the same meanings as defined above.)

Compound (XXII) can be obtained from Compound (XII) and a halogenated ethyl acetate according to the method of producing Compound (Ib) from Compound (Ia) or a similar method thereto. Compound (XXIII) can be obtained by treating Compound (XXII) with an alkyl lower alkoxide such as sodium methoxide, sodium ethoxide, and potassium tert-butoxide in a solvent such as a lower alcohol (e.g., methanol, ethanol), N,N-dimethylformamide, dimethyl sulfoxide, and tetrahydrofuran, at a temperature of room temperature to the boiling point of the solvent employed for 0.5 to 24 hours. Compound (XXIV) can be obtained by reacting Compound (XXIII) with ammonia, a primary amine, or a secondary amine in a solvent such as a lower alcohol (e.g., methanol, ethanol), N,N-dimethylformamide, dimethyl sulfoxide, and tetrahydrofuran, at a temperature of 50° C. to the boiling point of the solvent employed for 0.5 to 24 hours, or without a solvent at a temperature of 50° to 200° C. for 0.5 to 24 hours. Then, Compound (XIXa) can be obtained by reacting Compound (XXIV) with phthalimide in the presence of triphenylphosphine and the like, and diethyl azodicarboxylate and the like, in a solvent such as tetrahydrofuran, at a temperature of 0° C. to the boiling point of the solvent employed for 0.5 to 48 hours.

As for the starting compounds, Compound (II) can be obtained according to the method described in Tetrahedron Lett., 28, 5651 (1987) or a similar method thereto, and Compound (III) can be obtained according to the method described in J. Am. Chem. Soc., 67, 423 (1945), J. Med. Chem., 32, 1681 (1989), J. Med. Chem., 33, 749 (1990), or Chem. Pharm. Bull., 21, 1481 (1973), or a similar method thereto.

The intermediates and the desired compounds in the processes described above can be isolated and purified by purification methods conventionally used in organic synthetic chemistry, for example, filtration, extraction, washing, drying, concentration, recrystallization, and various kinds of chromatography. The intermediates may also be subjected to the subsequent reaction without purification.

In the case where a salt of Compound (I) is desired and it is produced in the form of the desired salt, it can be subjected to purification as such. In the case where Compound (I) is produced in the free state and its salt is desired, Compound (I) is dissolved or suspended in a suitable solvent, followed by addition of an appropriate acid or base to form a salt, and then the salt can be isolated.

Compounds (I) and pharmaceutically acceptable salts thereof may be in the form of adducts with water or various solvents, which are also within the scope of the present invention.

Examples of Compounds (I) obtained in the above processes are shown in Table 1.

TABLE 1

| Compd No. | $R^1$ | $R^2$ | $R^3$ | $-NR^{10}R^{11}$ |
|---|---|---|---|---|
| 1 | $OCH_2OCH_3$ | $OCH_2OCH_3$ | H | piperazinyl-(2-chlorophenyl) |
| 2 | $OCH_2OCH_3$ | $OCH_2OCH_3$ | $-(CH_2)_2-N(CH_3)_2$ | piperazinyl-(2-chlorophenyl) |
| 3 | $OCH_2OCH_3$ | $OCH_2OCH_3$ | $-(CH_2)_2-$morpholinyl | piperazinyl-(2-chlorophenyl) |
| 4 | $OCH_2OCH_3$ | $OCH_2OCH_3$ | $-(CH_2)_2-N(CH_3)_2$ | $-N(H)-(CH_2)_2-CH_3$ |
| 5 | $OCH_2OCH_3$ | $OCH_2OCH_3$ | $-(CH_2)_2-N(CH_3)_2$ | $-N(H)-CH(CH_3)_2$ |
| 6 | $OCH_2OCH_3$ | $OCH_2OCH_3$ | $-(CH_2)_2-N(CH_3)_2$ | piperidinyl |

TABLE 1-continued

| | | | | |
|---|---|---|---|---|
| 7 | OCH$_2$OCH$_3$ | OCH$_2$OCH$_3$ | —(CH$_2$)$_2$—N(CH$_3$)$_2$ | 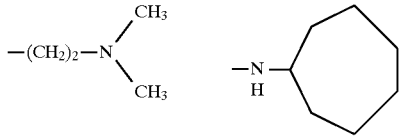 |
| 8 | OH | OH | H | 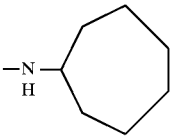 |
| 9 | OH | OH | —(CH$_2$)$_2$—N(CH$_3$)$_2$ | 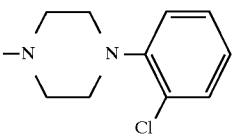 |
| 10 | OH | OH | —(CH$_2$)$_2$—N⟨morpholino⟩ | 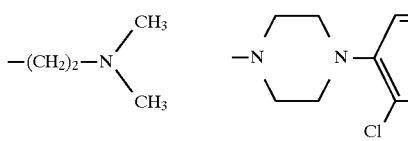 |
| 11 | OH | OH | —(CH$_2$)$_2$—N(CH$_3$)$_2$ | —NH—(CH$_2$)$_2$—CH$_3$ |
| 12 | OH | OH | —(CH$_2$)$_2$—N(CH$_3$)$_2$ | —NH—CH(CH$_3$)$_2$ |
| 13 | OH | OH | —(CH$_2$)$_2$—N(CH$_3$)$_2$ | 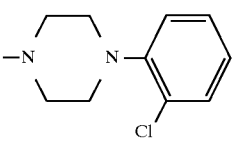 |
| 14 | OH | OH | —(CH$_2$)$_2$—N(CH$_3$)$_2$ | 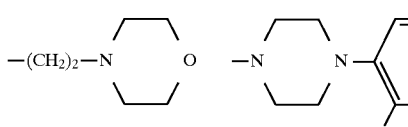 |
| 15 | OCH$_2$OCH$_3$ | OCH$_2$OCH$_3$ | —(CH$_2$)$_2$—N(CH$_3$)$_2$ | —N(CH$_2$CH$_3$)$_2$ |
| 16 | OCH$_2$OCH$_3$ | OCH$_2$OCH$_3$ | —(CH$_2$)$_2$—N(CH$_3$)$_2$ | 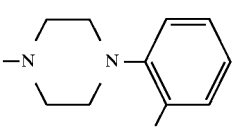 |
| 17 | OCH$_2$OCH$_3$ | OCH$_2$OCH$_3$ | —(CH$_2$)$_2$—N(CH$_3$)$_2$ | 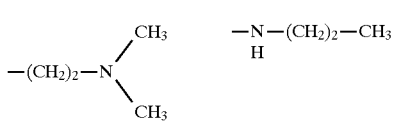 |
| 18 | OCH$_2$OCH$_3$ | OCH$_2$OCH$_3$ | —(CH$_2$)$_2$—N(CH$_3$)$_2$ | 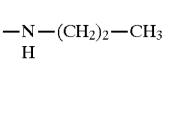 |

TABLE 1-continued

| # | | | | |
|---|---|---|---|---|
| 19 | OCH₂OCH₃ | OCH₂OCH₃ | —(CH₂)₂—N(CH₃)₂ | —N(piperazine)N-phenyl |
| 20 | OCH₂OCH₃ | OCH₂OCH₃ | —(CH₂)₂—N(CH₃)₂ | —N(piperazine)N-CH₂-phenyl |
| 21 | OCH₂OCH₃ | OCH₂OCH₃ | —(CH₂)₂—N(pyrrolidine) | —N(piperazine)N-(2-chlorophenyl) |
| 22 | OCH₂OCH₃ | OCH₂OCH₃ | —(CH₂)₂—N(piperidine) | —N(piperazine)N-(2-chlorophenyl) |
| 23 | OCH₂OCH₃ | OCH₂OCH₃ | —(CH₂)₃—N(CH₃)₂ | —N(piperazine)N-(2-chlorophenyl) |
| 24 | OCH₂OCH₃ | OCH₂OCH₃ | —(CH₂)₄—N(CH₃)₂ | —N(piperazine)N-(2-chlorophenyl) |
| 25 | OCH₂OCH₃ | OCH₂OCH₃ | —(CH₂)₃—N(morpholine) | —N(piperazine)N-(2-chlorophenyl) |
| 26 | OCH₂OCH₃ | OCH₂OCH₃ | —(CH₂)₄—N(morpholine) | —N(piperazine)N-(2-chlorophenyl) |
| 27 | OCH₂OCH₃ | OCH₂OCH₃ | —(CH₂)₃—N(pyrrolidine) | —N(piperazine)N-(2-chlorophenyl) |
| 28 | OCH₂OCH₃ | OCH₂OCH₃ | —(CH₂)₄—N(pyrrolidine) | —N(piperazine)N-(2-chlorophenyl) |
| 29 | OCH₃ | OCH₃ | H | —N(piperazine)N-(2-chlorophenyl) |

TABLE 1-continued

| | | | | |
|---|---|---|---|---|
| 30 | OCH₃ | OCH₃ | —(CH₂)₂—N(CH₃)₂ | —N(piperazinyl)-(2-chlorophenyl) |
| 31 | OCH₃ | OCH₃ | —(CH₂)₂—N(morpholino) | —N(piperazinyl)-(2-chlorophenyl) |
| 32 | OCH₃ | OCH₃ | —(CH₂)₂—N(pyrrolidinyl) | —N(piperazinyl)-(2-chlorophenyl) |
| 33 | OH | OH | —(CH₂)₂—N(CH₃)₂ | —N(CH₂CH₃)₂ |
| 34 | OH | OH | —(CH₂)₂—N(CH₃)₂ | —N(morpholino) |
| 35 | OH | OH | —(CH₂)₂—N(CH₃)₂ | —NH—C₆H₄—(CH₂)₂CH₃ (para) |
| 36 | OH | OH | —(CH₂)₂—N(CH₃)₂ | —NH—cyclooctyl |
| 37 | OH | OH | —(CH₂)₂—N(CH₃)₂ | —N(piperazinyl)-phenyl |
| 38 | OH | OH | —(CH₂)₂—N(CH₃)₂ | —N(piperazinyl)-CH₂-phenyl |
| 39 | OH | OH | —(CH₂)₂—N(pyrrolidinyl) | —N(piperazinyl)-(2-chlorophenyl) |
| 40 | OH | OH | —(CH₂)₂—N(piperidinyl) | —N(piperazinyl)-(2-chlorophenyl) |

TABLE 1-continued

| | | | | |
|---|---|---|---|---|
| 41 | OH | OH | −(CH₂)₃−N(CH₃)₂ | −N(piperazinyl)−(2-chlorophenyl) |
| 42 | OH | OH | −(CH₂)₄−N(CH₃)₂ | −N(piperazinyl)−(2-chlorophenyl) |
| 43 | OH | OH | −(CH₂)₃−N(morpholino) | −N(piperazinyl)−(2-chlorophenyl) |
| 44 | OH | OH | −(CH₂)₄−N(morpholino) | −N(piperazinyl)−(2-chlorophenyl) |
| 45 | OH | OH | −(CH₂)₃−N(pyrrolidinyl) | −N(piperazinyl)−(2-chlorophenyl) |
| 46 | OH | OH | −(CH₂)₄−N(pyrrolidinyl) | −N(piperazinyl)−(2-chlorophenyl) |

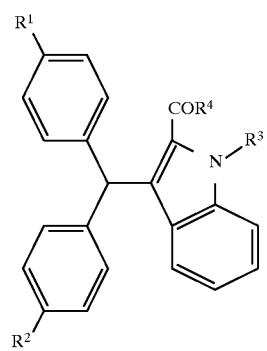

| Compd. No. | $R^1$ | $R^2$ | $R^3$ | $R^4$ |
|---|---|---|---|---|
| 47 | OCH₂OCH₃ | OCH₂OCH₃ | −(CH₂)₂−N(CH₃)₂ | OCH₂CH₃ |
| 48 | OCH₂OCH₃ | OCH₂OCH₃ | −(CH₂)₂−N(CH₃)₂ | OH |

TABLE 1-continued

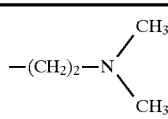

| Compd. No. | R¹ | R² | R³ | —NR¹⁰R¹¹ |
|---|---|---|---|---|
| 49 | OCH$_2$OCH$_3$ | OCH$_2$OCH$_3$ | —(CH$_2$)$_2$—N(CH$_3$)$_2$ | —N(H)—(CH$_2$)$_2$—N(CH$_3$)$_2$ |
| 50 | OCH$_2$OCH$_3$ | OCH$_2$OCH$_3$ | —(CH$_2$)$_2$—N(CH$_3$)$_2$ | —N(CH$_3$)—(CH$_2$)$_2$—N(CH$_3$)$_2$ |
| 51 | OCH$_2$OCH$_3$ | OCH$_2$OCH$_3$ | —(CH$_2$)$_2$—N(CH$_3$)$_2$ | —N(H)—(CH$_2$)$_2$—pyrrolidinyl |
| 52 | OCH$_2$OCH$_3$ | OCH$_2$OCH$_3$ | —(CH$_2$)$_2$—N(CH$_3$)$_2$ | —N(H)—(CH$_2$)$_3$—(2-oxopyrrolidin-1-yl) |
| 53 | OCH$_2$OCH$_3$ | OCH$_2$OCH$_3$ | —(CH$_2$)$_2$—N(CH$_3$)$_2$ | —N(H)—(CH$_2$)$_2$—piperidinyl |
| 54 | OCH$_2$OCH$_3$ | OCH$_2$OCH$_3$ | —(CH$_2$)$_2$—N(CH$_3$)$_2$ | —N(H)—(CH$_2$)$_2$—morpholinyl |
| 55 | OCH$_2$OCH$_3$ | OCH$_2$OCH$_3$ | —(CH$_2$)$_2$—N(CH$_3$)$_2$ | —N(H)—(CH$_2$)$_3$—morpholinyl |
| 56 | OCH$_2$OCH$_3$ | OCH$_2$OCH$_3$ | —(CH$_2$)$_2$—N(CH$_3$)$_2$ | —N(H)—CH$_2$—(2-pyridyl) |
| 57 | OCH$_2$OCH$_3$ | OCH$_2$OCH$_3$ | —(CH$_2$)$_2$—N(CH$_3$)$_2$ | —N(H)—CH$_2$—(3-pyridyl) |
| 58 | OCH$_2$OCH$_3$ | OCH$_2$OCH$_3$ | —(CH$_2$)$_2$—N(CH$_3$)$_2$ | —N(H)—CH$_2$—(4-pyridyl) |

TABLE 1-continued

| # | | | | |
|---|---|---|---|---|
| 59 | OCH₂OCH₃ | OCH₂OCH₃ | —(CH₂)₂—N(CH₃)₂ | —NH—(CH₂)₂-(2-pyridyl) |
| 60 | OCH₂OCH₃ | OCH₂OCH₃ | —(CH₂)₂—N(CH₃)₂ | —NH—(CH₂)₂-(4-pyridyl) |
| 61 | OCH₂OCH₃ | OCH₂OCH₃ | —(CH₂)₂—N(CH₃)₂ | —NH—CH₂-(1-ethylpyrrolidin-2-yl) |
| 62 | OCH₂OCH₃ | OCH₂OCH₃ | —(CH₂)₂—N(CH₃)₂ | —NH—(CH₂)₂-(1-methylpyrrolidin-2-yl) |
| 63 | OCH₂OCH₃ | OCH₂OCH₃ | —(CH₂)₂—N(CH₃)₂ | —NH—(CH₂)₃-(3-methylpiperidin-1-yl) |
| 64 | OCH₂OCH₃ | OCH₂OCH₃ | —(CH₂)₂—N(CH₃)₂ | —NH—(CH₂)₃-(imidazol-1-yl) |
| 65 | OCH₂OCH₃ | OCH₂OCH₃ | —(CH₂)₂—N(CH₃)₂ | —NH—CH₂-(tetrahydrofuran-2-yl) |
| 66 | OCH₂OCH₃ | OCH₂OCH₃ | —(CH₂)₂—N(CH₃)₂ | —NH—CH₂-(thien-2-yl) |
| 67 | OCH₂OCH₃ | OCH₂OCH₃ | —(CH₂)₂—N(CH₃)₂ | —NH—CH₂-(furan-2-yl) |
| 68 | OCH₂OCH₃ | OCH₂OCH₃ | —(CH₂)₂—N(CH₃)₂ | —NH—(CH₂)₂-(1-methylpyrrol-2-yl) |
| 69 | OH | OH | —(CH₂)₂—N(CH₃)₂ | —NH—(CH₂)₂—N(CH₃)₂ |
| 70 | OH | OH | —(CH₂)₂—N(CH₃)₂ | —N(CH₃)—(CH₂)₂—N(CH₃)₂ |
| 71 | OH | OH | —(CH₂)₂—N(CH₃)₂ | —NH—(CH₂)₂-(pyrrolidin-1-yl) |

TABLE 1-continued

| | | | | |
|---|---|---|---|---|
| 72 | OH | OH | —(CH₂)₂—N(CH₃)₂ | —N(H)—(CH₂)₃—N(pyrrolidin-2-one) 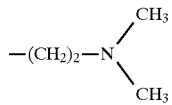 |
| 73 | OH | OH | —(CH₂)₂—N(CH₃)₂ | —N(H)—(CH₂)₂—N(piperidine) 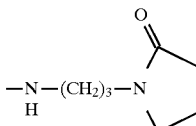 |
| 74 | OH | OH | —(CH₂)₂—N(CH₃)₂ | —N(H)—(CH₂)₂—N(morpholine) 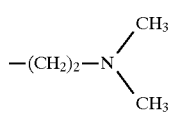 |
| 75 | OH | OH | —(CH₂)₂—N(CH₃)₂ | —N(H)—(CH₂)₃—N(morpholine) 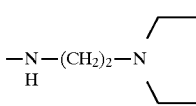 |
| 76 | OH | OH | —(CH₂)₂—N(CH₃)₂ | —N(H)—CH₂—(2-pyridyl) 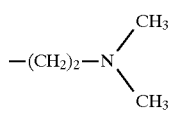 |
| 77 | OH | OH | —(CH₂)₂—N(CH₃)₂ | —N(H)—CH₂—(3-pyridyl) 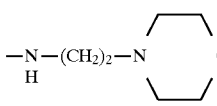 |
| 78 | OH | OH | —(CH₂)₂—N(CH₃)₂ | —N(H)—CH₂—(4-pyridyl) 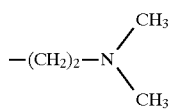 |
| 79 | OH | OH | —(CH₂)₂—N(CH₃)₂ | —N(H)—(CH₂)₂—(2-pyridyl) 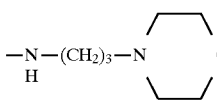 |
| 80 | OH | OH | —(CH₂)₂—N(CH₃)₂ | —N(H)—(CH₂)₂—(4-pyridyl) 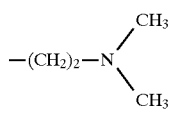 |
| 81 | OH | OH | —(CH₂)₂—N(CH₃)₂ | —N(H)—CH₂—(1-ethylpyrrolidin-2-yl) 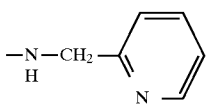 |
| 82 | OH | OH | —(CH₂)₂—N(CH₃)₂ | —N(H)—(CH₂)₂—(1-methylpyrrolidin-2-yl) 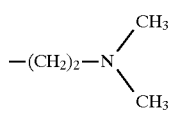 |
| 83 | OH | OH | —(CH₂)₂—N(CH₃)₂ | —N(H)—(CH₂)₃—N(3-methylpiperidine) 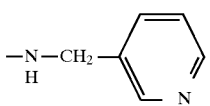 |

TABLE 1-continued

| 84 | OH | OH | —(CH₂)₂—N(CH₃)₂ | —NH—(CH₂)₃—(imidazol-1-yl) |
| 85 | OH | OH | —(CH₂)₂—N(CH₃)₂ | —NH—CH₂—(tetrahydrofuran-2-yl) |
| 86 | OH | OH | —(CH₂)₂—N(CH₃)₂ | —NH—CH₂—(thiophen-2-yl) |
| 87 | OH | OH | —(CH₂)₂—N(CH₃)₂ | —NH—CH₂—(furan-2-yl) |

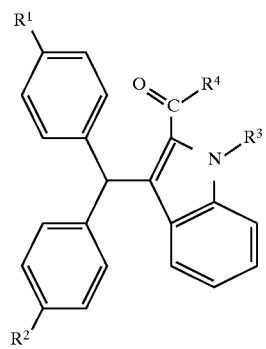

| Compd. No. | R¹ | R² | R³ | R⁴ |
|---|---|---|---|---|
| 88 | H | H | H | —N(piperazin-1-yl)—(2-chlorophenyl) |
| 89 | H | H | —(CH₂)₂—N(CH₃)₂ | —N(piperazin-1-yl)—(2-chlorophenyl) |
| 90 | H | H | —(CH₂)₂—N(morpholino) | —N(piperazin-1-yl)—(2-chlorophenyl) |
| 91 | H | H | —(CH₂)₂—N(pyrrolidin-1-yl) | —N(piperazin-1-yl)—(2-chlorophenyl) |
| 92 | H | H | —(CH₂)₂—N(CH₃)₂ | OCH₂CH₃ |

TABLE 1-continued

| # | | | | |
|---|---|---|---|---|
| 93 | H | H | —(CH$_2$)$_2$—N(CH$_3$)$_2$ | OH |
| 94 | H | H | —(CH$_2$)$_2$—N(CH$_3$)$_2$ | —NH—(CH$_2$)$_2$—CH$_3$ |
| 95 | H | H | —(CH$_2$)$_2$—N(CH$_3$)$_2$ | —NH—CH(CH$_3$)$_2$ |
| 96 | H | H | —(CH$_2$)$_2$—N(CH$_3$)$_2$ | —N(CH$_2$CH$_3$)$_2$ |
| 97 | H | H | —(CH$_2$)$_2$—N(CH$_3$)$_2$ | —N(piperidinyl) |
| 98 | H | H | —(CH$_2$)$_2$—N(CH$_3$)$_2$ | —NH—(cycloheptyl) |
| 99 | H | H | —(CH$_2$)$_2$—N(CH$_3$)$_2$ | —NH—(cyclooctyl) |
| 100 | H | H | —(CH$_2$)$_2$—N(CH$_3$)$_2$ | —N(morpholinyl) |
| 101 | H | H | —(CH$_2$)$_2$—N(CH$_3$)$_2$ | —N(piperazinyl)-phenyl |
| 102 | H | H | —(CH$_2$)$_2$—N(CH$_3$)$_2$ | —N(piperazinyl)-N—CH$_2$-phenyl |
| 103 | H | H | —(CH$_2$)$_2$—N(CH$_3$)$_2$ | —NH-(4-(CH$_2$)$_2$CH$_3$-phenyl) |
| 104 | H | H | —(CH$_2$)$_2$—N(CH$_3$)$_2$ | —NH—(CH$_2$)$_2$—N(CH$_3$)$_2$ |
| 105 | H | H | —(CH$_2$)$_2$—N(CH$_3$)$_2$ | —N(CH$_3$)—(CH$_2$)$_2$—N(CH$_3$)$_2$ |

TABLE 1-continued

| | | | | |
|---|---|---|---|---|
| 106 | H | H | —(CH₂)₂—N(CH₃)₂ | —NH—(CH₂)₂—N(piperidine) |
| 107 | H | H | —(CH₂)₂—N(CH₃)₂ | —NH—(CH₂)₃—N(morpholine) |
| 108 | H | H | —(CH₂)₂—N(CH₃)₂ | —NH—(CH₂)₃—N(2-pyrrolidinone) |
| 109 | H | H | —(CH₂)₂—N(CH₃)₂ | —NH—(CH₂)₃—N(imidazole) |
| 110 | H | H | —(CH₂)₂—N(CH₃)₂ | —NH—CH₂—(2-pyridyl) |
| 111 | H | H | —(CH₂)₂—N(CH₃)₂ | —NH—(CH₂)₂—(2-pyridyl) |
| 112 | H | H | —(CH₂)₂—N(CH₃)₂ | —NH—CH₂—(1-ethylpyrrolidin-2-yl) |
| 113 | H | H | —(CH₂)₂—N(CH₃)₂ | —NH—(CH₂)₂—(1-methylpyrrolidin-2-yl) |
| 114 | H | H | —(CH₂)₂—N(CH₃)₂ | —NH—CH₂—(tetrahydrofuran-2-yl) |
| 115 | H | H | —(CH₂)₂—N(CH₃)₂ | —NH—CH₂—(2-thienyl) |
| 116 | H | H | —(CH₂)₂—N(CH₃)₂ | —NH—CH₂—(2-furyl) |
| 117 | H | H | —(CH₂)₂—N(CH₃)₂ | —NH—(CH₂)₃—(2-methylpiperidin-1-yl) |
| 118 | H | H | —(CH₂)₂—N(pyrrolidine) | OH |

5,891,902

TABLE 1-continued

| # | | | | |
|---|---|---|---|---|
| 119 | H | H | —(CH₂)₂—N⟨pyrrolidine⟩ | —NH—CH(CH₃)₂ |
| 120 | H | H | —(CH₂)₂—N⟨pyrrolidine⟩ | —N⟨piperazine⟩N—CH₂—C₆H₅ |
| 121 | H | H | —(CH₂)₂—N⟨pyrrolidine⟩ | —NH—(CH₂)₃—N⟨morpholine⟩O |
| 122 | H | H | —(CH₂)₂—N⟨piperidine⟩ | OH |
| 123 | H | H | —(CH₂)₂—N⟨piperidine⟩ | —NH—CH(CH₃)₂ |
| 124 | H | H | —(CH₂)₂—N⟨piperidine⟩ | —N⟨piperazine⟩N—CH₂—C₆H₅ |
| 125 | H | H | —(CH₂)₂—N⟨piperidine⟩ | —NH—(CH₂)₃—N⟨morpholine⟩O |
| 126 | H | H | —(CH₂)₂—N⟨morpholine⟩O | OH |
| 127 | H | H | —(CH₂)₂—N⟨morpholine⟩O | —NH—CH(CH₃)₂ |
| 128 | H | H | —(CH₂)₂—N⟨morpholine⟩O | —N⟨piperazine⟩N—CH₂—C₆H₅ |
| 129 | H | H | —(CH₂)₂—N⟨morpholine⟩O | —NH—(CH₂)₃—N⟨morpholine⟩O |
| 130 | F | F | —(CH₂)₂—N(CH₃)₂ | OCH₂CH₃ |
| 131 | F | F | —(CH₂)₂—N(CH₃)₂ | OH |
| 132 | F | F | —(CH₂)₂—N(CH₃)₂ | —NH—CH(CH₃)₂ |

TABLE 1-continued

| | | | | |
|---|---|---|---|---|
| 133 | F | F | −(CH₂)₂−N(CH₃)₂ | −N(piperazine)N−CH₂−phenyl |
| 134 | F | F | −(CH₂)₂−N(CH₃)₂ | −NH−(CH₂)₃−N(morpholine) |
| 135 | H | H | −(CH₂)₂−N(CH₃)₂ | −NH−(CH₂)₃−CH₃ |
| 136 | H | H | −(CH₂)₂−N(CH₃)₂ | −NH−CH₂−CH=CH₂ |
| 137 | H | H | −(CH₂)₂−N(CH₃)₂ | −NH−CH₂−CH(CH₃)₂ |
| 138 | H | H | −(CH₂)₂−N(CH₃)₂ | −NH−cyclopropyl |
| 139 | H | H | −(CH₂)₂−N(CH₃)₂ | −NH−cyclobutyl |
| 140 | H | H | −(CH₂)₂−N(CH₃)₂ | −NH−CH(CH₃)(CH₂CH₃) |
| 141 | H | H | −(CH₂)₂−N(CH₃)₂ | −NH−cyclopentyl |
| 142 | H | H | −(CH₂)₂−N(CH₃)₂ | −NH−cyclohexyl |
| 143 | H | H | −(CH₂)₂−N(CH₃)₂ | −NH−CH₃ |
| 144 | H | H | −(CH₂)₂−N(CH₃)₂ | −NH−(CH₂)₄−CH₃ |
| 145 | H | H | −(CH₂)₂−N(CH₃)₂ | −NH−CH₂CH₃ |
| 146 | H | H | −(CH₂)₂−N(CH₃)₂ | −NH−(4-methoxyphenyl) |

TABLE 1-continued

| | | | | |
|---|---|---|---|---|
| 147 | H | H | —(CH₂)₂—N(CH₃)₂ | —NH—C₆H₅ |
| 148 | H | H | —(CH₂)₂—N(pyrrolidinyl) | —NH—(CH₂)₂—CH₃ |
| 149 | H | H | —(CH₂)₂—N(pyrrolidinyl) | —NH—(CH₂)₂—N(piperidinyl) |
| 150 | H | H | —(CH₂)₂—N(pyrrolidinyl) | —NH—C₆H₄—(CH₂)₂CH₃ |
| 151 | H | H | —(CH₂)₃—N(CH₃)₂ | OCH₂CH₃ |
| 152 | H | H | —(CH₂)₃—N(CH₃)₂ | OH |
| 153 | H | H | —(CH₂)₃—N(CH₃)₂ | —NH—CH(CH₃)₂ |
| 154 | H | H | —(CH₂)₃—N(CH₃)₂ | —NH—(CH₂)₂—CH₃ |
| 155 | H | H | —(CH₂)₃—N(CH₃)₂ | —NH—cyclooctyl |
| 156 | H | H | —(CH₂)₃—N(CH₃)₂ | —NH—(CH₂)₂—N(piperidinyl) |
| 157 | H | H | —(CH₂)₃—N(CH₃)₂ | —NH—C₆H₄—(CH₂)₂CH₃ |
| 158 | H | H | —(CH₂)₃—N(CH₃)₂ | —NH—(CH₂)₃—N(2-oxopyrrolidinyl) |
| 159 | H | H | —(CH₂)₃—N(pyrrolidinyl) | OCH₂CH₃ |

TABLE 1-continued

| 160 | H | H | —(CH$_2$)$_3$—N(pyrrolidine) | OH |
| --- | --- | --- | --- | --- |
| 161 | H | H | —(CH$_2$)$_3$—N(pyrrolidine) | —N(H)—CH(CH$_3$)$_2$ |
| 162 | H | H | —(CH$_2$)$_3$—N(pyrrolidine) | —N(H)—(CH$_2$)$_2$—CH$_3$ |
| 163 | H | H | —(CH$_2$)$_3$—N(pyrrolidine) | —N(H)—cyclooctyl |
| 164 | H | H | —(CH$_2$)$_3$—N(pyrrolidine) | —N(H)—(CH$_2$)$_2$—N(piperidine) |
| 165 | H | H | —(CH$_2$)$_3$—N(pyrrolidine) | —N(H)—C$_6$H$_4$—(CH$_2$)$_2$CH$_3$ |
| 166 | H | H | —(CH$_2$)$_3$—N(pyrrolidine) | —N(H)—(CH$_2$)$_3$—N(2-pyrrolidinone) |
| 167 | H | H | —(CH$_2$)$_4$—N(CH$_3$)$_2$ | OCH$_2$CH$_3$ |
| 168 | H | H | —(CH$_2$)$_4$—N(CH$_3$)$_2$ | OH |
| 169 | H | H | —(CH$_2$)$_4$—N(CH$_3$)$_2$ | —N(H)—CH(CH$_3$)$_2$ |
| 170 | H | H | —(CH$_2$)$_4$—N(CH$_3$)$_2$ | —N(H)—(CH$_2$)$_2$—CH$_3$ |
| 171 | H | H | —(CH$_2$)$_4$—N(CH$_3$)$_2$ | —N(H)—cyclooctyl |
| 172 | H | H | —(CH$_2$)$_4$—N(CH$_3$)$_2$ | —N(H)—C$_6$H$_4$—(CH$_2$)$_2$CH$_3$ |

TABLE 1-continued

| 173 | H | H | —(CH₂)₄—N(CH₃)₂ | —N(H)—(CH₂)₃—N(2-oxopyrrolidinyl) |
| 174 | H | H | —(CH₂)₄—N(pyrrolidinyl) | OCH₂CH₃ |
| 175 | H | H | —(CH₂)₄—N(pyrrolidinyl) | OH |
| 176 | H | H | —(CH₂)₄—N(pyrrolidinyl) | —N(H)—CH(CH₃)₂ |
| 177 | H | H | —(CH₂)₄—N(pyrrolidinyl) | —N(H)—(CH₂)₂—CH₃ |
| 178 | H | H | —(CH₂)₄—N(pyrrolidinyl) | —N(H)—cyclooctyl |
| 179 | H | H | —(CH₂)₄—N(pyrrolidinyl) | —N(H)—C₆H₄—(CH₂)₂CH₃ |
| 180 | H | H | —(CH₂)₄—N(pyrrolidinyl) | —N(H)—(CH₂)₃—N(2-oxopyrrolidinyl) |
| 181 | Cl | Cl | —(CH₂)₂—N(CH₃)₂ | OCH₂CH₃ |
| 182 | Cl | Cl | —(CH₂)₂—N(CH₃)₂ | OH |
| 183 | Cl | Cl | —(CH₂)₂—N(CH₃)₂ | —N(H)—(CH₂)₂—CH₃ |
| 184 | Cl | Cl | —(CH₂)₂—N(CH₃)₂ | —N(H)—C₆H₄—(CH₂)₂CH₃ |
| 185 | CH₃ | CH₃ | —(CH₂)₂—N(piperidinyl) | OCH₂CH₃ |

TABLE 1-continued

| # | | | | |
|---|---|---|---|---|
| 186 | CH₃ | CH₃ | —(CH₂)₂—N(piperidine) | OH |
| 187 | CH₃ | CH₃ | —(CH₂)₂—N(piperidine) | —NH—(CH₂)₃—N(morpholine) |
| 188 | CH₃ | CH₃ | —(CH₂)₂—N(piperidine) | —NH—CH(CH₃)₂ |
| 189 | CH₃ | CH₃ | —(CH₂)₂—N(piperidine) | —NH—(CH₂)₃—N(imidazole) |
| 190 | CH₃ | CH₃ | —(CH₂)₂—N(pyrrolidine) | OCH₂CH₃ |
| 191 | CH₃ | CH₃ | —(CH₂)₂—N(pyrrolidine) | OH |
| 192 | CH₃ | CH₃ | —(CH₂)₂—N(pyrrolidine) | —NH—(CH₂)₃—N(morpholine) |
| 193 | CH₃ | CH₃ | —(CH₂)₂—N(pyrrolidine) | —NH—CH(CH₃)₂ |
| 194 | CH₃ | CH₃ | —(CH₂)₂—N(pyrrolidine) | —NH—(CH₂)₃—N(imidazole) |
| 195 | CH₃ | CH₃ | —(CH₂)₂—N(morpholine) | OCH₂CH₃ |
| 196 | CH₃ | CH₃ | —(CH₂)₂—N(morpholine) | OH |
| 197 | CH₃ | CH₃ | —(CH₂)₂—N(morpholine) | —NH—(CH₂)₃—N(morpholine) |
| 198 | CH₃ | CH₃ | —(CH₂)₂—N(morpholine) | —NH—CH(CH₃)₂ |
| 199 | CH₃ | CH₃ | —(CH₂)₂—N(morpholine) | —NH—(CH₂)₃—N(imidazole) |
| 200 | CH₃ | CH₃ | —(CH₂)₂—N(CH₃)₂ | OCH₂CH₃ |

TABLE 1-continued

| # | | | | |
|---|---|---|---|---|
| 201 | CH₃ | CH₃ | —(CH₂)₂—N(CH₃)₂ | OH |
| 202 | CH₃ | CH₃ | —(CH₂)₂—N(CH₃)₂ | —NH—(CH₂)₃—N(morpholine) |
| 203 | CH₃ | CH₃ | —(CH₂)₂—N(CH₃)₂ | —NH—CH(CH₃)₂ |
| 204 | CH₃ | CH₃ | —(CH₂)₂—N(CH₃)₂ | —NH—(CH₂)₃—N(imidazole) |
| 205 | OH | H | —(CH₂)₂—N(CH₃)₂ | —NH—(CH₂)₂—CH₃ |
| 206 | OH | H | —(CH₂)₂—N(CH₃)₂ | —NH—CH(CH₃)₂ |
| 207 | OH | H | —(CH₂)₂—N(CH₃)₂ | —NH—C₆H₄—(CH₂)₂CH₃ |
| 208 | OH | H | —(CH₂)₂—N(CH₃)₂ | —NH—(CH₂)₃—N(morpholine) |
| 209 | OH | H | —(CH₂)₂—N(CH₃)₂ | —NH—(CH₂)₃—N(2-pyrrolidinone) |
| 210 | OH | H | —(CH₂)₂—N(CH₃)₂ | —NH—(cyclooctyl) |
| 211 | OH | H | —(CH₂)₂—N(pyrrolidine) | —NH—(CH₂)₂—CH₃ |
| 212 | OH | H | —(CH₂)₂—N(pyrrolidine) | —NH—CH(CH₃)₂ |
| 213 | OH | H | —(CH₂)₂—N(pyrrolidine) | —NH—(CH₂)₃—N(morpholine) |

TABLE 1-continued

| 214 | OH | H | —(CH₂)₂—N(pyrrolidine) | | —N(H)—(CH₂)₃—N(pyrrolidin-2-one) |
| --- | --- | --- | --- | --- | --- |
| 215 | —O(CH₂)₂—N(CH₃)₂ | H | H | | —N(H)—CH(CH₃)₂ |
| 216 | —O(CH₂)₂—N(CH₃)₂ | H | H | | —N(H)—(CH₂)₂—CH₃ |
| 217 | —O(CH₂)₂—N(CH₃)₂ | H | H | | —N(H)—cyclooctyl |
| 218 | —O(CH₂)₂—N(CH₃)₂ | H | H | | —N(H)—C₆H₄—(CH₂)₂CH₃ |
| 219 | —O(CH₂)₂—N(CH₃)₂ | H | H | | —N(H)—(CH₂)₃—N(pyrrolidin-2-one) |
| 220 | —O(CH₂)₂—N(pyrrolidine) | H | H | | —N(H)—CH(CH₃)₂ |
| 221 | —O(CH₂)₂—N(pyrrolidine) | H | H | | —N(H)—(CH₂)₂—CH₃ |
| 222 | —O(CH₂)₂—N(pyrrolidine) | H | H | | —N(H)—cyclooctyl |
| 223 | —O(CH₂)₂—N(pyrrolidine) | H | H | | —N(H)—C₆H₄—(CH₂)₂CH₃ |
| 224 | —O(CH₂)₂—N(pyrrolidine) | H | H | | —N(H)—(CH₂)₃—N(pyrrolidin-2-one) |
| 225 | —O(CH₂)₂—N(CH₃)₂ | H | —(CH₂)₂—N(CH₃)₂ | | OCH₂CH₃ |
| 226 | —O(CH₂)₂—N(CH₃)₂ | H | —(CH₂)₂—N(CH₃)₂ | | OH |

TABLE 1-continued

| # | R1 | R2 | R3 | R4 |
|---|---|---|---|---|
| 227 | —O(CH₂)₂—N(CH₃)₂ | H | —(CH₂)₂—N(CH₃)₂ | —NH—CH(CH₃)₂ |
| 228 | —O(CH₂)₂—N(CH₃)₂ | H | —(CH₂)₂—N(CH₃)₂ | —NH—(CH₂)₂—CH₃ |
| 229 | —O(CH₂)₂—N(CH₃)₂ | H | —(CH₂)₂—N(CH₃)₂ | —NH—cyclooctyl |
| 230 | —O(CH₂)₂—N(CH₃)₂ | H | —(CH₂)₂—N(CH₃)₂ | —NH—C₆H₄—(CH₂)₂CH₃ |
| 231 | —O(CH₂)₂—N(CH₃)₂ | H | —(CH₂)₂—N(CH₃)₂ | —NH—(CH₂)₃—N(2-pyrrolidinone) |
| 232 | —O(CH₂)₂—N(pyrrolidinyl) | H | —(CH₂)₂—N(pyrrolidinyl) | OCH₂CH₃ |
| 233 | —O(CH₂)₂—N(pyrrolidinyl) | H | —(CH₂)₂—N(pyrrolidinyl) | OH |
| 234 | —O(CH₂)₂—N(pyrrolidinyl) | H | —(CH₂)₂—N(pyrrolidinyl) | —NH—CH(CH₃)₂ |
| 235 | —O(CH₂)₂—N(pyrrolidinyl) | H | —(CH₂)₂—N(pyrrolidinyl) | —NH—(CH₂)₂—CH₃ |
| 236 | —O(CH₂)₂—N(pyrrolidinyl) | H | —(CH₂)₂—N(pyrrolidinyl) | —NH—cyclooctyl |
| 237 | —O(CH₂)₂—N(pyrrolidinyl) | H | —(CH₂)₂—N(pyrrolidinyl) | —NH—C₆H₄—(CH₂)₂CH₃ |
| 238 | —O(CH₂)₂—N(pyrrolidinyl) | H | —(CH₂)₂—N(pyrrolidinyl) | —NH—(CH₂)₃—N(2-pyrrolidinone) |
| 239 | H | H | —(CH₂)₂—NH(CH₃) | —NH—(CH₂)₃—N(2-pyrrolidinone) |

TABLE 1-continued
| 240 | H | H | —(CH₂)₂—NH₂ | 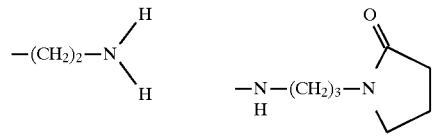 |
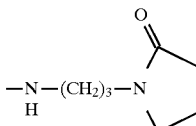
| Compd. No. | R¹ | R² | R³ | —R⁴ |
|---|---|---|---|---|
| 241 | OCH₂OCH₃ | OCH₂OCH₃ | H | 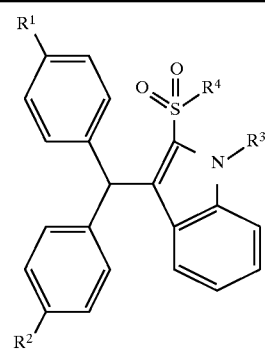 |
| 242 | OCH₂OCH₃ | OCH₂OCH₃ | —(CH₂)₂—N(CH₃)₂ | 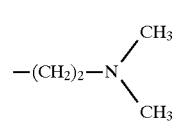 |
| 243 | OCH₂OCH₃ | OCH₂OCH₃ | —(CH₂)₂—N(morpholine) | 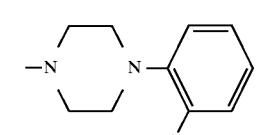 |
| 244 | OCH₂OCH₃ | OCH₂OCH₃ | H | 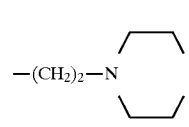 |
| 245 | OCH₂OCH₃ | OCH₂OCH₃ | H | —N(CH₂CH₃)₂ |
| 246 | OCH₂OCH₃ | OCH₂OCH₃ | H | 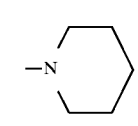 |
| 247 | OCH₂OCH₃ | OCH₂OCH₃ | H | 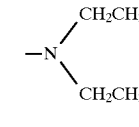 |
| 248 | OCH₂OCH₃ | OCH₂OCH₃ | H | 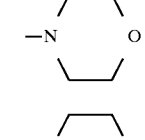 |

TABLE 1-continued

| 249 | OCH₂OCH₃ | OCH₂OCH₃ | —(CH₂)₂—N(CH₃)₂ | piperidinyl |
| 250 | OCH₂OCH₃ | OCH₂OCH₃ | —(CH₂)₂—N(CH₃)₂ | —N(CH₂CH₃)₂ |
| 251 | OCH₂OCH₃ | OCH₂OCH₃ | —(CH₂)₂—N(CH₃)₂ | morpholinyl |
| 252 | OCH₂OCH₃ | OCH₂OCH₃ | —(CH₂)₂—N(CH₃)₂ | 4-phenylpiperazinyl |
| 253 | OCH₂OCH₃ | OCH₂OCH₃ | —(CH₂)₂—N(CH₃)₂ | 4-benzylpiperazinyl |
| 254 | OH | OH | H | 4-(2-chlorophenyl)piperazinyl |
| 255 | OH | OH | —(CH₂)₂—N(CH₃)₂ | 4-(2-chlorophenyl)piperazinyl |
| 256 | OH | OH | —(CH₂)₂—morpholinyl | 4-(2-chlorophenyl)piperazinyl |
| 257 | OH | OH | —(CH₂)₂—N(CH₃)₂ | piperidinyl |
| 258 | OH | OH | —(CH₂)₂—N(CH₃)₂ | —N(CH₂CH₃)₂ |
| 259 | OH | OH | —(CH₂)₂—N(CH₃)₂ | morpholinyl |
| 260 | OH | OH | —(CH₂)₂—N(CH₃)₂ | 4-phenylpiperazinyl |
| 261 | OH | OH | —(CH₂)₂—N(CH₃)₂ | 4-benzylpiperazinyl |

TABLE 1-continued

| | | | | |
|---|---|---|---|---|
| 262 | H | H | H | —N(CH₂CH₃)₂ |
| 263 | H | H | H | —N(piperidine) |
| 264 | H | H | —(CH₂)₂—N(CH₃)₂ | —N(piperidine) |
| 265 | H | H | H | —NH—CH(CH₃)₂ |
| 266 | CH₃ | CH₃ | H | —NH—CH(CH₃)₂ |
| 267 | F | F | H | —NH—CH(CH₃)₂ |
| 268 | Cl | Cl | H | —NH—CH(CH₃)₂ |
| 269 | OCH₂OCH₃ | OCH₂OCH₃ | H | —NH—CH(CH₃)₂ |
| 270 | OH | OH | H | —NH—CH(CH₃)₂ |
| 271 | OH | H | H | —NH—CH(CH₃)₂ |
| 272 | —O—(CH₂)₂—N(CH₃)₂ | H | H | —NH—CH(CH₃)₂ |
| 273 | H | H | —(CH₂)₂—N(CH₃)₂ | —NH—CH₃ |
| 274 | H | H | —(CH₂)₂—N(pyrrolidine) | —NH—CH₃ |
| 275 | H | H | —(CH₂)₂—N(CH₃)₂ | —NH—CH(CH₃)₂ |
| 276 | H | H | —(CH₂)₂—N(pyrrolidine) | —NH—CH(CH₃)₂ |

TABLE 1-continued

| | | | | |
|---|---|---|---|---|
| 277 | H | H | —(CH₂)₂—N(CH₃)(CH₃) | —N(H)—(CH₂)₃—N[pyrrolidinone] |
| 278 | H | H | —(CH₂)₂—N[pyrrolidine] | —N(H)—(CH₂)₃—N[pyrrolidinone] |

The inhibitory effect of the compounds of the present invention on bone absorption is shown below by test examples.

Test Example 1

Inhibitory effect on bone absorption

The calvaria was excised from a newborn dd mouse (5 to 6 days old) under sterile conditions. The calvaria was washed with a modified Dulbecco phosphate buffer physiological saline solution containing neither calcium nor magnesium (a product of Gibco Oriental), and divided into two parts along the center suture. A half of the calvaria was cultivated in a modified Dulbecco Eagle medium (1.5 ml) (a product of Gibco Oriental) containing 2.5% fetal calf serum and 15% equine serum which had been inactivated by heating at 56° C. for 20 minutes. The test compound was dissolved in dimethyl sulfoxide and 10 μl of the resulting solution was added to the culture medium to give the final concentrations of $3 \times 10^{-6}$M, $1 \times 10^{-5}$M, and $3 \times 10^{-5}$M. PTH (parathyroid hormone) was dissolved in a 0.15M saline solution (pH 3) and 3 μl of the resulting solution was added to the culture medium to give the final concentration of $1 \times 10^{-8}$M. The culturing was carried out under the condition of 95% air and 5% carbon dioxide and at a temperature of 37° C. for 96 hours. At 48 hours after the start of the culturing, the culture medium was renewed and the test compound and PTH treated as defined above were added thereto. For examining the effect of the test compound on calcium liberation (bone absorption) from the PTH enhanced bone, a control group, a group using PTH ($1 \times 10^{-8}$M), and a group using both the test compound ($3 \times 10^{-6}$M, $1 \times 10^{-5}$M, $3 \times 10^{-5}$M) and PTH were prepared. The amount of the bone absorption was determined by measuring the amount of calcium accumulated in the culture as collected after 96 hours of culturing. The total calcium concentration in the culture was measured with Calcium C Test Wako. The inhibition rate was calculated using the following equation and the result was shown in terms of 50% inhibitory concentration ($IC_{50}$). The results are shown in Table 2.

Inhibition of bone absorption from PTH enhanced bone

Inhibition rate (%) = $[(C_P - C_D)/(C_P - C_0)] \times 100$ $C_0$: The total calcium concentration in the culture containing neither the test compound nor PTH.

$C_P$: The total calcium concentration in the culture treated with only PTH.

$C_D$: The total calcium concentration in the culture treated with both the test compound and PTH.

TABLE 2

| Compound No. | Inhibitory effect on bone absorption ($IC_{50}$; μM) |
|---|---|
| 8 | >30 |
| 9 | 11.5 |
| 10 | 9.6 |
| 11 | >30 |
| 12 | >30 |
| 13 | 15.0 |
| 14 | 11.9 |
| 95 | 14.3 |
| 97 | 9.1 |
| 98 | 17.5 |
| 100 | 11.2 |
| 101 | 10.9 |
| 102 | 14.3 |
| 107 | 3.7 |
| 108 | 14.3 |
| 109 | 13.7 |
| 143 | 13.0 |
| 148 | 18.1 |
| 150 | 16.7 |
| 183 | 14.3 |
| 205 | 10.8 |
| 206 | 10.5 |
| 254 | 14.1 |
| 257 | 13.7 |
| 258 | 13.3 |
| 264 | 13.7 |

Test Example 2

Inhibitory effect on decrease of bone density by ovariectomy

The experiment was carried out using 10-weeks-old female SD strain rats (Charles River Japan Inc.) The ovaries on both sides of the rats were excised under anesthesia using Nembutal. The test compound (10 mg/kg) was dissolved or suspended in distilled water for injection (a product of Otsuka Pharmaceutical Co., Ltd.) and administered orally once a day from the first day after the operation for 3 weeks. For the control group, distilled water for injection alone was administered. The rat was slaughtered by neck dislocation, the right hindlimb was ablated, and then the bone density of the neck was measured according to a DEXA (DXA) method [Japan Clinic, 52 (9), 2329–2334 (1994)] using bone mineral measuring apparatus DCS-600 (Aloka Co., Ltd.) The inhibition rate of decrease in the bone density of the test compound-administered group was calculated from the decrease of the bone density in the test compound-administered group and that in the control group. The results are shown in Table 3.

TABLE 3

| Compd No. | Inhibition rate of decrease in bone density (%) |
|---|---|
| 9 | 97 |
| 10 | 33 |

Test Example 3
Inhibitory effect on decrease of bone density by ovariectomy

The experiment was carried out using 13-weeks-old female SD strain rats (Japan Crea Co. Ltd.) The animals were subjected to sham operation or bilateral ovariectomy under Nembutal anesthesia. The test compound (10 mg/kg) was dissolved or suspended in 0.5% methylcellulose (Shin-Etsu Chemical Co., Ltd.) and administered orally once a day from the first day after the operation for 6 weeks. For the sham-operated group and the ovariectomized control group, 0.5% methylcellulose (Shin-Etsu Chemical Co., Ltd.) was administered orally. The rat was slaughtered by femoral artery bleeding, the right hindlimb was ablated, and then the bone mineral content (BMC) and bone density (BD) of the tibia was measured according to a DEXA (DXA) method [Japan Clinic, 52 (9), 2329–2334 (1994)] using bone mineral measuring apparatus DCS-600 (Aloka Co., Ltd.) Tibial BMC and BD in the sham-operated, ovariectomized control, and test compound-treated ovariectomized group are shown in Table 4.

TABLE 4

|  | BMC | BD |
|---|---|---|
| sham-operated group | 257.76 ± 7.52 | 125.37 ± 1.42 |
| ovariectomized control group | 233.48 ± 4.29 | 110.43 ± 1.38 |
| Compound 108-treated ovariectomized group | 268.81 ± 7.38 | 126.95 ± 1.78 |

The inhibitory effect of the compounds of the present application on bone resorption was also determined by their inhibitory effect on the excretion of urinary hydroxyproline which is elevated by ovariectomy of the animals tested, according to the report of Kalu DN et al. [Bone and Mineral., 14, 175 (1991)].

Test Example 4
Inhibitory effect on the increase of urinary hydroxyproline excretion by ovariectomy 12-weeks-old female SD strain rats (Japan Clea Co., Ltd.) were acclimated for 1 week during which they were given tap water and a standard diet (F2; Funabashi Farmas) ad libitum. The experiment was carried out using the rats weighing 270–310 g. After the animals were subjected to sham operation or bilateral ovariectomy, they were allowed free access to water passed through ion exchange resin instead of tap water, and were housed in individual cages. The test compound (10 mg/kg) was suspended in 0.3% Tween or 0.5% methylcellulose, and the obtained suspension was orally administered to the ovariectomized rats once a day for two weeks starting from the day following ovariectomy (0.5 ml/100 g body weight). 0.3% Tween or 0.5% methylcellulose was similarly administered to sham-operated rats and ovariectomized control rats. After the final administration, the rats were placed in individual metabolic cages and fasted during 24 hours, and urine was collected The volume of the collected urine was measured and the urine was centrifuged at 3,000 rpm for 15 min at 4° C. The concentration of hydroxyproline in the supernatant was measured by the method of Ikeda et al. [Ann. Rep. Tokyo Metr. Res. Lab. P. H., 36, 277–282 (1985)] and the concentration of creatinine in the supernatant was measured with creatinine test WAKO (Wako Pure Chem.) The amount of urinary hydroxyproline excretion was expressed by the molar ratio of the amount of hydroxyproline to the amount of creatinine. The rate of inhibition on increase of the amount of urinary hydroxyproline excretion in ovariectomized rats treated with the test compound compared to that of the control group was calculated using the following equation. The results are shown in Table 5.

Inhibition rate (%)=[(P1−P2)/(P1−P3)]×100

P1: The amount of urinary hydroxyproline excretion in ovariectomized rats treated with 0.3% Tween (mmol/mmol).

P2: The amount of urinary hydroxyproline excretion in ovariectomized rats treated with the test compound (mmol/mmol).

P3: The amount of urinary hydroxyproline in sham-operated rats treated with 0.3% Tween (mmol/mmol).

TABLE 5

| Compd No. | Inhibition rate of increase of the amount of urinary hydroxyproline excretion |
|---|---|
| 70 | 100 |
| 73 | 100 |
| 75 | 30 |
| 77 | 30 |
| 78 | 100 |
| 80 | 100 |
| 81 | 100 |
| 82 | 100 |
| 85 | 100 |
| 91 | 43 |
| 93 | 100 |
| 95 | 100 |
| 98 | 100 |
| 102 | 100 |
| 107 | 100 |
| 108 | 100 |
| 109 | 87 |
| 138 | 70 |
| 143 | 57 |
| 148 | 53 |
| 150 | 77 |
| 183 | 40 |
| 184 | 47 |
| 207 | 59 |
| 256 | 32 |
| 258 | 22 |
| 264 | 100 |

Compounds (I) and pharmaceutically acceptable salts thereof can be formulated into generally employed dose forms such as tablets, capsules, and syrups, and administered orally or parenterally through intramuscular injection, intravenous injection, drip infusion, or rectal administration using suppositories. For preparing these dose forms for oral or parenteral administration, generally known techniques are applied. For example, the preparations may contain various excipients, lubricants, binders, disintegrating agents, isotonizing agents, emulsifiers, and the like.

Examples of the carriers which can be used are water, injectable distilled water, physiological saline, glucose, fructose, sucrose, mannitol, lactose, starch, cellulose, methyl cellulose, carboxymethyl cellulose, hydroxypropyl cellulose, alginic acid, talc, sodium citrate, calcium carbonate, calcium hydrogenphosphate, magnesium stearate, urea, silicone resins, sorbitan fatty acid esters, and glycerin fatty acid esters.

The effective dose and administration schedule of Compound (I) or a pharmaceutically acceptable salt thereof varies depending upon the mode of administration, the age, body weight and conditions of a patient, etc. However, generally, Compound (I) or a pharmaceutically acceptable salt thereof is administered in a dose of 0.1 to 10 mg/kg/day in 1 to 4 parts.

Certain embodiments of the present invention are illustrated in the following Examples and Reference Examples.

BEST MODE FOR CARRYING OUT THE INVENTION

EXAMPLE 1

1-{3-{Bis[4-(methoxymethoxy)phenyl] methyl}indol-2-ylcarbonyl}-4-(2-chlorophenyl) piperazine (Compound 1)

Boron trifluoride-ether complex (0.36 ml, 2.94 mmol) was added dropwise at 0° C. to a solution of 4,4'-bis (methoxymethoxy)benzhydrol (8.96 g, 29.43 mmol) and 1-(2-chlorophenyl)-4-(indol-2-ylcarbonyl)piperazine (10.0 g, 29.43 mmol) in 200 ml of methylene chloride, followed by stirring at 0° C. to room temperature for 2 hours. A saturated aqueous solution of sodium bicarbonate was added to the reaction solution for neutralization followed by extraction with chloroform. The resulting organic layer was washed with a saturated aqueous solution of sodium bicarbonate and a saturated aqueous solution of sodium chloride, and dried over magnesium sulfate, and the solvent was distilled off under reduced pressure to give a crude product. The obtained crude product was recrystallized from ethanol to, give 15.1 g (yield: 82%) of the title compound.

$^1$H-NMR(CDCl$_3$) δ(ppm): 2.65–2.85 (4H, m), 3.43 (6H, s), 3.45–3.65 (4H, m), 5.11 (4H, s), 5.77 (1H, s), 6.8–6.85 (1H, m), 6.9–7.05 (2H, m), 6.92 (4H, d, J=8.4Hz), 7.1–7.25 (3H, m), 7.17 (4H, d, J=8.4 Hz), 7.3–7.35 (2H, m), 8.72 (1H, s).

IR(KBr tab.): 1608, 1509, 1481, 1439, 1233, 1153 cm$^{-1}$
Melting Point: 178.9°–180.0° C.

EXAMPLE 2

1-{3-{Bis[4-(methoxymethoxy)phenyl]methyl}-1-(2-dimethylaminoethyl)indol-2-ylcarbonyl}-4-(2-chlorophenyl)-piperazine (Compound 2)

To a solution of Compound 1 (2.0 g, 3.19 mmol) obtained in Example 1 in 30 ml of N,N-dimethylformamide was portionwise added sodium hydride (60% in oil, 270 mg, 6.71 mmol) with stirring at 0° C., and 2-dimethylaminoethylchloride hydrochloride (460 mg, 3.19 mmol) was added thereto, followed by heating to 80° C. and then stirring for one hour. A saturated aqueous solution of ammonium chloride was added to the reaction solution for neutralization, and water was added thereto followed by extraction with ethyl acetate. The resulting organic layer was washed with a saturated aqueous solution of sodium chloride and dried over magnesium sulfate, and the solvent was distilled off under reduced pressure to give 2.9 g of a crude product. The obtained crude product was purified with silica gel column chromatography (ethyl acetate/hexane=1/1– ethyl acetate alone) to give 2.1 g (yield: 94%) of the title compound.

$^1$H-NMR(CDCl$_3$) δ(ppm): 2.15–2.4 (2H, m), 2.32 (6H, s), 2.5–2.9 (3H, m), 3.0–3.2 (2H, m), 3.2–3.3 (1H, m), 3.41 (3H, 3), 3.43 (3H, s), 3.65–3.8 (1H, m), 3.95–4.2 (2H, m), 4.3–4.45 (1H, m), 5.11 (4H, s), 5.67 (1H, s), 6.75–6.85 (1H, m), 6.85–7.05 (6H, m), 7.05–7.3 (7H, m), 7.3–7.4 (2H, m).

IR(neat): 1639, 1508, 1459, 1438, 1229, 1153 cm$^{-1}$

EXAMPLE 3

1-{3-{Bis[4-(methoxymethoxy)phenyl]methyl}-1-(2-morpholinoethyl)indol-2-ylcarbonyl}-4-(2-chlorophenyl)-piperazine (Compound 3)

Substantially the same procedure as in Example 2 was repeated using Compound 1 (2.0 g, 3.19 mmol) obtained in Example 1 and 2-morpholinoethylchloride hydrochloride (600 mg, 3.19 mmol) to give 2.1 g (yield: 89%) of the title compound.

$^1$H-NMR(CDCl$_3$) δ(ppm): 2.1–2.25 (1H, m), 2.45–2.7 (6H, m), 2.75–2.95 (2H, m), 3.0–3.15 (2H, m), 3.15–3.3 (1H, m), 3.41 (3H, s), 3.44 (3H, s), 3.6–3.8 (5H, m), 3.9–4.2 (2H, m), 4.25–4.45 (1H, m), 5.11 (2H, s), 5.15 (2H, s), 5.67 (1H, s), 6.75–7.45 (16H, m).

IR(KBr tab.): 1635, 1509, 1432, 1233, 1152, 1004 cm$^{-1}$

EXAMPLE 4

N-Propyl-3-{bis[4-(methoxymethoxy)phenyl] methyl}-1-(2-dimethylaminoethyl)indole-2-carboxamide (Compound 4)

1-(3-Dimethylaminopropyl)-3-ethylcarbodiimide hydrochloride (728 mg, 3.80 mmol) was added to a solution of 3-{bis[4-(methoxymethoxy)phenyl]methyl}-1-(2-dimethylaminoethyl)indole-2-carboxylic acid (1.0 g, 1.90 mmol) obtained in Example 48 and propylamine (0.23 ml, 2.85 mmol) in 10 ml of methylene chloride, followed by stirring at room temperature for 3.5 hours. Water was added to the reaction solution followed by extraction with chloroform. The resulting organic layer was washed successively with 2N hydrochloric acid, a saturated aqueous solution of sodium bicarbonate, and a saturated aqueous solution of sodium chloride, and dried over magnesium sulfate, and the solvent was distilled off under reduced pressure to give 1.2 g (quantitative) of the title compound.

$^1$H-NMR(CDCl$_3$) δ(ppm): 0.86 (3H, t, J=7.4 Hz), 1.4–1.6 (2H, m), 2.25 (6H, s), 2.85–2.95 (2H, m), 3.25–3.35 (2H, m), 3.46 (6H, s), 4.44 (2H, t, J=6.6 Hz), 5.14 (4H, s), 5.99 (1H, s), 6.85–7.0 (6H, m), 7.10 (4H, d, J=6.6 Hz), 7.15–7.25 (1H, m), 7.34 (1H, d, J=8.3 Hz).

In the following Examples 5 to 7, substantially the same procedure as in Example 4 was repeated using corresponding amines in place of propylamine to give the desired compounds.

EXAMPLE 5

N-Isopropyl-3-{bis[4-(methoxymethoxy)phenyl] methyl}-1-(2-dimethylaminoethyl)indole-2-carboxamide (Compound 5)

$^1$H-NMR(CDCl$_3$) δ(ppm): 1.12 (6H, d, J=6.6 Hz), 2.24 (6H, s), 2.7–2.8 (2H, br), 3.46 (6H, s), 4.15–4.3 (1H, m), 4.4–4.5 (2H, m), 5.14 (4H, s), 5.93 (1H, s), 6.85–6.95 (6H, m), 7.10 (4H, d, J=8.9 Hz), 7.15–7.25 (1H, m), 7.3–7.4 (1H, m).

EXAMPLE 6

1-{3-{Bis[4-(methoxymethoxy)phenyl]methyl}-1-(2-dimethylaminoethyl)indol-2-ylcarbonyl}piperidine (Compound 6)

$^1$H-NMR(CDCl$_3$) δ(ppm): 0.95–1.1 (1H, m), 1.1–1.3 (1H, m), 1.4–1.8 (4H, m), 2.31 (6H, s), 2.55–2.85 (3H, m), 3.0–3.1 (1H, m), 3.4–3.5 (1H, m), 3.44 (3H, s), 3.46 (3H, s), 3.65–3.75 (1H, m), 4.0–4.15 (1H, m), 4.25–4.4 (1H, m), 5.11 (2H, s), 5.14 (2H, s), 5.59 (1H, s), 6.8–7.0 (4H, m), 7.0–7.2 (7H, m), 7.33 (1H, d, J=8.2 Hz).

EXAMPLE 7

N-Cycloheptyl-3-{bis[4-(methoxymethoxy)phenyl]methyl}-1-(2-dimethylaminoethyl)indole-2-carboxamide (Compound 7)

$^1$H-NMR(CDCl$_3$) δ(ppm): 1.2–1.4 (2H, m), 1.4–1.6 (8H, m), 1.9–2.0 (2H, m), 2.23 (6H, s), 2.7–2.8 (2H, m), 3.46 (6H, s), 4.0–4.2 (1H, m), 4.45 (2H, t, J=6.9 Hz), 5.14 (4H, s), 5.94 (1H, s), 6.8–6.95 (6H, m), 7.09 (4H, d, J=8.5 Hz), 7.15–7.25 (1H, m), 7.35 (1H, d, J=8.2 Hz).

EXAMPLE 8

1-{3-[Bis(4-hydroxyphenyl)methyl]indol-2-ylcarbonyl}-4-(2-chlorophenyl)piperazine (Compound 8)

Compound 1 (1.43 g, 2.28 mmol) obtained in Example 1 was dissolved in a mixed solvent of tetrahydrofuran (20 ml) and ethanol (20 ml), and 5 ml of 2N hydrochloric acid was added thereto, followed by heating under reflux for 0.5 hours. The solvent was distilled off under reduced pressure, and a saturated aqueous solution of sodium bicarbonate was added thereto followed by extraction with ethyl acetate. The resulting organic layer was washed with a saturated aqueous solution of sodium chloride and dried over magnesium sulfate, and the solvent was distilled off under pressure. The resulting residue was washed with diethyl ether/ethyl acetate and crystallized to give 1.1 g (yield: 88%) of the title compound.

$^1$H-NMR(DMSO-d$_6$) δ(ppm): 2.5–2.9 (2H, m), 3.2–3.6 (6H, m), 5.59 (1H, s), 6.64 (4H, d, J=8.7 Hz), 6.8–6.9 (1H, m), 6.98 (4H, d, J=8.7 Hz), 7.0–7.15 (4H, m), 7.25–7.45 (3H, m), 9.16 (2H, s), 11.35 (1H, s).

IR(KBr tab.): 1611, 1509, 1477, 1434, 1233 cm$^{-1}$

Melting Point: 226°–230° C.

EXAMPLE 9

1-{3-[Bis(4-hydroxyphenyl)methyl]-1-(2-dimethylaminoethyl)indol-2-ylcarbonyl}-4-(2-chlorophenyl)piperazine methanesulfonate (Compound 9 methanesulfonate)

Compound 2 (13.1 g, 18.4 mmol) obtained in Example 2 was dissolved in a mixed solvent of tetrahydrofuran (50 ml) and ethanol (100 ml), and 20 ml of 2N hydrochloric acid was added thereto, followed by heating under reflux for 4 hours. The solvent was distilled off under reduced pressure, and a saturated aqueous solution of sodium bicarbonate and ethyl acetate were added thereto for neutralization. At this time, crystals were gradually precipitated. The aqueous layer was separated off and a saturated aqueous solution of sodium chloride was added to the suspending organic layer for washing. The aqueous layer was separated off, and crystals were collected by filtration from the suspending organic layer and dried under reduced pressure to give 8.8 g (yield: 79%) of the free base of the title compound. The crystals were suspended in 500 ml of ethyl acetate, and methanesulfonic acid (0.95 ml, 14.6 mmol) was added thereto, followed by stirring at room temperature. The precipitated crystals were collected by filtration and dried under reduced pressure to give 10.9 g (quantitative) of the title compound.

$^1$H-NMR(DMSO-d$_6$) δ(ppm): 2.15–2.3 (1H, m), 2.33 (3H, s), 2.5–2.65 (1H, m), 2.7–2.95 (7H, m), 2.95–3.2 (2H, m), 3.3–3.5 (3H, m), 3.6–3.75 (1H, m), 3.8–3.95 (1H, m), 4.2–4.4 (1H, m), 4.5–4.7 (1H, m), 5.49 (1H, s), 6.55–6.7 (4H, m), 6.8–7.1 (8H, m), 7.15– 7.35 (2H, m), 7.39 (1H, d, J=7.9 Hz), 7.60 (1H, d, J=8.3 Hz), 9.20 (1H, s), 9.27 (1H, s), 9.55–9.7 (1H, br).

IR(KBr tab.): 1609, 1512, 1481, 1442, 1210 cm$^{-1}$

Melting Point: 148°–151° C.

In the following Examples 10 to 14, substantially the same procedure as in Example 9 was repeated using corresponding Compounds 3 to 7 in place of Compound 2 to give the desired compounds.

EXAMPLE 10

1-{3-[Bis(4-hydroxyphenyl)methyl]-1-(2-morpholinoethyl)indol-2-ylcarbonyl}-4-(2-chlorophenyl)-piperazine methanesulfonate (Compound 10 methanesulfonate)

$^1$H-NMR(DMSO-d$_6$) δ(ppm): 2.2–2.35 (1H, m), 2.38 (3H, s), 2.55–2.7 (1H, m), 2.7–2.9 (1H, m), 3.0–3.5 (7H, m), 3.6–3.8 (4H, m), 3.85–4.1 (4H, m), 4.25–4.5 (1H, m), 4.5–4.7 (1H, m), 5.68 (1H, s), 6.55–6.75 (4H, m), 6.8–7.1 (7H, m), 7.1–7.35 (3H, m), 7.38 (1H, d, J=7.9 Hz), 7.61(1H, d, J=8.4 Hz), 9.1–9.35 (2H, br), 9.85–10.1 (1H, br).

IR(KBr tab.): 1612, 1509, 1480, 1445, 1209 cm$^{-1}$

Melting Point: 167°–170° C.

EXAMPLE 11

N-Propyl-3-[bis(4-hydroxyphenyl)methyl]-1-(2-dimethylaminoethyl)indole-2-carboxamide methanesulfonate (Compound 11 methanesulfonate)

$^1$H-NMR(DMSO-d$_6$) δ(ppm): 0.89 (3H, t, J=7.3 Hz), 1.45–1.6 (2H, m), 2.33 (3H, s), 2.82 (6H, s), 3.15–3.3 (2H, m), 3.4–3.5 (2H, m), 4.45–4.55 (2H, m), 5.73 (1H, s), 6.64 (4H, d, J=7.9 Hz), 6.85–6.95 (2H, m), 6.91 (4H, d, J=7.9 Hz), 7.15–7.25 (1H, m), 7.57 (1H, d, J=8.2 Hz), 8.1–8.2 (1H, m), 9.20 (2H, s), 9.7–9.8 (1H, br).

EXAMPLE 12

N-Isopropyl-3-[bis(4-hydroxyphenyl)methyl]-1-(2-dimethylaminoethyl)indole-2-carboxamide methanesulfonate Compound 12 methanesulfonate)

$^1$H-NMR(DMSO-d$_6$) δ(ppm): 1.15 (6H, d, J=6.6 Hz), 2.32 (3H, s), 2.83 (6H, s), 3.4–3.5 (2H, m), 4.0–4.15 (1H, m), 4.45–4.6 (2H, m), 5.71 (1H, s), 6.65 (4H, d, J=8.0 Hz), 6.85–6.95 (2H, m), 6.91 (4H, d, J=8.0 Hz), 7.15–7.25 (1H, m), 7.57 (1H, d, J=8.2 Hz), 7.86 (1H, d, J=7.2 Hz), 9.21 (2H, br), 9.75–9.9 (1H, br).

EXAMPLE 13

1-{3-[Bis(4-hydroxyphenyl)methyl]-1-(2-dimethylaminoethyl)indol-2-ylcarbonyl)piperidine methanesulfonate (Compound 13 methanesulfonate)

$^1$H-NMR(DMSO-d$_6$) δ(ppm): 1.1–1.3 (2H, m), 1.4–1.6 (4H, m), 2.32 (3H, s), 2.75–2.95 (8H, m), 3.1–3.4 (3H, m), 3.6–3.7 (1H, m), 4.15–4.3 (1H, m), 4.5–4.65 (1H, m), 5.40 (1H, s), 6.5–6.7 (4H, m), 6.8–7.0 (5H, m), 7.05 (1H, d, J=7.9 Hz), 7.15–7.25 (1H, m), 7.57 (1H, d, J=8.6 Hz), 9.15 (1H, s), 9.20 (1H, s), 9.5–9.7 (1H, br).

EXAMPLE 14

N-Cycloheptyl-3-[bis(4-hydroxyphenyl)methyl]-1-(2-dimethylaminoethyl)indole-2-carboxamide methanesulfonate (Compound 14 methanesulfonate)

$^1$H-NMR(DMSO-d$_6$) δ(ppm): 1.4–1.7 (10H, m), 1.8–1.95 (2H, m), 2.31 (3H, s), 2.81 (6H, s), 3.4–3.5 (2H, m), 3.9–4.0

(1H, m), 4.45–4.55 (2H, m), 5.69 (1H, s), 6.65 (4H, d, J=8.4 Hz), 6.8–6.95 (2H, m), 6.90 (4H, d, J=8.4 Hz), 7.15–7.25 (1H, m), 7.56(1H, d, J=8.3 Hz), 7.88 (1H, d, J=7.6 Hz), 9.20 (2H, s), 9.5–9.7 (1H, br).

In the following examples 15 to 20, substantially the same procedure as in Example 4 was repeated using corresponding amines in place of propylamine to give the desired compounds.

EXAMPLE 15

N,N-Diethyl-3-{bis[4-(methoxymethoxy)phenyl]methyl}-1-(2-dimethylaminoethyl)indole-2-carboxamide (Compound 15)

$^1$H-NMR(CDCl$_3$) δ(ppm): 0.78 (3H, t, J=7.1 Hz), 1.22 (3H, t, J=7.1 Hz), 2.36 (6H, s), 2.6–2.9 (4H, m), 3.05–3.2 (2H, m), 3.43 (3H, s), 3.47 (3H, s), 3.95–4.15 (1H, m), 4.3–4.45 (1H, m), 5.10 (2H, s), 5.14 (2H, s), 5.54 (1H, s), 6.8–7.0 (5H, m), 7.07 (2H, d, J=8.6 Hz), 7.15–7.25 (4H, m), 7.36 (1H, d, J=7.9 Hz).

EXAMPLE 16

4-{3-{Bis[4-(methoxymethoxy)phenyl]methyl}-1(2-dimethylaminoethyl)indol-2-ylcarbonyl}morpholine (Compound 16)

$^1$H-NMR(CDCl$_3$) δ(ppm): 2.29 (6H, s), 2.5–2.7 (2H, m), 2.85–3.1 (3H, m), 3.2–3.35 (1H, m), 3.44(3H, s), 3.46 (3H, s), 3.55–3.75 (4H, m), 4.0–4.15 (1H, m), 4.25–4.4(1H, m), 5.11 (2H, s), 5.14 (2H, s), 5.62 (1H, s), 6.8–7.0 (5H, m), 7.0–7.1 (2H, m), 7.15–7.25 (4H, m), 7.32 (1H, d, J=8.2 Hz).

EXAMPLE 17

N-(4-Propylphenyl)-3-{bis[4-(methoxymethoxy)phenyl]methyl}-1-(2-dimethylaminoethyl)indole-2-carboxamide (Compound 17)

$^1$H-NMR(CDCl$_3$) δ(ppm): 0.93 (3H, t, J=7.4 Hz), 1.5–1.7 (2H, m), 2.22 (6H, s), 2.56 (2H, t, J=7.1 Hz), 2.85–2.95 (2H, m), 3.46 (6H, s), 4.45–4.55 (2H, m), 5.14 (4H, s), 6.11 (1H, s), 6.85–7.0 (5H, m), 7.0–7.1 (1H, m), 7.1–7.2 (6H, m), 7.2–7.3 (1H, m), 7.3–7.4 (3H, m), 9.25–9.35 (1H, br).

EXAMPLE 18

N-Cyclooctyl-3-{bis[4-(methoxymethoxy)phenyl]methyl}-1-(2-dimethylaminoethyl)indole-2-carboxamide (Compound 18)

$^1$H-NMR(CDCl$_3$) δ(ppm): 1.35–1.6 (14H, m), 2.28 (6H, s), 2.7–2.9 (2H, m), 3.46 (6H, s), 4.1–4.2 (1H, m), 4.45–4.55 (2H, m), 5.14 (4H, s), 5.94 (1H, s), 6.55–6.65 (1H, m), 6.8–6.9 (2H, m), 6.93 (4H, d, J=8.4 Hz), 7.09 (4H, d, J=8.4 Hz), 7.15–7.25 (1H, m), 7.37 (1H, d, J=8.2 Hz).

EXAMPLE 19

1-{3-{Bis[4-(methoxymethoxy)phenyl]methyl}-1-(2-dimethylaminoethyl)indol-2-ylcarbonyl}-4-phenylpiperazine (Compound 19)

$^1$H-NMR(CDCl$_3$) δ(ppm): 2.31 (6H, s), 2.35–2.5 (1H, m), 2.6–2.8 (3H, m), 3.0–3.15 (2H, m), 3.15–3.3 (2H, m), 3.42 (3H, s), 3.43 (3H, s), 3.65–3.8 (2H, m), 4.0–4.15 (1H, m), 4.3–4.45 (1H, m), 5.09 (4H, s), 5.64 (1H, s), 6.75–7.0 (8H, m), 7.0–7.25 (8H, m), 7.35 (1H, d, J=8.4 Hz).

EXAMPLE 20

1-Benzyl-4-{3-{bis[4-(methoxymethoxy)phenyl]methyl}-1-(2-dimethylaminoethyl)indol-2-ylcarbonyl}piperazine (Compound 20)

$^1$H-NMR(CDCl$_3$) δ(ppm): 1.75–1.85 (1H, m), 2.0–2.1 (1H, m), 2.30(6H, s), 2.35–2.45 (2H, m), 2.5–2.8 (2H, m), 2.85–3.0 (1H, m), 3.05–3.2 (1H, m), 3.3–3.45 (2H, m), 3.44 (3H, s), 3.46 (3H, s), 3.6–3.75 (2H, m), 4.0–4.15 (1H, m), 4.25–4.4 (1H, m), 5.11 (2H, s), 5.14 (2H, s), 5.60 (1H, s), 6.8–6.95 (5H, m), 7.0–7.35 (12H, m).

In the following Examples 21 to 22, substantially the same procedure as in Example 2 was repeated using corresponding substituted ethylchloride hydrochlorides in place of 2-dimethylaminoethylchloride hydrochloride to give the desired compounds.

EXAMPLE 21

1-{3-{Bis[4-(methoxymethoxy)phenyl]methyl}-1-[2-(1-pyrrolidinyl)ethyl]indol-2-ylcarbonyl}-4-(2-chlorophenyl)piperazine (Compound 21)

$^1$H-NMR(CDCl$_3$) δ(ppm): 1.8–1.95 (4H, m), 2.15–2.3 (1H, m), 2.5–2.65 (1H, m), 2.65–2.8 (3H, m), 2.8–3.15 (6H, m), 3.2–3.3 (1H, m), 3.41 (3H, s), 3.44 (3H, s), 3.7–3.85 (1H, m), 3.85–4.0 (1H, m), 4.1–4.25 (1H, m), 4.4–4.6 (1H, m), 5.11 (4H, s), 5.67 (1H, s), 6.75–6.85 (1H, m), 6.85–7.0 (6H, m), 7.0–7.25 (7H, m), 7.33 (1H, dd, J=7.9, 1.3 Hz), 7.4–7.45 (1H, m).

EXAMPLE 22

1-{3-{Bis[4-(methoxymethoxy)phenyl]methyl}-1-(2-piperidinoethyl)indol-2-ylcarbonyl}-4-(2-chlorophenyl)piperazine (Compound 22)

$^1$H-NMR(CDCl$_3$) δ(ppm): 1.4–1.5 (2H, m), 1.5–1.65 (4H, m), 2.1–2.2 (1H, m), 2.45–2.55 (4H, m), 2.55–2.7 (2H, m), 2.7–2.9 (2H, m), 2.95–3.2 (2H, m), 3.2–3.35 (1H, m), 3.39 (3H, s), 3.42 (3H, s), 3.65–3.8 (1H, m), 3.95–4.05 (1H, m), 4.05–4.2 (1H, m), 4.3–4.45 (1H, m), 5.10 (4H, s), 5.68 (1H, s), 6.80 (1H, dd, J=7.9, 1.3 Hz), 6.85–7.05 (6H, m), 7.05–7.25 (7H, m), 7.32 (1H, dd, J=7.9, 1.3 Hz), 7.371 (1H, d, J=8.2 Hz).

EXAMPLE 23

1-{3-{Bis[4-(methoxymethoxy)phenyl)methyl}-1-(3-dimethylaminopropyl)indol-2-ylcarbonyl}-4-(2-chlorophenyl)piperazine (Compound 23)

1-{3-{Bis[4-(methoxymethoxy)phenyl]methyl}-1-(3-chloropropyl)indol-2-ylcarbonyl}-4-(2-chlorophenyl)piperazine (1.5 g, 2.13 mmol) obtained in Reference Example 2 was dissolved in a mixed solvent of ethanol (30 ml) and methanol (20 ml), and an aqueous solution of dimethylamine (50%, 5 ml) was added thereto. The resulting solution was heated to 50° to 60° C. and stirred for a total of 50 hours while an aqueous solution of dimethylamine was added thereto suitably. The solvent was distilled off under reduced pressure, and a saturated aqueous solution of sodium bicarbonate was added thereto followed by extraction with ethyl acetate. The resulting organic layer was washed with a saturated aqueous solution of sodium chloride and dried over magnesium sulfate, and the solvent was distilled off under reduced pressure to give 1.45 g of a crude product. The obtained crude product was purified with silica gel column chromatography (chloroform/methanol=50/1–20/1) to give 1.35 g (yield :89%) of the title compound.

$^1$H-NMR(CDCl$_3$) δ(ppm): 2.0–2.25 (4H, m), 2.34 (6H, s), 2.4–2.5 (1H, m), 2.5–2.6 (1H, m), 2.8–3.0 (2H, m), 3.05–3.3 (2H, m), 3.40 (3H, s), 3.44 (3H, s), 3.7–3.8 (1H, m), 3.85–4.1 (2H, m), 4.25–4.4 (1H, m), 5.10 (2H, s), 5.12 (2H, s), 5.68 (1H, s), 6.75–7.0 (7H, m), 7.0–7.3 (7H, m), 7.33 (1H, dd, J=7.9, 1.5 Hz), 7.37(1H, d, J=8.4 Hz).

EXAMPLE 24

1-{3-{Bis[4-(methoxymethoxy)phenyl]methyl}-1-(4-dimethylaminobutyl)indol-2-ylcarbonyl}-4-(2-chlorophenyl)piperazine (Compound 24)

Substantially the same procedure as in Example 23 was repeated using 1-{3-{bis[4-(methoxymethoxy)phenyl]methyl}-1-(4-chlorobutyl)indol-2-ylcarbonyl}-4-(2-chlorophenyl)piperazine (1.5 g, 2.09 mmol) obtained in Reference Example 3 and an aqueous solution of dimethylamine to give 1.58 g (quantitative) of the title compound.

$^1$H-NMR(CDCl$_3$) δ(ppm): 1.5–1.65 (2H, m), 1.75–2.0 (2H, m), 2.1–2.2(1H, m), 2.26(6H, s), 2.25–2.35 (2H, m), 2.5–2.6 (1H, m), 2.8–2.9 (1H, m), 2.95–3.15 (2H, m), 3.15–3.25 (1H, m), 3.40 (3H, s), 3.44 (3H, s), 3.65–3.8 (1H, m), 3.9–4.05 (2H, m), 4.2–4.35 (1H, m), 5.05–5.15 (4H, m), 5.68 (1H, s), 6.75–6.85 (1H, m), 6.85–7.0(6H, m), 7.05–7.25 (7H, m), 7.33 (2H, dd, J=7.9, 1.7 Hz).

In the following Examples 25 to 28, substantially the same procedure as in Example 23 or 24 was repeated using a compound obtained in Reference Example 3 or 4 and corresponding amines in place of an aqueous solution of dimethylamine to give the desired compounds.

EXAMPLE 25

1-{3-{Bis[4-(methoxymethoxy)phenyl]methyl}-1-(3-morpholinopropyl)indol-2-ylcarbonyl}-4-(2-chlorophenyl)piperazine (Compound 25)

$^1$H-NMR(CDCl$_3$) δ(ppm): 1.5–1.8 (1H, br), 2.0–2.2 (3H, m), 2.4–2.6 (6H, m), 2.8–2.9 (1H, m), 2.9–3.0 (1H, m), 3.05–3.25 (2H, m), 3.40 (3H, s), 3.44 (3H, s), 3.65–3.85 (5H, m), 3.85–4.0 (1H, m), 4.0–4.15 (1H, m), 4.25–4.4 (1H, m), 5.1–5.25 (4H, m), 5.68 (1H, s), 6.8–6.85 (1H, m), 6.85–7.05 (6H, m), 7.1–7.25 (7H, m), 7.33 (1H, dd, J=7.9, 1.3 Hz), 7.37 (1H, d, J=8.2 Hz).

EXAMPLE 26

1-{3-{Bis[4-(methoxymethoxy)phenyl]methyl}-1-(4-morpholinobutyl)indol-2-ylcarbonyl}-4-(2-chlorophenyl)piperazine (Compound 26)

$^1$H-NMR(CDCl$_3$) δ(ppm): 1.45–1.6 (2H, m), 1.7–2.0 (2H, m), 2.05–2.2 (1H, m), 2.3–2.45 (6H, m), 2.5–2.6 (1H, m), 2.75–2.9 (1H, m), 2.95–3.3 (3H, m), 3.40 (3H, s), 3.44 (3H, s), 3.65–3.75 (5H, m), 3.9–4.1 (2H, m), 4.2–4.3 (1H, m), 5.05–5.2 (4H, m), 5.69 (1H, s), 6.75–6.85 (1H, m), 6.85–7.05 (6H, m), 7.05–7.25 (7H, m), 7.3–7.4 (2H, m).

EXAMPLE 27

1-{3-{Bis[4-(methoxymethoxy)phenyl]methyl}-1-[3-(1-pyrrolidinyl)propyl]indol-2-ylcarbonyl}-4-(2-chlorophenyl)piperazine (Compound 27)

$^1$H-NMR(CDCl$_3$) δ(ppm): 1.75–1.9(4H, m), 1.95–2.2 (3H, m), 2.45–2.65 (7H, m), 2.75–2.9 (1H, m), 2.9–3.0 (1H, m), 3.0–3.1 (1H, m), 3.1–3.25 (1H, m), 3.40 (3H, s), 3.44 (3H, s), 3.65–3.75 (1H, m), 3.9–4.15 (2H, m), 4.25–4.4 (1H, m), 5.05–5.15 (4H, m), 5.69 (1H, s), 6.75–6.85 (1H, m), 6.85–7.0 (6H, m), 7.05–7.25 (7H, m), 7.33 (1H, dd, J=7.9, 1.5 Hz), 7.38 (1H, d, J=8.2 Hz).

EXAMPLE 28

1-{3-{Bis[4-(methoxymethoxy)phenyl]methyl}-1-[4-(1-pyrrolidinyl)butyl]indol-2-ylcarbonyl}-4-( 2-chlorophenyl)piperazine (Compound 28)

$^1$H-NMR(CDCl$_3$) δ(ppm): 1.5–1.65 (2H, m), 1.7–2.0 (7H, m), 2.05–2.2 (1H, m), 2.4–2.6 (6H, m), 2.8–2.9 (1H, m), 2.95–3.15 (2H, m), 3.15–3.3 (1H, m), 3.40 (3H, s), 3.44 (3H, s), 3.65–3.75 (1H, m), 3.9–4.1 (2H, m), 4.2–4.35 (1H, m), 5.05–5.15 (4H, m), 5.68 (1H, s), 6.80(1H, dd, J=7.9, 1.3 Hz), 6.85–7.05 (6H, m), 7.05–7.25 (7H, m), 7.3–7.4 (2H, m).

EXAMPLE 29

1-{3-[Bis(4-methoxyphenyl)methyl]indol-2-ylcarbonyl}-4-(2-chlorophenyl)piperazine (Compound 29)

Substantially the same procedure as in Example 1 was repeated using 4,4'-dimethoxybenzhydrol (2.37 g, 9.71 mmol) and 1-(2-chlorophenyl)-4-(indol-2-ylcarbonyl)piperazine (3.0 g, 8.83 mmol) to give 4.0 g (yield: 81%) of the title compound.

$^1$H-NMR(CDCl$_3$) δ(ppm): 2.65–2.85 (4H, m), 3.5–3.65 (4H, m), 3.75 (6H, s), 5.79 (1H, s), 6.75–6.9 (1H, m), 6.79 (4H, d, J=8.6 Hz), 6.9–7.05 (2H, m), 7.1–7.25 (3H, m), 7.17 (4H, d, J=8.6 Hz), 7.3–7.4 (2H, m), 8.48 (1H, s).

EXAMPLE 30

1-{3-[Bis(4-methoxyphenyl)methyl]-1-(2-dimethylaminoethyl)indol-2-ylcarbonyl}-4-(2-chlorophenyl)piperazine (Compound 30)

Substantially the same procedure as in Example 2 was repeated using Compound 29 (1.0 g, 1.77 mmol) obtained in Example 29 and 2-dimethylaminoethylchloride hydrochloride (266 mg, 1.85 mmol) to give 0.75 g (yield: 67%) of the title compound.

$^1$H-NMR(CDCl$_3$) δ(ppm): 2.1–2.2 (1H, m), 2.3–2.45 (1H, m), 2.40 (6H, s), 2.45–2.6 (1H, m), 2.65–2.9 (2H, m), 3.0–3.15 (2H, m), 3.15–3.3 (1H, m), 3.7–3.85 (1H, m), 3.75 (3H, s), 3.76 (3H, s), 3.9–4.05 (1H, m), 4.05–4.2 (1H, m), 4.4–4.55 (1H, m), 5.67 (1H, s), 6.7–6.9 (6H, m), 6.9–7.05 (2H, m), 7.05–7.15 (2H, m), 7.15–7.3 (4H, m), 7.33 (1H, dd, J=7.9, 1.5 Hz), 7.39 (1H, d, J=8.4 Hz).

In the following Examples 31 to 32, substantially the same procedure as in Example 30 was repeated using corresponding substituted aminoethylchloride hydrochlorides in place of 2-dimethylaminochloride hydrochloride to give the desired compounds.

EXAMPLE 31

1-{3-[Bis(4-methoxyphenyl)methyl]-1-(2-morpholinoethyl)indol-2-ylcarbonyl}-4-(2-chlorophenyl)piperazine (Compound 31)

$^1$H-NMR(CDCl$_3$) δ(ppm): 2.05–2.2 (1H, m), 2.45–2.6 (5H, m), 2.6–2.75 (1H, m), 2.75–2.9 (2H, m), 2.95–3.2 (2H, m), 3.2–3.3 (1H, m), 3.6–3.8 (5H, m), 3.75 (6H, s), 3.95–4.2 (2H, m), 4.3–4.45 (1H, m), 5.69(1H, s), 6.7–6.85 (5H, m), 6.9–7.05 (2H, m), 7.05–7.15 (3H, m), 7.15–7.3 (4H, m), 7.3–7.4 (2H, m).

EXAMPLE 32

1-{3-[Bis(4-methoxyphenyl)methyl]-1-[2-(1-pyrrolidinyl)ethyl]indol-2-ylcarbonyl}-4-(2-chlorophenyl)piperazine (Compound 32)

$^1$H-NMR(CDCl$_3$) δ(ppm); 1.55–1.7 (2H, m), 1.75–1.9 (3H, m), 2.05–2.15 (1H, m), 2.5–2.7 (4H, m), 2.7–2.9 (2H, m), 2.9–3.3 (4H, m), 3.6–3.8 (1H, m), 3.75 (6H, s), 4.0–4.2 (2H, m), 4.3–4.45 (1H, m), 5.69 (1H, s), 6.75 (4H, d, J=8.9 Hz), 6.82 (1H, d, J=8.6 Hz), 6.9–7.0 (2H, m), 7.05–7.15 (3H, m), 7.15–7.25 (4H, m), 7.3–7.4 (2H, m)

In the following Examples 33 to 46, substantially the same procedure as in Example 9 was repeated using corresponding Compound 15 to Compound 28 in place of Compound 2 to give the desired compounds.

EXAMPLE 33

N,N-Diethyl-3-[bis(4-hydroxyphenyl)methyl]-1(2-dimethylaminoethyl)indole-2-carboxamide methanesulfonate (Compound 33 methanesulfonate)

$^1$H-NMR(DMSO-d$_6$) δ(ppm): 0.80 (3H, t, J=6.9 Hz), 1.18 (3H, t, J=6.9 Hz), 2.32 (3H, s), 2.7–2.9 (6H, m), 3.1–3.3 (1H, m), 3.3–3.5 (4H, m), 3.5–3.7 (1H, m), 4.1–4.3 (1H, m), 4.5–4.7 (1H, m), 5.33 (1H, s), 6.60 (2H, d, J=8.4 Hz), 6.66 (2H, d, J=8.4 Hz), 6.84 (2H, d, J=8.4 Hz), 6.9–7.0 (3H, m), 7.05 (1H, d, J=7.9 Hz), 7.20 (1H, t, J=7.6 Hz), 7.58 (1H, d, J=8.2 Hz), 9.16 (1H, s), 9.24 (1H, s), 9.55–9.65 (1H, br).

IR(KBr tab.): 3420, 1610, 1590, 1512, 1450, 1202 cm$^{-1}$

Melting Point: 186°–187° C.

EXAMPLE 34

4-{3-[Bis(4-hydroxyphenyl)methyl]-1-(2-dimethylaminoethyl)indol-2-ylcarbonyl}morpholine methanesulfonate (Compound 34 methanesulfonate)

$^1$H-NMR(DMSO-d$_6$) δ(ppm): 2.33 (3H, s), 2.86 (6H, br), 2.95–3.05 (1H, m), 3.05–3.2 (1H, m), 3.2–3.5 (4H, m), 3.5–3.7 (4H, m), 4.2–4.35 (1H, m), 4.5–4.65 (1H, m), 5.45 (1H, s), 6.55–6.75 (4H, m), 6.8–7.1 (6H, m), 7.22 (1H, t, J=7.6 Hz), 7.58 (1H, d, J=8.6 Hz), 9.20 (1H, s), 9.25 (1H, s), 9.55–9.65 (1H, br).

IR(KBr tab.): 3400, 1611, 1513, 1217 cm$^{-1}$

Melting Point: 206°–208° C.

EXAMPLE 35

N-(4-Propylphenyl)-3-[bis(4-hydroxyphenyl)methyl]-1-(2-dimethylaminoethyl)indole-2-carboxamide methanesulfonate (Compound 35 methanesulfonate)

$^1$H-NMR(DMSO-d$_6$) δ(ppm): 0.90 (3H, t, J=7.3 Hz), 1.5–1.7 (2H, m), 2.32 (3H, s), 2.54 (2H, t, J=7.3 Hz), 2.83 (6H, s), 3.35–3.5 (2H, m), 4.5–4.65 (2H, m), 5.77 (1H, s), 6.63 (4H, d, J=8.2 Hz), 6.9–7.1 (6H, m), 7.1–7.3 (3H, m), 7.45–7.55 (2H, m), 7.61 (1H, d, J=7.9 Hz), 9.20 (2H, s), 9.55–9.7 (1H, br), 10.16 (1H, s).

IR(KBr tab.): 3400, 1612, 1513, 1206 cm$^{-1}$

Melting Point: .188°–189° C.

EXAMPLE 36

N-Cyclooctyl-3-[bis(4-hydroxyphenyl)methyl]-1-(2-dimethylaminoethyl)indole-2-carboxamide methanesulfonate (Compound 36 methanesulfonate)

$^1$H-NMR(DMSO-d$_6$) δ(ppm): 1.4–1.9 (14H, m), 2.32 (3H, s), 2.82 (6H, s), 3.35–3.5 (2H, m), 3.9–4.1 (1H, m), 4.45–4.6 (2H, m), 5.69 (1H, s), 6.65 (4H, d, J=7.9 Hz), 6.85–6.95 (6H, m), 7.15–7.25 (1H, m), 7.57 (1H, d, J=8.6 Hz), 7.90 (1H, d, J=7.9 Hz), 9.23 (2H, s), 9.6–9.7 (1H, br).

IR(KBr tab.): 3380, 3250, 1645, 1613, 1538, 1511, 1225 cm$^{-1}$

Melting Point: 268°–270° C. (decomposition)

EXAMPLE 37

1-{3-[Bis(4-hydroxyphenyl)methyl]-1-(2-dimethylaminoethyl)indol-2-ylcarbonyl}-4-phenylpiperazine (Compound 37)

$^1$H-NMR(DMSO-d$_6$) δ(ppm): 2.18 (6H, s), 2.5–2.65 (3H, m), 2.75–2.9 (1H, m), 3.05–3.35 (4H, m), 3.65–3.8 (2H, m), 4.0–4.15 (1H, m), 4.2–4.35 (1H, m), 5.47 (1H, s), 6.5–6.7 (4H, m), 6.7–6.95 (6H, m), 6.95–7.25 (6H, m), 7.43 (1H, d, J=8.4 Hz), 9.07 (1H, s), 9.15 (1H, s).

EXAMPLE 38

1-Benzyl-4-{3-[bis(4-hydroxyphenyl)methyl]-1-(2-dimethylaminoethyl)indol-2-ylcarbonyl}piperazine (Compound 38)

$^1$H-NMR(DMSO-d$_6$) δ(ppm): 1.75–1.9 (1H, m), 2.0–2.2 (2H, m), 2.17 (6H, s), 2.25–2.45 (2H, m), 2.9–3.05 (1H, m), 3.05–3.2 (1H, m), 3.3–3.5 (3H, m), 3.5–3.7 (2H, m), 3.95–4.1 (1H, m), 4.2–4.35 (1H, m), 5.42 (1H, s), 6.55–6.7 (4H, m), 6.8–6.9 (3H, m), 6.9–7.05 (3H, m), 7.05–7.15 (1H, m), 7.15–7.35 (5H, m), 7.42 (1H, d, J=7.9 Hz), 9.10 (1H, s), 9.17 (1H, s).

EXAMPLE 39

1-{3-[Bis(4-hydroxyphenyl)methyl]-1-[2-(1-pyrrolidinyl)ethyl]indol-2-ylcarbonyl}-4-(2-chlorophenyl)piperazine methanesulfonate (Compound 39 methanesulfonate)

$^1$H-NMR(DMSO-d$_6$) δ(ppm): 1.8–1.9 (2H, m), 1.9–2.05 (2H, m), 2.2–2.35 (1H, m), 2.35 (3H, s), 2.55–2.65 (1H, m), 2.75–3.15 (4H, m), 3.25–3.35 (2H, m), 3.45–3.55 (2H, m), 3.55–3.75 (3H, m), 3.8–3.95 (1H, m), 4.2–4.35 (1H, m), 4.5–4.65 (1H, m), 5.49 (1H, s), 6.55–6.75 (4H, m), 6.85–7.1 (8H, m), 7.2–7.35 (2H, m), 7.39 (1H, d, J=8.0 Hz), 7.60 (1H, d, J=7.4 Hz), 9.18 (1H, s), 9.26 (1H, s), 9.7–9.8 (1H, br).

EXAMPLE 40

1-{3-[Bis(4-hydroxyphenyl)methyl]-1-(2-piperidinoethyl)indol-2-ylcarbonyl}-4-(2-chlorophenyl) piperazine methanesulfonate (Compound 40 methanesulfonate)

$^1$H-NMR(DMSO-d$_6$) δ(ppm): 1.3–1.5 (1H, m), 1.55–1.9 (6H, m), 2.2–2.3 (1H, m), 2.40 (3H, s), 2.55–2.7 (1H, m), 2.7–3.2 (6H, m), 3.35–3.6 (3H, m), 3.6–3.75; (1H, m), 3.8–3.95 (1H, m), 4.3–4.45 (1H, m), 4.55–4.7 (1H, m), 5.49 (1H, s), 6.55–6.7 (4H, m), 6.8–7.1 (8H, m), 7.15–7.35 (2H, m), 7.37 (1H, d, J=7.9 Hz), 7.60 (1H, d, J=7.6 Hz), 9.23 (1H, s), 9.31 (1H, s), 9.2–9.4 (1H, br).

EXAMPLE 41

1-{3-[Bis(4-hydroxyphenyl)methyl]-1-(3-dimethylaminopropyl)indol-2-ylcarbonyl}-4-(2-chlorophenyl)piperazine methanesulfonate (Compound 41 methanesulfonate)

$^1$H-NMR(DMSO-d$_6$) δ(ppm): 2.0–2.25 (3H, m), 2.33 (3H, s), 2.5–2.65 (1H, m), 2.76 (6H, s), 2.9–3.0 (1H, m), 3.05–3.15 (2H, m), 3.15–3.3 (1H, m), 3.55–3.7 (1H, m), 3.7–3.9 (1H, m), 3.9–4.05 (2H, m), 4.25–4.45 (2H, m), 5.49 (1H, s), 6.6–6.75 (4H, m), 6.85–7.0 (4H, m), 7.0–7.1 (4H, m), 7.15–7.25 (1H, m), 7.25–7.35 (1H, m), 7.39 (1H, dd, J=7.9, 1.3 Hz), 7.55 (1H, d, J=7.9 Hz), 9.18 (1H, s), 9.25 (1H, s), 9.25–9.35 (1H, br).

EXAMPLE 42

1-{3-[Bis(4-hydroxyphenyl)methyl]-1-(4-dimethylaminobutyl)indol-2-ylcarbonyl}-4-(2-chlorophenyl)piperazine methanesulfonate (Compound 42 methanesulfonate)

$^1$H-NMR(DMSO-d$_6$) δ(ppm): 1.6–1.9 (4H, m), 2.15–2.3 (1H, m), 2.40 (3H, s), 2.80 (6H, s), 2.5–3.3 (7H, m), 3.55–3.75 (1H, m), 3.9–4.1 (2H, m), 4.3–4.5 (1H, m), 5.58 (1H, s), 6.65–6.85 (4H, m), 6.9–7.05 (4H, m), 7.05–7.2 (4H, m), 7.2–7.3 (1H, m), 7.3–7.4 (1H, m), 7.4–7.55 (1H, m), 7.55–7.7 (1H, m), 9.25 (1H, s), 9.32 (1H, s), 9.2–9.4 (1H, br).

EXAMPLE 43

1-{3-[Bis(4-hydroxyphenyl)methyl]-1(3-morpholinopropyl)indol-2-ylcarbonyl}-4-(2-chlorophenyl)piperazine methanesulfonate
(Compound 43 methanesulfonate)

$^1$H-NMR(DMSO-d$_6$) δ(ppm): 2.05–2.3 (3H, m), 2.34 (3H, s), 2.55–2.65 (1H, m), 2.7–2.8 (1H, m), 2.9–3.2 (5H, m), 3.2–3.5 (4H, m), 3.55–3.7 (3H, m), 3.85–4.05 (4H, m), 4.25–4.4 (1H, m), 5.49 (1H, s), 6.6–6.75 (4H, m), 6.85–7.0 (4H, m), 7.0–7.1 (4H, m), 7.15–7.25 (1H, m), 7.25–7.35 (1H, m), 7.39 (1H, dd, J=7.9, 1.8 Hz), 7.55 (1H, d, J=7.4 Hz), 9.17 (1H, s), 9.25 (1H, s), 9.5–9.65 (1H, br).

EXAMPLE 44

1-{3-[Bis(4-hydroxyphenyl)methyl]-1-(4-morpholinobutyl)indol-2-ylcarbonyl}-4-(2-chlorophenyl)piperazine methanesulfonate
(Compound 44 methanesulfonate)

$^1$H-NMR(DMSO-d$_6$) δ(ppm): 1.55–1.7 (2H, m), 1.7–1.85 (2H, m), 2.1–2.25 (1H, m), 2.33 (3H, s), 2.5–2.65 (1H, m), 2.7–2.8 (1H, m), 2.85–3.15 (5H, m), 3.15–3.25 (1H, m), 3.25–3.4 (4H, m), 3.55–3.7 (3H, m), 3.8–4.0 (3H, m), 4.25–4.4 (1H, m), 5.49 (1H, s), 6.6–6.7 (4H, m), 6.85–6.96 (4H, m), 7.0–7.1 (4H, m), 7.1–7.2 (1H, m), 7.15–7.25 (1H, m), 7.37 (1H, dd, J=7.9, 1.4 Hz), 7.53 (1H, d, J=8.2 Hz), 9.17 (1H, s), 9.24 (1H, s), 9.4–9.55 (1H, br).

EXAMPLE 45

1-{3-[Bis(4-hydroxyphenyl)methyl]-1-[3-(1-pyrrolidinyl)propyl]indol-2-ylcarbonyl}-4-(2-chlorophenyl)piperazine methanesulfonate
(Compound 45 methanesulfonate)

$^1$H-NMR(DMSO-d$_6$) δ(ppm): 1.8–2.25 (7H, m), 2.33 (3H, s), 2.5–2.65 (1H, m), 2.7–2.8 (1H, m), 2.9–3.05 (2H, m), 3.05–3.3 (5H, m), 3.4–3.7 (3H, m), 3.75–4.1 (2H, m), 4.25–4.4 (1H, m), 5.49 (1H, s), 6.6–6.75(4H, m), 6.85–7.0 (4H, m), 7.0–7.1 (4H, m), 7.15–7.25 (1H, m), 7.25–7.35 (1H, m), 7.39 (1H, dd, J=7.9, 1.2 Hz), 7.56 (1H, d, J=8.6 Hz), 9.17 (1H, s), 9.25 (1H, s), 9.4–9.55 (1H, br).

EXAMPLE 46

1-{3-[Bis(4-hydroxyphenyl)methyl]-1-[4-(1-pyrrolidinyl)butyl]indol-2-ylcarbonyl}-4-(2-chlorophenyl)piperazine methanesulfonate
(Compound 46 methanesulfonate)

$^1$H-NMR(DMSO-d$_6$) δ(ppm): 1.5–1.65 (2H, m), 1.65–2.0 (6H, m), 2.1–2.25 (1H, m), 2.32 (3H, s), 2.5–2.7 (1H, m), 2.7–2.85 (1H, m), 2.85–3.15 (5H, m), 3.15–3.3 (1H, m), 3.35–3.55 (3H, m), 3.55–3.65 (1H, m), 3.8–4.0 (2H, m), 4.25–4.4 (1H, m), 5.50 (1H, s), 6.6–6.75 (4H, m), 6.85–7.0 (4H, m), 7.0–7.1 (4H, m), 7.1–7.2 (1H, m), 7.25–7.35 (1H, m), 7.39 (1H, dd, J=7.9, 1.3 Hz), 7.52 (1H, d, J=8.2 Hz), 9.16 (1H, s), 9.24 (1H, s), 9.25–9.4 (1H, br).

EXAMPLE 47

Ethyl 3-{bis[4-(methoxymethoxy)phenyl]methyl}-1-(2-dimethylaminoethyl)indole-2-carboxylate Substantially the same procedure as in Example 2 was repeated using ethyl 3-{bis[4-(methoxymethoxy)phenyl]methyl]indole-2-carboxylate (12.9 g, 27.0 mmol) obtained in Reference Example 1 and 2-dimethylaminoethylchloride hydrochloride (3.98 g, 27.6 mmol) to give 16.4 g (quantitative) of the title compound as a crude product, which was used as a starting material for Example 48 without further purification.

$^1$H-NMR(CDCl$_3$) δ(ppm): 1.37 (3H, t, J=7.2 Hz), 2.34 (6H, s), 2.6–2.75 (2H, m), 3.45 (6H, s), 4.35 (2H, q, J=7.2 Hz), 4.5–4.65 (2H, m), 5.13 (4H, s), 6.47 (1H, s), 6.8–7.05 (6H, m), 7.09 (4H, d, J=8.5 Hz), 7.1–7.2 (1H, m), 7.39 (1H, d, J=8.6 Hz).

EXAMPLE 48

3-{Bis[4-(methoxymethoxy)phenyl]methyl}-1-(2-dimethylaminoethyl)indole-2-carboxylic acid The crude ethyl 3-{bis[4-(methoxymethoxy)phenyl]methyl}-1-(2-dimethylaminoethyl)indole-2-carboxylate (16.4 g, approximately 27.0 mmol) obtained in Example 47 was dissolved in 100 ml of ethanol, and a 2N aqueous sodium hydroxide solution (40 ml) was added thereto, followed by heating under reflux for 3 hours. The solvent was distilled off under reduced pressure, water was added to dissolve the residue, and the pH of the solution was adjusted to 5 by adding 2N hydrochloric acid, followed by extraction with chloroform. The resulting organic layer was washed with water and a saturated aqueous solution of sodium chloride, and dried over magnesium sulfate, and the solvent was distilled off under reduced pressure to give 14.4 g of a crude product. The obtained crude product was crystallized from ethyl acetate to give 8.9 g (yield: 64%) of the title compound.

$^1$H-NMR(CDCl$_3$) δ(ppm): 2.39 (6H, 3), 3.18 (2H, t, J=6.0 Hz), 3.45 (6H, s), 4.74 (2H, t, J=6.0 Hz), 5.12 (4H, s), 6.68 (1H, s), 6.88 (4H, d, J=8.9 Hz), 6.9–7.0 (1H, m), 7.15–7.25 (3H, m), 7.18 (4H, d, J=8.9 Hz).

EXAMPLE 49

N-(2-Dimethylaminoethyl)-3-{bis[4-(methoxymethoxy)phenyl]methyl}-1-(2-dimethylaminoethyl)indole-2-carboxamide
(Compound 49)

1-(3-Dimethylaminopropyl)-3-ethylcarbodiimide hydrochloride (1.48 g, 7.71 mmol) was added to a solution of 3-{bis[4-(methoxymethoxy)phenyl]methyl}-1-(2-dimethylaminoethyl)indole-2-carboxylic acid (2.0 g, 3.86 mmol) obtained in Example 48 and N,N-dimethylethylenediamine (0.64 ml, 5.78 mmol) in 30 ml of methylene chloride, followed by stirring at room temperature for 4.5 hours. Water was added to the reaction solution followed by extraction with chloroform. The resulting organic layer was washed successively with 2N hydrochloric acid, a saturated aqueous solution of sodium bicarbonate, and a saturated aqueous solution of sodium chloride, and dried over magnesium sulfate, and the solvent was distilled off under reduced pressure to give 2.48 g (quantitative) of the title compound.

$^1$H-NMR(CDCl$_3$) δ(ppm): 2.14 (6H, s), 2.23 (6H, s), 2.38 (2H, t, J=6.1 Hz), 2.75 (2H, t, J=6.9 Hz), 3.4–3.5 (2H, m), 3.46 (6H, s), 4.43 (2H, t, J=6.9 Hz), 5.14 (4H, s), 6.60 (1H, s), 6.85–6.95 (1H, m), 6.92 (4H, d, J=8.9 Hz),7.01 (1H, d, J=8.3 Hz), 7.12 (4H, d, J=8.9 Hz), 7.15–7.25 (2H, m), 7.33 (1H,d, J=8.3 Hz).

In the following Examples 50 to 68, substantially the same procedure as in Example 49 was repeated using corresponding amines in place of N,N-dimethylethylenediamine to give the desired compounds.

EXAMPLE 50

N-(2-Dimethylaminoethyl)-N-methyl-3-{bis[4-(methoxymethoxy)phenyl]methyl}-1-(2-dimethylaminoethyl)indole-2-carboxamide (Compound 50)

$^1$H-NMR(CDCl$_3$) δ(ppm): 2.27 (12H, s), 2.47 (2H, t, J=6.5 Hz), 2.56 (3H, s), 2.55–2.75 (2H, m), 3.44 (3H, s), 3.48 (3H, s), 3.45–3.55 (2H, m), 4.05–4.35 (2H, m), 5.11 (2H, s), 5.15 (2H, s), 5.65 (1H, s), 6.8–7.0 (5H, m), 7.08 (2H, d, J=8.6 Hz), 7.15–7.3 (4H, m), 7.33 (1H, d, J=8.6 Hz).

EXAMPLE 51

N-[2-(1-Pyrrolidinyl)ethyl]-3-{bis[4-(methoxymethoxy)phenyl]methyl}-1-(2-dimethylaminoethyl)indole-2-carboxamide (Compound 51)

$^1$H-NMR(CDCl$_3$) δ(ppm): 1.6–1.7 (4H, m), 2.22 (6H, s), 2.4–2.5 (4H, m), 2.60 (2H, t, J=6.3 Hz), 2.74 (2H, t, J=6.8 Hz), 3.46 (6H, s), 3.49 (2H, q, J=6.3 Hz), 4.43 (2H, t, J=6.8 Hz), 5.13 (4H, s), 6.02 (1H, s), 6.85–6.95 (1H, m), 6.91 (4H, d, J=8.7 Hz), 7.02 (1H, d, J=7.9 Hz), 7.12 (4H, d, J=8.7 Hz), 7.19 (1H, t, J=8.2 Hz), 7.3–7.4 (1H, m), 7.32 (1H, d, J=8.2 Hz).

EXAMPLE 52

N-[3-(2-Oxo-1-pyrrolidinyl)propyl]-3-{bis[4-(methoxymethoxy)phenyl]methyl}-1-(2-dimethylaminoethyl)indole-2-carboxamide (Compound 52)

$^1$H-NMR(CDCl$_3$) δ(ppm): 1.7–1.8 (2H, m), 1.95–2.05 (2H, m), 2.19 (6H, s), 2.37 (2H, t, J=8.1 Hz), 2.79 (2H, t, J=6.4 Hz), 3.2–3.4 (6H, m), 3.46 (6H, s), 4.40 (2H, t, J=6.4 Hz), 5.14 (4H, s), 6.07 (1H, s), 6.85–6.95 (1H, m), 6.91 (4H, d, J=8.5 Hz), 7.01 (1H, d, J=7.9 Hz), 7.12 (4H, d, J=8.5 Hz), 7.15–7.25 (1H, m), 7.31 (1H, d, J=8.6 Hz), 7.95–8.0 (1H, m).

EXAMPLE 53

N-(2-Piperidinoethyl)-3-{bis[4-(methoxymethoxy)phenyl]methyl}-1-(2-dimethylaminoethyl)indole-2-carboxamide (Compound 53)

$^1$H-NMR(CDCl$_3$) δ(ppm): 1.3–1.5 (6H, m), 2.21 (6H, s), 2.3–2.4 (4H, m), 2.43 (2H, t, J=6.3 Hz), 2.74 (2H, t, J=6.7 Hz), 3.46 (6H, s), 3.4–3.5 (2H, m), 4.44 (2H, t, J=6.7 Hz), 5.14 (4H, s), 6.02 (1H, s), 6.85–6.95 (1H, m), 6.91 (4H, d, J=8.7 Hz), 7.03 (1H, d, J=7.9 Hz), 7.12 (4H, d, J=8.6 Hz), 7.15–7.25 (1H, m), 7.33 (1H, d, J=8.6 Hz).

EXAMPLE 54

N-(2-Morpholinoethyl)-3-{bis[4-(methoxymethoxy)phenyl]methyl}-1-(2-dimethylaminoethyl)indole-2-carboxamide (Compound 54)

$^1$H-NMR(CDCl$_3$) δ(ppm): 2.22 (6H, s), 2.3–2.35 (4H, m), 2.46 (2H, t, J=6.1 Hz), 2.75 (2H, t, J=6.6 Hz), 3.45–3.6 (6H, m), 3.46 (6H, s), 4.45 (2H, t, J=6.6 Hz), 5.13 (4H, s), 6.03 (1H, s), 6.85–6.95 (1H, m), 6.91 (4H, d, J=8.7 Hz), 7.02 (1H, d, J=7.9 Hz), 7.11 (4H, d, J=8.7 Hz), 7.15–7.25 (2H, m), 7.33 (1H, d, J=8.2 Hz).

EXAMPLE 55

N-(3-Morpholinopropyl)-3-{bis[4-(methoxymethoxy)phenyl]methyl}-1-(2-dimethylaminoethyl)indole-2-carboxamide (Compound 55)

$^1$H-NMR(CDCl$_3$) δ(ppm): 1.6–1.75 (2H, m), 2.2–2.3 (2H, m), 2.26 (6H, s), 2.3–2.4 (4H, m), 2.80 (2H, t, J=6.6 Hz), 3.4–3.5 (2H, m), 3.46 (6H, s), 3.55–3.65 (4H, m), 4.43 (2H, t, J=6.6 Hz), 5.14 (4H, s), 5.99 (1H, s), 6.85–7.0 (2H, m), 6.91 (4H, d, J=8.6 Hz), 7.11 (4H, d, J=8.6 Hz), 7.15–7.25 (1H, m), 7.3–7.4 (2H, m).

EXAMPLE 56

N-(2-Pyridylmethyl)-3-{bis[4-(methoxymethoxy)phenyl]methyl}-1-(2-dimethylaminoethyl)indole-2-carboxamide (Compound 56)

$^1$H-NMR(CDCl$_3$) δ(ppm): 2.18 (6H, s), 2.83 (2H, br t, J=6.1 Hz), 3.46 (6H, s), 4.48 (2H, t, J=6.6 Hz), 4.69 (2H, d, J=5.3 Hz), 5.13 (4H, s), 6.14 (1H, s), 6.85–6.95 (1H, m), 6.88 (4H, d, J=8.7 Hz), 7.0–7.1 (1H, m), 7.09 (4H, d, J=8.7 Hz), 7.15–7.3 (3H, m), 7.35–7.4 (1H, m), 7.62 (1H, td, J=7.6, 1.8 Hz), 8.35–8.5 (2H, m).

EXAMPLE 57

N-(3-Pyridylmethyl)-3-{bis[4-(methoxymethoxy)phenyl]methyl}-1-(2-dimethylaminoethyl)indole-2-carboxamide (Compound 57)

$^1$H-NMR(CDCl$_3$) δ(ppm): 2.03 (6H, s), 2.78 (2H, t, J=5.9 Hz), 3.46 (6H, s), 4.40 (2H, t, J=5.9 Hz), 4.56 (2H, d, J=5.6 Hz), 5.13 (4H, s), 6.11 (1H, s), 6.85–7.05 (2H, m), 6.89 (4H, d, J=8.5 Hz), 7.06 (4H, d, J=8.5 Hz), 7.15–7.35 (3H, m), 7.5–7.6 (1H, m), 8.52 (2H, br s), 8.5–8.65 (1H, br).

EXAMPLE 58

N-(4-Pyridylmethyl)-3-(bis[4-(methoxymethoxy)phenyl]methyl}-1-(2-dimethylaminoethyl)indole-2-carboxamide (Compound 58)

$^1$H-NMR(CDCl$_3$) δ(ppm): 2.03 (6H, s), 2.80 (2H, t, J=5.9 Hz), 3.46 (6H, s), 4.40 (2H, t, J=5.9 Hz), 4.55 (2H, d, J=5.6 Hz), 5.13 (4H, s), 6.20 (1H, s), 6.85–6.95 (1H, m), 6.90 (4H, d, J=8.6 Hz), 7.00 (1H, d, J=7.9 Hz), 7.05–7.15 (2H, m), 7.09 (4H, d, J=8.6 Hz), 7.15–7.25 (2H, m), 8.51 (2H, d, J=5.9 Hz), 8.85–8.95 (1H, m).

EXAMPLE 59

N-[2-(2-Pyridyl)ethyl]-3-{bis[4-(methoxymethoxy)phenyl]methyl}-1-(2-dimethylaminoethyl)indole-2-carboxamide (Compound 59)

$^1$H-NMR(CDCl$_3$) δ(ppm): 2.1–2.2 (6H, br), 2.75–2.85 (2H, m), 3.03 (2H, t, J=6.3 Hz), 3.46 (6H, s), 3.80 (2H, q, J=6.2 Hz), 4.35–4.45 (2H, m), 5.14 (4H, s), 6.02 (1H, s), 6.85–7.1 (4H, m), 6.90 (4H, d, J=8.5 Hz), 7.05 (4H, d, J=8.5 Hz), 7.15–7.25 (1H, m), 7.3–7.4 (1H, m), 7.46 (1H, dd, J=7.6, 2.0 Hz), 7.9–8.05 (1H, br), 8.36 (1H, d, J=4.0 Hz).

EXAMPLE 60

N-[2-(4-Pyridyl)ethyl]-3-{bis[4-(methoxymethoxy)phenyl]methyl}-1-(2-dimethylaminoethyl)indole-2-carboxamide (Compound 60)

$^1$H-NMR(CDCl$_3$) δ(ppm): 1.90 (6H, s), 2.70 (2H, t, J=5.9 Hz), 2.83 (2H, t, J=6.6 Hz), 3.45 (6H, s), 3.63 (2H, t, J=6.6

Hz), 4.30 (2H, t, J=5.9 Hz), 5.14 (4H, s), 6.20 (1H, s), 6.85–6.95 (3H, m), 6.93 (4H, d, J=8.6 Hz), 7.00 (1H, d, J=8.3 Hz), 7.10 (4H, d, J=8.6 Hz), 7.15–7.3 (2H, m), 8.38 (2H, d, J=5.9 Hz), 8.45–8.5 (1H, m).

EXAMPLE 61

N-[(1-Ethyl-2-pyrrolidinyl)methyl]-3-{bis[4-(methoxymethoxy)phenyl]methyl}-1-(2-dimethylaminoethyl)indole-2-carboxamide (Compound 61)

$^1$H-NMR(CDCl$_3$) δ(ppm): 0.97 (3H, t, J=7.1 Hz), 1.4–1.8 (4H, m), 2.05–2.25 (2H, m), 2.19 (6H, s), 2.5–2.6 (1H, m), 2.7–2.8 (3H, m), 2.95–3.05 (1H, m), 3.15–3.25 (1H, m), 3.46 (6H, s), 3.7–3.8 (1H, m), 4.43 (2H, t, J=6.9 Hz), 5.13 (4H, s), 6.01 (1H, s), 6.85–6.95 (1H, m), 6.91 (4H, d, J=8.6 Hz), 7.01 (1H,d, J=7.9 Hz), 7.05–7.15 (4H, m), 7.15–7.25 (1H, m), 7.33 (1H, d, J=8.3 Hz).

EXAMPLE 62

N-[2-(1-Methyl-2-pyrrolidinyl)ethyl]-3-{bis[4-(methoxymethoxy)phenyl]methyl}-1-(2-dimethylaminoethyl)indole-2-carboxamide (Compound 62)

$^1$H-NMR(CDCl$_3$) δ(ppm): 1.4–1.55 (2H, m), 1.55–1.75 (2H, m), 1.75–1.95 (2H, m), 1.95–2.15 (2H, m), 2.22 (9H, s), 2.76 (2H, t, J=6.5 Hz), 2.9–3.0 (1H, m), 3.3–3.55 (2H, m), 3.46 (6H, s), 4.41 (2H, t, J=6.5 Hz), 5.14 (4H, s), 6.03 (1H, s), 6.85–6.95 (1H, m), 6.92 (4H, d, J=8.4 Hz), 7.00 (1H, d, J=7.9 Hz), 7.11 (4H, d, J=8.4 Hz), 7.15–7.25 (1H, m), 7.32 (1H, d, J=8.6 Hz), 7.55–7.65 (1H, m).

EXAMPLE 63

N-[3-(2-Methylpiperidino)propyl]-3-{bis[4-(methoxymethoxy)phenyl]methyl}-1-(2-dimethylaminoethyl)indole-2-carboxamide (Compound 63)

$^1$H-NMR(CDCl$_3$) δ(ppm): 0.99 (3H, d, J=6.2 Hz), 1.2–1.3 (2H, m), 1.3–1.8 (6H, m), 2.0–2.15 (1H, m), 2.22 (6H, s), 2.2–2.4 (2H, m), 2.65–2.8 (2H, m), 2.77 (2H, t, J=6.6 Hz), 3.3–3.45 (2H, m), 3.46 (6H, s), 4.40 (2H, t, J=6.6 Hz), 5.14 (4H, s), 6.03 (1H, s), 6.85–6.95 (1H, m), 6.91 (4H, d, J=8.2 Hz), 7.02 (1H, d, J=8.3 Hz), 7.2–7.25 (4H, m), 7.25–7.35 (1H, m), 7.31 (1H, d, J=8.3 Hz).

EXAMPLE 64

N-[3-(1-Imidazolyl)propyl]-3-{bis[4-(methoxymethoxy)phenyl]methyl}-1-(2-dimethylaminoethyl)indole-2-carboxamide (Compound 64)

$^1$H-NMR(CDCl$_3$) δ(ppm): 1.9–2.0 (2H, m), 2.24 (6H, s), 2.87 (2H, t, J=6.4 Hz), 3.34 (2H, q, J=6.9 Hz), 3.45 (6H, s), 3.85 (2H, t, J=6.9 Hz), 4.42 (2H, t, J=6.4 Hz), 5.13 (4H, s), 6.07 (1H, s), 6.85–6.95 (3H, m), 6.92 (4H, d, J=8.6 Hz), 7.05–7.15 (1H, m), 7.10 (4H, d, J=8.6 Hz), 7.2–7.25 (1H, m), 7.35–7.45 (2H, m), 7.65–7.8 (1H, br).

EXAMPLE 65

N-(2-Tetrahydrofuranylmethyl)-3-{bis[4-(methoxymethoxy)phenyl]methyl}-1-(2-dimethylaminoethyl)indole-2-carboxamide (Compound 65)

$^1$H-NMR(CDCl$_3$) δ(ppm): 1.4–2.0 (4H, m), 2.20 (6H, s), 2.7–2.85 (2H, m), 3.3–3.45 (1H, m), 3.46 (6H, s), 3.55–3.75 (3H, m), 3.9–4.0 (1H, m), 4.35–4.5 (2H, m), 5.14 (4H, s), 6.09 (1H, s), 6.85–6.95 (5H, m), 7.01 (1H, d, J=7.9 Hz), 7.1–7.25 (5H, m), 7.32 (1H, d, J=8.6 Hz), 7.95–8.05 (1H, m).

EXAMPLE 66

N-(2-Thienylmethyl)-3-{bis[4-(methoxymethoxy)phenyl]methyl}-1-(2-dimethylaminoethyl)indole-2-carboxamide (Compound 66)

$^1$H-NMR(CDCl$_3$) δ(ppm): 2.04 (6H, s), 2.75 (2H, t, J=6.2 Hz), 3.46 (6H, s), 4.41 (2H, t, J=6.2 Hz), 4.74 (2H, d, J=5.3 Hz), 5.13 (4H, s), 6.10 (1H, s), 6.85–7.0 (3H, m), 6.88 (4H, d, J=8.6 Hz), 7.0–7.1 (1H, m), 7.07 (4H, d, J=8.6 Hz), 7.15–7.3 (3H, m), 8.5–8.6 (1H, m).

EXAMPLE 67

N-(2-Furylmethyl)-3-{bis[4-(methoxymethoxy)phenyl]methyl}-1-(2-dimethylaminoethyl)indole-2-carboxamide (Compound 67)

$^1$H-NMR(CDCl$_3$) δ(ppm): 2.08 (6H, s), 2.76 (2H, t, J=6.3 Hz), 3.46 (6H, s), 4.40 (2H, t, J=6.3 Hz), 4.56 (2H, d, J=4.7 Hz), 5.13 (4H, s), 6.07 (1H, s), 6.23 (1H, d, J=2.0 Hz), 6.3–6.35 (1H, m), 6.85–6.95 (1H, m), 6.89 (4H, d, J=8.7 Hz), 7.0–7.1 (1H, m), 7.08 (4H, d, J=8.7 Hz), 7.15–7.35 (2H, m), 7.37 (1H, br s), 8.4–8.45 (1H, m).

EXAMPLE 68

N-[2-(1-Methyl-2-pyrrolyl)ethyl]-3-{bis[4-(methoxymethoxy)phenyl]methyl}-1-(2-dimethylaminoethyl)indole-2-carboxamide (Compound 68)

$^1$H-NMR(CDCl$_3$) δ(ppm): 2.09 (6H, s), 2.73 (2H, t, J=6.3 Hz), 2.80 (2H, t, J=6.7 Hz), 3.46 (6H, s), 3.47 (3H, s), 3.60 (2H, q, J=6.7 Hz), 4.37 (2H, t, J=6.3 Hz), 5.14 (4H, s), 5.75–5.8 (1H, m), 5.95–6.0 (1H, m), 6.07 (1H, s), 6.45–6.5 (1H, m), 6.85–7.05 (2H, m), 6.91 (4H, d, J=8.6 Hz), 7.08 (4H, d, J=8.6 Hz), 7.15–7.25 (1H, m), 7.29 (1H, d, J=8.3 Hz), 7.85–7.95 (1H, m).

EXAMPLE 69

N-(2-Dimethylaminoethyl)-3-[bis(4-hydroxyphenyl)methyl]-1-(2-dimethylaminoethyl)indole-2-carboxamide (Compound 69)

Compound 49 (2.48 g, 4.21 mmol) obtained in Example 49 was dissolved in ethanol (50 ml), and 15 ml of 2N hydrochloric acid was added thereto, followed by heating under reflux for 2 hours. After cooling the reaction solution, a saturated aqueous solution of sodium bicarbonate was added thereto for neutralization. A little amount of ethyl acetate was added to the mixture followed by stirring at room temperature. The resulting crystals were collected by filtration, washed with water, and dried under reduced pressure to give 1.6 g (yield: 81%) of the title compound.

$^1$H-NMR(DMSO-d$_6$) δ(ppm): 2.11 (6H, s), 2.15 (6H, s), 2.36 (2H, t, J=6.4 Hz), 2.5–2.6 (2H, m), 3.3–3.4 (2H, m), 4.32 (2H, t, J=6.4 Hz), 5.78 (1H, s), 6.62 (4H, d, J=8.6 Hz), 6.83 (1H, t, J=7.5 Hz), 6.9–7.0 (1H, m), 6.93 (4H, d, J=8.6 Hz), 7.12 (1H, t, J=7.5 Hz), 7.4–7.45 (1H, m), 8.15–8.25 (1H, m), 9.05–9.15 (2H, br).

In the following Examples 70 to 87, substantially the same procedure as in Example 69 was repeated using corresponding Compounds 50 to 67 in place of Compound 49 to give the desired compounds.

EXAMPLE 70

N-(2-Dimethylaminoethyl)-N-methyl-3-[bis(4-hydroxyphenyl)methyl]-1-(2-dimethylaminoethyl)indole-2-carboxamide (Compound 70)

$^1$H-NMR(DMSO-d$_6$) δ(ppm): 2.17 (6H, s), 2.22 (6H, s), 2.4–2.55 (4H, m), 2.63 (3H, s), 3.35–3.65 (2H, m), 4.0–4.3 (2H, m), 5.47 (1H, s), 6.58 (2H, d, J=8.6 Hz), 6.65 (2H, d, J=8.6 Hz), 6.8–6.9 (3H, m), 7.0–7.15 (4H, m), 7.39 (1H, d, J=8.3 Hz), 9.03 (1H, s), 9.10 (1H, s).

EXAMPLE 71

N-[2-(1-Pyrrolidinyl)ethyl]-3-[bis(4-hydroxyphenyl)methyl]-1-(2-dimethylaminoethyl)indole-2-carboxamide (Compound 71)

$^1$H-NMR(DMSO-d$_6$) δ(ppm): 1.55–1.7 (4H, m), 2.12 (6H, s), 2.35–2.5 (4H, m), 2.5–2.65 (4H, m), 3.3–3.45 (2H, m), 4.25–4.35 (2H, m), 5.82 (1H, s), 6.62 (4H, d, J=8.4 Hz), 6.83 (1H, t, J=7.6 Hz), 6.94 (4H, d, J=8.4 Hz), 7.01 (1H, d, J=8.1 Hz), 7.12 (1H, t, J=7.6 Hz), 7.39 (1H, d, J=8.6 Hz), 8.0–8.1 (1H, br), 9.05 (2H, s).

EXAMPLE 72

N-[3-(2-Oxo-1-pyrrolidinyl)propyl]-3-[bis(4-hydroxyphenyl)methyl]-1-(2-dimethylaminoethyl)indole-2-carboxamide (Compound 72)

$^1$H-NMR(DMSO-d$_6$) δ(ppm): 1.6–1.75 (2H, m), 1.85–2.0 (2H, m), 2.12 (6H, s), 2.23 (2H, t, J=7.9 Hz), 2.5–2.6 (2H, m), 3.15–3.25 (4H, m), 3.25–3.35 (2H, m), 4.29 (2H, t, J=6.3 Hz), 5.77 (1H, s), 6.62 (4H, d, J=8.4 Hz), 6.8–6.85 (1H, m), 6.93 (4H, d, J=8.4 Hz), 6.9–7.0 (1H, m), 7.1–7.15 (1H, m), 7.42 (1H, d, J=8.3 Hz), 8.4–8.5 (1H, m), 9.13 (2H, s).

EXAMPLE 73

N-(2-Piperidinoethyl)-3-[bis(4-hydroxyphenyl)methyl]-1-(2-dimethylaminoethyl)indole-2-carboxamide (Compound 73)

$^1$H-NMR(DMSO-d$_6$) δ(ppm): 1.3–1.5 (6H, m), 2.11 (6H, s), 2.25–2.35 (4H, m), 2.40 (2H, t, J=6.3 Hz), 2.57 (2H, t, J=6.4 Hz), 3.3–3.4 (2H, m), 4.34 (2H, t, J=6.4 Hz), 5.81 (1H, s), 6.62 (4H, d, J=8.2 Hz), 6.8–6.9 (1H, m), 6.93 (4H, d, J=8.2 Hz), 6.99 (1H, d, J=7.9 Hz), 7.1–7.2 (1H, m), 7.42 (1H, d, J=8.3 Hz), 8.1–8.2 (1H, m), 9.10 (2H, s).

EXAMPLE 74

N-(2-Morpholinoethyl)-3-[bis(4-hydroxyphenyl)methyl]-1-(2-dimethylaminoethyl)indole-2-carboxamide (Compound 74)

$^1$H-NMR(DMSO-d$_6$) δ(ppm): 2.11 (6H, s), 2.3–2.4 (4H, m), 2.44 (2H, t, J=6.3 Hz), 2.57 (2H, t, J=6.4 Hz), 3.39 (2H, t, J=6.3 Hz), 3.45–3.5 (4H, m), 4.34 (2H, t, J=6.4 Hz), 5.81 (1H, s), 6.63 (4H, d, J=8.4 Hz), 6.83 (1H, t, J=7.6 Hz), 6.94 (4H, d, J=8.4 Hz), 6.99 (1H, d, J=7.6 Hz), 7.12 (1H, t, J=7.6 Hz), 7.42 (1H, d, J=7.6 Hz), 8.26 (3H, s).

EXAMPLE 75

N-(3-Morpholinopropyl)-3-[bis(4-hydroxyphenyl)methyl]-1-(2-dimethylaminoethyl)indole-2-carboxamide (Compound 75)

$^1$H-NMR(DMSO-d$_6$) δ(ppm): 1.55–1.7 (2H, m), 2.13 (6H, s), 2.25–2.35 (2H, m), 2.5–2.6 (2H, m), 3.2–3.35 (2H, m), 3.5–3.6 (4H, m), 4.28 (2H, t, J=6.7 Hz), 5.80 (1H, s), 6.62 (4H, d, J=8.4 Hz), 6.8–6.9 (1H, m), 6.9–7.0 (1H, m), 6.93 (4H, d, J=8.4 Hz), 7.05–7.15 (1H, m), 7.42 (1H, d, J=8.4 Hz), 8.37 (1H, t, J=5.4 Hz), 9.12 (2H, s).

EXAMPLE 76

N-(2-Pyridylmethyl)-3-[(bis(4-hydroxyphenyl)methyl]-1-(2-dimethylaminoethyl)indole-2-carboxamide (Compound 76)

$^1$H-NMR(DMSO-d$_6$) δ(ppm): 2.07 (6H, s), 2.62 (2H, t, J=6.3 Hz), 4.38 (2H, t, J=6.3 Hz), 4.59 (2H, d, J=5.6 Hz), 5.93 (1H, s), 6.62 (4H, d, J=8.5 Hz), 6.84 (1H, t, J=7.4 Hz), 6.9–7.0 (1H, m), 6.92 (4H, d, J=8.5 Hz), 7.13 (1H, t, J=7.6 Hz), 7.2–7.3 (2H, m), 7.39 (1H, d, J=8.6 Hz), 7.69 (1H, td, J=7.6, 1.6 Hz), 8.49 (1H, d, J=5.0 Hz), 9.03 (2H, s), 9.15 (1H, t, J=5.6 Hz).

EXAMPLE 77

N-(3-Pyridylmethyl)-3-[bis(4-hydroxyphenyl)methyl]-1-(2-dimethylaminoethyl)indole-2-carboxamide (Compound 77)

$^1$H-NMR(DMSO-d$_6$) δ(ppm): 2.03 (6H, s), 2.45–2.55 (2H, m), 4.2–4.3 (2H, m), 4.47 (2H, d, J=5.6 Hz), 5.77 (1H, s), 6.61 (4H, d, J=8.2 Hz), 6.8–6.95 (2H, m), 6.87 (4H, d, J=8.2 Hz), 7.05–7.15 (1H, m), 7.25–7.35 (1H, m), 7.42 (1H, d, J=8.3 Hz), 7.67 (1H, d, J=8.4 Hz), 8.47 (1H, d, J=4.6 Hz), 8.57 (1H, s), 9.1–9.2 (1H, m), 9.13 (2H, s).

EXAMPLE 78

N-(4-Pyridylmethyl)-3-[bis(4-hydroxyphenyl)methyl]-1-(2-dimethylaminoethyl)indole-2-carboxamide (Compound 78)

$^1$H-NMR(DMSO-d$_6$) δ(ppm): 2.06 (6H, s), 2.5–2.6 (2H, m), 4.31 (2H, t, J=6.4 Hz), 4.48 (2H, d, J=5.6 Hz), 5.87 (1H, s), 6.63 (4H, d, J=8.6 Hz), 6.8–6.95 (2H, m), 6.90 (4H, d, J=8.6 Hz), 7.1–7.25 (3H, m), 7.35–7.45 (1H, m), 8.45–8.5 (2H, m), 9.0–9.15 (2H, br), 9.25–9.35 (1H, m).

EXAMPLE 79

N-[2-(2-Pyridyl)ethyl]-3-[bis(4-hydroxyphenyl)methyl]-1-(2-dimethylaminoethyl)indole-2-carboxamide (Compound 79)

$^1$H-NMR(DMSO-d$_6$) δ(ppm): 2.02 (6H, s), 2.45–2.55 (2H, m), 2.98 (2H, t, J=6.9 Hz), 3.65 (2H, q, J=6.4 Hz), 4.25 (2H, t, J=6.4 Hz), 5.77 (1H, s), 6.62 (4H, d, J=8.4 Hz), 6.75–7.0 (2H, m), 6.89 (4H, d, J=8.4 Hz), 7.05–7.2 (3H, m), 7.39 (1H, d, J=8.4 Hz), 7.59 (1H, td, J=7.6, 2.0 Hz), 8.43 (1H, d, J=4.9 Hz), 8.59 (1H, t, J=5.4 Hz), 9.09 (2H, s).

EXAMPLE 80

N-[2-(4-Pyridyl)ethyl]-3-[bis(4-hydroxyphenyl)methyl]-1-(2-dimethylaminoethyl)indole-2-carboxamide (Compound 80)

$^1$H-NMR(DMSO-d$_6$) δ(ppm): 1.96 (6H, s), 2.45–2.55 (2H, m), 2.83 (2H, t, J=6.6 Hz), 3.55 (2H, q, J=6.6 Hz), 4.23 (2H, t, J=6.2 Hz), 5.80 (1H, s), 6.63 (4H, d, J=8.3 Hz), 6.8–7.0 (2H, m), 6.89 (4H, d, J=8.3 Hz), 7.05–7.15 (3H, m), 7.39 (1H, d, J=8.3 Hz), 8.36 (2H, d, J=5.9 Hz), 8.7–8.8 (1H, m), 9.11 (2H, s).

EXAMPLE 81

N-[(1-Ethyl-2-pyrrolidinyl)methyl]-3-[bis(4-hydroxyphenyl)methyl]-1-(2-dimethylaminoethyl)indole-2-carboxamide (Compound 81)

$^1$H-NMR(DMSO-d$_6$) δ(ppm): 0.98 (3H, t, J=7.1 Hz), 1.45–1.85 (4H, m), 2.0–2.2 (2H, m), 2.12 (6H, s), 2.5–2.6

(3H, m), 2.75–2.85 (1H, m), 2.95–3.05 (1H, m), 3.05–3.2 (1H, m), 3.4–3.5 (1H, m), 4.31 (2H, t, J=6.3 Hz), 5.78 (1H, s),6.62 (4H, d, J=8.3 Hz), 6.83 (1H, t, J=7.2 Hz), 6.9–7.0 (1H, m), 6.93 (4H, d, J=8.3 Hz), 7.12 (1H, t, J=7.3 Hz), 7.42 (1H, d, J=7.3 Hz), 8.0–8.1 (1H, m), 9.13 (2H, s).

EXAMPLE 82

N-[2-(1-Methyl-2-pyrrolidinyl)ethyl]-3-[bis(4-hydroxyphenyl)methyl]-1-(2-dimethylaminoethyl) indole-2-carboxamide (Compound 82)

$^1$H-NMR(DMSO-d$_6$) δ(ppm): 1.35–1.5 (2H, m), 1.5–1.7 (2H, m), 1.75–1.9 (2H, m), 1.95–2.05 (2H, m), 2.14 (6H, s), 2.17 (3H, s), 2.58 (2H, t, J=6.6 Hz), 2.85–2.95 (1H, m), 3.25–3.35 (2H, m), 4.30 (2H, t, J=6.6 Hz), 5.77 (1H, s), 6.62 (4H, d, J=8.4 Hz), 6.75–6.85 (1H, m), 6.9–7.0 (1H, m), 6.93 (4H, d, J=8.4 Hz), 7.11 (1H, t, J=7.3 Hz), 7.40 (1H, d, J=8.2 Hz), 8.3–8.4 (1H, m), 9.09 (2H, s).

EXAMPLE 83

N-[3-(2-Methylpiperidino)propyl]-3-[bis(4-hydroxyphenyl)methyl]-1-(2-dimethylaminoethyl) indole-2-carboxamide (Compound 83)

$^1$H-NMR(DMSO-d$_6$) δ(ppm): 0.94 (3H, d, J=6.3 Hz), 1.05–1.3 (2H, m), 1.3–1.7 (6H, m), 1.95–2.1 (1H, m), 2.13 (6H, s), 2.1–2.3 (2H, m), 2.5–2.6 (2H, m), 2.6–2.75 (2H, m), 3.2–3.3 (2H, m), 4.28 (2H, t, J=6.6 Hz), 5.74 (1H, s), 6.62 (4H, d, J=8.6 Hz), 6.8–6.9 (1H, m), 6.9–7.0 (1H, m), 6.92 (4H, d, J=8.6 Hz), 7.05–7.15 (1H, m), 7.43 (1H, d, J=8.3 Hz), 8.3–8.4 (1H, br), 9.14 (2H, brs).

EXAMPLE 84

N-[3-(1-Imidazolyl)propyl]-3-[bis(4-hydroxyphenyl) methyl]-1-(2-dimethylaminoethyl)indole-2-carboxamide (Compound 84)

$^1$H-NMR(CDCl$_3$-CD$_3$OD) δ(ppm): 1.9–2.0 (2H, m), 2.13 (6H, s), 2.58 (2H, t, J=6.7 Hz), 3.21 (2H, t, J=6.9 Hz), 3.98 (2H, t, J=6.9 Hz), 4.29 (2H, t, J=6.7 Hz), 5.78 (1H, s), 6.64 (4H, d, J=8.4 Hz), 6.8–6.9 (1H, m), 6.9–7.0 (2H, m), 6.95 (4H, d, J=8.4 Hz), 7.1–7.2 (1H, m), 7.16 (1H, s), 7.43 (1H, d, J=8.4 Hz), 7.64 (1H, s).

EXAMPLE 85

N-(2-Tetrahydrofuranylmethyl)-3-[bis(4-hydroxyphenyl)methyl]-1-(2-dimethylaminoethyl) indole-2-carboxamide (Compound 85)

$^1$H-NMR(DMSO-d$_6$) δ(ppm): 1.5–1.6 (1H, m), 1.75–2.0 (3H, m), 2.12 (6H, s), 2.6–2.7 (2H, m), 3.3–3.4 (2H, m), 3.6–3.8 (2H, m), 3.9–4.0 (1H, m), 4.33 (2H, t, J=6.3 Hz), 5.86 (1H, s), 6.62 (4H, d, J=8.3 Hz), 6.83 (1H, t, J=7.9 Hz),6.9–7.0 (5H, m), 7.13 (1H, t, J=7.9 Hz), 7.37 (1H, d, J=7.9 Hz), 8.66 (1H,t, J=5.6 Hz), 9.02 (2H, s).

EXAMPLE 86

N-(2-Thienylmethyl)-3-[bis(4-hydroxyphenyl) methyl]-1-(2-dimethylaminoethyl)indole-2-carboxamide (Compound 86)

$^1$H-NMR(DMSO-d$_6$) δ(ppm): 2.05 (6H, s), 2.45–2.55 (2H, m), 4.27 (2H, t, J=6.6 Hz), 4.62 (2H, d, J=5.6 Hz), 5.78 (1H, s), 6.61 (4H, d, J=8.2 Hz), 6.8–6.9 (1H, m), 6.89 (4H, d, J=8.2 Hz), 6.95–7.05 (3H, m), 7.12 (1H, t, J=7.6 Hz), 7.35–7.45 (2H, m), 9.14 (2H, s), 9.29 (1H, t, J=5.6 Hz).

EXAMPLE 87

N-(2-Furylmethyl)-3-[bis(4-hydroxyphenyl)methyl]-1-(2-dimethylaminoethyl)indole-2-carboxamide (Compound 87)

$^1$H-NMR(DMSO-d$_6$) δ(ppm): 2.05 (6H, s), 2.45–2.55 (2H, m), 4.28 (2H, t, J=6.3 Hz), 4.46 (2H, d, J=5.6 Hz), 5.77 (1H, s), 6.28 (1H, d, J=3.0 Hz), 6.41 (1H, br s), 6.61 (4H, d, J=8.6 Hz), 6.8–7.0 (2H, m), 6.89 (4H, d, J=8.6 Hz), 7.1–7.15 (1H, m), 7.43 (1H, d, J=8.3 Hz), 7.59 (1H, br s), 9.1–9.2 (1H, m), 9.14 (2H, s).

EXAMPLE 88

2-[4-(2-Chlorophenyl)piperazinylcarbonyl]-3-(diphenylmethyl)indole (Compound 88)

Benzhydryl acetate (2.2 g, 9.71 mmol) and 2-[4-(2-chlorophenyl)piperazinylcarbonyl]indole (3.0 g, 8.83 mmol) were dissolved in a mixed solvent of methylene chloride (50 ml) and chloroform (50 ml), and methanesulfonic acid (1.72 ml, 26.5 mmol) was added thereto, followed by stirring at room temperature for 3 hours. A saturated aqueous solution of sodium bicarbonate was added to the reaction solution for neutralization followed by extraction with chloroform. The resulting organic layer was washed with a saturated aqueous solution of sodium bicarbonate and a saturated aqueous solution of sodium chloride, and dried over magnesium sulfate, and the solvent was distilled off under reduced pressure to give 6.5 g of a crude product. The obtained crude product was washed with ethanol (60 ml) under heating to give 4.0 g (yield: 89%) of the title compound.

$^1$H-NMR(CDCl$_3$) δ(ppm): 2.65–2.8 (4H, m), 3.5–3.65 (4H, m), 5.90 (1H, s), 6.8–6.9 (1H, m), 6.9–7.05 (2H, m), 7.1–7.4 (15H, m), 8.50 (1H, s).

EXAMPLE 89

2-[4-(2-Chlorophenyl)piperazinylcarbonyl]-1-(2-dimethylaminoethyl)-3-(diphenylmethyl)indole (Compound 89)

To a solution of Compound 88 (1.0 g, 1.98 mmol) obtained in Example 88 in 10 ml of N,N-dimethylformamide was portionwise added sodium hydride (60% in oil, 166 mg, 4.15 mmol) with stirring at room temperature, and 2-dimethylaminoethylchloride hydrochloride (298 mg, 2.07 mmol) was added thereto, followed by heating to 80° C. and then stirring for one hour. A saturated aqueous solution of ammonium chloride was added to the reaction solution for neutralization, water was added thereto, and the resulting crystals were collected by filtration to give 1.1 g of a crude product. The obtained crude product was recrystallized from ethanol (65 ml) to give 0.67 g (yield: 59%) of the title compound.

$^1$H-NMR(CDCl$_3$) δ(ppm): 2.1–2.25 (1H, m), 2.37 (6H, s), 2.45–2.55 (1H, m), 2.65–2.9 (3H, m), 3.0–3.15 (2H, m), 3.15–3.25 (1H, m), 3.65–3.8 (1H, m), 3.9–4.0 (1H, m), 4.05–4.2 (1H, m), 4.35–4.5 (1H, m), 5.77 (1H, s), 6.76 (1H, dd, J=7.9, 1.5 Hz), 6.9–7.0 (2H, m), 7.05–7.4 (15H, m).

EXAMPLE 90

2-[4-(2-Chlorophenyl)piperazinylcarbonyl]-3-(diphenylmethyl)-1-(2-morpholinoethyl)indole (Compound 90)

Substantially the same procedure as in Example 89 was repeated using Compound 88 (1.0 g, 1.98 mmol) obtained in Example 88 and 2-morpholinoethylchloride hydrochloride (385 mg, 2.07 mmol) to give 0.91 g (yield: 74%) of the title compound.

$^1$H-NMR(CDCl$_3$) δ(ppm): 2.0–2.15 (1H, m), 2.45–2.65 (5H, m), 2.65–2.9 (3H, m), 2.9–3.15 (2H, m), 3.15–3.3 (1H, m), 3.6–3.8 (5H, m), 3.9–4.2 (2H, m), 4.3–4.5 (1H, m), 5.78 (1H, s), 6.76 (1H, dd, J=7.9, 1.5 Hz), 6.9–7.0 (2H, m), 7.05–7.4 (15H, m).

EXAMPLE 91

2-[4-(2-Chlorophenyl)piperazinylcarbonyl]-3-(diphenylmethyl)-1-(2-pyrrolidinylethyl)indole (Compound 91)

Substantially the same procedure as in Example 89 was repeated using Compound 88 (0.95 g, 1.88 mmol) obtained in Example 88 and 2-pyrrolidinylethylchloride hydrochloride (335 mg, 1.97 mmol) to give 0.61 g (yield: 54%) of the title compound.

$^1$H-NMR(CDCl$_3$) δ(ppm): 1.58 (2H, br s), 1.7–1.85 (3H, m), 2.0–2.1 (1H, m), 2.45–2.55 (1H, m), 2.61 (4H, br s), 2.75–2.85 (2H, m), 2.85–3.3 (4H, m), 3.65–3.8 (1H, m), 3.95–4.2 (2H, m), 4.3–4.5 (1H, m), 5.79 (1H, s), 6.7–6.8 (1H, m), 6.9–7.05 (2H, m), 7.10 (1H, d, J=7.9 Hz), 7.15–7.4 (14H, m).

EXAMPLE 92

Ethyl 1-(2-dimethylaminoethyl)-3-(diphenylmethyl)indole-2-carboxylate (Compound 92)

Substantially the same procedure as in Example 89 was repeated using ethyl 3-(diphenylmethyl)indole-2-carboxylate (8.5 g, 23.9 mmol) obtained in Reference Example 4 and 2-dimethylaminoethylchloride hydrochloride (3.8 g, 26.3 mmol) to give 7.0 g (yield: 69%) of the title compound.

$^1$H-NMR(CDCl$_3$) δ(ppm): 1.35 (3H, t, J=7.2 Hz), 2.33 (6H, s), 2.6–2.7 (2H, m), 4.34 (2H, q, J=7.2 Hz), 4.55–4.65 (2H, m), 6.57 (1H, s), 6.8–6.95 (2H, m), 7.1–7.3 (11H, m), 7.39 (1H, d, J=8.3 Hz).

EXAMPLE 93

1-(2-Dimethylaminoethyl)-3-(diphenylmethyl)indole-2-carboxylic acid (Compound 93)

Compound 92 (7.0 g, 16.5 mmol) obtained in Example 92 was dissolved in ethanol (50 ml), and a 2N aqueous sodium hydroxide solution (25 ml) was added thereto, followed by heating under reflux. After 4 hours, a 2N aqueous sodium hydroxide solution (10 ml) was added thereto, followed by heating under reflux for one hour. The reaction solution was concentrated under reduced pressure, water was added, and the pH of the solution was adjusted to 5. A little amount of chloroform was added to the mixture followed by stirring. The precipitated crystals were collected by filtration, washed with water, and dried under reduced pressure to give 5.7 g (yield: 87%) of the title compound.

$^1$H-NMR(CDCl$_3$) δ(ppm): 2.45 (6H, s), 3.27 (2H, t, J=5.9 Hz), 4.77 (2H, t, J=5.9 Hz), 6.81 (1H, s), 6.89 (1H, t, J=7.6 Hz), 7.05–7.2 (12H, m), 7.33 (1H, d, J=8.3 Hz).

EXAMPLE 94

N-Propyl-1-(2-dimethylaminoethyl)-3-(diphenylmethyl)indole-2-carboxamide (Compound 94)

1-(3-Dimethylaminopropyl)-3-ethylcarbodiimide hydrochloride (1.45 g, 7.53 mmol) was added to a solution of Compound 93 (1.5 g, 3.76 mmol) obtained in Example 93 and propylamine (0.47 ml, 5.65 mmol) in 50 ml of methylene chloride, followed by stirring at room temperature for 4.5 hours. Water was added to the reaction solution followed by extraction with chloroform. The resulting organic layer was washed successively with water and a saturated aqueous solution of sodium chloride, and dried over magnesium sulfate, and the solvent was distilled off under reduced pressure to give a crude product. The obtained crude product was purified with silica gel column chromatography (chloroform/methanol=40/1) followed by recrystallization from diisopropyl ether to give 0.98 g (yield: 59%) of the title compound.

$^1$H-NMR(CDCl$_3$) δ(ppm): 0.85 (3H, t, J=7.4 Hz), 1.4–1.55 (2H, m), 2.19 (6H, s), 2.76 (2H, t, J=6.6 Hz), 3.25–3.35 (2H, m), 4.42 (2H, t, J=6.6 Hz), 6.14 (1H, s), 6.85–6.95 (2H, m), 7.15–7.35 (13H, m).

In the following Examples 95 to 117, substantially the same procedure as in Example 94 was repeated using corresponding amines in place of propylamine to give the desired compounds.

EXAMPLE 95

N-Isopropyl-1-(2-dimethylaminoethyl)-3-(diphenylmethyl)indole-2-carboxamide (Compound 95)

$^1$H-NMR(CDCl$_3$) δ(ppm): 1.10 (6H, d, J=6.6 Hz), 2.23 (6H, s), 2.78 (2H, t, J=6.9 Hz), 4.15–4.3 (1H, m), 4.46 (2H, t, J=6.9 Hz), 6.06 (1H, s), 6.67 (1H, br d, J=7.3 Hz), 6.8–6.9 (2H, m), 7.1–7.3 (11H, m), 7.35 (1H, d, J=8.6 Hz).

EXAMPLE 96

N,N-Diethyl-1-(2-dimethylaminoethyl)-3-(diphenylmethyl)indole-2-carboxamide (Compound 96)

$^1$H-NMR(CDCl$_3$) δ(ppm): 0.73 (3H, t, J=7.3 Hz), 1.22 (3H, t, J=7.3 Hz), 2.31 (6H, s), 2.5–2.8 (3H, m), 3.0–3.15 (1H, m), 3.4–3.5 (2H, m), 4.0–4.1 (1H, m), 4.15–4.25 (1H, m), 5.65 (1H, s), 6.9–7.0 (1H, m), 7.1–7.35 (13H, m).

EXAMPLE 97

1-(2-Dimethylaminoethyl)-3-(diphenylmethyl)-2-(piperidinocarbonyl)indole (Compound 97)

$^1$H-NMR(CDCl$_3$) δ(ppm)) 0.8–1.0 (1H, m), 1.0–1.2 (1H, m), 1.4–1.6 (4H, m), 2.30 (6H, s), 2.5–2.8 (3H, m), 3.0–3.1 (1H, m), 3.4–3.5 (1H, m), 3.65–3.75 (1H, m), 4.0–4.15 (1H, m), 4.25–4.4 (1H, m), 5.70 (1H, s), 6.92 (1H, t, J=7.4 Hz), 7.1–7.3 (13H, m).

EXAMPLE 98

N-Cycloheptyl-1-(2-dimethylaminoethyl)-3-(diphenylmethyl)indole-2-carboxamide (Compound 98)

$^1$H-NMR(CDCl$_3$) δ(ppm): 1.2–1.35 (2H, m), 1.35–1.65 (8H, m), 1.85–2.0 (2H, m), 2.23 (6H, s), 2.78 (2H, t, J=6.9 Hz), 4.0–4.15 (1H, m), 4.46 (2H, t, J=6.9 Hz), 6.06 (1H, s), 6.69 (1H, br d, J=7.6 Hz), 6.85–6.9 (2H, m), 7.15–7.3 (11H, m), 7.35 (1H, d, J=8.2 Hz).

EXAMPLE 99

N-Cyclooctyl-1-(2-dimethylaminoethyl)-3-(diphenylmethyl)indole-2-carboxamide (Compound 99)

$^1$H-NMR(CDCl$_3$) δ(ppm): 1.2–1.35 (2H, m), 1.35–1.6 (10H, m), 1.7–1.85 (2H, m), 2.20 (6H, s), 2.74 (2H, t, J=6.9

Hz), 4.05–4.2 (1H, m), 4.45 (2H, t, J=6.9 Hz), 6.07 (1H, s), 6.55–6.65 (1H, m), 6.8–6.85 (2H, m), 7.1–7.35 (12H, m).

EXAMPLE 100

1-(2-Dimethylaminoethyl)-3-(diphenylmethyl)-2-(morpholinocarbonyl)indole (Compound 100)

$^1$H-NMR(CDCl$_3$) δ(ppm): 2.28 (6H, s), 2.5–2.7 (2H, m), 2.7–2.9 (2H, m), 2.9–3.1 (1H, m), 3.1–3.3 (1H, m), 3.5–3.75 (4H, m), 3.95–4.15 (1H, m), 4.2–4.4 (1H, m), 5.73 (1H, s), 6.93 (1H, t, J=7.4 Hz), 7.05–7.4 (13H, m).

EXAMPLE 101

1-(2-Dimethylaminoethyl)-3-(diphenylmethyl)-2-(4-phenylpiperazinylcarbonyl)indole (Compound 101)

$^1$H-NMR(CDCl$_3$) δ(ppm): 2.28 (6H, s), 2.3–2.4 (1H, m), 2.5–2.75 (3H, m), 2.9–3.25 (4H, m), 3.7–3.85 (2H, m), 4.0–4.15 (1H, m), 4.25–4.4 (1H, m), 5.75 (1H, s), 6.77 (2H, d, J=8.6 Hz), 6.85–6.95 (2H, m), 7.1–7.3 (15H, m).

EXAMPLE 102

2-(4-Benzylpiperazinylcarbonyl)-1-(2-dimethylaminoethyl)-3-(diphenylmethyl)indole (Compound 102)

$^1$H-NMR(CDCl$_3$) δ(ppm): 1.6–1.7 (1H, m), 1.95–2.05 (1H, m), 2.3–2.45 (2H, m), 2.33 (6H, s), 2.55–2.8 (2H, m), 2.8–2.95 (1H, m), 3.05–3.15 (1H, m), 3.3–3.45 (2H, m), 3.6–3.7 (2H, m), 4.0–4.15 (1H, m), 4.3–4.45 (1H, m), 5.70 (1H, s), 7.13 (1H, t, J=6.9 Hz), 7.05–7.4 (18H, m).

EXAMPLE 103

N-(4-Propylphenyl)-1-(2-dimethylaminoethyl)-3-(diphenylmethyl)indole-2-carboxamide (Compound 103)

$^1$H-NMR(CDCl$_3$) δ(ppm): 0.93 (3H, t, J=7.4 Hz), 1.55–1.7 (2H, m), 2.16 (6H, s), 2.55 (2H, t, J=7.6 Hz), 2.82 (2H, t, J=6.2 Hz), 4.48 (2H, t, J=6.2 Hz), 6.25 (1H, s), 6.85–7.0 (2H, m), 7.13 (2H, d, J=8.6 Hz), 7.2–7.4 (14H, m), 9.47 (1H, br s).

EXAMPLE 104

N-(2-Dimethylaminoethyl)-1-(2-dimethylaminoethyl)-3-(diphenylmethyl)indole-2-carboxamide (Compound 104)

$^1$H-NMR(CDCl$_3$) δ(ppm): 2.16 (6H, s), 2.27 (6H, s), 2.41 (2H, t, J=6.1 Hz), 2.75–2.85 (2H, m), 3.47 (2H, q, J=6.0 Hz), 4.46 (2H, t, J=6.7 Hz), 6.13 (1H,s), 6.8–6.9 (1H, m), 6.96 (1H, d, J=7.9 Hz), 7.15–7.3 (11H, m), 7.36 (1H, d, J=8.6 Hz).

EXAMPLE 105

N-(2-Dimethylaminoethyl)-N-methyl-1-(2-dimethylaminoethyl)-3-(diphenylmethyl)indole-2-carboxamide (Compound 105)

$^1$H-NMR(CDCl$_3$) δ(ppm): 2.27 (12H, s), 2.4–2.5 (2H, m), 2.51 (3H, s), 2.5–2.7 (2H, m), 3.45–3.55 (2H, m), 4.05–4.2 (1H, m), 4.2–4.35 (1H, m), 5.76 (1H, s), 6.9–7.0 (1H, m), 7.1–7.3 (13H, m).

EXAMPLE 106

N-(2-Piperidinoethyl)-1-(2-dimethylaminoethyl)-3-(diphenylmethyl)indole-2-carboxamide (Compound 106)

$^1$H-NMR(CDCl$_3$) δ(ppm): 1.3–1.5 (6H, m), 2.20 (6H, s), 2.25–2.35 (4H, m), 2.41 (2H, t, J=6.3 Hz), 2.74 (2H, t, J=6.7 Hz), 3.4–3.5 (2H, m), 4.44 (2H, t, J=6.7 Hz), 6.14 (1H, s), 6.8–6.9 (1H, m), 6.99 (1H, d, J=7.9 Hz), 7.15–7.3 (12H, m), 7.33 (1H, d, J=8.6 Hz).

EXAMPLE 107

N-(3-Morpholinopropyl)-1-(2-dimethylaminoethyl)-3-(diphenylmethyl)indole-2-carboxamide (Compound 107)

$^1$H-NMR(CDCl$_3$) δ(ppm): 1.55–1.7 (2H, m), 2.2–2.35 (6H, m), 2.26 (6H, s), 2.75–2.9 (2H, br), 3.41 (2H, q, J=6.6 Hz), 3.55–3.65 (4H, m), 4.44 (2H, t, J=6.6 Hz), 6.12 (1H, s), 6.8–6.95 (2H, m), 7.1–7.3 (11H, m), 7.3–7.4 (2H, m).

EXAMPLE 108

N-[3-(2-Oxopyrrolidinyl)propyl]-1-(2-dimethylaminoethyl)-3-(diphenylmethyl)indole-2-carboxamide (Compound 108)

$^1$H-NMR(CDCl$_3$) δ(ppm): 1.65–1.8 (2H, m), 1.9–2.1 (2H, m), 2.18 (6H, s), 2.36 (2H, t, J=8.1 Hz), 2.79 (2H, t, J=6.4 Hz), 3.24 (2H, t, J=7.1 Hz), 3.3–3.4 (4H, m), 4.40 (2H, t, J=6.4 Hz), 6.19 (1H, s), 6.85–6.9 (1H, m), 6.95 (1H, d, J=7.6 Hz), 7.15–7.3 (11H, m), 7.31 (1H, d, J=8.2 Hz), 7.9–8.0 (1H, m).

EXAMPLE 109

N-[3-(1-Imidazolyl)propyl]-1-(2-dimethylaminoethyl)-3-(diphenylmethyl)indole-2-carboxamide (Compound 109)

$^1$H-NMR(CDCl$_3$) δ(ppm): 1.85–2.0 (2H, m), 2.19 (6H, s), 2.8–2.9 (2H, m), 3.33 (2H, q, J=6.6 Hz), 3.80 (2H, t, J=6.9Hz), 4.40 (2H, t, J=5.7 Hz), 6.23 (1H, s), 6.84 (1H, s), 6.89 (2H, d, J=3.6 Hz), 7.05 (1H, s), 7.15–7.4 (13H, m), 7.85–8.0 (1H, br).

EXAMPLE 110

N-(2-Pyridylmethyl)-1-(2-dimethylaminoethyl)-3-(diphenylmethyl)indole-2-carboxamide (Compound 110)

$^1$H-NMR(CDCl$_3$) δ(ppm): 2.15 (6H, s), 2.82 (2H, t, J=6.5 Hz), 4.48 (2H, t, J=6.5 Hz), 4.67 (2H, d, J=5.4 Hz), 6.28 (1H, s), 6.89 (1H, t, J=8.4 Hz), 6.98 (1H, d, J=8.4 Hz), 7.1–7.3 (13H, m), 7.34 (1H, d, J=8.4 Hz), 7.60 (1H, td, J=7.9, 1.5 Hz), 8.43 (1H, d, J=4.4 Hz), 8.4–8.55 (1H, br).

EXAMPLE 111

N-[2-(2-Pyridyl)ethyl]-1-(2-dimethylaminoethyl)-3-(diphenylmethyl)indole-2-carboxamide (Compound 111)

$^1$H-NMR(CDCl$_3$) δ(ppm): 2.10 (6H, s), 2.7–2.8 (2H, m), 3.02 (2H, t, J=6.4 Hz), 3.79 (2H, q, J=6.4 Hz), 4.38 (2H, t, J=6.4 Hz), 6.16 (1H, s), 6.8–7.0 (3H, m), 7.0–7.1 (1H, m), 7.1–7.3 (11H, m), 7.32 (1H, d, J=8.4 Hz), 7.42 (1H, td, J=7.4, 2.0 Hz), 7.9–8.1 (1H, br), 8.35 (1H, d, J=3.0 Hz).

EXAMPLE 112

N-[(1-Ethyl-2-pyrrolidinyl)methyl]-1-(2-dimethylaminoethyl)-3-(diphenylmethyl)indole-2-carboxamide (Compound 112)

$^1$H-NMR(CDCl$_3$) δ(ppm): 0.95 (3H, t, J=7.3 Hz), 1.35–1.6 (2H, m), 1.6–1.8 (2H, m), 2.0–2.2 (2H, m), 2.23

(6H, s), 2.4–2.5 (1H, m), 2.55–2.65 (3H, m), 2.9–3.0 (1H, m), 3.05–3.15 (1H, m), 3.65–3.75 (1H, m), 4.43 (2H, t, J=6.7 Hz), 6.13 (1H, s), 6.8–6.9 (1H, m), 6.97 (1H, d, J=7.9 Hz), 7.15–7.3 (12H, m), 7.33 (1H, d, J=8.6 Hz).

EXAMPLE 113

N-[2-(1-Methyl-2-pyrrolidinyl)ethyl]-1-(2-dimethylaminoethyl)-3-(diphenylmethyl)indole-2-carboxamide (Compound 113)

$^1$H-NMR(CDCl$_3$) δ(ppm): 1.4–1.6 (2H, m), 1.6–2.0 (4H, m), 2.05–2.2 (2H, m), 2.21 (6H, s), 2.24 (3H, s), 2.78 (2H, d, J=6.4 Hz), 3.0–3.1 (1H, m), 3.3–3.6 (2H, m), 4.42 (2H, t, J=6.4 Hz), 6.18 (1H, s), 6.8–6.9 (1H, m), 6.95 (1H, d, J=7.9 Hz), 7.15–7.3 (11H, m), 7.32 (1H, d, J=8.6 Hz), 7.7–7.8 (1H, m).

EXAMPLE 114

N-[(2-Tetrahydrofuranyl)methyl]-1-(2-dimethylaminoethyl)-3-(diphenylmethyl)indole-2-carboxamide (Compound 114)

$^1$H-NMR(CDCl$_3$) δ(ppm): 1.4–1.55 (1H, m), 1.7–1.95 (3H, m), 2.19 (6H, s), 2.7–2.9 (2H, m), 3.35–3.45 (1H, m), 3.55–3.7 (3H, m), 3.9–4.0 (1H, m), 4.35–4.5 (2H, m), 6.22 (1H, s), 6.85–6.95 (1H, m), 6.97 (1H, d, J=7.9 Hz), 7.15–7.3 (11H, m), 7.32 (1H, d, J=8.3 Hz), 8.05–8.1 (1H, m).

EXAMPLE 115

N-(2-Thienylmethyl)-1-(2-dimethylaminoethyl)-3-(diphenylmethyl)indole-2-carboxamide (Compound 115)

$^1$H-NMR(CDCl$_3$) δ(ppm): 2.02 (6H, s), 2.75 (2H, t, J=6.3 Hz), 4.41 (2H, t, J=6.3 Hz), 4.73 (2H, d, J=5.3 Hz), 6.23 (1H, s), 6.8–7.0 (4H, m), 7.15–7.35 (13H, m), 8.6–8.7 (1H, m).

EXAMPLE 116

N-(2-Furylmethyl)-1-(2-dimethylaminoethyl)-3-(diphenylmethyl)indole-2-carboxamide (Compound 116)

$^1$H-NMR(CDCl$_3$) δ(ppm): 2.06 (6H, s), 2.76 (2H, t, J=6.1 Hz), 4.40 (2H, t, J=6.1 Hz), 4.56 (2H, d, J=5.3 Hz), 6.21 (1H, s), 6.2–6.25 (1H, m), 6.3–6.35 (1H, m), 6.85–6.95 (1H, m), 6.99 (1H, d, J=7.6 Hz), 7.15–7.35 (12H, m), 7.19 (1H, br s), 8.5–8.6 (1H, m).

EXAMPLE 117

N-[3-(2-Methylpiperidino)propyl])1-(2-dimethylaminoethyl)-3-(diphenylmethyl)indole-2-carboxamide (Compound 117)

$^1$H-NMR(CDCl$_3$) δ(ppm): 1.03 (3H, d, J=6.3 Hz), 1.2–1.35 (2H, m), 1.5–1.8 (6H, m), 2.15–2.25 (1H, m), 2.21 (6H, s), 2.3–2.45 (2H, m), 2.7–2.9 (2H, m), 2.79 (2H, t, J=6.4 Hz), 3.38 (2H, q, J=6.4 Hz), 4.41 (2H, t, J=6.4 Hz), 6.17 (1H, s), 6.85–6.95 (1H, m), 6.97 (1H, d, J=7.6 Hz), 7.15–7.3 (11H, m), 7.31 (1H, d, J=8.3 Hz), 7.85–8.05 (1H, br).

EXAMPLE 118

3-(Diphenylmethyl)-1-(2-pyrrolidinylethyl)indole-2-carboxylic acid (Compound 118)

Substantially the same procedure as in Example 89 was repeated using ethyl 3-(diphenylmethyl)indole-2-carboxylate (5.0 g, 14.1 mmol) obtained in Reference Example 4 and 2-pyrrolidinylethylchloride hydrochloride (2.63 g, 15.5 mmol) to give 7.05 g of ethyl 3-(diphenylmethyl)-1-(2-pyrrolidinylethyl)indole-2-carboxylate. Then, substantially the same procedure as in Example 93 was repeated using the obtained compound to give 4.7 g (yield: 79%, 2 steps) of the title compound.

$^1$H-NMR(DMSO-d$_6$) δ(ppm): 1.7–1.85 (4H, br), 2.7–2.9 (4H, br), 3.48 (2H, t, J=5.7 Hz), 4.77 (2H, t, J=5.7 Hz), 6.77 (1H, s), 6.85–6.95 (1H, m), 7.05–7.3 (12H, m), 7.35 (1H, d, J=8.3 Hz), 7.85 (1H, s).

In the following Examples 119 to 121, substantially the same procedure as in Example 94 was repeated using Compound 118 in place of Compound 93 and using corresponding amines in place of propylamine to give the desired compounds.

EXAMPLE 119

N-Isopropyl-3-(diphenylmethyl)-1-(2-pyrrolidinylethyl)indole-2-carboxamide (Compound 119)

$^1$H-NMR(CDCl$_3$) δ(ppm): 1.11 (6H, d, J=6.6 Hz), 1.6–1.75 (4H, br), 2.25–2.4 (4H, br), 2.97 (2H, t, J=6.6 Hz), 4.15–4.3 (1H, m), 4.47 (2H, t, J=6.6 Hz), 6.15 (1H, s), 6.8–6.95 (2H, m), 7.15–7.3 (11H, m), 7.35 (1H, d, J=8.3 Hz), 7.55–7.7 (1H, br).

EXAMPLE 120

2-(4-Benzylpiperazinylcarbonyl)-3-(diphenylmethyl)-1-(2-pyrrolidinylethyl)indole (Compound 120)

$^1$H-NMR(CDCl$_3$) δ(ppm): 1.6–1.7 (1H, m), 1.75–1.85 (4H, m), 1.95–2.05 (1H, m), 2.25–2.5 (2H, m), 2.55–2.65 (4H, m), 2.7–3.0 (3H, m), 3.05–3.15 (1H, m), 3.3–3.45 (2H, m), 3.65–3.75 (2H, m), 4.05–4.2 (1H, m), 4.25–4.4 (1H, m), 5.72 (1H, s), 6.85–6.95 (1H, m), 7.08 (1H, d, J=8.3 Hz), 7.1–7.35 (16H, m), 7.35 (1H, d, J=8.3 Hz).

EXAMPLE 121

N-(3-Morpholinopropyl)-3-(diphenylmethyl)-1-(2-pyrrolidinylethyl)indole-2-carboxamide (Compound 121)

$^1$H-NMR(CDCl$_3$) δ(ppm): 1.6–1.75 (6H, m), 2.25–2.5 (10H, m), 2.99 (2H, t, J=6.6 Hz), 3.39 (2H, td, J=6.9, 5.9 Hz), 3.55–3.65 (4H, m), 4.45 (2H, t, J=6.6 Hz), 6.17 (1H, s), 6.85–6.95 (1H, m), 6.97 (1H, d, J=7.6 Hz), 7.15–7.3 (11H, m), 7.34 (1H, d, J=8.3 Hz), 7.95–8.05 (1H, br).

EXAMPLE 122

3-(Diphenylmethyl)-1-(2-piperidinoethyl)indole-2-carboxylic acid (Compound 122)

Substantially the same procedure as in Example 89 was repeated using ethyl 3-(diphenylmethyl)indole-2-carboxylate (5.0 g, 14.1 mmol) obtained in Reference Example 4 and 2-piperidinoethylchloride hydrochloride (2.85 g, 15.5 mmol) to give 7.20 g of ethyl 3-(diphenylmethyl)-1-(2-piperidinoethyl)indole-2-carboxylate. Then, substantially the same procedure as in Example 93 was repeated using the obtained compound to give 5.3 g (yield: 85%, 2 steps) of the title compound.

$^1$H-NMR(CDCl$_3$) δ(ppm): 1.4–1.65 (6H, m), 2.3–2.6 (4H, m), 3.12 (2H, t, J=5.4 Hz), 4.72 (2H, t, J=5.4 Hz), 6.83 (1H, s), 6.85–7.0 (1H, m), 7.1–7.35 (13H, m).

In the following Examples 123 to 125, substantially the same procedure as in Example 94 was repeated using Compound 122 in place of Compound 93 and using corresponding amines in place of propylamine to give the desired compounds.

EXAMPLE 123

N-Isopropyl-3-(diphenylmethyl)-1-(2-piperidinoethyl)indole-2-carboxamide (Compound 123)

$^1$H-NMR(CDCl$_3$) δ(ppm): 1.12 (6H, d, J=6.6 Hz), 1.3–1.45 (2H, m), 1.45–1.55 (4H, m), 2.25–2.35 (4H, m), 2.74 (2H, t, J=6.9 Hz), 4.15–4.3 (1H, m), 4.49 (2H, t, J=6.9 Hz), 6.08 (1H, s), 6.75–6.9 (3H, m), 7.15–7.3 (11H, m), 7.36 (1H, d, J=8.3 Hz).

EXAMPLE 124

2-(4-Benzylpiperazinylcarbonyl)-3-(diphenylmethyl)-1-(2-piperidinoethyl)indole (Compound 124)

$^1$H-NMR(CDCl$_3$) δ(ppm): 1.4–1.5 (2H, m), 1.5–1.65 (4H, m), 1.65–1.8 (2H, m), 1.95–2.05 (1H, m), 2.25–2.4 (1H, m), 2.4–2.65 (5H, m), 2.7–2.9 (2H, m), 3.05–3.15 (1H, m), 3.25–3.35 (2H, m), 3.6–3.8 (2H, m), 4.05–4.2 (1H, m), 4.25–4.4 (1H, m), 5.71 (1H, s), 6.91 (1H, t, J=7.3 Hz), 7.08 (1H, d, J=7.9 Hz), 7.15–7.3 (16H, m), 7.35 (1H, d, J=8.3 Hz).

EXAMPLE 125

N-(3-Morpholinopropyl)-3-(diphenylmethyl)-1-(2-piperidinoethyl)indole-2-carboxamide (Compound 125)

$^1$H-NMR(CDCl$_3$) δ(ppm): 1.3–1.55 (6H, m), 1.65–1.75 (2H, m), 2.2–2.4 (10H, m), 2.80 (2H, t, J=6.4 Hz), 3.42 (2H, td, J=6.9, 6.3 Hz), 3.6–3.7 (4H, m), 4.45 (2H, t, J=6.4 Hz), 6.17 (1H, s), 6.85–6.95 (1H, m), 6.96 (1H, d, J=7.6 Hz), 7.15–7.3 (11H, m), 7.34 (1H, d, J=8.6 Hz), 8.05–8.15 (1H, br).

EXAMPLE 126

3-(Diphenylmethyl)-1-(2-morpholinoethyl)indole-2-carboxylic acid (Compound 126)

Substantially the same procedure as in Example 89 was repeated using ethyl 3-(diphenylmethyl)indole-2-carboxylate (5.0 g, 14.1 mmol) obtained in Reference Example 4 and 2-morpholinoethylchloride hydrochloride (2.88 g, 15.5 mmol) to give 7.24 g of ethyl 3-(diphenylmethyl)-1-(2-morpholinoethyl)indole-2-carboxylate. Then, substantially the same procedure as in Example 93 was repeated using the obtained compound to give 5.6 g (yield: 88%, 2 steps) of the title compound.

$^1$H-NMR(CDCl$_3$) δ(ppm): 2.3–2.45 (4H, br), 3.03 (2H, t, J=5.6 Hz), 3.4–3.5 (4H, m), 4.66 (2H, t, J=5.6 Hz), 6.68 (1H, s), 6.9–7.0 (1H, m), 7.06 (1H, d, J=8.2 Hz), 7.15–7.3 (12H, m).

In the following Examples 127 to 129, substantially the same procedure as in Example 94 was repeated using Compound 126 in place of Compound 93 and using corresponding amines in place of propylamine to give the desired compounds.

EXAMPLE 127

N-Isopropyl-3-(diphenylmethyl)-1-(2-morpholinoethyl)indole-2-carboxamide (Compound 127)

$^1$H-NMR(CDCl$_3$) δ(ppm): 1.10 (6H, d, J=6.6 Hz), 2.25–2.35 (4H, m), 2.76 (2H, t, J=7.1 Hz), 3.55–3.65 (4H, m), 4.15–4.3 (1H, m), 4.51 (2H, t, J=7.1 Hz), 6.00 (1H, s), 6.11 (1H, br d, J=7.6 Hz), 6.75–6.9 (2H, m), 7.15–7.35 (11H, m), 7.36 (1H, d, J=8.2 Hz).

EXAMPLE 128

2-(4-Benzylpiperazinylcarbonyl)-3-(diphenylmethyl)-1-(2-morpholinoethyl)indole (Compound 128)

$^1$H-NMR(CDCl$_3$) δ(ppm): 1.6–1.7 (1H, m), 1.9–2.0 (1H, m), 2.3–2.65 (7H, m), 2.75–2.9 (2H, m), 3.05–3.15 (1H, m), 3.25–3.45 (2H, m), 3.65–3.75 (6H, m), 4.0–4.15 (1H, m), 4.25–4.4 (1H, m), 5.71 (1H, s), 6.85–6.95 (1H, m), 7.05–7.4 (18H, m).

EXAMPLE 129

N-(3-Morpholinopropyl)-3-(diphenylmethyl)-1-(2-morpholinoethyl)indole-2-carboxamide (Compound 129)

$^1$H-NMR(CDCl$_3$) δ(ppm): 1.6–1.75 (2H, m), 2.25–2.45 (10H, m), 2.77 (2H, t, J=6.9 Hz), 3.35–3.45 (2H, m), 3.55–3.65 (8H, m), 4.48 (2H, t, J=6.9 Hz), 6.05 (1H, s), 6.8–6.95 (3H, m), 7.15–7.35 (11H, m), 7.35 (1H, d, J=8.3 Hz).

EXAMPLE 130

Ethyl 3-[bis(4-fluorophenyl)methyl]-1-(2-dimethylaminoethyl)indole-2-carboxylate (Compound 130)

Substantially the same procedure as in Example 89 was repeated using ethyl 3-[bis(4-fluorophenyl)methyl]indole-2-carboxylate (5.0 g, 12.8 mmol) obtained in Reference Example 5 and 2-dimethylaminoethylchloride hydrochloride (1.93 g, 13.4 mmol) to give 6.8 g (quantitative) of the title compound.

$^1$H-NMR(CDCl$_3$) δ(ppm): 1.46 (3H, t, J=7.2 Hz), 2.43 (6H, s), 2.7–2.8 (2H, m), 4.46 (2H, q, J=7.2 Hz), 4.65–4.75 (2H, m), 6.59 (1H, s), 6.95–7.1 (6H, m), 7.15–7.25 (4H, m), 7.35–7.4 (1H, m), 7.50 (1H, d, J=8.5 Hz).

EXAMPLE 131

3-[Bis(4-fluorophenyl)methyl]-1-(2-dimethylaminoethyl)indole-2-carboxylic acid (Compound 131)

Substantially the same procedure as in Example 93 was repeated using Compound 130 (6.8 g, 12.8 mmol) obtained in Example 130 to give 3.6 g (yield: 65%) of the title compound.

$^1$H-NMR(DMSO-d$_6$) δ(ppm): 2.45 (6H, s), 3.28 (2H, t, J=5.6 Hz), 4.73 (2H, t, J=5.6 Hz), 6.74 (1H, s), 6.85–6.95 (1H, m), 6.97 (1H, d, J=7.9 Hz), 7.0–7.2 (9H, m), 7.59 (1H, d, J=8.3 Hz).

In the following Examples 132 to 134, substantially the same procedure as in Example 94 was repeated using Compound 131 in place of Compound 93 and using corresponding amines in place of propylamine to give the desired compounds.

EXAMPLE 132

N-Isopropyl-3-[bis(4-fluorophenyl)methyl]-1-(2-dimethylaminoethyl)indole-2-carboxamide (Compound 132)

$^1$H-NMR(CDCl$_3$) δ(ppm): 1.15 (6H, d, J=6.6 Hz), 2.12 (6H, s), 2.78 (2H, t, J=6.4 Hz), 4.15–4.3 (1H, m), 4.42 (2H,

EXAMPLE 133

2-(4-Benzylpiperazinylcarbonyl)-3-[bis(4-fluorophenyl)methyl]-1-(2-dimethylaminoethyl) indole (Compound 133)

$^1$H-NMR(CDCl$_3$) δ(ppm): 1.65–1.75 (1H, m), 2.0–2.1 (1H, m), 2.28 (6H, s), 2.3–2.4 (1H, m), 2.45–2.55 (1H, m), 2.55–2.75 (2H, m), 2.85–2.95 (1H, m), 3.05–3.15 (1H, m), 3.3–3.45 (2H, m), 3.55–3.65 (2H, m), 4.0–4.15 (1H, m), 4.25–4.4 (1H, m), 5.66 (1H, s), 6.85–7.15 (8H, m), 7.2–7.4 (9H, m).

EXAMPLE 134

N-(3-Morpholinopropyl)-3-[bis(4-fluorophenyl)methyl]-1-(2-dimethylaminoethyl)indole-2-carboxamide (Compound 134)

$^1$H-NMR(CDCl$_3$) δ(ppm): 1.65–1.85 (2H, m), 2.17 (6H, s), 2.25–2.4 (6H, m), 2.81 (2H, t, J=5.9 Hz), 3.42 (2H, q, J=6.9 Hz), 3.6–3.7 (4H, m), 4.38 (2H, t, J=5.9 Hz), 6.17 (1H, s), 6.85–7.0 (6H, m), 7.1–7.25 (5H, m), 7.31 (1H, d, J=8.3 Hz), 8.25–8.35 (1H, m).

EXAMPLE 135

N-[3-(2-Oxopyrrolidinyl)propyl]-1-(2-dimethylaminoethyl)-3-(diphenylmethyl)indole-2-carboxamide hydrochloride (Compound 108 hydrochloride)

A solution of hydrogen chloride in 10 ml of ethyl acetate was added to a suspension of Compound 108 (12.85 g) obtained in Example 108 in 70 ml of ethanol, followed by stirring. Then, ethanol (45 ml) was added to the reaction solution followed by recrystallization to give 12.2 g (yield: 89%) of the title compound.

$^1$H-NMR(CDCl$_3$) δ(ppm): 1.55–1.65 (2H, m), 1.95–2.05 (2H, m), 2.33 (2H, t, J=8.1 Hz), 2.88 (3H, s), 2.90 (3H, s), 3.18 (2H, t, J=6.9 Hz), 3.25–3.35 (4H, m), 3.45–3.55 (2H, m), 4.85–4.95 (2H, m), 5.97 (1H, s), 6.05 (1H, t, J=5.6 Hz), 6.79 (1H, d, J=7.9 Hz), 6.89 (1H, t, J=7.1 Hz), 7.1–7.2 (4H, m), 7.2–7.35 (7H, m), 7.78 (1H, d, J=8.3 Hz), 12.93 (1H, br).

In the following Examples 136 to 148, substantially the same procedure as in Example 94, and then substantially the same procedure as in Example 135 were repeated using corresponding amines in place of propylamine to give the desired compounds.

EXAMPLE 136

N-Butyl-1-(2-dimethylaminoethyl)-3-(diphenylmethyl)indole-2-carboxamide hydrochloride (Compound 135 hydrochloride)

$^1$H-NMR(CDCl$_3$) δ(ppm): 0.88 (3H, t, J=7.3 Hz), 1.15–1.3 (2H, m), 1.3–1.45 (2H, m), 2.91 (6H, s), 3.29 (2H, dt, J=5.6, 6.9 Hz), 3.55–3.65 (2H, m), 4.8–4.9 (2H, m), 5.76 (1H, t, J=5.6 Hz), 5.95 (1H, s), 6.77 (1H, d, J=8.2 Hz), 6.88 (1H, t, J=6.5 Hz), 7.1–7.2 (4H, m), 7.2–7.35 (7H, m), 7.79 (1H, d, J=8.6 Hz), 13.0 (1H, br).

EXAMPLE 137

N-Allyl-1-(2-dimethylaminoethyl)-3-(diphenylmethyl)indole-2-carboxamide hydrochloride (Compound 136 hydrochloride)

$^1$H-NMR(CDCl$_3$) δ(ppm): 2.90 (3H, s), 2.92 (3H, s), 3.55–3.65 (2H, m), 3.92 (2H, t, J=5.7 Hz), 4.8–4.9 (2H, m), 5.10 (1H, d, J=12.5 Hz), 5.15 (1H, d, J=5.3 Hz), 5.7–5.85 (1H, m), 5.85–5.9 (1H, m), 5.96 (1H, s), 6.80 (1H, d, J=7.9 Hz), 6.90 (1H, t, J=7.5 Hz), 7.1–7.2 (4H, m), 7.2–7.4 (7H, m), 7.80 (1H, d, J=8.6 Hz), 13.04 (1H, br).

EXAMPLE 138

N-Isobutyl-1-(2-dimethylaminoethyl)-3-(diphenylmethyl)indole-2-carboxamide hydrochloride (Compound 137 hydrochloride)

$^1$H-NMR(CDCl$_3$) δ(ppm): 0.78 (6H, d, J=6.6 Hz), 1.5–1.7 (1H, m), 2.90 (3H, s), 2.92 (3H, s), 3.13 (2H, t, J=6.4 Hz), 3.55–3.65 (2H, m), 4.8–4.9 (2H, m), 5.75–5.85 (1H, m), 5.97 (1H, s), 6.78 (1H, d, J=8.2 Hz), 6.88 (1H, t, J=7.6 Hz), 7.05–7.2 (4H, m), 7.2–7.35 (7H, m), 7.79 (1H, d, J=8.6 Hz), 13.03 (1H, br).

EXAMPLE 139

N-Cyclopropyl-1-(2-dimethylaminoethyl)-3-(diphenylmethyl)indole-2-carboxamide hydrochloride (Compound 138 hydrochloride)

$^1$H-NMR(CDCl$_3$) δ(ppm): 0.35–0.45 (2H, m), 0.75–0.85 (2H, m), 2.75–2.85 (1H, m), 2.91 (3H, s), 2.93 (3H, s), 3.55–3.65 (2H, m), 4.85–4.95 (2H, m), 5.86 (2H, s), 6.74 (1H, d, J=7.9 Hz), 6.88 (1H, t, J=7.1 Hz), 7.05–7.15 (4H, m), 7.2–7.4 (7H, m), 7.82 (1H, d, J=7.9 Hz), 13.06 (1H, br).

EXAMPLE 140

N-Cyclobutyl-1-(2-dimethylaminoethyl)-3-(diphenylmethyl)indole-2-carboxamide hydrochloride (Compound 139 hydrochloride)

$^1$H-NMR(CDCl$_3$) δ(ppm): 1.55–1.75 (4H, m), 2.25–2.35 (2H, m), 2.90 (3H, s), 2.91 (3H, s), 3.55–3.65 (2H, m), 4.35–4.45 (1H, m), 4.75–4.85 (2H, m), 5.95–6.0 (1H, m), 5.96 (1H, s), 6.75 (1H, d, J=7.9 Hz), 6.88 (1H, t, J=7.4 Hz), 7.1–7.2 (4H, m), 7.25–7.4 (7H, m), 7.79 (1H, d, J=8.6 Hz), 13.02 (1H, br).

EXAMPLE 141

N-(sec-Butyl)-1-(2-dimethylaminoethyl)-3-(diphenylmethyl)indole-2-carboxamide hydrochloride (Compound 140 hydrochloride)

$^1$H-NMR(CDCl$_3$) δ(ppm): 0.82 (3H, t, J=6.9 Hz), 1.06 (3H, d, J=6.6 Hz), 1.25–1.4 (2H, m), 2.91 (6H, s), 3.55–3.65 (2H, m), 3.95–4.05 (1H, m), 4.85–4.95 (2H, m), 5.63 (1H, d, J=7.9 Hz), 5.95 (1H, s), 6.73 (1H, d, J=8.3 Hz), 6.87 (1H, t, J=7.6 Hz), 7.05–7.15 (4H, m), 7.2–7.4 (7H, m), 7.79 (1H, d, J=7.8 Hz), 13.05 (1H, br).

EXAMPLE 142

N-Cyclopentyl-1-(2-dimethylaminoethyl)-3-(diphenylmethyl)indole-2-carboxamide hydrochloride (Compound 141 hydrochloride)

$^1$H-NMR(CDCl$_3$) δ(ppm): 1.1–1.25 (2H, m), 1.5–1.75 (4H, m), 1.85–2.0 (2H, m), 2.91 (6H, s), 3.55–3.65 (2H, m), 4.2–4.3 (1H, m), 4.8–4.9 (2H, m), 5.78 (1H, d, J=7.3 Hz), 5.94 (1H, s), 6.73 (1H, d, J=7.2 Hz), 6.87 (1H, t, J=6.7 Hz), 7.05–7.15 (4H, m), 7.25–7.4 (7H, m), 7.78 (1H, d, J=8.6 Hz), 13.0 (1H, br).

EXAMPLE 143

N-Cyclohexyl-1-(2-dimethylaminoethyl)-3-(diphenylmethyl)indole-2-carboxamide hydrochloride (Compound 142 hydrochloride)

$^1$H-NMR(CDCl$_3$) δ(ppm): 0.9–1.05 (2H, m), 1.05–1.2 (1H, m), 1.2–1.45 (3H, m), 1.55–1.7 (2H, m), 1.85–1.95

(2H, m), 2.90 (3H, s), 2.92 (3H, s), 3.55–3.65 (2H, m), 3.75 (1H, m), 4.75–4.85 (2H, m), 5.69 (1H, d, J=7.9 Hz), 5.93 (1H, s), 6.75 (1H, d, J=7.9 Hz), 6.87 (1H, t, J=7.6 Hz), 7.05–7.15 (4H, m), 7.2–7.35 (7H, m), 7.78 (1H, d, J=8.2 Hz), 13.03 (1H, br).

EXAMPLE 144

N-Methyl-1-(2-dimethylaminoethyl)- 3-(diphenylmethyl)indole-2-carboxamide hydrochloride (Compound 143 hydrochloride)

$^1$H-NMR(CDCl$_3$) δ(ppm): 2.83 (3H, d, J=5.0 Hz), 2.90 (3H, s), 2.92 (3H, s), 3.5–3.6 (2H, m), 4.75–4.85 (2H, m), 5.7–5.8 (1H, m), 5.92 (1H, s), 6.83 (1H, d, J=7.9 Hz), 6.91 (1H, t, J=7.3 Hz), 7.05–7.15 (4H, m), 7.2–7.35 (7H, m), 7.79 (1H, d, J=8.6 Hz), 13.03 (1H, br).

EXAMPLE 145

N-Pentyl-1-(2-dimethylaminoethyl)-3-(diphenylmethyl)indole-2-carboxamide hydrochloride (Compound 144 hydrochloride)

$^1$H-NMR(CDCl$_3$) δ(ppm): 0.86 (3H, t, J=7.3 Hz), 1.05–1.45 (6H, m), 2.90 (3H, s), 2.92 (3H, s), 3.29 (2H, dt, J=5.6, 7.0 Hz), 3.55–3.65 (2H, m), 4.8–4.9 (2H, m), 5.76 (1H, t, J=5.6 Hz), 5.95 (1H, s), 6.78 (1H, d, J=8.2 Hz), 6.89 (1H, t, J=7.1 Hz), 7.1–7.2 (4H, m), 7.2–7.35 (7H, m), 7.79 (1H, d, J=8.6 Hz), 13.04 (1H, br).

EXAMPLE 146

N-Ethyl-1-(2-dimethylaminoethyl)-3-(diphenylmethyl)indole-2-carboxamide hydrochloride (Compound 145 hydrochloride)

$^1$H-NMR(CDCl$_3$) δ(ppm): 1.07 (3H, t, J=7.3 Hz), 2.90 (3H, s), 2.92 (3H, s), 3.33 (2H, dq, J=5.3, 7.3 Hz), 3.55–3.65 (2H, m), 4.75–4.9 (2H, m), 5.75 (1H, t, J=5.3 Hz), 5.94 (1H, s), 6.78 (1H, d, J=8.2 Hz), 6.89 (1H, t, J=7.6 Hz), 7.05–7.15 (4H, m), 7.2–7.35 (7H, m), 7.79 (1H, d, J=7.9 Hz), 13.0 (1H, br).

EXAMPLE 147

N-(4-Methoxyphenyl)-1-(2-dimethylaminoethyl)- 3-(diphenylmethyl)indole-2-carboxamide hydrochloride (Compound 46 hydrochloride)

$^1$H-NMR(CDCl$_3$) δ(ppm): 2.90 (3H, s), 2.91 (3H, s), 3.55–3.65 (2H, m), 3.80 (3H, s), 4.85–4.95 (2H, m), 6.07 (1H, s), 6.75–6.95 (4H, m), 7.1–7.25 (6H, m), 7.25–7.4 (7H, m), 7.46 (1H, s), 7.85 (1H, d, J=8.6 Hz), 13.09 (1H, br).

EXAMPLE 148

N-Phenyl-1-(2-dimethylaminoethyl)-3-(diphenylmethyl)indole-2-carboxamide hydrochloride (Compound 147 hydrochloride)

$^1$H-NMR(CDCl$_3$) δ(ppm): 2.89 (6H, s), 3.55–3.65 (2H, m), 4.8–4.9 (2H, m), 6.06 (1H, s), 6.8–6.95 (2H, m), 7.1–7.4 (16H, m), 7.81 (1H, d, J=8.6 Hz), 8.42 (1H, s), 12.47 (1H, br).

In the following Examples 149 to 151, substantially the same procedure as in Example 94, and then substantially the same procedure as in Example 135 were repeated using Compound 118 in place of Compound 93 and using corresponding amines in place of propylamine to give the desired compounds.

EXAMPLE 149

N-Propyl-3-(diphenylmethyl)-1-(2-pyrrolidinylethyl) indole-2-carboxamide hydrochloride (Compound 148 hydrochloride)

$^1$H-NMR(CDCl$_3$) δ(ppm): 0.83 (3H, d, J=7.4 Hz), 1.3–1.5 (2H, m), 2.0–2.3 (4H, m), 2.9–3.05 (2H, m), 3.2–3.3 (2H, m), 3.6–3.9 (4H, m), 4.75–4.85 (2H, m), 5.77 (1H, t, J=5.3 Hz), 5.95 (1H, s), 6.78 (1H, d, J=8.3 Hz), 6.88 (1H, t, J=7.6 Hz), 7.05–7.2 (4H, m), 7.2–7.4 (7H, m), 7.81 (1H, d, J=8.6 Hz), 12.86 (1H, br).

EXAMPLE 150

N-(2-Piperidinoethyl)-3-(diphenylmethyl)-1-(2-pyrrolidinylethyl)indole-2-carboxamide 2 hydrochloride (Compound 149 2 hydrochloride)

$^1$H-NMR(CDCl$_3$) δ(ppm): 1.75–1.9 (4H, m), 2.0–2.3 (6H, m), 2.55–2.9 (4H, m), 3.2–3.3 (2H, m), 3.55–3.8 (8H, m), 4.84 (2H, t, J=7.4 Hz), 6.04 (1H, s), 6.9–6.95 (2H, m), 7.15–7.35 (11H, m), 7.46 (1H, d, J=8.6 Hz), 7.81 (1H, t, J=5.9 Hz), 11.54 (1H, br), 12.50 (1H, br).

EXAMPLE 151

N-(4-Propylphenyl)-3-(diphenylmethyl)-1-(2-pyrrolidinylethyl)indole-2-carboxamide hydrochloride (Compound 150 hydrochloride)

$^1$H-NMR(CDCl$_3$) δ(ppm): 0.93 (3H, t, J=7.4 Hz), 1.5–1.65 (2H, m), 2.05–2.35 (4H, m), 2.56 (2H, t, J=7.6 Hz), 2.9–3.05 (2H, m), 3.6–3.85 (4H, m), 4.85–4.95 (2H, m), 6.07 (1H, s), 6.79 (1H, d, J=8.2 Hz), 6.90 (1H, t, J=7.4 Hz), 7.05–7.2 (6H, m), 7.2–7.4 (9H, m), 7.48 (1H, s), 7.87 (1H, t, J=8.6 Hz), 12.91 (1H, br).

EXAMPLE 152

Ethyl 1-(3-dimethylaminopropyl)-3-(diphenylmethyl)indole-2-carboxylate (Compound 151)

Substantially the same procedure as in Example 89 was repeated using ethyl 3-(diphenylmethyl)indole-2-carboxylate (40.0 g, 113 mmol) obtained in Reference Example 4 and 3-dimethylaminopropylchloride hydrochloride (19.6 g, 124 mmol) to give 55.4 g (quantitative) of the title compound.

$^1$H-NMR(CDCl$_3$) δ(ppm): 1.35 (3H, t, J=7.3 Hz), 2.05–2.25 (2H, m), 2.39 (6H, s), 2.40–2.65 (2H, br), 4.33 (2H, q, J=7.3 Hz), 4.56 (2H, t, J=6.9 Hz), 6.57 (1H, s), 6.83–6.94 (2H, m), 7.16–7.43 (12H, m).

EXAMPLE 153

1-(3-Dimethylaminopropyl)-3-(diphenylmethyl) indole-2-carboxylic acid (Compound 152)

Substantially the same procedure as in Example 93 was repeated using Compound 151 (55.4 g) obtained in Example 152 to give 48.3 g (yield: 94%) of the title compound.

$^1$H-NMR(DMSO-d$_6$) δ(ppm): 2.28 (2H, t, J=6.3 Hz), 2.55 (6H, s), 2.68 (2H, t, J=5.9 Hz), 4.59 (2H, t, J=6.3 Hz), 6.74 (1H, s), 6.86 (1H, t, J=7.6 Hz), 7.02 (1H, d, J=7.9 Hz), 7.12–7.31 (11H, m), 7.52 (1H, d, J=8.3 Hz).

In the following Examples 154 to 159, substantially the same procedure as in Example 94 was repeated using Compound 152 in place of Compound 93 and using corresponding amines in place of propylamine to give the desired compounds.

EXAMPLE 154

N-Isopropyl-1-(3-dimethylaminopropyl)-3-(diphenylmethyl)indole-2-carboxamide (Compound 153)

$^1$H-NMR(CDCl$_3$) δ(ppm): 1.07 (6H, d, J=6.6 Hz), 1.94–2.05 (2H, m), 2.16 (6H, s), 2.23 (2H, t, J=6.9 Hz), 4.14–4.26 (1H, m), 4.41 (2H, t, J=7.3 Hz), 5.93 (1H, s), 5.96 (1H, s), 6.77–6.87 (2H, m), 7.15–7.38 (12H, m).

EXAMPLE 155

N-Propyl-1-(3-dimethylaminopropyl)-3-(diphenylmethyl)indole-2-carboxamide (Compound 154)

$^1$H-NMR(CDCl$_3$) δ(ppm): 0.83 (3H, t, J=7.3 Hz), 1.38–1.51 (2H, m), 1.96–2.06 (2H, m), 2.15 (6H, s), 2.23 (2H, t, J=6.9 Hz), 3.23 (2H, dt, J=6.9, 7.3 Hz), 4.40 (2H, t, J=6.9 Hz), 5.99 (1H, s), 6.37 (1H, t, J=5.6 Hz), 6.84–6.86 (1H, m), 7.15–7.39 (12H, m).

EXAMPLE 156

N-Cyclooctyl-1-(3-dimethylaminopropyl)-3-(diphenylmethyl)indole-2-carboxamide (Compound 155)

$^1$H-NMR(CDCl$_3$) δ(ppm): 1.25–1.60 (14H, m), 1.94–2.04 (2H, m), 2.17 (6H, s), 2.24 (2H, t, J=6.9 Hz), 4.06–4.19 (1H, m), 4.41 (2H, t, J=6.9 Hz), 5.93 (1H, s), 5.97 (1H, s), 6.77–6.83 (2H, m), 7.15–7.39 (12H, m).

EXAMPLE 157

N-(2-piperidinoethyl)-1-(3-dimethylaminopropyl)-3-(diphenylmethyl)indole-2-carboxamide (Compound 156)

$^1$H-NMR(CDCl$_3$) δ(ppm): 1.30–1.45 (6H, m), 1.95–2.05 (2H, m), 2.16 (6H, s), 2.24 (2H, t, J=7.3 Hz), 2.20–2.30 (4H, m), 2.38 (2H, t, J=6.3 Hz), 3.44 (2H, dt, J=6.3, 5.9 Hz), 4.39 (2H, t, J=6.9 Hz), 6.05 (1H, s), 6.66 (1H, t, J=5.0 Hz), 6.83–6.98 (2H, m), 7.15–7.39 (12H, m).

EXAMPLE 158

N-(4-Propylphenyl)-1-(3-dimethylaminopropyl)-3-(diphenylmethyl)indole-2-carboxamide (Compound 157)

$^1$H-NMR(CDCl$_3$) δ(ppm): 0.93 (3H, t, J=7.3 Hz), 1.55–1.69 (2H, m), 1.99–2.09 (2H, m), 2.13 (6H, s), 2.22 (2H, t, J=6.9 Hz), 2.55 (2H, t, J=7.6 Hz), 4.47 (2H, t, J=7.3 Hz), 6.09 (1H, s), 6.87 (2H, d, J=3.6 Hz), 7.09–7.43 (17H, m), 7.99 (1H, s).

EXAMPLE 159

N-[3-(2-Oxopyrrolidinyl)propyl]-1-(3-dimethylaminopropyl)-3-(diphenylmethyl)indole-2-carboxamide (Compound 158)

$^1$H-NMR(CDCl$_3$) δ(ppm): 1.63–1.73 (2H, m), 1.95–2.15 (4H, m), 2.21 (6H, s), 2.25–2.40 (2H, br), 2.36 (2H, t, J=7.9 Hz), 3.20–3.32 (4H, m), 3.36 (2H, t, J=6.9 Hz), 4.38 (2H, t, J=6.9 Hz), 6.02 (1H, s), 6.83–6.91 (2H, m), 7.16–7.38 (12H, m).

EXAMPLE 160

Ethyl 3-(diphenylmethyl)-1-(3-pyrrolidinylpropyl)indole-2-carboxylate (Compound 159)

To a solution of ethyl 3-(diphenylmethyl)-1-(3-chloropropyl)indole-2-carboxylate (39.64 g, 91.8 mmol) obtained in Reference Example 6 in 400 ml of ethanol was added pyrrolidine (41.4 ml, 496 mmol) with stirring at room temperature, followed by heating under reflux for 20 hours. Water and a saturated aqueous solution of sodium bicarbonate were added to the reaction solution followed by extraction with ethyl acetate. The resulting organic layer was washed successively with water and a saturated aqueous solution of sodium chloride, and dried over magnesium sulfate, and the solvent was distilled off under reduced pressure to give 46.5 g (quantitative) of the title compound.

$^1$H-NMR(CDCl$_3$) δ(ppm): 1.35 (3H, t, J=7.3 Hz), 1.70–1.95 (4H, m), 1.74–1.79 (2H, m), 2.35–2.55 (6H, m), 4.33 (2H, q, J=6.9 Hz), 4.56 (2H, t, J=6.9 Hz), 6.58 (1H, s), 6.81–6.93 (2H, m), 7.16–7.28 (11H, m), 7.42 (1H, d, J=8.3 Hz).

EXAMPLE 161

3-(Diphenylmethyl)-1-(3-pyrrolidinylpropyl)indole-2-carboxylic acid (Compound 160)

Substantially the same procedure as in Example 93 was repeated using Compound 159 (46.5 g) obtained in Example 160 to give 34.1 g (yield: 78%) of the title compound.

$^1$H-NMR(CDCl$_3$) δ(ppm): 1.60–1.75 (4H, m), 2.25–2.40 (2H, m), 2.45–2.70 (4H, br), 2.70 (2H, t, J=5.6 Hz), 4.62 (2H, t, J=5.6 Hz), 6.77 (1H, s), 6.88–6.94 (1H, m), 7.09–7.32 (13H, m).

In the following Examples 162 to 167, substantially the same procedure as in Example 94 was repeated using Compound 160 in place of Compound 93 and using corresponding amines in place of propylamine to give the desired compounds.

EXAMPLE 162

N-Isopropyl-3-(diphenylmethyl)3–1(3-pyrrolidinylpropyl)indole-2-carboxamide (Compound 161)

$^1$H-NMR(CDCl$_3$) δ(ppm): 1.07 (6H, d, J=6.6 Hz), 1.70–1.80 (4H, m), 2.01–2.12 (2H, m), 2.45–2.55 (6H, m), 4.13–4.26 (1H, m), 4.43 (2H, t, J=6.9 Hz), 5.72 (1H, d, J=7.9 Hz), 5.94 (1H, s), 6.76–6.86 (2H, m), 7.16–7.40 (12H, m).

EXAMPLE 163

N-Propyl-3-(diphenylmethyl)-1-(3-pyrrolidinylpropyl)indole-2-carboxamide (Compound 162)

$^1$H-NMR(CDCl$_3$) δ(ppm): 0.83 (3H, t, J=7.3 Hz), 1.38–1.52 (2H, m), 1.65–1.75 (4H, m), 2.00–2.11 (2H, m), 2.35–2.45 (6H, m), 3.27 (2H, dt, J=6.9, 5.9 Hz), 4.42 (2H, t, J=6.9 Hz), 5.98 (1H, s), 6.38 (1H, t, J=5.3 Hz), 6.81–6.88 (2H, m), 7.15–7.39 (12H, m).

EXAMPLE 164

N-Cyclooctyl-3-(diphenylmethyl)-1-(3-pyrrolidinylpropyl)indole-2-carboxamide (Compound 163)

$^1$H-NMR(CDCl$_3$) δ(ppm): 1.25–1.85 (18H, m), 1.99–2.10 (2H, m), 2.40–2.55 (6H, m), 4.07–4.17 (1H, m), 4.44 (2H, t, J=6.9 Hz), 5.79 (1H, d, J=7.9 Hz), 5.95 (1H, s), 6.76–6.85 (2H, m), 7.14–7.40 (12H, m).

EXAMPLE 165

N-(2-Piperidinoethyl)-3-(diphenylmethyl)-1-(3-pyrrolidinylpropyl)indole-2-carboxamide (Compound 164)

$^1$H-NMR(CDCl$_3$) δ(ppm): 1.30–1.45 (6H, m), 1.70–1.80 (4H, m), 2.04–2.12 (2H, m), 2.25–2.35 (4H, m), 2.39 (2H, t, J=6.3 Hz), 2.40–2.50 (6H, m), 3.43 (2H, dt, J=6.3, 5.9 Hz), 4.42 (2H, t, J=6.9 Hz), 6.04 (1H, s), 6.71 (1H, t, J=5.3 Hz), 6.83–6.98 (2H, m), 7.15–7.39 (12H, m).

EXAMPLE 166

N-(4-Propylphenyl)-3-(diphenylmethyl)-1-(3-pyrrolidinylpropyl)indole-2-carboxamide (Compound 165)

$^1$H-NMR(CDCl$_3$) δ(ppm): 0.93 (3H, t, J=7.3 Hz), 1.55–1.75 (6H, m), 2.03–2.14 (2H, m), 2.35–2.50 (6H, m), 2.55 (2H, t, J=7.3 Hz), 4.49 (2H, t, J=7.3 Hz), 6.08 (1H, s), 6.84–6.90 (2H, m), 7.08–7.43 (16H, m), 7.88 (1H, s).

EXAMPLE 167

N-[3-(2-Oxopyrrolidinyl)propyl]-3-(diphenylmethyl)-1-(3-pyrrolidinylpropyl)indole-2-carboxamide (Compound 166)

$^1$H-NMR(CDCl$_3$) δ(ppm): 1.50–1.90 (8H, m), 1.95–2.25 (4H, m), 2.30–2.65 (4Hr br), 2.36 (2H, t, J=7.9 Hz), 3.20–3.31 (4H, m), 3.37 (2H, t, J=6.9 Hz), 4.40 (2H, t, J=6.9 Hz), 6.01 (1H, s), 6.83–6.92 (2H, m), 7.16–7.38 (12H, m).

EXAMPLE 168

Ethyl 1-(4-dimethylaminobutyl)-3-(diphenylmethyl)indole-2-carboxylate (Compound 167)

Substantially the same procedure as in Example 160 was repeated using ethyl 1-(4-chlorobutyl)-3-(diphenylmethyl)indole-2-carboxylate (39.84 g, 89.3 mmol) obtained in Reference Example 7 and an aqueous solution of dimethylamine (50%, 90 ml, 893 mmol) to give 29.2 g (yield: 72%) of the title compound.

$^1$H-NMR(CDCl$_3$) δ(ppm): 1.35 (3H, t, J=6.9 Hz), 1.40–1.60 (2H, m), 1.70–1.90 (2H, m), 2.18 (6H, s), 2.26 (2H, t, J=7.6 Hz), 4.34 (2H, q, J=7.3 Hz), 4.50 (2H, t, J=7.6 Hz), 6.57 (1H, s), 6.81–6.93 (2H, m), 7.16–7.38 (12H, m).

EXAMPLE 169

1-(4-Dimethylaminobutyl)-3-(diphenylmethyl)indole-2-carboxylic acid (Compound 168)

Substantially the same procedure as in Example 93 was repeated using Compound 167 (29.2 g) obtained in Example 168 to give 22.8 g (yield: 83%) of the title compound.

$^1$H-NMR(CDCl$_3$) δ(ppm): 1.50–1.70 (2H, m), 1.75–1.95 (2H, m), 2.42 (6H, s), 2.74 (2H, t, J=7.6 Hz), 4.69 (2H, t, J=6.3 Hz), 6.79 (1H, s), 6.85 (1H, t, J=6.9 Hz), 7.01 (1H, d, J=8.3 Hz), 7.10–7.28 (12H, m).

In the following Examples 170 to 174, substantially the same procedure as in Example 94 was repeated using Compound 168 in place of Compound 93 and using corresponding amines in place of propylamine to give the desired compounds.

EXAMPLE 170

N-Isopropyl-1-(4-dimethylaminobutyl)-3-(diphenylmethyl)indole-2-carboxamide (Compound 169)

$^1$H-NMR(CDCl$_3$) δ(ppm): 1.69 (6H, d, J=6.6 Hz), 1.42–1.53 (2H, m), 1.76–1.88 (2H, m), 2.17 (6H, s), 2.25 (2H, t, J=7.3 Hz), 4.13–4.26 (1H, m), 4.38 (2H, t, J=7.6 Hz), 5.57 (1H, d, J=7.9 Hz), 5.92 (1H, s), 6.76–6.86 (2H, m), 7.15–7.36 (12H, m).

EXAMPLE 171

N-Propyl-1-(4-dimethylaminobutyl)-3-(diphenylmethyl)indole-2-carboxamide (Compound 170)

$^1$H-NMR(CDCl$_3$) δ(ppm): 0.83 (3H, t, J=7.3 Hz), 1.37–1.52 (4H, m), 1.76–1.87 (2H, m), 2.16 (6H, s), 2.23 (2H, t, J=7.6 Hz), 3.28 (2H, dt, J=6.9, 5.9 Hz), 4.39 (2H, t, J=7.3 Hz), 5.73 (1H, t, J=5.6 Hz), 5.94 (1H, s), 6.83–6.84 (2H, m), 7.16–7.36 (12H, m).

EXAMPLE 172

N-Cyclooctyl-1-(4-dimethylaminobutyl)-3-(diphenylmethyl)indole-2-carboxamide (Compound 171)

$^1$H-NMR(CDCl$_3$) δ(ppm): 1.30–1.90 (18H, m), 2.16 (6H, s), 2.25 (2H, t, J=7.3 Hz), 4.11–4.16 (1H, m), 4.39 (2H, t, J=7.3 Hz), 5.68 (1H, d, J=7.9 Hz), 5.94 (1H, s), 6.76–6.85 (2H, m), 7.15–7.35 (12H, m).

EXAMPLE 173

N-(4-Propylphenyl)-1-(4-dimethylaminobutyl)-3-(diphenylmethyl)indole-2-carboxamide (Compound 172)

$^1$H-NMR(CDCl$_3$) δ(ppm): 0.93 (3H, t, J=7.3 Hz), 1.44–1.55 (2H, m), 1.55–1.68 (2H, m), 1.75–1.95 (2H, m), 2.14 (6H, s), 2.25 (2H, t, J=7.3 Hz), 2.55 (2H, t, J=7.6 Hz), 4.43 (2H, t, J=7.3 Hz), 6.04 (1H, s), 6.81–6.89 (2H, m), 7.08–7.39 (16H, m), 7.44 (1H, s).

EXAMPLE 174

N-[3-(2-Oxopyrrolidinyl)propyl]-1-(4-dimethylaminobutyl)-3-(diphenylmethyl)indole-2-carboxamide (Compound 173)

$^1$H-NMR(CDCl$_3$) δ(ppm): 1.43–1.54 (2H, m), 1.62–1.72 (2H, m), 1.76–1.87 (2H, m), 1.96–2.06 (2H, m), 2.18 (6H, s), 2.26 (2H, t, J=7.6 Hz), 2.36 (2H, t, J=7.6 Hz), 3.19–3.32 (4H, m), 3.35 (2H, t, J=6.9 Hz), 4.35 (2H, t, J=7.6 Hz), 5.95 (1H, s), 6.14 (1H, t, J=5.9 Hz), 6.85 (2H, d, J=4.0 Hz), 7.16–7.35 (12H, m).

EXAMPLE 175

Ethyl 3-(diphenylmethyl)-1-(4-pyrrolidinylbutyl)indole-2-carboxylate (Compound 174)

Substantially the same procedure as in Example 160 was repeated using ethyl 1-(4-chlorobutyl)-3-(diphenylmethyl)indole-2-carboxylate (40.0 g, 89.7 mmol) obtained in Reference Example 7 and pyrrolidine (40.4 ml, 484 mmol) to give 43.0 g (quantitative) of the title compound.

$^1$H-NMR(CDCl$_3$) δ(ppm): 1.45–1.65 (2H, m), 1.65–1.90 (6H, m), 2.35–2.55 (6H, m), 4.33 (2H, q, J=7.3 Hz), 4.50 (2H, t, J=7.3 Hz), 6.57 (1H, s), 6.81–6.93 (2H, m), 7.16–7.38 (12H, m).

EXAMPLE 176

3-(Diphenylmethyl)-1-(4-pyrrolidinylbutyl)indole-2-carboxylic acid (Compound 175)

Substantially the same procedure as in Example 93 was repeated using Compound 174 (43.0 g) obtained in Example 175 to give 25.5 g (yield: 63%) of the title compound.

¹H-NMR(CDCl₃) δ(ppm): 1.60–1.95 (8H, m), 2.76–2.82 (2H, t, J=7.9 Hz), 2.70–3.15 (4H, br), 4.66 (2H, t, J=6.3 Hz), 6.77 (1H, s), 6.83 (1H, t, J=6.9 Hz), 7.36 (1H, d, J=7.9 Hz), 7.10–7.28 (12H, m).

In the following Examples 177 to 181, substantially the same procedure as in Example 94 was repeated using Compound 175 in place of Compound 93 and using corresponding amines in place of propylamine to give the desired compounds.

EXAMPLE 177

N-Isopropyl-3-(diphenylmethyl)-1-(4-pyrrolidinylbutyl)indole-2-carboxamide (Compound 176)

¹H-NMR(CDCl₃) δ(ppm): 1.07 (6H, d, J=6.6 Hz), 1.50–1.70 (2H, m), 1.70–1.95 (6H, m), 2.45–2.65 (6H, m), 4.13–4.25 (1H, m), 4.37 (2H, t, J=7.3 Hz), 5.57 (1H, d, J=7.9 Hz), 5.92 (1H, s), 6.76–6.86 (2H, m), 7.15–7.36 (12H, m).

EXAMPLE 178

N-Propyl-3-(diphenylmethyl)-1-(4-pyrrolidinylbutyl)indole-2-carboxamide (Compound 177)

¹H-NMR(CDCl₃) δ(ppm): 0.83 (3H, t, J=7.6 Hz), 1.35–1.60 (4H, m), 1.70–1.95 (6H, m), 2.35–2.55 (6H, m), 3.28 (2H, dt, J=6.6, 7.3 Hz), 4.38 (2H, t, J=7.3 Hz), 5.74 (1H, t, J=5.6 Hz), 5.93 (1H, s), 6.83–6.88 (2H, m), 7.16–7.36 (12H, m).

EXAMPLE 179

N-Cyclooctyl-3-(diphenylmethyl)-1-(4-pyrrolidinylbutyl)indole-2-carboxamide (Compound 178)

¹H-NMR(CDCl₃) δ(ppm): 1.25–1.95 (22H, m), 2.35–2.60 (6H, m), 4.05–4.20 (1H, m), 4.38 (2H, t, J=7.3 Hz), 5.67 (1H, d, J=7.9 Hz), 5.94 (1H, s), 6.76–6.85 (2H, m), 7.15–7.36 (12H, m).

EXAMPLE 180

N-(4-Propylphenyl)-3-(diphenylmethyl)-1-(4-pyrrolidinylbutyl)indole-2-carboxamide (Compound 179)

¹H-NMR(CDCl₃) δ(ppm): 0.93 (3H, t, J=7.3 Hz), 1.50–1.80 (10H, m), 1.80–1.95 (2H, m), 2.40–2.60 (6H, m), 4.43 (2H, t, J=7.3 Hz), 6.04 (1H, s), 6.81–6.90 (2H, m), 7.08–7.39 (16H, m), 7.45 (1H, m).

EXAMPLE 181

N-[3-(2-Oxopyrrolidinyl)propyl]-3-(diphenylmethyl)-1-(4-pyrrolidinylbutyl)indole-2-carboxamide (Compound 180)

¹H-NMR(CDCl₃) δ(ppm): 1.50–1.95 (12H, m), 2.02 (2H, m), 2.36 (2H, t, J=7.6 Hz), 2.35–2.70 (4H, br), 3.19–3.32 (4H, m), 3.36 (2H, t, J=6.9 Hz), 4.34 (2H, t, J=7.3 Hz), 5.96 (1H, s), 6.24 (1H, br), 6.85–6.87 (2H, m), 7.17–7.35 (12H, m).

EXAMPLE 182

Ethyl 3-[bis(4-chlorophenyl)methyl]-1-(2-dimethylaminoethyl)indole-2-carboxylate (Compound 181)

Substantially the same procedure as in Example 89 was repeated using ethyl 3-[bis(4-chlorophenyl)methyl]indole-2-carboxylate (5.0 g, 11.8 mmol) obtained in Reference Example 8 and 2-dimethylaminoethylchloride hydrochloride (1.78 g, 12.4 mmol) to give 6.3 g (quantitative) of the title compound.

¹H-NMR(CDCl₃) δ(ppm): 1.36 (3H, t, J=7.1 Hz), 2.33 (6H, s), 2.66 (2H, dd, J=7.6, 7.9 Hz), 4.36 (2H, q, J=7.1 Hz), 4.59 (2H, dd, J=7.6, 7.9 Hz), 6.49 (1H, s), 6.85–6.95 (2H, m), 7.15 (4H, d, J=7.7 Hz), 7.2–7.35 (5H, m), 7.41 (1H, d, J=8.6 Hz).

EXAMPLE 183

3-[Bis(4-chlorophenyl)methyl]-1-(2-dimethylaminoethyl)indole-2-carboxylic acid (Compound 182)

Substantially the same procedure as in Example 93 was repeated using Compound 181 (6.3 g) obtained in Example 182 to give 4.2 g (yield: 77%) of the title compound.

¹H-NMR(CDCl₃) δ(ppm): 2.60 (6H, s), 3.34 (2H, t, J=6.4 Hz), 4.87 (2H, t, J=6.4 Hz), 6.77 (1H, s), 6.9–7.0 (1H, m), 7.04 (1H, d, J=7.9 Hz), 7.1–7.2 (8H, m), 7.2–7.35 (2H, m).

In the following Examples 184 and 185, substantially the same procedure as in Example 94, and then substantially the same procedure as in Example 135 were repeated using Compound 182 in place of Compound 93 and using corresponding amines in place of propylamine to give the desired compounds.

EXAMPLE 184

N-Propyl-3-[bis(4-chlorophenyl)methyl]-1-(2-dimethylaminoethyl)indole-2-carboxamide hydrochloride (Compound 183 hydrochloride)

¹H-NMR(CDCl₃) δ(ppm): 0.88 (3H, t, J=7.3 Hz), 1.4–1.55 (2H, m), 2.90 (3H, s), 2.91 (3H, s), 3.28 (2H, dt, J=5.9, 7.3 Hz), 3.5–3.6 (2H, m), 4.8–4.9 (2H, m), 5.72 (1H, t, J=5.9 Hz), 5.87 (1H, s), 6.80 (1H, d, J=7.9 Hz), 6.91 (1H, t, J=7.3 Hz), 7.06 (4H, d, J=8.2 Hz), 7.25–7.4 (5H, m), 7.81 (1H, d, J=8.6 Hz), 13.1 (1H, br).

EXAMPLE 185

N-(4-propylphenyl)-3-[bis(4-chlorophenyl)methyl]-1-(2-dimethylaminoethyl)indole-2-carboxamide hydrochloride (Compound 184 hydrochloride)

¹H-NMR(CDCl₃) δ(ppm): 0.94 (3H, t, J=7.3 Hz), 1.55–1.7 (2H, m), 2.57 (2H, t, J=7.6 Hz), 2.83 (3H, s), 2.85 (3H, s), 3.5–3.6 (2H, m), 4.65–4.75 (2H, m), 6.02 (1H, s), 6.78 (1H, d, J=8.3 Hz), 6.94 (1H, t, J=7.5 Hz), 7.05–7.4 (13H, m), 7.8–7.9 (2H, m), 12.9 (1H, br).

EXAMPLE 186

Ethyl 3-[bis(4-methylphenyl)methyl]-1-(2-piperidinoethyl)indole-2-carboxylate (Compound 185)

Substantially the same procedure as in Example 89 was repeated using ethyl 3-[bis(4-methylphenyl)methyl]-indole-2-carboxylate (5.0 g, 13.04 mmol) obtained in Reference Example 9 and 2-piperidinoethylchloride hydrochloride (2.64 g, 14.34 mmol) to give 6.8 g (quantitative) of the title compound.

¹H-NMR(CDCl₃) δ(ppm): 1.37 (3H, t, J=7.3 Hz), 1.4–1.5 (2H, m), 1.5–1.6 (4H, m), 2.30 (6H, s), 2.4–2.55 (4H, m), 2.6–2.7 (2H, m), 4.34 (2H, q, J=7.3 Hz), 4.55–4.65 (2H, m), 6.49 (1H, s), 6.8–6.9 (1H, m), 6.95–7.1 (9H, m), 7.2–7.3 (1H, m), 7.40 (1H, d, J=8.6 Hz).

EXAMPLE 187

3-[Bis(4-methylphenyl)methyl]-1-(2-piperidinoethyl)indole-2-carboxylic acid (Compound 186)

Substantially the same procedure as in Example 93 was repeated using Compound 185 (6.8 g) obtained in Example 186 to give 5.1 g (yield: 84%) of the title compound.

$^1$H-NMR(CDCl$_3$) δ(ppm): 1.4–1.7 (6H, m), 2.27 (6H, s), 2.3–2.6 (4H, m), 3.05–3.15 (2H, m), 4.65–4.75 (2H, m), 6.70 (1H, s), 6.85–6.95 (1H, m), 7.00 (4H, d, J=7.9 Hz), 7.1–7.2 (7H, m).

In the following Examples 188 to 190, substantially the same procedure as in Example 94, and then, if necessary, substantially the same procedure as in Example 135 were repeated using Compound 186 in place of Compound 93 and using corresponding amines in place of propylamine to give the desired compounds.

EXAMPLE 188

N-(3-Morpholinopropyl)-3-(bis(4-methylphenyl)methyl]-1-(2-piperidinoethyl)indole-2-carboxamide 2 hydrochloride (Compound 187 2 hydrochloride)

$^1$H-NMR(CDCl$_3$) δ(ppm): 1.8–2.0 (6H, m), 2.1–2.25 (4H, m), 2.32 (6H, s), 2.75–3.1 (4H, m), 3.3–3.65 (8H, m), 3.9–4.0 (2H, m), 4.1–4.25 (2H, m), 4.9–5.0 (2H, m), 5.86 (1H, s), 6.71 (1H, br), 6.8–6.95 (2H, m), 7.03 (4H, d, J=8.1 Hz), 7.09 (4H, d, J=8.1 Hz), 7.2–7.3 (1H, m), 7.61 (1H, d, J=8.3 Hz), 12.0 (1H, br), 12.5 (1H, br).

EXAMPLE 189

N-Isopropyl-3-[bis(4-methylphenyl)methyl]-1-(2-piperidinoethyl)indole-2-carboxamide hydrochloride (Compound 188 hydrochloride)

$^1$H-NMR(CDCl$_3$) δ(ppm): 1.07 (6H, d, J=6.6 Hz), 1.85–2.0 (4H, m), 2.25–2.4 (2H, m), 2.33 (6H, s), 2.7–2.9 (2H, m), 3.45–3.65 (4H, m), 4.05–4.2 (1H, m), 4.85–4.95 (2H, m), 5.70 (1H, d, J=7.9 Hz), 5.83 (1H, s), 6.78 (1H, d, J=7.9 Hz), 6.88 (1H, t, J=7.3 Hz), 7.01 (4H, d, J=8.1 Hz), 7.10 (4H, d, J=8.1 Hz), 7.25–7.3 (1H, m), 7.87 (1H, d, J=8.3 Hz), 12.57 (1H, br).

EXAMPLE 190

N-[3-(1-Imidazolyl)propyl]-3-[bis(4-methylphenyl)methyl]-1-(2-piperidinoethyl)indole- 2-carboxamide (Compound 189)

$^1$H-NMR(CDCl$_3$) δ(ppm): 1.3–1.45 (2H, m), 1.65–1.8 (4H, m), 1.9–2.0 (2H, m), 2.2–2.3 (4H, m), 2.30 (6H, s), 2.80 (2H, t, J=6.3 Hz), 3.3–3.4 (2H, m), 3.89 (2H, t, J=7.2 Hz), 4.42 (2H, t, J=6.3 Hz), 6.14 (1H, s), 6.85–7.0 (3H, m), 7.0–7.1 (9H, m), 7.15–7.25 (1H, m), 7.33 (1H, d, J=8.2 Hz), 7.40 (1H, s), 8.36 (1H, br).

EXAMPLE 191

Ethyl 3-[bis(4-methylphenyl)methyl]-1-(2-pyrrolidinylethyl)indole-2-carboxylate (Compound 190)

Substantially the same procedure as in Example 89 was repeated using ethyl 3-[bis(4-methylphenyl)methyl]-indole-2-carboxylate (5.0 g, 13.04 mmol) obtained in Reference Example 9 and 2-pyrrolidinylethylchloride hydrochloride (2.45 g, 14.34 mmol) to give 6.7 g (quantitative) of the title compound.

$^1$H-NMR(CDCl$_3$) δ(ppm): 1.37 (3H, t, J=7.3 Hz), 1.7–1.9 (4H, m), 2.31 (6H, s), 2.6–2.7 (4H, m), 2.8–2.9 (2H, m), 4.34 (2H, q, J=7.3 Hz), 4.6–4.7 (2H, m), 6.49 (1H, s), 6.8–6.9 (1H, m), 6.95–7.15 (9H, m), 7.2–7.3 (1H, m), 7.41 (1H, d, J=8.6 Hz).

EXAMPLE 192

3-[Bis(4-methylphenyl)methyl]-1-(2-pyrrolidinylethyl)indole-2-carboxylic acid (Compound 191)

Substantially the same procedure as in Example 93 was repeated using Compound 190 (6.7 g) obtained in Example 191 to give 4.7 g (yield: 79%) of the title compound.

$^1$H-NMR(DMSO-d$_6$+CD$_3$OD) δ(ppm): 1.75–1.9 (4H, m), 2.33 (6H, s), 2.85–3.0 (4H, m), 3.55–3.7 (2H, m), 4.75–4.9 (2H, m), 6.71 (1H, s), 6.93 (1H, t, J=7.4 Hz), 7.05–7.25 (10H, m), 7.54 (1H, d, J=7.3 Hz).

In the following Examples 193 to 195, substantially the same procedure as in Example 94, and then, if necessary, substantially the same procedure as in Example 135 were repeated using Compound 191 in place of Compound 93 and using corresponding amines in place of propylamine to give the desired compounds.

EXAMPLE 193

N-(3-Morpholinopropyl)-3-[bis(4-methylphenyl)methyl]-1-(2-pyrrolidinylethyl)indole-2-carboxamide 2 hydrochloride (Compound 192 2 hydrochloride)

$^1$H-NMR(CDCl$_3$) δ(ppm): 2.05–2.2 (6H, m), 2.33 (6H, s), 2.8–3.0 (6H, m), 3.3–3.45 (4H, m), 3.55–3.65 (2H, m), 3.8–3.9 (2H, m), 3.9–4.0 (2H, m), 4.15–4.3 (2H, m), 4.8–4.95 (2H, m), 5.86 (1H, s),Å@6.48 (1H, br), 6.8–6.95 (2H, m), 7.02 (4H, d, J=8.1 Hz), 7.10 (4H, d, J=8.1 Hz), 7.25–7.3 (1H, m), 7.62 (1H, d, J=8.6 Hz), 12.58 (1H, br), 12.72 (1H, br).

EXAMPLE 194

N-Isopropyl-3-[bis(4-methylphenyl)methyl]-1-(2-pyrrolidinylethyl)indole-2-carboxamide hydrochloride (Compound 193 hydrochloride)

$^1$H-NMR(CDCl$_3$) δ(ppm): 1.07 (6H, d, J=6.6 Hz), 2.0–2.3 (4H, m), 2.33 (6H, s), 2.85–3.05 (2H, m), 3.55–3.7 (2H, m), 3.7–3.85 (2H, m), 4.05–4.2 (1H, m), 4.8–4.9 (2H, m), 5.71 (1H, d, J=7.9 Hz), 5.84 (1H, s), 6.78 (1H, d, J=7.9 Hz), 6.88 (1H, t, J=7.6 Hz), 7.01 (4H, d, J=8.3 Hz), 7.10 (4H, d, J=8.3 Hz), 7.25–7.35 (1H, m), 7.79 (1H, d, J=8.6 Hz), 12.86 (1H, br).

EXAMPLE 195

N-[3-(1-Imidazolyl)propyl]-3-[bis(4-methylphenyl)methyl]-1-(2-pyrrolidinylethyl)indole-2-carboxamide (Compound 194)

$^1$H-NMR(CDCl$_3$) δ(ppm): 1.55–1.7 (4H, m), 1.85–2.0 (2H, m), 2.29 (6H, s), 2.3–2.4 (4H, m), 3.00 (2H, t, J=6.3 Hz), 3.33 (2H, dd, J=6.0, 6.9 Hz), 3.83 (2H, t, J=7.3 Hz), 4.43 (2H, t, J=6.3 Hz), 6.15 (1H, s), 6.84 (1H, s), 6.8–7.0

(2H, m), 7.0–7.15 (9H, m), 7.15–7.25 (1H, m), 7.32 (1H, d, J=8.3 Hz), 7.38 (1H, s), 8.25 (1H, br).

EXAMPLE 196

Ethyl 3-[bis(4-methylphenyl)methyl]-1-(2-morpholinoethyl)indole-2-carboxylate (Compound 195)

Substantially the same procedure as in Example 89 was repeated using ethyl 3-[bis(4-methylphenyl)methyl]-indole-2-carboxylate (5.0 g, 13.04 mmol) obtained in Reference Example 9 and 2-morpholinoethylchloride hydrochloride (2.67 g, 14.34 mmol) to give 6.8 g (quantitative) of the title compound.

$^1$H-NMR(CDCl$_3$) δ(ppm): 1.37 (3H, t, J=7.3 Hz), 2.31 (6H, s), 2.45–2.55 (4H, m), 2.65–2.75 (2H, m), 3.6–3.7 (4H, m), 4.34 (2H, q, J=7.3 Hz), 4.6–4.7 (2H, m), 6.47 (1H, s), 6.8–6.9 (1H, m), 6.95–7.15 (9H, m), 7.2–7.3 (1H, m), 7.3–7.4 (1H, m).

EXAMPLE 197

3-[Bis(4-methylphenyl)methyl]-1-(2-morpholinoethyl)indole-2-carboxylic acid (Compound 196)

Substantially the same procedure as in Example 93 was repeated using Compound 195 (6.8 g) obtained in Example 196 to give 4.5 g (yield: 74%) of the title compound.

$^1$H-NMR(CDCl$_3$) δ(ppm): 2.29 (6H, s), 2.3–2.4 (4H, m), 3.02 (2H, t, J=5.6 Hz), 3.45–3.55 (4H, m), 4.62 (2H, t, J=5.6 Hz), 6.56 (1H, s), 6.9–7.0 (1H, m), 7.02 (4H, d, J=8.1 Hz), 7.12 (4H, d, J=8.1 Hz), 7.2–7.3 (3H, m).

In the following Examples 198 to 200, substantially the same procedure as in Example 94, and then, if necessary, substantially the same procedure as in Example 135 were repeated using Compound 196 in place of Compound 93 and using corresponding amines in place of propylamine to give the desired compounds.

EXAMPLE 198

N-(3-Morpholinopropyl)-3-[bis(4-methylphenyl)methyl]-1-(2-morpholinoethyl)indole-2-carboxamide 2 hydrochloride (Compound 197 2 hydrochloride)

$^1$H-NMR(CDCl$_3$) δ(ppm): 2.05–2.2 (2H, m), 2.32 (6H, s), 2.6–2.8 (2H, m), 2.9–3.3 (4H, m), 3.35–3.45 (4H, m), 3.45–3.6 (4H, m), 3.9–4.1 (4H, m), 4.1–4.3 (4H, m), 4.85–4.95 (2H, m), 5.88 (1H, s), 6.85–6.95 (2H, m), 7.0–7.15 (9H, m), 7.2–7.3 (1H, m), 7.68 (1H, d, J=8.2 Hz), 12.32 (1H, br), 12.75 (1H, br).

EXAMPLE 199

N-Isopropyl-3-[bis(4-methylphenyl)methyl]-1-(2-morpholinoethyl)indole-2-carboxamide hydrochloride (Compound 198 hydrochloride)

$^1$H-NMR(CDCl$_3$) δ(ppm): 1.07 (6H, d, J=6.6 Hz), 2.34 (6H, s), 2.95–3.15 (2H, m), 3.45–3.6 (4H, m), 3.95–4.05 (2H, m), 4.05–4.2 (1H, m), 4.30 (2H, t, J=11.9 Hz), 4.9–5.0 (2H, m), 5.72 (1H, d, J=7.6 Hz), 5.84 (1H, s), 6.79 (1H, d, J=8.2 Hz), 6.89 (1H, t, J=7.6 Hz), 7.01 (4H, d, J=8.2 Hz), 7.10 (4H, d, J=8.2 Hz), 7.25–7.3 (1H, m), 7.81 (1H, d, J=8.2 Hz), 13.55 (1H, br).

EXAMPLE 200

N-[3-(1-Imidazolyl)propyl]-3-[bis(4-methylphenyl)methyl]-1-(2-morpholinoethyl)indole-2-carboxamide (Compound 199)

$^1$H-NMR(CDCl$_3$) δ(ppm): 1.85–2.0 (2H, m), 2.32 (6H, s), 2.35–2.45 (4H, m), 2.78 (2H, t, J=6.9 Hz), 3.32 (2H, q, J=6.6 Hz), 3.5–3.6 (4H, m), 3.89 (2H, t, J=7.1 Hz), 4.48 (2H, t, J=6.9 Hz), 5.97 (1H, s), 6.76 (1H, t, J=6.6 Hz), 6.8–6.9 (3H, m), 7.0–7.15 (9H, m), 7.2–7.3 (1H, m), 7.35 (1H, d, J=8.3 Hz), 7.40 (1H, s).

EXAMPLE 201

Ethyl 3-[bis(4-methylphenyl)methyl]-1-(2-dimethylaminoethyl)indole-2-carboxylate (Compound 200)

Substantially the same procedure as in Example 89 was repeated using ethyl 3-[bis(4-methylphenyl)methyl]-indole-2-carboxylate (4.55 g, 11.86 mmol) obtained in Reference Example 9 and 2-dimethylaminoethylchloride hydrochloride (1.88 g, 13.05 mmol) to give 5.7 g (quantitative) of the title compound.

$^1$H-NMR(CDCl$_3$) δ(ppm): 1.37 (3H, t, J=6.9 Hz), 2.31 (6H, s), 2.37 (6H, s), 2.65–2.75 (2H, m), 4.34 (2H, q, J=6.9 Hz), 4.55–4.65 (2H, m), 6.49 (1H, s), 6.8–6.9 (1H, m), 6.9–7.15 (9H, m), 7.2–7.3 (1H, m), 7.40 (1H, d, J=8.3 Hz).

EXAMPLE 202

3-[Bis(4-methylphenyl)methyl]-1-(2-dimethylaminoethyl)indole-2-carboxylic acid (Compound 201)

Substantially the same procedure as in Example 93 was repeated using Compound 200 (5.7 g) obtained in Example 201 to give 3.5 g (yield: 68%) of the title compound.

$^1$H-NMR(CDCl$_3$) δ(ppm): 2.28 (6H, s), 2.37 (6H, s), 3.16 (2H, t, J=5.7 Hz), 4.71 (2H, t, J=5.7 Hz), 6.70 (1H, s), 6.85–6.95 (1H, m), 7.01 (4H, d, J=6.9 Hz), 7.15 (4H, d, J=6.9 Hz), 7.15–7.25 (3H, m).

In the following Examples 203 to 205, substantially the same procedure as in Example 94, and then, if necessary, substantially the same procedure as in Example 135 were repeated using Compound 201 in place of Compound 93 and using corresponding amines in place of propylamine to give the desired compounds.

EXAMPLE 203

N-(3-Morpholinopropyl)-3-[bis(4-methylphenyl)methyl]-1-(2-dimethylaminoethyl)indole-2-carboxamide 2 hydrochloride (Compound 202 2 hydrochloride)

$^1$H-NMR(CDCl$_3$) δ(ppm): 2.05–2.2 (2H, m), 2.31 (6H, s), 2.85–3.1 (4H, m), 2.93 (6H, s), 3.3–3.45 (4H, m), 3.5–3.6 (2H, m), 3.9–4.05 (2H, m), 4.05–4.25 (2H, m), 4.8–4.9 (2H, m), 5.89 (1H, s), 6.85–6.9 (2H, m), 7.05–7.1 (8H, m), 7.2–7.35 (2H, m), 7.65 (1H, d, J=8.3 Hz), 12.14 (2H, br).

EXAMPLE 204

N-Isopropyl-3-[bis(4-methylphenyl)methyl]-1-(2-dimethylaminoethyl)indole-2-carboxamide hydrochloride (Compound 203 hydrochloride)

$^1$H-NMR(CDCl$_3$) δ(ppm): 1.08 (6H, d, J=6.3 Hz), 2.34 (6H, s), 2.90 (3H, s), 2.92 (3H, s), 3.5–3.65 (2H, m), 4.05–4.2 (1H, m), 4.8–4.9 (2H, m), 5.72 (1H, d, J=7.9 Hz), 5.84 (1H, s), 6.79 (1H, d, J=7.3 Hz), 6.89 (1H, t, J=7.6 Hz), 7.00 (4H, d, J=7.9 Hz), 7.10 (4H, d, J=7.9 Hz), 7.25–7.3 (1H, m), 7.77 (1H, d, J=8.6 Hz), 13.05 (1H, br).

EXAMPLE 205

N-[3-(1-Imidazolyl)propyl]-3-[bis(4-methylphenyl)methyl]-1-(2-dimethylaminoethyl)indole-2-carboxamide (Compound 204)

$^1$H-NMR(CDCl$_3$) δ(ppm): 1.9–2.0 (2H, m), 2.17 (6H, s), 2.30 (6H, s), 2.78 (2H, t, J=6.3 Hz), 3.25–3.35 (2H, m), 3.82

(2H, t, J=7.1 Hz), 4.39 (2H, t, J=6.3 Hz), 6.11 (1H, s), 6.82 (1H, s), 6.85–6.95 (2H, m), 7.0–7.1 (9H, m), 7.2–7.35 (2H, m), 7.36 (1H, s), 7.6–7.7 (1H, m).

EXAMPLE 206

N-Propyl-1-(2-dimethylaminoethyl)-3-(4-hydroxybenzhydryl)indole-2-carboxamide hydrochloride (Compound 205 hydrochloride)

To a solution of N-propyl-3-(4-benzyloxybenzhydryl)-1-(2-dimethylaminoethyl)indole-2-carboxamide (1.95 g, 3.57 mmol) obtained in Reference Example 13 in 30 ml of ethanol was added 10% palladium on carbon (0.39 g, 50% aqueous), followed by stirring under a hydrogen atmosphere at 70° C. for 4.5 hours. The catalyst was filtered off and the solvent was distilled off under reduced pressure to give 1.65 g of a crude compound. The obtained crude product was crystallized from diethyl ether to give 1.42 g (yield :82%) of a free base of the title compound. Then, substantially the same procedure as in Example 135 was repeated using the free base (1.0 g) to give 0.92 g (yield: 86%) of the title compound.

$^1$H-NMR(CDCl$_3$) δ(ppm): 0.83 (3H, t, J=7.4 Hz), 1.35–1.5 (2H, m), 2.89 (6H, s), 3.2–3.35 (2H, m), 4.0–4.15 (2H, m), 4.7–4.85 (2H, m), 5.8–5.95 (2H, m), 6.38 (1H, s), 6.7–6.9 (4H, m), 6.96 (2H, d, J=8.6 Hz), 7.05–7.15 (2H, m), 7.15–7.35 (4H, m), 7.74 (1H, d, J=8.3 Hz), 12.73 (1H, br).

In the following Examples 207 to 215, substantially the same procedure as in Example 206 was repeated using Compounds obtained in Reference Examples 14 to 22 in place of N-propyl-3-(4-benzyloxybenzhydryl)-1-(2-dimethylaminoethyl)indole-2-carboxamide to give the desired compounds.

EXAMPLE 207

N-Isopropyl-1-(2-dimethylaminoethyl)-3-(4-hydroxybenzhydryl)indole-2-carboxamide hydrochloride (Compound 206 hydrochloride)

$^1$H-NMR(CDCl$_3$) δ(ppm): 1.06 (3H, d, J=6.3 Hz), 1.07 (3H, d, J=6.3 Hz), 2.89 (6H, s), 3.5–3.6 (2H, m), 4.0–4.15 (1H, m), 4.65–4.85 (2H, m), 5.74 (1H, d, J=7.6 Hz), 5.83 (1H, s), 6.36 (1H, s), 6.2–6.4 (4H, m), 6.96 (2H, d, J=8.6 Hz), 7.0–7.1 (2H, m), 7.1–7.35 (4H, m), 7.73 (1H, d, J=8.6 Hz), 12.74 (1H, br).

EXAMPLE 208

N-(4-Propylphenyl)-1-(2-dimethylaminoethyl)-3-(4-hydroxybenzhydryl)indole-2-carboxamide hydrochloride (Compound 207 hydrochloride)

$^1$H-NMR(CDCl$_3$) δ(ppm): 0.93 (3H, t, J=7.3 Hz), 1.5–1.65 (2H, m), 2.45–2.6 (2H, m), 2.90 (6H, s), 3.5–3.65 (2H, m), 4.3–4.45 (2H, m), 5.94 (1H, s), 5.98 (1H, s), 6.7–6.95 (4H, m), 7.00 (2H, d, J=8.3 Hz), 7.05–7.2 (6H, m), 7.2–7.35 (4H, m), 7.54 (1H, s), 7.82 (1H, d, J=8.6 Hz), 12.86 (1H, br).

EXAMPLE 209

N-(3-Morpholinopropyl)-1-(2-dimethylaminoethyl)-3-(4-hydroxybenzhydryl)indole-2-carboxamide 2 hydrochloride (Compound 208 2 hydrochloride)

$^1$H-NMR(DMSO-d$_6$) δ(ppm): 1.9–2.1 (2H, m), 2.85 (6H, s), 2.95–3.2 (4H, m), 3.2–3.5 (6H, m), 3.75–4.0 (4H, m), 4.55–4.7 (2H, m), 5.86 (1H, s), 6.67 (2H, d, J=8.3 Hz), 6.8–7.0 (4H, m), 7.1–7.3 (6H, m), 7.65 (1H, d, J=8.3 Hz), 8.47 (1H, t, J=5.6 Hz), 9.20 (1H, s), 10.81 (1H, br), 11.04 (1H, br).

EXAMPLE 210

N-[3-(2-Oxopyrrolidinyl)propyl]-1-(2-dimethylaminoethyl)-3-(4-hydroxybenzhydryl) indole-2-carboxamide hydrochloride (Compound 209 hydrochloride)

$^1$H-NMR(DMSO-d$_6$) δ(ppm): 1.6–1.75 (2H, m), 1.9–2.05 (2H, m), 2.25 (2H, t, J=7.9 Hz), 2.81 (6H, s), 3.15–3.3 (4H, m), 3.3–3.55 (4H, m), 4.5–4.65 (2H, m), 5.85 (1H, s), 6.66 (2H, d, J=8.3 Hz), 6.8–6.9 (2H, m), 6.95 (2H, d, J=8.3 Hz), 7.6–7.8 (6H, m), 7.67 (1H, d, J=8.2 Hz), 8.2–8.3 (1H, m), 9.24 (1H, s), 10.69 (1H, br).

EXAMPLE 211

N-Cyclooctyl-1-(2-dimethylaminoethyl)-3-(4-hydroxybenzhydryl)indole-2-carboxamide hydrochloride (Compound 210 hydrochloride)

$^1$H-NMR(DMSO-d$_6$) δ(ppm): 1.4–1.7 (12H, m), 1.7–1.9 (2H, m), 2.80 (6H, s), 3.3–3.45 (2H, m), 3.95–4.1 (1H, m), 4.55–4.65 (2H, m), 5.80 (1H, s), 6.66 (2H, d, J=8.6 Hz), 6.8–6.9 (2H, s), 6.94 (2H, d, J=8.6 Hz), 7.1–7.3 (6H, m), 7.67 (1H, d, J=8.2 Hz), 8.01 (1H, d, J=7.9 Hz), 9.26 (1H, s), 10.83 (1H, br).

EXAMPLE 212

N-Propyl-3-(4-hydroxybenzhydryl)-1-(2-pyrrolidinylethyl)indole-2-carboxamide hydrochloride (Compound 211 hydrochloride)

$^1$H-NMR(DMSO-d$_6$) δ(ppm): 0.91 (3H, t, J=7.3 Hz), 1.45–1.65 (2H, m), 1.75–2.05 (4H, m), 2.85–3.05 (2H, m), 3.05–3.4 (4H, m), 3.4–3.6 (2H, m), 4.45–4.6 (2H, m), 5.84 (1H, s), 6.66 (2H, d, J=8.3 Hz), 6.85–6.9 (2H, m), 6.94 (2H, d, J=8.3 Hz), 7.05–7.3 (6H, m), 7.62 (1H, d, J=6.3 Hz), 8.2–8.3 (1H, m), 9.21 (1H, s), 10.65 (1H, br).

EXAMPLE 213

N-Isopropyl-3-(4-hydroxybenzhydryl)-1-(2-pyrrolidinylethyl)indole-2-carboxamide hydrochloride (Compound 212 hydrochloride)

$^1$H-NMR(DMSO-d$_6$) δ(ppm): 1.17 (6H, d, J=6.6 Hz), 1.75–2.05 (4H, m), 2.85–3.05 (2H, m), 3.4–3.6 (4H, m), 4.0–4.15 (1H, m), 4.5–4.65 (2H, m), 5.83 (1H, s), 6.67 (2H, d, J=8.6 Hz), 6.85–6.9 (2H, m), 6.95 (2H, d, J=8.6 Hz), 7.05–7.3 (6H, m), 7.62 (1H, d, J=8.3 Hz), 7.84 (1H, br), 9.19 (1H, s), 10.64 (1H, br).

EXAMPLE 214

N-(3-Morpholinopropyl)-3-(4-hydroxybenzhydryl)-1-(2-pyrrolidinylethyl)indole-2-carboxamide 2 hydrochloride (Compound 213 2 hydrochloride)

$^1$H-NMR(DMSO-d$_6$) δ(ppm): 1.75–2.05 (6H, m), 2.9–3.2 (6H, m), 3.2–3.6 (8H, m), 3.75–4.0 (4H, m), 4.5–4.65 (2H, m), 5.85 (1H, s), 6.67 (2H, d, J=8.4 Hz), 6.85–6.9 (2H, m), 6.95 (2H, d, J=8.4 Hz), 7.1–7.3 (6H, m), 7.65 (1H, d, J=8.2 Hz), 8.5–8.6 (1H, m), 9.24 (1H, s), 11.05 (1H, br), 11.2 (1H, br).

EXAMPLE 215

N-[3-(2-Oxopyrrolidinyl)propyl]-3-(4-hydroxybenzhydryl)-1-(2-pyrrolidinylethyl)indole-2-carboxamide hydrochloride (Compound 214 hydrochloride)

$^1$H-NMR(CDCl$_3$) δ(ppm): 1.5–1.65 (2H, m), 1.95–2.2 (6H, m), 2.34 (2H, t, J=7.9 Hz), 2.8–3.0 (2H, m), 3.1–3.35 (6H, m), 3.5–3.65 (2H, m), 3.65–3.8 (2H, m), 4.7–4.85 (2H, m), 5.86 (1H, s), 6.0–6.1 (1H, m), 6.7–6.85 (4H, m), 6.95 (2H, d, J=8.3 Hz), 7.0–7.1 (2H, m), 7.1–7.3 (4H, m), 7.74 (1H, d, J=8.3 Hz), 12.45 (1H, br).

In the following Examples 216 to 220, substantially the same procedure as in Example 94 was repeated using 3-[4-(2-dimethylaminoethoxy)benzhydryl]-indole-2-carboxylic acid obtained in Reference Example 24 in place of Compound 93 and using corresponding amines in place of propylamine to give the desired compounds.

EXAMPLE 216

N-Isopropyl-3-[4-(2-dimethylaminoethoxy)benzhydryl]indole-2-carboxamide (Compound 215)

$^1$H-NMR(CDCl$_3$) δ(ppm): 1.01 (6H, d, J=6.6 Hz), 2.34 (6H, s), 2.73 (2H, t, J=5.9 Hz), 4.06 (2H, t, J=5.9 Hz), 4.05–4.20 (1H, m), 5.72 (1H, d, J=7.9 Hz), 6.01 (1H, s), 6.77–6.89 (4H, m), 7.07–7.45 (9H, m), 9.18 (1H, s).

EXAMPLE 217

N-Propyl-3-[4-(2-dimethylaminoethoxy)benzhydryl]-indole-2-carboxamide (Compound 216)

$^1$H-NMR(CDCl$_3$) δ(ppm): 0.79 (3H, t, J=7.3 Hz), 1.32–1.45 (2H, m), 2.35 (6H, s), 2.74 (2H, t, J=5.6 Hz), 3.21–3.29 (2H, m), 4.06 (2H, t, J=5.9 Hz), 5.82 (1H, t, J=5.6 Hz), 6.03 (1H, s), 6.76–6.88 (4H, m), 7.06–7.64 (9H, m), 9.14 (1H, s).

EXAMPLE 218

N-Cyclooctyl-3-[4-(2-dimethylaminoethoxy)benzhydryl]indole-2-carboxamide (Compound 217)

$^1$H-NMR(CDCl$_3$) δ(ppm): 1.25–1.90 (14H, br), 2.35 (6H, s), 2.74 (2H, t, J=5.6 Hz), 4.06 (2H, t, J=5.9 Hz), 4.05–4.20 (1H, m), 5.84 (1H, d, J=8.2 Hz), 6.01 (1H, s), 6.73–6.89 (4H, m), 7.06–7.65 (9H, m), 9.13 (1H, s).

EXAMPLE 219

N-(4-Propylphenyl)-3-[4-(2-dimethylaminoethoxy)benzhydryl]indole-2-carboxamide (Compound 218)

$^1$H-NMR(CDCl$_3$) δ(ppm): 0.92 (3H, t, J=7.3 Hz), 1.54–1.65 (2H, m), 2.35 (6H, s), 2.54 (2H, t, J=7.3 Hz),: 2.74 (2H, t, J=5.6 Hz), 4.07 (2H, t, J=5.6 Hz), 6.15 (1H, s), 6.74–6.92 (4H, m), 7.08–7.42 (13H, m), 7.58 (1H, s), 9.23 (1H, s).

EXAMPLE 220

N-[3-(2-Oxopyrrolidinyl)propyl]-3-[4-(2-dimethylaminoethoxy)benzhydryl]indole-2-carboxamide (Compound 219)

$^1$H-NMR(CDCl$_3$) δ(ppm): 1.67–1.76 (2H, m), 1.98–2.09 (2H, m), 2.35 (6H, s), 2.42 (2H, t, J=7.9 Hz), 2.75 (2H, t, J=5.6 Hz), 3.30–3.40 (4H, m), 4.05 (2H, t, J=5.6 Hz), 6.48 (1H, s), 6.81–6.93 (4H, m), 7.12–7.40 (9H, m), 9.54 (1H, s).

In the following Examples 221 to 225, substantially the same procedure as in Example 94 was repeated using 3-[4-(2-pyrrolidinylethoxy)benzhydryl]indole-2-carboxylic acid obtained in Reference Example 26 in place of Compound 93 and using corresponding amines in place of propylamine to give the desired compounds.

EXAMPLE 221

N-Isopropyl-3-[4-(2-pyrrolidinylethoxy)benzhydryl]indole-2-carboxamide (Compound 220)

$^1$H-NMR(CDCl$_3$) δ(ppm): 1.01 (6H, d, J=6.3 Hz), 1.75–1.90 (4H, br), 2.60–2.70 (4H, br), 2.91 (2H, t, J=5.9 Hz), 4.11 (2H, t, J=6.3 Hz), 4.10–4.25 (1H, m), 5.72 (1H, d, J=7.6 Hz), 6.01 (1H, s), 6.77–6.89 (4H, m), 7.07–7.40 (9H, m), 9.16 (1H, s).

EXAMPLE 222

N-Propyl-3-[4-(2-pyrrolidinylethoxy)benzhydryl]-indole-2-carboxamide (Compound 221)

$^1$H-NMR(CDCl$_3$) δ(ppm): 0.79 (3H, t, J=7.3 Hz), 1.32–1.45 (2H, m), 1.79–1.84 (4H, m), 2.55–2.70 (4H, br), 2.91 (2H, t, J=5.9 Hz), 3.21–3.29 (2H, m), 4.10 (2H, t, J=5.9 Hz), 5.82 (1H, t, J=5.6 Hz), 6.03 (1H, s), 6.76–6.89 (4H, m), 7.05–7.40 (9H, m), 9.15 (1H, s).

EXAMPLE 223

N-Cyclooctyl-3-[4-(2-pyrrolidinylethoxy)benzhydryl]indole-2-carboxamide (Compound 222)

$^1$H-NMR(CDCl$_3$) δ(ppm): 1.25–1.80 (14H, br), 1.80–1.90 (4H, br), 2.55–2.75 (4H, br), 2.93 (2H, t, J=5.9 Hz), 4.00–4.15 (1H, m), 4.12 (2H, t, J=5.9 Hz), 5.84 (1H, d, J=7.9 Hz), 6.01 (1H, s), 6.73–6.88 (4H, m), 7.06–7.64 (9H, m), 9.13 (1H, s).

EXAMPLE 224

N-(4-Propylphenyl)-3-[4-(2-pyrrolidinylethoxy)benzhydryl]indole-2-carboxamide (Compound 223)

$^1$H-NMR(CDCl$_3$) δ(ppm): 0.92 (3H, t, J=7.3 Hz), 1.54–1.67 (2H, m), 1.75–1.90 (4H, br), 2.54 (2H, t, J=7.3 Hz), 2.60–2.70 (4H, br), 2.93 (2H, t, J=5.9 Hz), 4.12 (2H, t, J=5.9 Hz), 6.15 (1H, s), 6.74–6.93 (4H, m), 7.08–7.42 (13H, m), 7.58 (1H, s), 9.24 (1H, s).

EXAMPLE 225

N-[3-(2-Oxopyrrolidinyl)propyl]-3-[4-(2-pyrrolidinylethoxy)benzhydryl]indole-2-carboxamide (Compound 224)

$^1$H-NMR(CDCl$_3$) δ(ppm): 1.67–1.76 (2H, m), 1.70–1.90 (4H, m), 1.97–2.08 (2H, m), 2.42 (2H, t, J=7.9 Hz), 2.55–2.75 (4H, br), 2.91 (2H, t, J=5.9 Hz), 3.30–3.39 (6H, m), 4.10 (2H, t, J=5.9 Hz), 6.48 (1H, s), 6.80–6.93 (4H, m), 7.12–7.39 (9H, m), 9.62 (1H, s).

EXAMPLE 226

Ethyl 3-[4-(2-dimethylaminoethoxy)benzhydryl]-1-(2-dimethylaminoethyl)indole-2-carboxylate (Compound 225)

Substantially the same procedure as in Example 160 was repeated using ethyl 3-[4-(2-chloroethoxy)-benzhydryl]-1-

(2-dimethylaminoethyl)indole-2-carboxylate (26.49 g, 52.5 mmol) obtained in Reference Example 27 and an aqueous solution of dimethylamine (50%, 39.4 ml, 787 mmol) to give 24.3 g (yield: 90%) of the title compound.

$^1$H-NMR(CDCl$_3$) δ(ppm): 1.36 (3H, t, J=7.3 Hz), 2.32 (6H, s), 2.34 (6H, s), 2.65–2.73 (4H, m), 4.03 (2H, t, J=5.9 Hz), 4.34 (2H, q, J=7.3 Hz), 4.60 (2H, t, J=7.6 Hz), 6.50 (1H, s), 6.79–6.95 (4H, m), 7.05–7.40 (9H, m).

EXAMPLE 227

3-[4-(2-Dimethylaminoethoxy)benzhydryl]-1-(2-dimethylaminoethyl)indole-2-carboxylic acid (Compound 226)

Substantially the same procedure as in Example 93 was repeated using Compound 225 (23.8 g) obtained in Example 226 to give 21.7 g (yield: 96%) of the title compound.

$^1$H-NMR(DMSO-d$_6$) δ(ppm): 2.17 (6H, s), 2.19 (6H, s), 2.45–2.60 (4H, m), 3.95 (2H, t, J=5.9 Hz), 4.63 (2H, t, J=7.3 Hz), 6.69–6.78 (3H, m), 6.96–7.33 (11H, m).

In the following Examples 228 to 232, substantially the same procedure as in Example 94, and then, if necessary, substantially the same procedure as in Example 135 were repeated using Compound 226 in place of Compound 93 and using corresponding amines in place of propylamine to give the desired compounds.

EXAMPLE 228

N-Isopropyl-3-[4-(2-dimethylaminoethoxy)benzhydryl]-1-(2-dimethylaminoethyl)indole-2-carboxamide (Compound 227)

$^1$H-NMR(CDCl$_3$) δ(ppm): 1.10 (6H, d, J=6.6 Hz), 2.21 (6H, s), 2.33 (6H, s), 2.69–2.76 (4H, m), 4.04 (2H, t, J=5.6 Hz), 4.15–4.27 (1H, m), 4.44 (2H, t, J=6.9 Hz), 5.98 (1H, s), 6.59 (1H, d, J=7.9 Hz), 6.81–6.86 (4H, m), 7.07–7.35 (9H, m).

EXAMPLE 229

N-Propyl-3-[4-(2-dimethylaminoethoxy)-benzhydryl]-1-(2-dimethylaminoethyl)indole-2-carboxamide (Compound 228)

$^1$H-NMR(CDCl$_3$) δ(ppm): 0.85 (3H, t, J=7.3 Hz), 1.41–1.55 (2H, m), 2.21 (6H, s), 2.33 (6H, s), 2.69–2.78 (4H, m), 3.31 (2H, dt, J=6.6, 6.9 Hz), 4.03 (2H, t, J=5.9 Hz), 4.43 (2H, t, J=6.6 Hz), 6.05 (1H, s), 6.79–6.92 (4H, m), 7.08–7.34 (9H, m).

EXAMPLE 230

N-Cyclooctyl-3-[4-(2-dimethylaminoethoxy)benzhydryl]-1-(2-dimethylaminoethyl)indole-2-carboxamide hydrochloride (Compound 229 hydrochloride)

$^1$H-NMR(DMSO-d$_6$) δ(ppm): 1.35–1.90 (14H, m), 2.77 (6H, s), 2.81 (6H, s), 3.30–3.55 (4H, m), 3.85–4.05 (1H, br), 4.20–4.40 (2H, br), 4.50–4.70 (2H, br), 5.84 (1H, s), 6.89–6.93 (4H, m), 7.08–7.27 (8H, m), 7.71 (1H, d, J=8.3 Hz), 8.36 (1H, d, J=7.6 Hz).

EXAMPLE 231

N-(4-Propylphenyl)-3-[4-(2-dimethylaminoethoxy)benzhydryl]-1-(2-dimethylaminoethyl)indole-2-carboxamide (Compound 230)

$^1$H-NMR(CDCl$_3$) δ(ppm): 1.36 (3H, t, J=7.3 Hz), 2.15–2.25 (2H, br), 2.37 (12H, s), 2.65–2.80 (4H, br), 4.07 (2H, t, J=5.6 Hz), 4.30–4.38 (2H, m), 4.63 (2H, t, J=7.9 Hz), 6.50 (1H, s), 6.79–6.91 (4H, m), 7.05–7.44 (13H, m).

EXAMPLE 232

N-[3-(2-Oxopyrrolidinyl)propyl]-3-[4-(2-dimethylaminoethoxy)benzhydryl]-1-(2-dimethylaminoethyl)indole-2-carboxamide (Compound 231)

$^1$H-NMR(CDCl$_3$) δ(ppm): 1.67–1.77 (2H, m), 1.95–2.07 (2H, m), 2.23 (6H, s), 2.33–2.39 (2H, m), 2.37 (6H, s), 2.76 (2H, t, J=5.6 Hz), 2.75–2.90 (2H, br), 3.24 (2H, t, J=6.9 Hz), 3.29–3.37 (4H, m), 4.06 (2H, t, J=5.6 Hz), 4.43 (2H, t, J=6.3 Hz), 6.10 (1H, s), 6.80–6.94 (4H, m), 7.09–7.35 (9H, m), 7.75 (1H, s).

EXAMPLE 233

Ethyl 3-[4-(2-pyrrolidinylethoxy)benzhydryl]-1-(2-pyrrolidinylethyl)indole-2-carboxylate (Compound 232)

Substantially the same procedure as in Example 160 was repeated using ethyl 3-[4-(2-chloroethoxy)benzhydryl]-1-(2-pyrrolidinylethyl)indole-2-carboxylate (36.7 g, 69.2 mmol) obtained in Reference Example 28 and pyrrolidine (32 ml, 380 mmol) to give 30.3 g (yield: 77%) of the title compound.

$^1$H-NMR(CDCl$_3$) δ(ppm): 1.36 (3H, t, J=7.3 Hz), 1.70–1.90 (8H, br), 2.50–2.80 (8H, br), 2.82–2.90 (4H, m), 4.07 (2H, t, J=5.9 Hz), 4.34 (2H, q, J=7.3 Hz), 4.63 (2H, t, J=7.9 Hz), 6.50 (1H, s), 6.79–6.95 (4H, m), 7.05–7.43 (9H, m).

EXAMPLE 234

3-[4-(2-Pyrrolidinylethoxy)benzhydryl]-1-(2-pyrrolidinylethyl)indole-2-carboxylic acid (Compound 233)

Substantially the same procedure as in Example 93 was repeated using Compound 232 (29.1 g) obtained in Example 233 to give 26.7 g (yield: 96%) of the title compound.

$^1$H-NMR(CDCl$_3$) δ(ppm): 1.60–1.90 (8H, br), 2.50–2.75 (8H, br), 2.85 (2H, t, J=5.9 Hz), 3.10–3.25 (2H, br), 4.00 (2H, t, J=5.9 Hz), 4.60–4.80 (2H, br), 6.70–6.91 (5H, m), 7.06–7.24 (9H, m).

In the following Examples 235 to 239, substantially the same procedure as in Example 94 was repeated using Compound 233 in place of Compound 93 and using corresponding amines in place of propylamine to give the desired compounds.

EXAMPLE 235

N-Isopropyl-3-[4-(2-pyrrolidinylethoxy)-benzhydryl]-1-(2-pyrrolidinylethyl)indole-2-carboxamide (Compound 234)

$^1$H-NMR(CDCl$_3$) δ(ppm): 1.11 (6H, d, J=6.9 Hz), 1.55–1.90 (10H, br), 2.25–2.55 (2H, br), 2.55–2.80 (4H, br), 2.80–3.10 (4H, br), 4.11 (2H, t, J=5.6 Hz), 4.10–4.30 (1H, m), 4.40–4.60 (2H, br), 6.05 (1H, s), 6.80–6.91 (4H, m), 7.09–7.36 (9H, m).

EXAMPLE 236

N-Propyl-3-[4-(2-pyrrolidinylethoxy)benzhydryl]-1-(2-pyrrolidinylethyl)indole-2-carboxamide (Compound 235)

$^1$H-NMR(CDCl$_3$) δ(ppm): 0.87 (3H, t, J=7.3 Hz), 1.40–1.55 (2H, m), 1.65–1.95 (8H, br), 2.35–2.85 (8H, br), 2.85–3.15 (4H, br), 3.20–3.40 (2H, m), 4.05–4.20 (2H, br), 4.45–4.55 (2H, br), 6.08 (1H, s), 6.79–6.92 (4H, m), 7.09–7.26 (9H, m).

EXAMPLE 237

N-Cyclooctyl-3-[4-(2-pyrrolidinylethoxy) benzhydryl]-1-(2-pyrrolidinylethyl)indole-2-carboxamide (Compound 236)

$^1$H-NMR(CDCl$_3$) δ(ppm): 1.35–1.90 (24H, m), 2.30–2.55 (2H, br), 2.55–2.75 (4H, br), 2.92 (2H, t, J=5.9 Hz), 2.90–3.10 (2H, br), 4.10 (2H, t, J=5.9 Hz), 4.05–4.20 (1H, m), 4.50 (2H, t, J=6.6 Hz), 6.05 (1H, s), 6.79–6.95 (4H, m), 7.05–7.46 (9H, m).

EXAMPLE 238

N-(4-Propylphenyl)-3-[4-(2-pyrrolidinylethoxy) benzhydryl]-1-(2-pyrrolidinylethyl)indole-2-carboxamide (Compound 237)

$^1$H-NMR(CDCl$_3$) δ(ppm): 0.94 (3H, t, J=7.3 Hz), 1.55–1.70 (6H, m), 1.75–1.90 (6H, br), 2.25–2.45 (2H, br), 2.56 (2H, t, J=7.6 Hz), 2.60–2.80 (4H, br), 2.85–3.15 (4H, br), 4.11 (2H, t, J=5.9 Hz), 4.50–4.60 (2H, br), 6.21 (1H, s), 6.78–7.36 (18H, m).

EXAMPLE 239

N-[3-(2-Oxopyrrolidinyl)propyl]-3-[4-(2-pyrrolidinylethoxy)benzhydryl]-1-(2-pyrrolidinylethyl)indole-2-carboxamide (Compound 238)

$^1$H-NMR(CDCl$_3$) δ(ppm): 1.60–1.90 (10H, m), 1.97–2.08 (2H, m), 2.30–2.50 (6H, m), 2.60–2.75 (4H, br), 2.95–3.00 (2H, br), 3.00–3.10 (2H, br), 3.24–3.32 (4H, m), 3.36 (2H, t, J=7.3 Hz), 4.10 (2H, t, J=5.9 Hz), 4.40–4.55 (2H, br), 6.14 (1H, s), 6.79–6.97 (4H, m), 7.10–7.67 (9H, m), 8.43 (1H, br).

EXAMPLE 240

N-[3-(2-Oxopyrrolidinyl)propyl]-3-(diphenylmethyl)-1-(2-methylaminoethyl)indole-2-carboxamide (Compound 239)

Substantially the same procedure as in Example 206 was repeated using N-[3-(2-oxopyrrolidinyl)propyl]-1-[2-(N-benzyloxycarbonyl-N-methylamino)ethyl]-3-(diphenylmethyl)indole-2-carboxamide (0.35 g, 0.54 mmol) obtained in Reference Example 30 to give 0.24 g (yield: 87%) of the title compound.

$^1$H-NMR(CDCl$_3$) δ(ppm): 1.6–1.75 (2H, m), 1.95–2.1 (2H, m), 2.37 (2H, t, J=7.6 Hz), 2.46 (3H, s), 3.2–3.4 (8H, m), 4.57 (2H, t, J=5.7 Hz), 6.02(1H, s), 6.9–6.95 (2H, m), 7.1–7.3 (12H, m), 7.39 (1H, d, J=8.2 Hz).

EXAMPLE 241

N-[3-(2-Oxopyrrolidinyl)propyl]-1-(2-aminoethyl)-3-(diphenylmethyl)indole-2-carboxamide (Compound 240)

Hydrazine hydrate (0.3 ml) was added to a solution of N-[3-(2-oxopyrrolidinyl)propyl]-3-(diphenylmethyl)-1-(2-phthalimideethyl)indole-2-carboxamide (0.553 g, 0.89 mmol) obtained in Reference Example 33 in 20 ml of ethanol, followed by stirring at 50° C. for 3 hours. The resulting precipitate was filtered off and washed with chloroform. The combined organic layer was concentrated under reduced pressure to give a crude product. The obtained crude product was purified with silica gel column chromatography (chloroform/methanol=10/1) to give 0.405 g (yield: 92%) of the title compound.

$^1$H-NMR(CDCl$_3$) δ(ppm): 1.68 (2H, t, J=6.6 Hz), 2.00 (2H, t, J=7.9 Hz), 2.35 (2H, t, J=7.9 Hz), 2.80–3.4 (10H, m), 4.35–4.5 (2H, s), 6.00 (1H, s), 6.8–6.95 (2H, m), 7.15–7.35 (13H, m).

EXAMPLE 242

3-(Bis[4-(methoxymethoxy)phenyl]methyl)-2-[4-(2-chlorophenyl)piperazinylsulfonyl]indole (Compound 241)

Boron trifluoride-ether complex (0.04 ml, 0.32 mmol) was added to a solution of 2-[4-(2-chlorophenyl) piperazinylsulfonyl]indole (1.2 g, 3.19 mmol) in 15 ml of methylene chloride, and a solution of 4,4'-bis(methoxymethoxy)benzhydrol (991 mg, 3.26 mmol) in 10 ml of methylene chloride was added thereto, followed by stirring at room temperature for 20 hours. Then, a solution of 4,4'-bis(methoxymethoxy)benzhydrol (490 mg, 1.60 mmol) in 10 ml of methylene chloride was further added to the reaction mixture to complete the reaction. A saturated aqueous solution of sodium bicarbonate was added to the reaction solution for neutralization followed by extraction with chloroform. The resulting organic layer was washed with a saturated aqueous solution of sodium bicarbonate and a saturated aqueous solution of sodium chloride, and dried over magnesium sulfate, and the solvent was distilled off under reduced pressure to give a crude product. The obtained crude product was crystallized from diisopropyl ether/hexane to give 1.9 g (yield: 90%) of the title compound.

$^1$H-NMR(CDCl$_3$) δ(ppm): 2.8–2.9 (4H, m), 3.05–3.15 (4H, m), 3.44 (6H, s), 5.12 (4H, s), 6.35 (1H, s), 6.85–7.0 (3H, m), 6.93 (4H, d, J=8.9 Hz), 7.15–7.25 (2H, m), 7.17 (4H, d, J=8.9 Hz), 7.25–7.35 (2H, m), 7.40 (1H, d, J=8.3 Hz), 8.71 (1H, br s).

EXAMPLE 243

3-{Bis[4-(methoxymethoxy)phenyl]methyl}-2-[4-(2-chlorophenyl)piperazinylsulfonyl]-1-(2-dimethylaminoethyl)-indole (Compound 242)

To a solution of Compound 241 (1.2 g, 1.81 mmol) obtained in Example 242 in 25 ml of N,N-dimethylformamide was portionwise added sodium hydride (60% in oil, 160 mg, 3.81 mmol) with stirring at 0° C., and 2-dimethylaminoethylchloride hydrochloride (260 mg, 1.81 mmol) was added thereto, followed by heating to 80° C. and then stirring for 7 hours. A saturated aqueous solution of ammonium chloride was added to the reaction solution for neutralization, and water was added thereto followed by extraction with ethyl acetate. The resulting organic layer was washed with a saturated aqueous solution of sodium chloride and dried over magnesium sulfate, and the solvent was distilled off under reduced pressure to give a crude product. The obtained crude product was purified with silica gel column chromatography (ethyl acetate/hexane=2/1) to give 1.1 g (yield: 85%) of the title compound.

$^1$H-NMR(CDCl$_3$) δ(ppm): 2.45 (6H, s), 2.75–2.9 (6H, m), 3.1–3.2 (4H, m), 3.43 (6H, s), 4.6–4.7 (2H, m), 5.12 (4H, s), 6.63 (1H, s), 6.85–7.05 (7H, m), 7.05–7.25 (6H, m), 7.3–7.4 (2H, m), 7.47 (1H, d, J=8.4 Hz).

EXAMPLE 244

3-{Bis [4-(methoxymethoxy)phenyl]methyl}-2-[4-(2-chlorophenyl)piperazinylsulfonyl]-1-(2-morpholinoethyl)-indole (Compound 243)

Substantially the same procedure as in Example 243 was repeated using Compound 241 (1.1 g, 1.66 mmol) obtained in Example 242 and 2-morpholinoethylchloride hydrochloride (310 mg, 1.66 mmol) to give 1.3 g (quantitative) of the title compound.

$^1$H-NMR(CDCl$_3$) δ(ppm): 2.5–2.6 (4H, m), 2.7–2.8 (2H, m), 2.8–2.9 (4H, m), 3.05–3.15 (4H, m), 3.43 (6H, s), 3.65–3.75 (4H, m), 4.55–4.65 (2H, m), 5.12 (4H, s), 6.62 (1H, s), 6.8–7.0 (3H, m), 6.91 (4H, d, J=8.6 Hz), 7.1–7.25 (2H, m), 7.13 (4H, d, J=8.6 Hz), 7.3–7.4 (2H, m), 7.43 (1H, d, J=8.3 Hz).

EXAMPLE 245

3-{Bis[4-(methoxymethoxy)phenyl]methyl}-2-(piperidinosulfonyl)indole (Compound 244)

To a solution of 2-(piperidinosulfonyl)indole (0.9 g, 3.40 mmol) and bis[4,4'-bis(methoxymethoxy)benzhydryl] ether (1.1 g, 1.87 mmol) in 20 ml of methylene chloride was added boron trifluoride-ether complex (0.04 ml, 0.32 mmol), followed by stirring at room temperature for 2 hours. A saturated aqueous solution of sodium bicarbonate was added to the reaction solution for neutralization followed by extraction with chloroform. The resulting organic layer was washed with a saturated aqueous solution of sodium bicarbonate and a saturated aqueous solution of sodium chloride, and dried over magnesium sulfate, and the solvent was distilled off under reduced pressure to give 2.4 g of a crude product. The obtained crude product was purified with silica gel column chromatography (ethyl acetate/hexane=1/3) to give 1.5 g (yield: 79%) of the title compound.

$^1$H-NMR(CDCl$_3$) δ(ppm): 1.2–1.35 (2H, m), 1.35–1.5 (4H, m), 2.85–2.95 (4H, m), 3.45 (6H, s), 5.13 (4H, s), 6.30 (1H, s), 6.91 (4H, d, J=8.4 Hz), 6.9–7.0 (1H, m), 7.05–7.15 (1H, m), 7.14 (4H, d, J=8.4 Hz), 7.2–7.3 (1H, m), 7.39 (1H, d, J=7.9 Hz), 8.77 (1H, s).

EXAMPLE 246

N,N-diethyl-3-{bis[4-(methoxymethoxy)phenyl]methyl}indole-2-sulfonamide (Compound 245)

Substantially the same procedure as in Example 245 was repeated using N,N-diethylindole-2-sulfonamide (1.0 g, 3.96 mmol) and bis[4,4'-bis(methoxymethoxy)benzhydryl] ether (1.29 g, 2.18 mmol) to give 1.56 g (yield: 73%) of the title compound.

$^1$H-NMR(CDCl$_3$) δ(ppm): 0.94 (6H, t, J=7.2 Hz), 3.06 (4H, q, J=7.2 Hz), 3.46 (6H, s), 5.13 (4H, s), 6.30 (1H, s), 6.85–6.95 (1H, m), 6.91 (4H, d, J=8.7 Hz), 7.05–7.15 (1H, m), 7.12 (4H, d, J=8.7 Hz), 7.2–7.3 (1H, m), 7.38 (1H, d, J=8.4 Hz), 8.83 (1H, s).

EXAMPLE 247

3-{Bis[4-(methoxymethoxy)phenyl]methyl}-2-(morpholinosulfonyl)indole (Compound 246)

Substantially the same procedure as in Example 245 was repeated using 2-(morpholinosulfonyl)indole (0.75 g, 2.82 mmol) and bis[4,4'-bis(methoxymethoxy)benzhydryl] ether (0.92 g, 1.55 mmol) to give 1.42 g (yield: 91%) of the title compound.

$^1$H-NMR(CDCl$_3$) δ(ppm): 2.85–2.95 (4H, m), 3.45 (6H, s), 3.45–3.55 (4H, m), 5.13 (4H, s), 6.31 (1H, s), 6.9–7.0 (1H, m), 6.92 (4H, d, J=8.4 Hz), 7.1–7.2 (1H, m), 7.13 (4H, d, J=8.4 Hz), 7.2–7.3 (1H, m), 7.39 (1H, d, J=8.3 Hz), 8.75–8.85 (1H, br).

EXAMPLE 248

3-{Bis[4-(methoxymethoxy)phenyl]methyl}-2-(4-phenylpiperazinylsulfonyl)indole (Compound 247)

Substantially the same procedure as in Example 245 was repeated using 2-(4-phenylpiperazinylsulfonyl)indole (1.0 g, 2.93 mmol) and bis[4,4'-bis(methoxymethoxy)benzhydryl] ether (0.95 g, 1.61 mmol) to give 1.63 g (yield: 89%) of the title compound.

$^1$H-NMR(CDCl$_3$) δ(ppm): 3.15–3.25 (8H, m), 3.46 (6H, s), 5.13 (4H, s), 5.34 (1H, s), 6.75 (2H, d, J=8.6 Hz), 6.9–7.0 (10H, m), 7.06 (1H, d, J=2.0 Hz), 7.21 (1H, t, J=6.9 Hz), 7.36 (1H, t, J=6.9 Hz), 7.45 (1H, d, J=8.3 Hz), 7.70 (1H, d, J=7.3 Hz), 8.88 (1H, s).

EXAMPLE 249

3-{Bis[4-(methoxymethoxy)phenyl]methyl}-2-(4-benzylpiperazinylsulfonyl)indole (Compound 248)

Substantially the same procedure as in Example 245 was repeated using 2-(4-benzylpiperazinylsulfonyl)indole (1.0 g, 2.81 mmol) and bis[4,4'-bis(methoxymethoxy)benzhydryl] ether (0.91 g, 1.55 mmol) to give 1.16 g (yield: 64%) of the title compound.

$^1$H-NMR(CDCl$_3$) δ(ppm): 2.2–2.3 (4H, m), 2.9–3.0 (4H, m), 3.36 (2H, s), 3.43 (6H, s), 5.11 (4H, s), 6.30 (1H, s), 6.9–7.0 (1H, m), 6.91 (4H, d, J=8.6 Hz), 7.1–7.2 (4H, m), 7.14 (4H, d, J=8.6 Hz), 7.2–7.3 (3H, m), 7.37 (1H, d, J=8.2 Hz), 8.67 (1H, s).

EXAMPLE 250

3-{Bis[4-(methoxymethoxy)phenyl]methyl}-1-(2-dimethylaminoethyl)-2-(piperidinosulfonyl)indole (Compound 249)

Substantially the same procedure as in Example 243 was repeated using Compound 244 (1.32 g, 2.40 mmol) obtained in Example 245 and 2-dimethylaminoethylchloride hydrochloride (345 mg, 2.40 mmol) to give 1.1 g (yield: 74%) of the title compound.

$^1$H-NMR(CDCl$_3$) δ(ppm): 1.41 (6H, br s), 2.37 (6H, s), 2.65–2.75 (2H, m), 2.9–3.0 (4H, m), 3.44 (6H, s), 4.5–4.6 (2H, m), 5.12 (4H, s), 6.64 (1H, s), 6.91 (4H, d, J=8.2 Hz), 6.85–6.95 (1H, m), 7.05–7.15 (1H, m), 7.12 (4H, d, J=8.2 Hz), 7.25–7.35 (1H, m), 7.41 (1H, d, J=8.3 Hz).

In the following Examples 251 to 254, substantially the same procedure as in Example 250 was repeated using corresponding Compounds 245 to 248 in place of Compound 244 to give the desired compounds.

EXAMPLE 251

N,N-Diethyl-3-{bis[4-(methoxymethoxy)phenyl]methyl}-1-(2-dimethylaminoethyl)indole-2-sulfonamide (Compound 250)

$^1$H-NMR(CDCl$_3$) δ(ppm): 0.91 (6H, t, J=7.3 Hz), 2.40 (6H, s), 2.7–2.8 (2H, m), 3.07 (4H, q, J=7.3 Hz), 3.46 (6H, s), 4.45–4.55 (2H, m), 5.13 (4H, s), 6.66 (1H, s), 6.85–6.95 (1H, m), 6.90 (4H, d, J=8.5 Hz), 7.0–7.1 (1H, m), 7.11 (4H, d, J=8.5 Hz), 7.25–7.35 (1H, m), 7.41 (1H, d, J=8.6 Hz).

EXAMPLE 252

3-{Bis[4-(methoxymethoxy)phenyl]methyl}-1-(2-dimethylaminoethyl)-2-(morpholinosulfonyl)indole (Compound 251)

$^1$H-NMR(CDCl$_3$) δ(ppm): 2.39 (6H, s), 2.65–2.75 (2H, m), 2.85–2.95 (4H, m), 3.4–3.5 (4H, m), 3.45 (6H, s), 4.5–4.6 (2H, m), 5.13 (4H, s), 6.59 (1H, s), 6.9–7.0 (1H, m), 6.91 (4H, d, J=8.6 Hz), 7.05–7.15 (1H, m), 7.10 (4H, d, J=8.6 Hz), 7.3–7.4 (1H, m), 7.42 (1H, d, J=8.6 Hz).

EXAMPLE 253

3-{Bis[4-(methoxymethoxy)phenyl]methyl}-1-(2-dimethylaminoethyl)-2-(4-phenylpiperazinylsulfonyl)indole (Compound 252)

$^1$H-NMR(CDCl$_3$) δ(ppm): 2.37 (6H, s), 2.65–2.75 (2H, m), 3.15–3.25 (4H, m), 3.3–3.4 (4H, m), 3.46 (6H, s), 4.5–4.6 (2H, m), 5.13 (4H, s), 5.35 (1H, s), 6.78 (2H, d, J=8.9 Hz), 6.85–7.0 (10H, m), 7.15–7.25 (2H, m), 7.35–7.45 (2H, m), 7.69 (1H, d, J=8.2 Hz).

EXAMPLE 254

2-(4-Benzylpiperazinylsulfonyl)-3-{bis[4-(methoxymethoxy)phenyl]methyl}-1-(2-dimethylaminoethyl)indole (Compound 253)

$^1$H-NMR(CDCl$_3$) δ(ppm): 2.2–2.3 (4H, m), 2.36 (6H, s), 2.65–2.75 (2H, m), 2.9–3.0 (4H, m), 3.39 (2H, s), 3.42 (6H, s), 4.5–4.6 (2H, m), 5.10 (4H, s), 6.60 (1H, s), 6.85–6.95 (1H, m), 6.89 (4H, d, J=8.7 Hz), 7.05–7.15 (1H, m), 7.10 (4H, d, J=8.7 Hz), 7.2–7.35 (6H, m), 7.40 (1H, d, J=8.3 Hz).

EXAMPLE 255

3-[Bis(4-hydroxyphenyl)methyl]-2-[4-(2-chlorophenyl)piperazinylsulfonyl]indole (Compound 254)

Compound 241 (1.0 g, 1.51 mmol) obtained in Example 242 was dissolved in a mixed solvent of tetrahydrofuran (10 ml) and ethanol (30 ml), and 20 ml of 2N hydrochloric acid was added thereto, followed by heating under reflux for 2 hours. The solvent was distilled off under reduced pressure, and a saturated aqueous solution of sodium bicarbonate was added thereto for neutralization. The mixture was stirred and the precipitated crystals were collected to give a crude product. The obtained crude product was washed with ethanol and a little amount of hexane to give 0.77 g (yield: 89%) of the title compound.

$^1$H-NMR(DMSO-d$_6$) δ(ppm): 2.75–2.9 (4H, m), 2.9–3.05 (4H, m), 6.16 (1H, s), 6.66 (4H, d, J=8.4 Hz), 6.85–7.05 (8H, m), 7.15–7.25 (2H, m), 7.25–7.35 (1H, m), 7.46 (1H, d, J=8.4 Hz), 9.21 (2H, s), 11.98 (1H, s).

In the following Examples 256 to 262, substantially the same procedure as in Example 255 was repeated using corresponding Compounds 242, 243, and 249 to 253 in place of Compound 241 to give the desired compounds.

EXAMPLE 256

3-[Bis(4-hydroxyphenyl)methyl]-2-[4-(2-chlorophenyl)piperazinylsulfonyl]-1-(2-dimethylaminoethyl)indole (Compound 255)

$^1$H-NMR(DMSO-d$_6$) δ(ppm): 2.28 (6H, s), 2.55–2.65 (2H, m), 2.8–2.9 (4H, m), 3.05–3.15 (4H, m), 4.5–4.6 (2H, m), 6.39 (1H, s), 6.65 (4H, d, J=8.6 Hz), 6.91 (4H, d, J=8.6 Hz), 6.8–6.9 (1H, m), 6.95–7.05 (3H, m), 7.2–7.4 (3H, m), 7.52 (1H, d, J=8.6 Hz), 9.15 (2H, s).

EXAMPLE 257

3-[Bis(4-hydroxyphenyl)methyl]-2-[4-(2-chlorophenyl)piperazinylsulfonyl]-1-(2-morpholinoethyl)indole (Compound 256)

$^1$H-NMR(DMSO-d$_6$) δ(ppm): 2.4–2.55 (4H, m), 2.55–2.65 (2H, m), 2.8–2.9 (4H, m), 3.05–3.15 (4H, m), 3.5–3.65 (4H, m), 4.5–4.65 (2H, m), 6.38 (1H, s), 6.65 (4H, d, J=8.4 Hz), 6.90 (4H, d, J=8.4 Hz), 6.9–7.1 (4H, m), 7.2–7.4 (3H, m), 7.58 (1H, d, J=8.9 Hz), 9.17 (2H, s).

EXAMPLE 258

3-[Bis(4-hydroxyphenyl)methyl]-1-(2-dimethylaminoethyl)-2-(piperidinosulfonyl)indole (Compound 257)

$^1$H-NMR(DMSO-d$_6$) δ(ppm): 1.42 (6H, br s), 2.29 (6H, s), 2.55–2.65 (2H, m), 2.96 (4H, br s), 4.45–4.55 (2H, m), 6.39 (1H, s), 6.63 (4H, d, J=8.6 Hz), 6.85–6.95 (1H, m), 6.88 (4H, d, J=8.6 Hz), 6.99 (1H, d, J=8.0 Hz), 7.25–7.3 (1H, m), 7.48 (1H, t, J=8.3 Hz), 9.10 (2H, s).

EXAMPLE 259

N,N-Diethyl-3-[bis(4-hydroxyphenyl)methyl]-1-(2-dimethylaminoethyl)indole-2-sulfonamide (Compound 258)

$^1$H-NMR(DMSO-d$_6$) δ(ppm): 0.89 (6H, t, J=6.9 Hz), 2.28 (6H, s), 2.5–2.65 (2H, m), 3.08 (4H, q, J=6.9 Hz), 4.4–4.5 (2H, m), 6.44 (1H, s), 6.64 (4H, d, J=8.2 Hz), 6.8–7.0 (2H, m), 6.87 (4H, d, J=8.2 Hz), 7.2–7.3 (1H, m), 7.47 (1H, d, J=8.4 Hz), 9.13 (2H, s).

EXAMPLE 260

3-[Bis(4-hydroxyphenyl)methyl]-1-(2-dimethylaminoethyl)-2-(morpholinosulfonyl)indole (Compound 259)

$^1$H-NMR(DMSO-d$_6$) δ(ppm): 2.27 (6H, s), 2.5–2.65 (2H, m), 2.85–2.95 (4H, m), 3.4–3.5 (4H, m), 4.45–4.55 (2H, m), 6.35 (1H, s), 6.65 (4H, d, J=8.3 Hz), 6.88 (4H, d, J=8.3 Hz), 6.85–6.95 (1H, m), 7.00 (1H, d, J=8.3 Hz), 7.25–7.35 (1H, m), 7.45–7.55 (1H, m), 9.05–9.2 (2H, br).

EXAMPLE 261

3-[Bis(4-hydroxyphenyl)methyl]-1-(2-dimethylaminoethyl)-2-(4-phenylpiperazinylsulfonyl)indole (Compound 260)

$^1$H-NMR(DMSO-d$_6$) δ(ppm): 2.22 (6H, s), 2.56 (2H, t, J=7.2 Hz), 3.1–3.25 (8H, m), 4.50 (2H, t, J=7.2 Hz), 5.19 (1H, s), 6.63 (4H, d, J=8.6 Hz), 6.7–6.95 (8H, m), 7.1–7.2 (2H, m), 7.3–7.4 (1H, m), 7.60 (1H, d, J=8.6 Hz), 7.70 (1H, d, J=7.9 Hz), 9.13 (2H, s).

EXAMPLE 262

2-(4-Benzylpiperazinylsulfonyl)-3-[bis(4-hydroxyphenyl)methyl]-1-(2-dimethylaminoethyl)indole (Compound 261)

$^1$H-NMR(CDCl$_3$) δ(ppm): 2.2–2.3 (4H, m), 2.36 (6H, s), 2.6–2.7 (2H, m), 2.95–3.05 (4H, m), 3.40 (2H, s), 4.45–4.55

(2H, m), 6.49 (1H, s), 6.70 (4H, d, J=8.3 Hz), 6.89 (1H, t, J=8.1 Hz), 6.98 (4H, d, J=8.3 Hz), 7.07 (1H, d, J=8.2 Hz), 7.15–7.35 (6H, m), 7.38 (1H, d, J=8.9 Hz).

EXAMPLE 263

N,N-Diethyl-3-(diphenylmethyl)indole-2-sulfonamide (Compound 262)

To a solution of benzhydryl acetate (0.77 g, 3.39 mmol) and N,N-diethylindole-2-sulfonamide (0.9 g, 3.39 mmol) in 20 ml of methylene chloride was added methanesulfonic acid (0.7 ml, 10.7 mmol), followed by stirring at room temperature for one hour. A saturated aqueous solution of sodium bicarbonate was added to the reaction solution for neutralization followed by extraction with chloroform. The resulting organic layer was washed with a saturated aqueous solution of sodium bicarbonate and a saturated aqueous solution of sodium chloride, and dried over magnesium sulfate, and the solvent was distilled off under reduced pressure to give a crude product. The obtained crude product was crystallized from diisopropyl ether to give 0.99 g (yield: 67%) of the title compound.

$^1$H-NMR(CDCl$_3$) δ(ppm): 0.90 (6H, t, J=7.2 Hz), 3.03 (4H, q, J=7.2 Hz), 6.42 (1H, s), 6.85–6.95 (1H, s), 7.05–7.3 (12H, m), 7.39 (1H, d, J=8.3 Hz), 8.86 (1H, br s).

EXAMPLE 264

3-(Diphenylmethyl)-2-(piperidinosulfonyl)indole (Compound 263)

Substantially the same procedure as in Example 263 was repeated using benzhydryl acetate (0.78 g, 3.41 mmol) and 2-(piperidinosulfonyl)indole (0.95 g, 3.59 mmol) to give 1.2 g (yield: 75%) of the title compound.

$^1$H-NMR(CDCl$_3$) δ(ppm): 1.2–1.3 (2H, m), 1.35–1.45 (4H, m), 2.8–2.9 (4H, m), 6.43 (1H, s), 6.94 (1H, td, J=8.2, 1.0 Hz), 7.14 (1H, d, J=7.6 Hz), 7.15–7.3 (11H, m), 7.39 (1H, d, J=8.2 Hz), 8.75–8.85 (1H, br).

EXAMPLE 265

1-(2-Dimethylaminoethyl)-3-(diphenylmethyl)-2-(piperidinosulfonyl)indole (Compound 264)

Substantially the same procedure as in Example 243 was repeated using Compound 263 (1.0 g, 2.25 mmol) obtained in Example 264 and 2-dimethylaminoethylchloride hydrochloride (360 mg, 2.47 mmol) to give 0.85 g (yield: 75%) of the title compound.

$^1$H-NMR(CDCl$_3$) δ(ppm): 1.3–1.45 (6H, br), 2.40 (6H, s), 2.7–2.8 (2H, m), 2.85–2.95 (4H, m), 4.5–4.6 (2H, m), 6.74 (1H, s), 6.91 (1H, td, J=6.9, 1.0 Hz), 7.01 (1H, d, J=8.2 Hz), 7.15–7.35 (11H, m), 7.43 (1H, d, J=8.6 Hz).

EXAMPLE 266

N-Isopropyl-3-(diphenylmethyl)indole-2-sulfonamide (Compound 265)

To a solution of benzhydrol (0.58 g, 3.15 mmol) and N-isopropylindole-2-sulfonamide (0.7 g, 3.12 mmol) in 15 ml of methylene chloride was added a solution of methanesulfonic acid (0.2 ml, 3.12 mmol) in 4 ml of methylene chloride, followed by stirring at room temperature for 2.5 hours. A saturated aqueous solution of sodium bicarbonate was added to the reaction solution for neutralization and the solvent was distilled off under reduced pressure, followed by extraction with ethyl acetate. The resulting organic layer was washed with a saturated aqueous solution of sodium chloride and dried over magnesium sulfate, and the solvent was distilled off under reduced pressure to give 1.4 g of a crude product. The obtained crude product was washed with ethanol to give 1.07 g (yield: 85%) of the title compound.

$^1$H-NMR(CDCl$_3$) δ(ppm): 0.62 (6H, t, J=6.3 Hz), 3.1–3.25 (1H, m), 3.80 (1H, d, J=7.3 Hz), 6.42 (1H, s), 6.9–7.2 (2H, m), 7.1–7.35 (11H, m), 7.40 (1H, d, J=8.3 Hz), 8.82 (1H, s).

EXAMPLE 267

N-Isopropyl-3-[bis(4-methylphenyl)methyl]indole-2-sulfonamide (Compound 266)

Substantially the same procedure as in Example 266 was repeated using 4,4'-dimethylbenzhydrol (0.96 g, 4.50 mmol) and N-isopropylindole-2-sulfonamide (1.00 g, 4.46 mmol) to give 1.44 g (yield: 75%) of the title compound.

$^1$H-NMR(CDCl$_3$) δ(ppm): 0.54 (6H, d, J=6.3 Hz), 2.22 (6H, s), 3.0–3.15 (1H, m), 3.69 (1H, d, J=6.9 Hz), 6.22 (1H, s), 6.8–6.9 (2H, m), 6.99 (4H, d, J=8.3 Hz), 7.02 (4H, d, J=8.3 Hz), 7.1–7.2 (1H, m), 7.29 (1H, d, J=8.3 Hz), 8.73 (1H, s).

EXAMPLE 268

N-Isopropyl-3-[bis(4-fluorophenyl)methyl]indole-2-sulfonamide (Compound 267)

Substantially the same procedure as in Example 266 was repeated using 4,4'-difluorobenzhydrol (0.99 g, 4.50 mmol) and N-isopropylindole-2-sulfonamide (1.00 g, 4.46 mmol) to give 1.56 g (yield: 80%) of the title compound.

$^1$H-NMR(CDCl$_3$) δ(ppm): 0.71 (6H, d, J=6.3 Hz), 3.15–3.3 (1H, m), 3.96 (1H, d, J=7.3 Hz), 6.38 (1H, s), 6.85–7.05 (6H, m), 7.15–7.25 (4H, m), 7.25–7.35 (1H, m), 7.42 (1H, d, J=8.3 Hz), 8.87 (1H, s).

EXAMPLE 269

N-Isopropyl-3-[bis(4-chlorophenyl)methyl]indole-2-sulfonamide (Compound 268)

Substantially the same procedure as in Example 266 was repeated using 4,4'-dichlorobenzhydrol (1.14 g, 4.50 mmol) and N-isopropylindole-2-sulfonamide (1.00 g, 4.46 mmol) to give 1.76 g (yield: 83%-) of the title compound.

$^1$H-NMR(CDCl$_3$) δ(ppm): 0.73 (6H, d, J=6.3 Hz), 3.15–3.3 (1H, m), 3.97 (1H, d, J=7.3 Hz), 6.36 (1H, s), 6.9–7.05 (2H, m), 7.15 (4H, d, J=8.6 Hz), 7.2–7.35 (5H, m), 7.42 (1H, d, J=8.6 Hz), 8.87 (1H, s).

EXAMPLE 270

N-Isopropyl-3-{bis[4-(methoxymethoxy)phenyl]methyl}indole-2-sulfonamide. (Compound 269)

Substantially the same procedure as in Example 245 was repeated using bis[4,4'-bis(methoxymethoxy)benzhydryl] ether (1.45 g, 2.45 mmol) and N-isopropylindole-2-sulfonamide (1.00 g, 4.46 mmol) to give 1.93 g (yield: 82%) of the title compound.

$^1$H-NMR(CDCl$_3$) δ(ppm): 0.67 (6H, d, J=6.6 Hz), 3.1–3.25 (1H, m), 3.46 (6H, s), 3.84 (1H, d, J=7.3 Hz), 5.15 (4H, s), 6.30 (1H, s), 6.9–7.0 (6H, m), 7.15 (4H, d, J=8.9 Hz), 7.2–7.3 (1H, m), 7.39 (1H, d, J=8.3 Hz), 8.81 (1H, s).

EXAMPLE 271

N-Isopropyl-3-[bis(4-hydroxyphenyl)methyl]indole-2-sulfonamide (Compound 270)

Substantially the same procedure as in Example 255 was repeated using Compound 269 (1.75 g, 3.34 mmol) obtained in Example 270 to give 1.22 g (yield: 84%) of the title compound.

¹H-NMR(DMSO-d₆) δ(ppm): 0.85 (6H, d, J=6.6 Hz), 3.15–3.3 (1H, m), 6.17 (1H, s), 6.63 (4H, d, J=8.3 Hz), 6.8–6.9 (1H, m), 6.96 (4H, d, J=8.3 Hz), 7.04 (1H, d, J=8.3 Hz), 7.1–7.2 (1H, m), 7.35 (1H, d, J=7.6 Hz), 7.43 (1H, d, J=8.3 Hz), 9.02 (2H, s), 11.51 (1H, s).

EXAMPLE 272

N-Isopropyl-3-(4-hydroxybenzhydryl)indole-2-sulfonamide (Compound 271)

N-Isopropyl-3-(4-benzyloxybenzhydryl)indole-2-sulfonamide (1.80 g, 3.52 mmol) obtained in Reference Example 34 was dissolved in a mixed solvent of ethanol (30 ml) and tetrahydrofuran (10 ml), and 10% palladium on carbon (0.36 g, 50% aqueous) was added thereto, followed by stirring under a hydrogen atmosphere for 4.5 hours. The catalyst was filtered off and the solvent was distilled off under reduced pressure to give 1.63 g of a crude compound. The obtained crude product was crystallized from diethyl ether to give 1.21 g (yield: 82%) of the title compound.

¹H-NMR(DMSO-d₆) δ(ppm): 0.83 (6H, d, J=6.6 Hz), 3.15–3.35 (1H, m), 6.26 (1H, s), 6.65 (2H, d, J=7.6 Hz), 6.8–7.05 (4H, m), 7.1–7.3 (6H, m), 7.44 (1H, d, J=8.3 Hz).

EXAMPLE 273

N-Isopropyl-3-[4-(2-dimethylaminoethoxy)benzhydryl]indole-2-sulfonamide hydrochloride (Compound 272 hydrochloride)

Substantially the same procedure as in Example 266 was repeated using 4-(2-dimethylaminoethoxy)benzhydrol (1.22 g, 4.50 mmol) and N-isopropylindole-2-sulfonamide (1.00 g, 4.46 mmol) to give 1.90 g (yield: 87%) of a free base of the title compound. This compound (1.5 g) was dissolved in 10 ml of ethanol and the pH of the solution was adjusted to 1 by addition of a solution of hydrogen chloride in ethyl acetate. The solvent was distilled off under reduced pressure followed by crystallization from ethanol to give 1.33 g (yield: 83%) of the title compound.

¹H-NMR(CDCl₃) δ(ppm): 0.78 (3H, d, J=6.6 Hz), 0.84 (3H, d, J=6.6 Hz), 2.86 (6H, s), 3.15–3.3 (1H, m), 3.3–3.5 (2H, m), 4.1–4.3 (2H, m), 5.33 (1H, d, J=6.9 Hz), 6.44 (1H, s), 6.53 (2H, d, J=8.6 Hz), 6.85–7.0 (2H, m), 7.07 (2H, d, J=8.6 Hz), 7.15–7.35 (6H, m), 7.46 (1H, d, J=8.3 Hz), 10.21 (1H, s).

EXAMPLE 274

N-Methyl-1-(2-dimethylaminoethyl)-3-(diphenylmethyl)indole-2-sulfonamide hydrochloride (Compound 273 hydrochloride)

To a solution of N-diphenylmethyl-N-methyl-1-(2-dimethylaminoethyl)indole-2-sulfonamide (1.97 g, 4.40 mmol) obtained in Reference Example 41 in 20 ml of chloroform was added methanesulfonic acid (0.57 ml, 8.80 mmol), followed by heating under reflux for 8 hours. A saturated aqueous solution of sodium bicarbonate was added to the reaction solution for neutralization followed by extraction with chloroform. The resulting organic layer was washed with a saturated aqueous solution of sodium chloride and dried over magnesium sulfate, and the solvent was distilled off under reduced pressure to give 2.04 g of a crude product. The obtained crude product was purified with silica gel column chromatography (chloroform/methanol=100/1) followed by crystallization from diethyl ether to give 1.09 g (yield: 55%) of a free base of the title compound. This compound (0.80 g) was dissolved in 10 ml of ethanol and the pH of the solution was adjusted to 1 by addition of a solution of hydrogen chloride in ethyl acetate. Water was added to the mixture followed by crystallization to give 0.52 g (yield: 60%) of the title compound.

¹H-NMR(CDCl₃) δ(ppm): 2.12 (3H, s), 2.73 (6H, s), 3.1–3.25 (2H, m), 4.95–5.1 (2H, m), 6.73 (1H, s), 6.85–6.95 (2H, m), 7.15–7.35 (12H, m), 7.47 (1H, d, J=8.6 Hz).

EXAMPLE 275

N-Methyl-3-(diphenylmethyl)-1-(2-pyrrolidinylethyl)indole-2-sulfonamide hydrochloride (Compound 274 hydrochloride)

Substantially the same procedure as in Example 274 was repeated using N-diphenylmethyl-N-methyl-1-(2-pyrrolidinylethyl)indole-2-sulfonamide (2.12 g, 4.48 mmol) obtained in Reference Example 42 to give 1.07 g (yield: 50%) of a free base of the title compound. Then, substantially the same procedure as in Example 274 was repeated using this compound (0.90 g) to give 0.95 g (yield: 98%) of the title compound.

¹H-NMR(CDCl₃) δ(ppm): 2.0–2.2 (4H, m), 2.16 (3H, d, J=5.3 Hz), 2.9–3.1 (2H, m), 3.4–3.5 (2H, m), 3.85–3.95 (2H, m), 5.1–5.2 (2H, m), 6.0–6.1 (1H, m), 6.71 (1H, s), 6.85–6.9 (2H, m), 7.1–7.3 (11H, m), 7.60 (1H, d, J=8.3 Hz), 12.26 (1H, br).

EXAMPLE 276

N-Isopropyl-1-(2-dimethylaminoethyl)-3-(diphenylmethyl)indole-2-sulfonamide hydrochloride (Compound 275 hydrochloride)

Substantially the same procedure as in Example 274 was repeated using N-diphenylmethyl-N-isopropyl-1-(2-dimethylaminoethyl)indole-2-sulfonamide (1.90 g, 3.99 mmol) obtained in Reference Example 43 to give 1.18 g (yield: 62%) of a free base of the title compound. Then, substantially the same procedure as in Example 274 was repeated using this compound (1.00 g) to give 0.84 g (yield: 78%) of the title compound.

¹H-NMR(CDCl₃) δ(ppm): 0.75 (6H, d, J=6.6 Hz), 2.75–3.0 (1H, m), 2.96 (6H, s), 3.35–3.45 (2H, m), 5.1–5.2 (2H, m), 6.08 (1H, d, J=8.3 Hz), 6.76 (1H, s), 6.85–6.95 (2H, m), 7.1–7.35 (11H, m), 7.64 (1H, d, J=8.3 Hz), 12.49 (1H, br).

EXAMPLE 277

N-Isopropyl-3-(diphenylmethyl)-1(2-pyrrolidinylethyl)indole-2-sulfonamide hydrochloride (Compound 276 hydrochloride)

Substantially the same procedure as in Example 274 was repeated using N-diphenylmethyl-N-isopropyl-1-(2-pyrrolidinylethyl)indole-2-sulfonamide (2.00 g, 3.99 mmol) obtained in Reference Example 44 to give 1.44 g (yield: 72%) of a free base of the title compound. Then, substantially the same procedure as in Example 274 was repeated using this compound (1.20 g) to give 1.12 g (yield: 87%) of the title compound.

¹H-NMR(CDCl₃) δ(ppm): 0.72 (6H, d, J=6.3 Hz), 2.05–2.2 (4H, m), 2.8–3.05 (3H, m), 3.4–3.5 (2H, m), 3.85–4.0 (2H, m), 5.1–5.2 (2H, m), 5.60 (1H, d, J=8.3 Hz), 6.74 (1H, s), 6.85–6.95 (2H, m), 7.15–7.35 (11H, m), 7.67 (1H, d, J=8.6 Hz).

EXAMPLE 278

N-[3-(2-Oxopyrrolidinyl)propyl]-1-(2-dimethylaminoethyl)-3-(diphenylmethyl)indole-2-sulfonamide hydrochloride (Compound 277 hydrochloride)

Substantially the same procedure as in Example 274 was repeated using N-diphenylmethyl-N-[3-(2-oxopyrrolidinyl)propyl]-1-(2-dimethylaminoethyl)indole-2-sulfonamide (1.23 g, 2.20 mmol) obtained in Reference Example 45 to give 0.96 g (yield: 78%) of a free base of the title compound. Then, substantially the same procedure as in Example 274 was repeated using this compound (0.96 g) to give 0.70 g (yield: 69%) of the title compound.

$^1$H-NMR(CDCl$_3$) δ(ppm): 1.1–1.3 (2H, m), 1.9–2.05 (2H, m), 2.25–2.4 (4H, m), 2.95 (3H, s), 2.97 (3H, s), 3.14 (2H, t, J=6.3 Hz), 3.23 (2H, t, J=6.9 Hz), 3.4–3.5 (2H, m), 5.05–5.15 (2H, m), 6.76 (1H, s), 6.85–7.0 (2H, m), 7.1–7.45 (12H, m), 7.85 (1H, d, J=8.3 Hz), 12.74 (1H, br).

EXAMPLE 279

N-[3-(2-Oxopyrrolidinyl)propyl]-3-(diphenylmethyl)-1-(2-pyrrolidinylethyl)indole-2-sulfonamide hydrochloride (Compound 278 hydrochloride)

Substantially the same procedure as in Example 274 was repeated using N-diphenylmethyl-N-[3-(2-oxopyrrolidinyl)propyl]-1-(2-pyrrolidinylethyl)indole-2-sulfonamide (1.62 g, 2.77 mmol) obtained in Reference Example 46 to give 0.50 g (yield: 31%) of a free base of the title compound. Then, substantially the same procedure as in Example 274 was repeated using this compound (0.50 g) to give 0.46 g (yield: 86%) of the title compound.

$^1$H-NMR(CDCl$_3$) δ(ppm): 1.2–1.35 (2H, m), 1.9–2.0 (2H, m), 2.05–2.2 (2H, m), 2.2–2.55 (6H, m), 3.0–3.2 (2H, m), 3.2–3.45 (4H, m), 3.55–3.7 (2H, m), 3.95–4.1 (2H, m), 5.15–5.3 (2H, m), 6.90 (1H, s), 7.0–7.1 (2H, m), 7.2–7.55 (12H, m), 8.01 (1H, d, J=7.6 Hz), 12.80 (1H, br).

REFERENCE EXAMPLE 1

Ethyl 3-{bis[4-(methoxymethoxy)phenyl]methyl}-indole-2-carboxylate

Substantially the same procedure as in Example 1 was repeated using 4,4'-bis(methoxymethoxy)benzhydrol (6.22 g, 32.9 mmol) and ethyl indole-2-carboxylate (10.0 g, 32.9 mmol) to give 12.9 g (yield: 89%) of the title compound.

$^1$H-NMR(CDCl$_3$) δ(ppm): 1.39 (3H, t, J=7.3 Hz), 3.46 (6H, s), 4.39 (2H, q, J=7.3 Hz), 5.14 (4H, s), 6.58 (1H, s), 6.85–6.95 (5H, m), 7.03 (1H, d, J=7.3 Hz), 7.13 (4H, d, J=8.2 Hz), 7.2–7.25 (1H, m), 7.36 (1H, d, J=8.6 Hz), 8.80 (1H, s).

REFERENCE EXAMPLE 2

1-{3-{Bis[4-(methoxymethoxy)phenyl]methyl}-1-(3-chloropropyl)indol-2-ylcarbonyl}-4-(2-chlorophenyl)piperazine To a solution of Compound 1 (5.0 g, 7.99 mmol) obtained in Example 1 in 50 ml of N,N-dimethylformamide was portionwise added sodium hydride (60%. in oil, 351 mg, 8.78 mmol) with stirring at room temperature, and 1-bromo-3-chloropropane (0.87 ml, 8.78 mmol) was added thereto, followed by stirring at room temperature for 4 hours. 1-Bromo-3-chloropropane (0.16 ml, 1.62 mmol) was added thereto and the mixture was stirred further for 4.5 hours. The reaction mixture was neutralized with a saturated aqueous solution of ammonium chloride, and water was added thereto followed by extraction with ethyl acetate. The resulting organic layer was washed with water and a saturated aqueous solution of sodium chloride and dried over magnesium sulfate, and the solvent was distilled off under reduced pressure to give 6.5 g of a crude product. The obtained crude product was purified with silica gel column chromatography (ethyl acetate/hexane=1/3–1/1) to give 5.35 g (yield: 95%) of the title compound.

$^1$H-NMR(CDCl$_3$) δ(ppm): 2.1–2.35 (3H, m), 2.5–2.65 (1H, m), 2.8–2.9 (1H, m), 2.9–3.15 (2H, m), 3.15–3.3 (1H, m), 3.40 (3H, s), 3.43 (3H, s), 3.45–3.65 (2H, m), 3.65–3.8 (1H, m), 3.9–4.05 (1H, m), 4.0–4.2 (1H, m), 4.4–4.6 (1H, m), 5.05–5.15 (4H, m), 5.69 (1H, s), 6.8–7.05 (7H, m), 7.15–7.3 (7H, m), 7.33 (1H, dd, J=7.9, 1.7 Hz), 7.40 (1H, d, J=8.2 Hz).

REFERENCE EXAMPLE 3

1-{3-{Bis[4-(methoxymethoxy)phenyl]methyl}-1-(4-chlorobutyl)indol-2-ylcarbonyl}-4-(2-chlorophenyl)piperazine Substantially the same procedure as in Reference Example 2 was repeated using Compound 1 (5.0 g, 7.99 mmol) and 1-bromo-4-chlorobutane (1.0 ml, 8.78 mmol) to give 5.3 g (yield: 93%) of the title compound.

$^1$H-NMR(CDCl$_3$) δ(ppm): 1.75–1.85 (2H, m), 1.9–2.1 (2H, m), 2.1–2.2 (1H, m), 2.5–2.6 (1H, m), 2.8–2.9 (1H, m), 2.9–3.15 (2H, m), 3.15–3.3 (1H, m), 3.40 (3H, s), 3.43 (3H, s), 3.5–3.6 (2H, m), 3.7–3.85 (1H, m), 3.9–4.05 (2H, m), 4.2–4.35 (1H, m), 5.05–5.15 (4H, m), 5.68 (1H, s), 6.75–7.0 (7H, m), 7.0–7.25 (7H, m), 7.3–7.4 (2H, m).

REFERENCE EXAMPLE 4

Ethyl 3-(diphenylmethyl)indole-2-carboxylate

Boron trifluoride-ether complex (0.65 ml, 5.29 mmol) was added to a solution of ethyl indole-2-carboxylate (10.0 g, 52.9 mmol) in 100 ml of methylene chloride, and a solution of benzhydryl acetate (11.4 g, 50.2 mmol) in 50 ml of methylene chloride was dropwise added thereto, followed by stirring at room temperature for 40 minutes. A saturated aqueous solution of sodium bicarbonate was added to the reaction solution for neutralization followed by extraction with chloroform. The resulting organic layer was washed with a saturated aqueous solution of sodium bicarbonate and a saturated aqueous solution of sodium chloride, and dried over magnesium sulfate, and the solvent was distilled off under reduced pressure to give a crude product. The obtained crude product was washed with diisopropyl ether to give 15.8 g (yield: 84%) of the title compound.

$^1$H-NMR(CDCl$_3$) δ(ppm): 1.38 (3H, t, J=7.2 Hz), 4.38 (2H, q, J=7.2 Hz), 6.69 (1H, s), 6.8–6.9 (1H, m), 6.97 (1H, d, J=7.9 Hz), 7.15–7.3 (11H, m), 8.35 (1H, d, J=8.2 Hz), 8.85–8.95 (1H, br).

REFERENCE EXAMPLE 5

Ethyl 3-[bis(4-fluorophenyl)methyl]indole-2-carboxylate

To a solution of 4,4'-difluorobenzhydrol (12.8 g, 58.1 mmol) and ethyl indole-2-carboxylate (10.0 g, 52.9 mmol) in 100 ml of methylene chloride was added methanesulfonic acid (3.4 ml, 52.9 mmol), followed by stirring at room temperature for one hour. Then, 4,4'-difluorobenzhydrol (1.0 g, 4.54 mmol) was further added to the reaction mixture followed by stirring for 1.5 hours to complete the reaction. A 2N aqueous sodium hydroxide solution was added to the reaction solution, and a saturated aqueous solution of ammonium chloride was further added thereto for neutralization followed by extraction with chloroform. The resulting organic layer was washed with a saturated aqueous solution of sodium bicarbonate and a saturated aqueous solution of sodium chloride, and dried over magnesium sulfate, and the solvent was distilled off under reduced pressure to give a crude product. The obtained crude product was recrystallized from ethanol to give 8.4 g (yield: 40%) of the title compound.

$^1$H-NMR(CDCl$_3$) δ(ppm): 1.39 (3H, t, J=7.2 Hz), 4.39 (2H, q, J=7.2 Hz), 6.63 (1H, s), 6.85–7.0 (6H, m), 7.1–7.2 (4H, m), 7.2–7.3 (1H, m), 7.38 (1H, d, J=8.3 Hz), 8.87 (1H, br s).

REFERENCE EXAMPLE 6

Ethyl 1-(3-chloropropyl)-3-(diphenylmethyl)indole-2-carboxylate

To a solution of ethyl 3-(diphenylmethyl)indole-2-carboxylate (38.0 g, 107 mmol) obtained in Reference Example 4 in 380 ml of N,N-dimethylformamide was added sodium hydride (60% in oil, 4.7 g, 118 mmol) under ice cooling, and 1-bromo-3-chloropropane (11.6 ml, 118 mmol) was added thereto, followed by stirring at room temperature for 21 hours. A saturated aqueous solution of ammonium chloride and water was added to the reaction solution followed by extraction with ethyl acetate. The resulting organic layer was washed with water and a saturated aqueous solution of, sodium chloride and dried over magnesium sulfate, and the solvent was distilled off under reduced pressure to give 51.1 g of a crude product. The obtained crude product was recrystallized from ethanol to give 40.6 g (yield: 88%) of the title compound.

$^1$H-NMR(CDCl$_3$) δ(ppm): 1.36 (3H, t, J=7.3 Hz), 2.26–2.36 (2H, m), 3.57 (2H, t, J=6.3 Hz), 4.34 (2H, q, J=7.3 Hz), 4.66 (2H, t, J=7.3 Hz), 6.58 (1H, s), 6.84–6.95 (2H, m), 7.15–7.30 (11H, m), 7.45 (1H, d, J=8.6 Hz).

REFERENCE EXAMPLE 7

Ethyl 1-(4-chlorobutyl)-3-(diphenylmethyl)indole-2-carboxylate

Substantially the same procedure as in Reference Example 6 was repeated using ethyl 3-(diphenylmethyl)indole-2-carboxylate (75.76 g, 213 mmol) obtained in Reference Example 4 and 1-bromo-4-chlorobutane (27 ml, 234 mmol) to give 82.0 g (yield: 84%) of the title compound.

$^1$H-NMR(CDCl$_3$) δ(ppm): 1.36 (3H, t, J=6.9 Hz), 1.78–1.88 (2H, m), 1.93–2.05 (2H, m), 3.55 (2H, t, J=6.6 Hz), 4.34 (2H, q, J=6.9 Hz), 4.52 (2H, t, J=7.3 Hz), 6.58 (1H, s), 6.83–6.94 (2H, m), 7.16–7.38 (12H, m).

REFERENCE EXAMPLE 8

Ethyl 3-[bis(4-chlorophenyl)methyl]indole-2-carboxylate

Substantially the same procedure as in Reference Example 5 was repeated using 4,4'-dichlorobenzhydrol (14.7 g, 58.1 mmol) and ethyl indole-2-carboxylate (10.0 g, 52.9 mmol) to give 21.0 g (yield: 94%) of the title compound.

$^1$H-NMR(CDCl$_3$) δ(ppm): 1.39 (3H, t, J=7.3 Hz), 4.39 (2H, q, J=7.3 Hz), 6.62 (1H, s), 6.9–6.95 (2H, m), 7.13 (4H, d, J=8.6 Hz), 7.2–7.35 (5H, m), 7.39 (1H, d, J=8.3 Hz), 8.87 (1H, s).

REFERENCE EXAMPLE 9

Ethyl 3-[bis(4-methylphenyl)methyl]indole-2-carboxylate

Substantially the same procedure as in Reference Example 4 was repeated using 4,4'-dimethylbenzhydrol (11.8 g, 55.5 mmol) and ethyl indole-2-carboxylate (10.0 g, 52.9 mmol) to give 19.8 g (yield: 97%) of the title compound.

$^1$H-NMR(CDCl$_3$) δ(ppm): 1.39 (3H, t, J=7.1 Hz), 2.31 (6H, s), 4.38 (2H, q, J=7.1 Hz), 6.60 (1H, s), 6.85–6.95 (1H, m), 7.0–7.15 (9H, m), 7.2–7.3 (1H, m), 7.35 (1H, d, J=8.6 Hz), 8.82 (1H, s).

REFERENCE EXAMPLE 10

Ethyl 3-(4-benzyloxybenzhydryl)indole-2-carboxylate

Substantially the same procedure as in Reference Example 4 was repeated using 4-benzyloxybenzhydrol (30.0 g, 103 mmol) and ethyl indole-2-carboxylate (18.5 g, 97.9 mmol) to give 42.7 g (yield: 95%) of the title compound.

$^1$H-NMR(CDCl$_3$) δ(ppm): 1.49 (3H, t, J=7.2 Hz), 4.48 (2H, q, J=7.2 Hz), 5.93 (2H, s), 6.72 (1H, s), 6.95–7.05 (3H, m), 7.08 (1H, d, J=7.9 Hz), 7.23 (2H, d, J=8.6 Hz), 7.25–7.55 (12H, m), 8.94 (1H, s).

REFERENCE EXAMPLE 11

3-(4-Benzyloxybenzhydryl)-1-(2-dimethylaminoethyl)indole-2-carboxylic acid

Substantially the same procedure as in Example 89 was repeated using ethyl 3-(4-benzyloxybenzhydryl)indole-2-carboxylate (20.0 g, 43.3 mmol) obtained in Reference Example 10 and 2-dimethylaminoethylchloride hydrochloride (6.55 g, 45.5 mmol) to give 26.3 g of ethyl 3-(4-benzyloxybenzhydryl)1-(2-dimethylaminoethyl)indole-2-carboxylate. Then, substantially the same procedure as in Example 93 was repeated using this compound (26.3 g) to give 19.8 g (yield: 91%, 2 steps) of the title compound.

$^1$H-NMR(CDCl$_3$) δ(ppm): 2.41 (6H, s), 3.18 (2H, t, J=6.1 Hz), 4.77 (2H, t, J=6.1 Hz), 5.00 (2H, s), 6.78 (1H, s), 6.84 (2H, d, J=8.9 Hz), 6.85–6.95 (1H, m), 7.1–7.45 (15H, m).

REFERENCE EXAMPLE 12

3-(4-Benzyloxybenzhydryl)-1-(2-pyrrolidinylethyl)indole-2-carboxylic acid

Substantially the same procedure as in Example 89 was repeated using ethyl 3-(4-benzyloxybenzhydryl)indole-2-carboxylate (20.0 g, 43.33 mmol) obtained in Reference Example 10 and 2-pyrrolidinylethylchloride hydrochloride (8.1 g, 47.66 mmol) to give 24.9 g of ethyl 3-(4-benzyloxybenzhydryl)-1-(2-pyrrolidinylethyl)indole-2-carboxylate. Then, substantially the same procedure as in Example 93 was repeated using this compound (24.9 g) to give 21.2 g (yield: 92%, 2 steps) of the title compound.

$^1$H-NMR(CDCl$_3$) δ(ppm): 1.65–1.85 (4H, m), 2.65–2.95 (4H, m), 3.35 (2H, t, J=6.1 Hz), 4.75–4.9 (2H, m), 5.00 (2H, s), 6.76 (1H, s), 6.83 (2H, d, J=8.9 Hz), 6.85–6.95 (1H, m), 7.05–7.45 (15H, m).

In the following Reference Examples 13 to 18, substantially the same procedure as in Example 94 was repeated using 3-(4-benzyloxybenzhydryl)-1-(2-dimethylaminoethyl)indole-2-carboxylic acid obtained in Reference Example 11 in place of Compound 93 and using corresponding amines in place of propylamine to give the desired compounds.

REFERENCE EXAMPLE 13

N-Propyl-3-(4-benzyloxybenzhydryl)-1-(2-dimethylaminoethyl)indole-2-carboxamide $^1$H-NMR(CDCl$_3$) δ(ppm): 0.85 (3H, t, J=7.4 Hz), 1.4–1.55 (2H, m), 2.22 (6H, s), 2.77 (2H, t, J=6.6 Hz), 3.31 (2H, q, J=6.6 Hz), 4.43 (2H, t, J=6.6 Hz), 5.03 (2H, s), 6.05 (1H, s), 6.85–6.95 (4H, m), 7.0–7.1 (1H, m), 7.11 (2H, d, J=8.6 Hz), 7.15–7.45 (12H, m).

REFERENCE EXAMPLE 14

N-Isopropyl-3-(4-benzyloxybenzhydryl)-1-(2-dimethylaminoethyl)indole-2-carboxamide $^1$H-NMR(CDCl$_3$) δ(ppm): 1.10 (6H, d, J=6.3 Hz), 2.20 (6H, s), 2.74 (2H, t, J=6.9 Hz), 4.15–4.3 (1H, m), 4.44 (2H, t, J=6.9 Hz), 5.04 (2H, s), 5.99 (1H, s), 6.63 (1H, d, J=7.6 Hz), 6.8–6.95 (4H, m), 7.10 (2H, d, J=8.6 Hz), 7.15–7.45 (12H, m).

REFERENCE EXAMPLE 15

N-(4-propylphenyl)-3-(4-benzyloxybenzhydryl)-1-(2-dimethylaminoethyl)indole-2-carboxamide $^1$H-NMR(CDCl$_3$) δ(ppm): 0.94 (3H, t, J=7.3 Hz), 1.55–1.7 (2H, m), 2.17 (6H, s), 2.5–2.6 (2H, m), 2.81 (2H, t, J=6.3 Hz), 4.48 (2H, t, J=6.3 Hz), 5.03 (2H, s), 6.17 (1H, s), 6.8–6.95 (3H, m), 7.00 (1H, d, J=8.3 Hz), 7.1–7.45 (18H, m), 9.32 (1H, s).

REFERENCE EXAMPLE 16

N-(3-Morpholinopropyl)-3-(4-benzyloxy-benzhydryl)-1-(2-dimethylaminoethyl)indole-2-carboxamide $^1$H-NMR(CDCl$_3$) δ(ppm): 1.6–1.75 (2H, m), 2.2–2.4 (6H, m), 2.22 (6H, s), 2.75 (2H, t, J=6.6 Hz), 3.35–3.45 (2H, m), 3.6–3.7 (4H, m), 4.40 (2H, t, J=6.6 Hz), 5.02 (2H, s), 6.05 (1H, s), 6.87 (2H, d, J=8.6 Hz), 6.9–7.0 (2H, m), 7.12 (2H, d, J=8.6 Hz), 7.15–7.5 (13H, m).

REFERENCE EXAMPLE 17

N-[3-(2-Oxopyrrolidinyl)propyl]-3-(4-benzyloxybenzhydryl)-1-(2-dimethylaminoethyl)indole-2-carboxamide $^1$H-NMR(CDCl$_3$) δ(ppm): 1.65–1.8 (2H, m), 1.9–2.1 (2H, m), 2.19 (6H, s), 2.35 (2H, t, J=8.1 Hz), 2.79 (2H, t, J=6.4 Hz), 3.24 (2H, t, J=7.1 Hz), 3.3–3.4 (4H, m), 4.41 (2H, t, J=6.4 Hz), 5.02 (2H, 3), 6.12 (1H, s), 6.87 (2H, d, J=8.6 Hz), 6.9–7.0 (1H, m), 7.13 (2H, d, J=8.6 Hz), 7.2–7.5 (13H, m), 7.8–7.9 (1H, m).

REFERENCE EXAMPLE 18

N-Cyclooctyl-3-(4-benzyloxybenzhydryl)-1-(2-dimethylaminoethyl)indole-2-carboxamide $^1$H-NMR(CDCl$_3$) δ(ppm): 1.3–1.6 (12H, m), 1.65–1.85 (2H, m), 2.20 (6H, s), 2.73 (2H, t, J=6.9 Hz), 4.05–4.2 (1H, m), 4.44 (2H, t, J=6.9 Hz), 5.03 (2H, s), 6.00 (1H, s), 6.63 (1H, d, J=8.3 Hz), 6.8–6.9 (4H, m), 7.10 (2H, d, J=8.5 Hz), 7.15–7.45 (12H, m).

In the following Reference Examples 19 to 22, substantially the same procedure as in Example 94 was repeated using 3-(4-benzyloxybenzhydryl)-1-( 2-pyrrolidinylethyl)indole-2-carboxylic acid obtained in Reference Example 12 in place of Compound 93 and using corresponding amines in place of propylamine to give the desired compounds.

REFERENCE EXAMPLE 19

N-Propyl-3-(4-benzyloxybenzhydryl)-1(2-pyrrolidinylethyl)indole-2-carboxamide $^1$H-NMR(CDCl$_3$) δ(ppm): 0.87 (3H, t, J=7.4 Hz), 1.6–1.75 (2H, m), 1.8–1.95 (4H, m), 2.3–2.45 (4H, m), 2.99 (2H, t, J=6.6 Hz), 3.25–3.35 (2H, m), 4.46 (2H, t, J=6.6 Hz), 5.03 (2H, s), 6.12 (1H, s), 6.85–6.95 (3H, m), 6.95 (1H, d, J=7.6 Hz), 7.1–7.45 (14H, m), 7.75–7.85 (1H, m).

REFERENCE EXAMPLE 20

N-Isopropyl-3-(4-benzyloxybenzhydryl)-1-(2-pyrrolidinylethyl)-indole-2-carboxamide $^1$H-NMR(CDCl$_3$) δ(ppm): 1.10 (6H, d, J=6.6 Hz), 1.55–1.65 (4H, m), 2.3–2.4 (4H, m), 2.97 (2H, t, J=6.6 Hz), 4.15–4.25 (1H, m), 4.47 (2H, t, J=6.6 Hz), 5.03 (2H, s), 6.08 (1H, s), 6.8–6.95 (4H, m), 7.1–7.45 (14H, m), 7.45–7.6 (1H, m).

REFERENCE EXAMPLE 21

N-(3-Morpholinopropyl)-3-(4-benzyloxybenzhydryl)-1-(2-pyrrolidinylethyl)indole-2-carboxamide $^1$H-NMR(CDCl$_3$) δ(ppm): 1.6–1.75 (6H, m), 2.25–2.45 (10H, m), 2.95–3.05 (2H, m), 3.3–3.45 (2H, m), 3.55–3.65 (4H, m), 4.45 (2H, t, J=6.6 Hz), 5.02 (2H, s), 6.10 (1H, s), 6.8–6.95 (3H, m), 6.97 (1H, d, J=8.0 Hz), 7.13 (2H, d, J=8.6 Hz), 7.15–7.45 (12H, m), 7.9–8.0 (1H, m).

REFERENCE EXAMPLE 22

N-[3-(2-Oxopyrrolidinyl)propyl]-3-(4-benzyloxybenzhydryl)-1-(2-pyrrolidinylethyl)indole-2-carboxamide $^1$H-NMR(CDCl$_3$) δ(ppm): 1.6–1.8 (6H, m), 1.95–2.2 (2H, m), 2.3–2.45 (6H, m), 3.03 (2H, t, J=6.2 Hz), 3.2–3.4 (6H, m), 4.46 (2H, t, J=6.2 Hz), 5.02 (2H, s), 6.17 (1H, s), 6.8–6.95 (3H, m), 6.98 (1H, d, J=7.9 Hz), 7.1–7.45 (14H, m), 8.4–8.6 (1H, m).

REFERENCE EXAMPLE 23

Ethyl 3-[4-(2-dimethylaminoethoxy)benzhydryl]-indole-2-carboxylate

Substantially the same procedure as in Reference Example 5 was repeated using 4-(2-dimethylaminoethoxy) benzhydrol (14.78 g, 54.5 mmol) and ethyl indole-2-carboxylate (11.3 g, 59.9 mmol) to give 20.8 g (yield: 86%) of the title compound.

$^1$H-NMR(CDCl$_3$) δ(ppm): 1.38 (3H, t, J=6.9 Hz), 2.32 (6H, s), 2.71 (2H, t, J=5.9 Hz), 4.03 (2H, t, J=5.9 Hz), 4.38 (2H, q, J=7.3 Hz), 6.61 (1H, s), 6.80–6.98 (4H, m), 7.09–7.36 (9H, m), 8.95 (1H, s).

REFERENCE EXAMPLE 24

3-[4-(2-Dimethylaminoethoxy)benzhydryl]indole-2-carboxylic acid

Substantially the same procedure as in Example 93 was repeated using ethyl 3-[4-(2-dimethylaminoethoxy)

benzhydryl]indole-2-carboxylate (20.8 g) obtained in Reference Example 23 to give 18.2 g (yield: 94%) of the title compound.

$^1$H-NMR(DMSO-d$_6$) δ(ppm): 2.30 (6H, s), 2.75 (2H, t, J=5.6 Hz), 4.03 (2H, t, J=5.9 Hz), 6.77–7.39 (14H, m), 11.45 (1H, s).

REFERENCE EXAMPLE 25

Ethyl 3-[4-(2-pyrrolidinylethoxy)benzhydryl]-indole-2-carboxylate

Substantially the same procedure as in Reference Example 5 was repeated using 4-(2-pyrrolidinylethoxy) benzhydrol (19.4 g, 65.1 mmol) and ethyl indole-2-carboxylate (13.55 g, 71.6 mmol) to give 31.2 g (quantitative) of the title compound.

$^1$H-NMR(CDCl$_3$) δ(ppm): 1.39 (3H, t, J=7.3 Hz), 1.60–1.85 (4H, m), 2.50–2.70 (4H, m), 2.88 (2H, t, J=6.3 Hz), 4.08 (2H, t, J=6.3 Hz), 4.38 (2H, q, J=6.9 Hz), 6.61 (1H, s), 6.79–6.99 (4H, m), 7.10–7.40 (9H, m), 8.83 (1H, s).

REFERENCE EXAMPLE 26

3-[4-(2-Pyrrolidinylethoxy)benzhydryl]indole-2-carboxylic acid

Substantially the same procedure as in Example 93 was repeated using ethyl 3-[4-(2-pyrrolidinylethoxy)benzhydryl] indole-2-carboxylate (29.17 g, 62.2 mmol) obtained in Reference Example 25 to give 24.8 g (yield: 90%) of the title compound.

$^1$H-NMR(DMSO-d$_6$) δ(ppm): 1.60–1.80 (4H, br), 2.65–2.80 (4H, br), 2.97 (2H, t, J=5.6 Hz), 4.08 (2H, t, J=5.9 Hz), 6.72–7.37 (14H, m), 11.35 (1H, s).

REFERENCE EXAMPLE 27

Ethyl 3-[4-(2-chloroethoxy)benzhydryl]-1-(2-dimethylaminoethyl)indole-2-carboxylate Substantially the same procedure as in Reference Example 5 was repeated using 4-(2-chloroethoxy) benzhydrol (17.66 g, 67.2 mmol) and ethyl 1-(2-dimethylaminoethyl)indole-2-carboxylate (19.2 g, 73.9 mmol) to give 27.6 g (yield: 81%) of the title compound.

$^1$H-NMR(CDCl$_3$) δ(ppm): 1.36 (3H, t, J=7.3 Hz), 2.34 (6H, s), 2.68 (2H, t, J=7.6 Hz), 3.79 (2H, t, J=5.9 Hz), 4.20 (2H, t, J=5.9 Hz), 4.35 (2H, q, J=7.3 Hz), 4.60 (2H, t, J=7.6 Hz), 6.51 (1H, s), 6.79–6.95 (4H, m), 7.08–7.42 (9H, m).

REFERENCE EXAMPLE 28

3-[4-(2-Chloroethoxy)benzhydryl]-1-(2-pyrrolidinylethyl)indole-2-carboxylate

Substantially the same procedure as in Reference Example 5 was repeated using 4-(2-chloroethoxy) benzhydrol (17.6 g, 67 mmol) and ethyl 1-(2-pyrrolidinylethyl)indole-2-carboxylate (21.1 g, 73.6 mmol) to give 37.4 g (quantitative) of the title compound.

$^1$H-NMR(CDCl$_3$) δ(ppm): 1.36 (3H, t, J=7.3 Hz), 1.75–1.90 (4H, br), 2.55–2.75 (4H, br), 2.87 (2H, t, J=7.9 Hz), 3.79 (2H, t, J=5.9 Hz), 4.20 (2H, t, J=5.9 Hz), 4.34 (2H, q, J=7.3 Hz), 4.65 (2H, t, J=7.9 Hz), 6.51 (1H, s), 6.79–6.95 (4H, m), 7.08–7.45 (9H, m).

REFERENCE EXAMPLE 29

1-[2-(N-Benzyloxycarbonyl-N-methylamino)ethyl]-3-(diphenylmethyl)indole-2-carboxylic acid Substantially the same procedure as in Example 89 was repeated using 3-(diphenylmethyl)indole-2-carboxylic acid (1.23 g, 3.47 mmol) obtained in Reference Example 4 and 2-(N-benzyloxycarbonyl-N-methylamino)ethylchloride (0.79 g, 3.47 mmol) to give 0.93 g (yield: 49%) of ethyl 1-[2-(N-benzyloxycarbonyl-N-methylamino)ethyl]-3-(diphenylmethyl)indole-2-carboxylate. Then, to a solution of this compound (0.93 g, 1.70 mmol) in a mixed solvent of ethanol (12 ml) and water (2 ml) was added lithium hydroxide (0.36 g, 8.51 mmol), followed by heating under reflux for 3 hours. The solvent was distilled off under reduced pressure and a saturated aqueous solution of ammonium chloride was added thereto for neutralization, followed by extraction with ethyl acetate. The resulting organic layer was washed with a saturated aqueous solution of ammonium chloride and a saturated aqueous solution of sodium chloride and dried over magnesium sulfate, and the solvent was distilled off under reduced pressure to give a crude product. The obtained crude product was crystallized from ethanol to give 0.65 g (yield: 74%) of the title compound.

$^1$H-NMR(CDCl$_3$) δ(ppm): 2.61, 2.81 (3H, each s), 3.55–3.75 (2H, m), 4.55–4.65, 4.65–4.75 (2H, each m), 5.11 (2H, s), 6.69, 6.72 (1H, each s), 6.75–6.95 (2H, m), 7.02 (1H, br s), 7.1–7.4 (15H, m), 7.48 (1H, d, J=8.6 Hz).

REFERENCE EXAMPLE 30

N-[3-(2-Oxopyrrolidinyl)propyl]-1-[2-(N-benzyloxycarbonyl-N-methylamino)ethyl]-3-(diphenylmethyl)indole-2-carboxamide Substantially the same procedure as in Example 94 was repeated using 1-[2-(N-benzyloxycarbonyl-N-methylamino) ethyl]-3-(diphenylmethyl)indole-2-carboxylic acid (0.57 g, 1.10 mmol) obtained in Reference Example 29 and 1-(3-aminopropyl)-2-pyrrolidinone (0.23 ml, 1.65 mmol) to give 0.46 g (yield: 65%) of the title compound.

$^1$H-NMR(CDCl$_3$) δ(ppm): 1.6–1.75 (2H, m), 1.95–2.1 (2H, m), 2.35 (2H, t, J=7.9 Hz), 2.64, 2.75 (3H, each s), 3.15–3.4 (6H, m), 3.6–3.75 (2H, m), 4.4–4.55 (2H, m), 4.98, 5.05 (2H, each s), 5.94, 5.97 (1H, each s), 6.05–6.15, 6.15–6.25 (1H, each m), 6.8–6.9 (2H, m), 7.0–7.5(17H, m).

REFERENCE EXAMPLE 31

5-Diphenylmethyl-1,2-dihydro-4H-indolo[2,1-c][1,4]oxazin-4-one

Substantially the same procedure as in Example 89 was repeated using 3-(diphenylmethyl)indole-2-carboxylic acid (2.0 g, 5.6 mmol) obtained in Reference Example 4 and 2-bromoethyl acetate (0.8 ml, 7.2 mmol) to give 2.4 g (yield: 97%) of ethyl 1-(2-acetoxyethyl)-3-(diphenylmethyl)indole-2-carboxylate. Then, to a suspension of this compound (1.87 g, 4.25 mmol) in 15 ml of methanol was added sodium methoxide (0.98 ml, 5.10 mmol), followed by stirring at room temperature for 2 hours. A saturated aqueous solution of ammonium chloride was added thereto for neutralization followed by extraction with chloroform. The resulting organic layer was washed with a saturated aqueous solution of sodium chloride and dried over magnesium sulfate, and the solvent was distilled off under reduced pressure to give 1.55 g (quantitative) of the title compound.

$^1$H-NMR(CDCl$_3$) δ(ppm): 4.32 (2H, t, J=5.3 Hz), 4.72 (2H, t, J=5.3 Hz), 6.85 (1H, s), 6.93–6.99 (1H, m), 7.11 (1H, d, J=8.3 Hz), 7.19–7.37 (12H, m).

REFERENCE EXAMPLE 32

N-[3-(2-Oxopyrrolidinyl)propyl]-3-(diphenylmethyl) -1-(2-hydroxyethyl)indole-2-carboxamide 5-Diphenylmethyl-1,2-dihydro-4H-indolo[2,1-c]-[1,4] oxazin-4-one (1.12 g, 3.2 mmol) obtained in Reference Example 31 and 1-(3-aminopropyl)-2-pyrrolidinone (0.9 ml, 6.4 mmol) were mixed and the mixture was stirred at 100° C. for 6 hours. Water was added to the reaction solution followed by extraction with chloroform. The resulting organic layer was washed with a saturated aqueous solution of sodium chloride and the solvent was distilled off under reduced pressure to give a crude product. The obtained crude product was purified with silica gel column chromatography (chloroform/methanol=20/1) to give 1.12 g (yield: 71%) of the title compound.

$^1$H-NMR(CDCl$_3$) δ(ppm): 1.71 (2H, q, J=6.9 Hz), 2.08 (2H, q, J=7.3 Hz), 2.39 (2H, t, J=7.9 Hz), 3.20–3.43 (6H, m), 4.06 (2H, t, J=5.3 Hz), 4.44 (2H, t, J=5.0 Hz), 6.08 (1H, s), 6.82–7.00 (3H, m), 7.11–7.38 (12H, m).

REFERENCE EXAMPLE 33

N-[3-(2-Oxopyrrolidinyl)propyl]-3-(diphenyl-methyl)-1-(2-phthalimideethyl)indole-2-carboxamide To a solution of N-[3-(2-oxopyrrolidinyl)propyl]-3-(diphenylmethyl)-1-(2-hydroxyethyl)indole-2-carboxamide (1.0 g, 2.02 mmol), triphenylphosphine (0.795 g, 3.03 mmol), and phthalimide (0.446 g, 3.03 mmol) in 30 ml of tetrahydrofuran was dropwise added diethyl azodicarboxylate (0.48 ml, 3.03 mmol), followed by stirring at room temperature for 2 hours and then being allowed to stand overnight. Water was added to the reaction mixture followed by extraction with ethyl acetate. The resulting organic layer was washed with a saturated aqueous solution of sodium chloride and dried over magnesium sulfate, and the solvent was distilled off under reduced pressure to give a crude product. The obtained crude product was purified with silica gel column chromatography (ethyl acetate) to give 0.70 g (yield: 56%) of the title compound.

$^1$H-NMR(CDCl$_3$) δ(ppm): 1.56–1.7 (2H, m), 1.90–2.07 (2H, m), 2.37 (2H, t, J=7.9 Hz), 3.12–3.27 (4H, m), 3.35 (2H, t, J=6.9 Hz), 4.05 (2H, t, J=5.9 Hz), 4.68 (2H, t, J=5.9 Hz), 5.93 (1H, s), 6.10(1H, t, J=5.9 Hz), 6.62–6.78(2H, m), 6.96 (1H, dt, J=1.3, 6.6 Hz), 7.10–7.32 (11H, m), 7.55–7.65 (4H, m).

REFERENCE EXAMPLE 34

N-Isopropyl-3-(4-benzyloxybenzhydryl)indole-2-sulfonamide

Substantially the same procedure as in Example 266 was repeated using 4-benzyloxybenzhydrol (1.31 g, 4.50 mmol) and N-isopropylindole-2-sulfonamide (1.00 g, 4.46 mmol) to give 1.92 g (yield: 84%) of the title compound.

$^1$H-NMR(CDCl$_3$) δ(ppm): 0.61 (3H, d, J=6.3 Hz), 0.63 (3H, d, J=6.3 Hz), 3.1–3.25 (1H, m), 3.75–3.85 (1H, m), 5.04 (2H, s), 6.36 (1H, s), 6.85–7.0 (4H, m), 7.14 (2H, d, J=8.6 Hz), 7.2–7.45 (12H, m), 8.78 (1H, br).

REFERENCE EXAMPLE 35

N-Diphenylmethyl-N-methyl-1-benzenesulfonylindole-2-sulfonamide

To a solution of N-diphenylmethyl-1-benzenesulfonylindole-2-sulfonamide (12.40 g, 24.67 mmol) in 120 ml of N,N-dimethylformamide was portionwise added sodium hydride (60% in oil, 1.18 g, 29.61 mmol) with stirring at 0° C., and iodomethane (1.85 ml, 29.61 mmol) was added thereto. The resulting solution was heated to 50° C. and stirred for 3 hours, followed by stirring at 70° C. for 3.5 hours. The reaction solution was neutralized with a saturated aqueous solution of ammonium chloride, and water was added thereto followed by extraction with chloroform. The resulting organic layer was washed with water and a saturated aqueous solution of sodium chloride and dried over magnesium sulfate, and the solvent was distilled off under reduced pressure to give 18.1 g of a crude product. The obtained crude product was washed with ethanol under heating to give 11.0 g (yield: 86%) of the title compound.

$^1$H-NMR(CDCl$_3$) δ(ppm): 2.95 (3H, s), 6.44 (1H, s), 7.15–7.55 (17H, m), 8.09 (2H, d, J=7.6 Hz), 8.22 (1H, d, J=9.2 Hz).

REFERENCE EXAMPLE 36

N-Diphenylmethyl-N-isopropyl-1-benzenesulfonylindole-2-sulfonamide

To a solution of N-isopropyl-1-benzenesulfonylindole-2-sulfonamide (10.0 g, 26.42 mmol), triphenylphosphine (10.4 g, 39.63 mmol), and benzhydrol (7.30 g, 39.63 mmol) in 100 ml of tetrahydrofuran was dropwise added a solution of diethyl azodicarboxylate (6.24 ml, 39.63 mmol) in 100 ml of tetrahydrofuran with stirring, followed by stirring at room temperature for 2 hours. Water was added to the reaction mixture followed by extraction with ethyl acetate. The resulting organic layer was washed with a saturated aqueous solution of sodium chloride and dried over magnesium sulfate, and the solvent was distilled off under reduced pressure to give 34.5 g of a crude product. The obtained crude product was purified with silica gel column chromatography (ethyl acetate/hexane=1/9) followed by crystallization from ethanol to give 11.4 g (yield: 79%) of the title compound.

$^1$H-NMR(CDCl$_3$) δ(ppm): 1.27 (6H, d, J=6.6 Hz), 4.6–4.75 (1H, m), 6.26 (1H, s), 6.62 (1H, s), 7.1–7.5 (16H, m), 7.93 (2H, d, J=7.3 Hz), 8.22 (1H, d, J=8.6 Hz).

REFERENCE EXAMPLE 37

N-Diphenylmethyl-N-[3-(2-oxopyrrolidinyl)propyl]-1-benzenesulfonylindole-2-sulfonamide Substantially the same procedure as in Reference Example 36 was repeated using N-[3-(2-oxopyrrolidinyl)propyl]-1-benzenesulfonylindole-2-sulfonamide (10.0 g, 21.67 mmol) and benzhydrol (6.00 g, 32.50 mmol) to give 4.85 g (yield: 36%) of the title compound.

$^1$H-NMR(CDCl$_3$) δ(ppm): 1.2–1.4 (2H, m), 1.8–2.0 (2H, m), 2.29 (2H, t, J=8.1 Hz), 2.97 (2H, t, J=6.6 Hz), 3.07 (2H, t, J=7.1 Hz), 3.55–3.7 (2H, m), 6.45 (1H, s), 7.1–7.35 (7H, m), 7.35–7.6 (8H, m), 7.6–7.75 (2H, m), 8.03 (2H, d, J=7.6 Hz), 8.18 (1H, d, J=8.6 Hz).

REFERENCE EXAMPLE 38

N-Diphenylmethyl-N-methylindole-2-sulfonamide

To a solution of N-diphenylmethyl-N-methyl-1-benzenesulfonyl-indole-2-sulfonamide (10.70 g, 20.71 mmol) obtained in Reference Example 35 in 100 ml of ethanol was added a 2N aqueous sodium hydroxide solution (35 ml), followed by heating under reflux for 2.5 hours. The solvent was distilled off under reduced pressure, and water and ethyl acetate were added, followed by extraction with ethyl acetate. The resulting organic layer was washed with water, a saturated aqueous solution of sodium bicarbonate, and a saturated aqueous solution of sodium chloride, and dried over magnesium sulfate, and the solvent was distilled off under reduced pressure to give 8.38 g of a crude product. The obtained crude product was washed with diethyl ether to give 7.22 g (yield: 93%) of the title compound.

$^1$H-NMR(CDCl$_3$) δ(ppm): 2.73 (3H, s), 6.54 (1H, s), 6.93 (1H, d, J=2.0 Hz), 7.05–7.35 (13H, m), 7.62 (1H, d, J=7.9 Hz), 8.16 (1H, s).

REFERENCE EXAMPLE 39

N-Diphenylmethyl-N-isopropylindole-2-sulfonamide

Substantially the same procedure as in Reference Example 38 was repeated using N-diphenylmethyl-N-isopropyl-1-benzenesulfonylindole-2-sulfonamide (11.0 g, 20.20 mmol) obtained in Reference Example 36 to give 7.30 g (yield: 89%) of the title compound.

$^1$H-NMR(CDCl$_3$) δ(ppm): 1.19 (6H, d, J=6.6 Hz), 4.25–4.4 (1H, m), 5.98 (1H, s), 6.83 (1H, s), 7.0–7.2 (3H, m), 7.2–7.4 (101H, m), 7.59 (1H, d, J=7.9 Hz).

REFERENCE EXAMPLE 40

N-Diphenylmethyl-N-[3-(2-oxopyrrolidinyl)propyl]indole-2-sulfonamide

Substantially the same procedure as in Reference Example 38 was repeated using N-diphenylmethyl-N-[3-(2-oxopyrrolidinyl)propyl]-1-benzenesulfonylindole-2-sulfonamide (4.80 g, 7.65 mmol) obtained in Reference Example 37 to give 2.97 g (yield: 80%) of the title compound.

$^1$H-NMR(CDCl$_3$) δ(ppm): 1.35–1.55 (2H, m), 1.85–2.0 (2H, m), 2.34 (2H, t, J=7.7 Hz), 2.98 (2H, t, J=6.4 Hz), 3.05–3.15 (2H, m), 3.36 (2H, t, J=7.6 Hz), 6.41 (1H, s), 6.96 (1H, d, J=2.0 Hz), 7.0–7.1 (4H, m), 7.1–7.35 (9H, m), 7.62 (1H, d, J=8.3 Hz), 8.85–9.05 (1H, m).

REFERENCE EXAMPLE 41

N-Diphenylmethyl-N-methyl-1-(2-dimethylaminoethyl)indole-2-sulfonamide

Substantially the same procedure as in Example 243 was repeated using N-diphenylmethyl-N-methylindole-2-sulfonamide (2.00 g, 5.31 mmol) obtained in Reference Example 38 and 2-dimethylaminoethylchloride hydrochloride (0.84 g, 5.84 mmol) to give 2.01 g (yield: 85%) of the title compound.

$^1$H-NMR(CDCl$_3$) δ(ppm): 2.26 (6H, s), 2.55–2.65 (2H, m), 2.80 (3H, s), 4.15–4.25 (2H, m), 6.53 (1H, s), 7.00 (1H, s), 7.05–7.15 (4H, m), 7.15–7.4 (9H, m), 7.64 (1H, d, J=7.9 Hz).

REFERENCE EXAMPLE 42

N-Diphenylmethyl-N-methyl-1-(2-pyrrolidinylethyl)indole-2-sulfonamide

Substantially the same procedure as in Example 243 was repeated using N-diphenylmethyl-N-methylindole-2-sulfonamide (2.00 g, 5.31 mmol) obtained in Reference Example 38 and 2-pyrrolidinylethylchloride hydrochloride (0.99 g, 5.84 mmol) to give 2.30 g (yield: 91%) of the title compound.

$^1$H-NMR(CDCl$_3$) δ(ppm): 1.65–1.8 (4H, m), 2.45–2.6 (4H, m), 2.7–2.8 (2H, m), 2.80 (3H, s), 4.2–4.3 (2H, m), 6.53 (1H, s), 7.00 (1H, s), 7.0–7.15 (4H, m), 7.15–7.4 (9H, m), 7.64 (1H, d, J=7.9 Hz).

REFERENCE EXAMPLE 43

N-Diphenylmethyl-N-isopropyl-1-(2-dimethylaminoethyl)indole-2-sulfonamide

Substantially the same procedure as in Example 243 was repeated using N-diphenylmethyl-N-isopropylindole-2-sulfonamide (2.0 g, 4.94 mmol) obtained in Reference Example 39 and 2-dimethylaminoethylchloride hydrochloride (0.79 g, 5.44 mmol) to give 2.05 g (yield: 87%) of the title compound.

$^1$H-NMR(CDCl$_3$) δ(ppm): 1.27 (6H, d, J=6.6 Hz), 2.26 (6H, s), 2.5–2.6 (2H, m), 3.9–4.05 (1H, m), 4.1–4.2 (2H, m), 6.25 (1H, s), 6.89 (1H, s), 7.1–7.2 (1H, m), 7.2–7.35 (12H, m), 7.57 (1H, d, J=8.3 Hz).

REFERENCE EXAMPLE 44

N-Diphenylmethyl-N-isopropyl-1-(2-pyrrolidinylethyl)indole-2-sulfonamide

Substantially the same procedure as in Example 243 was repeated using N-diphenylmethyl-N-isopropylindole-2-sulfonamide (2.0 g, 4.94 mmol) obtained in Reference Example 39 and 2-pyrrolidinylethylchloride hydrochloride (0.93 g, 5.44 mmol) to give 2.26 g (yield: 91%) of the title compound.

$^1$H-NMR(CDCl$_3$) δ(ppm): 1.27 (6H, d, J=6.9 Hz), 1.65–1.8 (4H, m), 2.45–2.6 (4H, m), 2.65–2.8 (2H, m), 3.85–4.0 (1H, m), 4.15–4.25 (2H, m), 6.25 (1H, s), 6.88 (1H, s), 7.05–7.2 (1H, m), 7.2–7.35 (12H, m), 7.56 (1H, d, J=7.9 Hz).

REFERENCE EXAMPLE 45

N-Diphenylmethyl-N-[3-(2-oxopyrrolidinyl)propyl]-1-(2-dimethylaminoethyl)indole-2-sulfonamide Substantially the same procedure as in Example 243 was repeated using N-diphenylmethyl-N-[3-(2-oxopyrrolidinyl)propyl]indole-2-sulfonamide (1.40 g, 2.87 mmol) obtained in Reference Example 40 and 2-dimethylaminoethylchloride hydrochloride (0.46 g, 3.16 mmol) to give 1.23 g (yield: 77%) of the title compound.

$^1$H-NMR(CDCl$_3$) δ(ppm): 1.2–1.4 (2H, m), 1.8–2.0 (2H, m), 2.2–2.35 (2H, m), 2.26 (6H, s), 2.45–2.6 (2H, m), 2.9–3.05 (4H, m), 3.2–3.35 (2H, m), 3.85–4.0 (2H, m), 6.54 (1H, s), 6.95–7.4 (14H, m), 7.64 (1H, d, J=8.3 Hz).

REFERENCE EXAMPLE 46

N-Diphenylmethyl-N-[3-(2-oxopyrrolidinyl)propyl]-1-(2-pyrrolidinylethyl)indole-2-sulfonamide Substantially the same procedure as in Example 243 was repeated using N-diphenylmethyl-N-[3-(2-oxopyrrolidinyl)propyl]indole-2-sulfonamide (1.40 g, 2.87 mmol) obtained in Reference Example 40 and 2-pyrrolidinylethylchloride hydrochloride (0.54 g, 3.16 mmol) to give 1.62 g (yield: 97%) the title compound.

$^1$H-NMR(CDCl$_3$) δ(ppm): 1.2–1.4 (2H, m), 1.8–1.95 (6H, m), 2.29 (2H, t, J=8.5 Hz), 2.45–2.7 (4H, m), 2.7–2.9 (2H, m), 2.9–3.05 (4H, m), 3.2–3.35 (2H, m), 3.95–4.15 (2H, m), 6.52 (1H, s), 6.9–7.0 (4H, m), 7.09 (1H, s), 7.1–7.4 (9H, m), 7.64 (1H, d, J=7.9 Hz).

INDUSTRIAL APPLICABILITY

According to the present invention, there can be provided indole derivatives which are useful as therapeutic agents for osteoporosis.

We claim:

1. An indole derivative represented by formula (I):

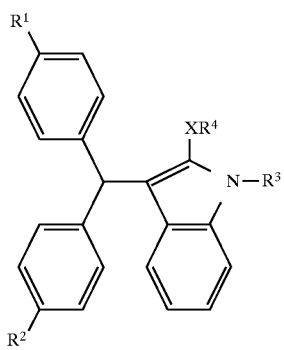

wherein $R^1$ and $R^2$ independently represent hydrogen, lower alkyl, hydroxy, lower alkoxy, halogen, —O—$(CH_2)_n$—$OR^5$ wherein $R^5$ represents hydrogen or lower alkyl, and n is an integer of 1 to 6, or

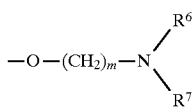

wherein $R^6$ and $R^7$ independently represent hydrogen or lower alkyl, or $R^6$ and $R^7$ are combined together with the adjacent nitrogen atom to form a substituted or unsubstituted alicyclic heterocyclic group, and m represents an integer of 2 to 6, $R^3$ represents hydrogen, lower alkyl, or

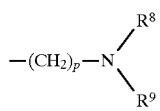

wherein $R^8$ and $R^9$ independently represent hydrogen or lower alkyl, or $R^8$ and $R^9$ are combined together with the adjacent nitrogen atom to form a substituted or unsubstituted alicyclic heterocyclic group, and p represents an integer of 2 to 6, $R^4$ represents hydroxy, lower alkoxy, substituted or unsubstituted aryloxy, or —$NR^{10}R^{11}$ wherein $R^{10}$ and $R^{11}$ independently represent hydrogen, lower alkyl, alicyclic alkyl, lower alkenyl, substituted or unsubstituted aryl, a substituted or unsubstituted heterocyclic group,

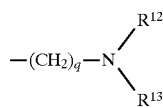

wherein $R^{12}$ and $R^{13}$ independently represent hydrogen or lower alkyl, or $R^{12}$ and $R^{13}$ are combined together with the adjacent nitrogen atom to form a substituted or unsubstituted alicyclic heterocyclic group, and q represents an integer of 2 to 6, or —$(CH_2)_r$—$R^{14}$ wherein $R^{14}$ represents substituted or unsubstituted aryl or a substituted or unsubstituted heterocyclic group, and r is an integer of 1 to 6, or $R^{10}$ and $R^{11}$ are combined together with the adjacent nitrogen atom to form a substituted or unsubstituted alicyclic heterocyclic group, and X represents CO or $SO_2$, with the proviso that when $R^3$ is hydrogen or lower alkyl, and X is CO, $R^4$ is —$NR^{10}R^{11}$ or pharmaceutically acceptable salts thereof.

2. An indole derivative according to claim 1, wherein $R^1$ and $R^2$ independently represent hydroxy, lower alkoxy, —O—$(CH_2)_n$—$OR^5$ wherein $R^5$ represents hydrogen or lower alkyl and n is an integer of 1 to 6, or

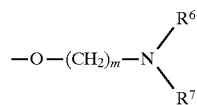

wherein $R^6$ and $R^7$ independently represent hydrogen or lower alkyl, or $R^6$ and $R^7$ are combined together with the adjacent nitrogen atom to form a substituted or unsubstituted alicyclic heterocyclic group; and m is an integer from 2 to 6, $R^4$ represents —$NR^{10b}R^{11b}$ wherein $R^{10b}$ and $R^{11b}$ independently represent hydrogen, lower alkyl, alicyclic alkyl, substituted or unsubstituted aryl, or a substituted or unsubstituted heterocyclic group, or $R^{10b}$ and $R^{11b}$ are combined together with the adjacent nitrogen atom to form a substituted or unsubstituted alicyclic heterocyclic group, and X represents CO, or pharmaceutically acceptable salts thereof.

3. An indole derivative according to claim 2, wherein $R^1$ and $R^2$ represent hydroxy, or a pharmaceutically acceptable salt thereof.

4. An indole derivative according to claim 3, wherein $R^3$ represents

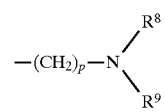

wherein $R^8$ and $R^9$ independently represent hydrogen or lower alkyl, or $R^8$ and $R^9$ are combined together with the adjacent nitrogen atom to form a substituted or unsubstituted alicyclic heterocyclic group; and p represents an integer of 2 to 6, or a pharmaceutically acceptable salt thereof.

5. An indole derivative according to claim 4, wherein $R^{10b}$ and $R^{11b}$ independently represent hydrogen, lower alkyl, or alicyclic alkyl, or $R^{10b}$ and $R^{11b}$ are combined together with the adjacent nitrogen atom to form a substituted or unsubstituted alicyclic heterocyclic group, or a pharmaceutically acceptable salt thereof.

6. 1-[3-[bis(4-hydroxyphenyl)methyl]-1-(2-dimethylaminoethyl)indol-2-ylcarbonyl]-4-(2-chlorophenyl)piperazine, or a pharmaceutically acceptable salt thereof.

7. An indole derivative according to claim 1, wherein $R^1$ and $R^2$ independently represent hydroxy, lower alkoxy, —O—$(CH_2)_n$—$OR^5$ wherein $R^5$ represents hydrogen or lower alkyl and n is an integer from 1 to 6, or

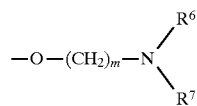

wherein $R^6$ and $R^7$ independently represent hydrogen or lower alkyl, or $R^6$ and $R^7$ are combined together with the adjacent nitrogen atom to form a substituted or unsubstituted alicyclic heterocyclic group; and m represents an integer of 2 to 6, $R^4$ represents —$NR^{10}R^{11a}$ wherein $R^{10}$ represents hydrogen, lower alkyl, alicyclic alkyl, lower alkenyl, substituted or unsubstituted aryl, a substituted or unsubstituted heterocyclic group; and $R^{10}$ and $R^{11a}$ represent

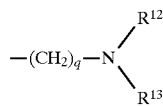

wherein $R^{12}$ and $R^{13}$ independently represent hydrogen or lower alkyl, or are combined together with the adjacent nitrogen atom form a substituted or unsubstituted alicyclic heterocyclic group; and q is an integer of 2 to 6, or —$(CH_2)_r$—$R^{14}$, wherein $R^{14}$ represents substituted or unsubstituted aryl or a substituted or unsubstituted heterocyclic group, and r is an integer of 1 to 6, or $R^{10}$ and $R^{11a}$ are combined together with the adjacent nitrogen atom to form a substituted or unsubstituted alicyclic heterocyclic group, and X represents CO, or pharmaceutically acceptable salts thereof.

8. An indole derivative according to claim 7, wherein $R^1$ and $R^2$ represent hydroxy, or a pharmaceutically acceptable salt thereof.

9. An indole derivative according to claim 7 or 8, wherein $R^3$ represents

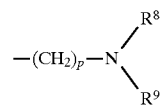

wherein $R^8$ and $R^9$ independently represent hydrogen or lower alkyl, or $R^8$ and $R^9$ are combined together with the adjacent nitrogen atom to form a substituted or unsubstituted alicyclic heterocyclic group, and p represents an integer of 2 to 6, or a pharmaceutically acceptable salt thereof.

10. An indole derivative according to claim 1, wherein $R^2$ represents hydrogen, lower alkyl, or halogen, and X represents CO, with the proviso that when $R^3$ is hydrogen or lower alkyl, $R^4$ is —$NR^{10}R^{11}$, or pharmaceutically acceptable salts thereof.

11. An indole derivative according to claim 10, wherein $R^1$ and $R^2$ represent hydrogen, or a pharmaceutically acceptable salt thereof.

12. An indole derivative according to claim 10 or 11, wherein $R^3$ represents

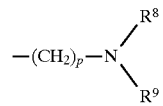

wherein $R^8$ and $R^9$ independently represent hydrogen or lower alkyl, or $R^8$ and $R^9$ are combined together with the adjacent nitrogen atom to form a substituted or unsubstituted alicyclic heterocyclic group, and p represents an integer of 2 to 6, or a pharmaceutically acceptable salt thereof.

13. An indole derivative according to claim 1, wherein X represents $SO_2$, or pharmaceutically acceptable salts thereof.

14. An indole derivative according to claim 13, wherein $R^1$ and $R^2$ represent hydrogen, or a pharmaceutically acceptable salt thereof.

15. An indole derivative according to claim 13 or 14, wherein $R^3$ represents

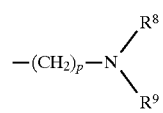

wherein $R^8$ and $R^9$ independently represent hydrogen or lower alkyl, or $R^8$ and $R^9$ are combined together with the adjacent nitrogen atom to form a substituted or unsubstituted alicyclic heterocyclic group, and p represents an integer of 2 to 6, or a pharmaceutically acceptable salt thereof.

16. A pharmaceutically acceptable composition comprising a pharmaceutically acceptable carrier and an effective amount of a compound according to claim 1 as an active ingredient.

* * * * *

UNITED STATES PATENT AND TRADEMARK OFFICE
CERTIFICATE OF CORRECTION

PATENT NO. : 5,891,902

DATED : April 6, 1999

INVENTOR(S) : DAISUKE MACHII ET AL.    Page 1 of 4

It is certified that error appears in the above-identified patent and that said Letters Patent is hereby corrected as shown below:

ON THE TITLE PAGE

[56] References Cited, "62141070" should read --62-141070--; and "63208571" should read --63-208571--.

COLUMN 18

Line 17, "conensing" should read --condensing--.

COLUMN 67

Line 46, "(1x10⁻" should read --(1x10$^{-8}$M),--; and
Line 47, "8M)," should be deleted.

COLUMN 68

Line 49, "Inc.)" should read --Inc.).--.

COLUMN 70

Line 5, "Chem.)" should read --Chem.).--.

COLUMN 73

Line 31, "under" should --under reduced--; and
Line 55, "were" should read --was--.

UNITED STATES PATENT AND TRADEMARK OFFICE
CERTIFICATE OF CORRECTION

PATENT NO. : 5,891,902

DATED : April 6, 1999

INVENTOR(S): DAISUKE MACHII ET AL.

It is certified that error appears in the above-identified patent and that said Letters Patent is hereby corrected as shown below:

COLUMN 74

Line 42, "Compound" should read --(Compound--.

COLUMN 76

Line 35, "7.371" should read --7.37--.

COLUMN 79

Line 46, ".188°" should read --188°--.

COLUMN 98

Line 53, "7.59" should read --7.54--.

COLUMN 101

Line 46, "46" should read --146--.

COLUMN 110

Line 48, "Å@6.48" should read --6.48--.

COLUMN 122

Line 15, Left Margin should be closed up.

UNITED STATES PATENT AND TRADEMARK OFFICE
CERTIFICATE OF CORRECTION

PATENT NO. : 5,891,902

DATED : April 6, 1999

INVENTOR(S) : DAISUKE MACHII ET AL.

It is certified that error appears in the above-identified patent and that said Letters Patent is hereby corrected as shown below:

COLUMN 126

Line 42, "83%-)" should read --83%)--.

COLUMN 131

Line 35, "of," should read --of--.

COLUMN 133

Line 58, "(2H,3)" should read --(2H,s)--.

COLUMN 134

Line 6, "-1( 2-" should read -- -1(2- --.

COLUMN 142

Line 62, "group;" should read --group,--; and
Line 66, "group;" should read --group,--.

UNITED STATES PATENT AND TRADEMARK OFFICE
CERTIFICATE OF CORRECTION

PATENT NO. : 5,891,902

DATED : April 6, 1999

INVENTOR(S) : DAISUKE MACHII ET AL.

It is certified that error appears in the above-identified patent and that said Letters Patent is hereby corrected as shown below:

<u>COLUMN 143</u>

```
Line 8, "form" should read --to form--; and
Line 9, "group;" should read --group,--.
```

Signed and Sealed this

Twenty-fifth Day of April, 2000

Attest:

Q. TODD DICKINSON

*Attesting Officer*    *Director of Patents and Trademarks*